(12) United States Patent
Gotteland et al.

(10) Patent No.: US 12,280,052 B2
(45) Date of Patent: Apr. 22, 2025

(54) COMPOSITIONS AND METHODS FOR THE TREATMENT OF ADENOMYOSIS AND RECTOVAGINAL ENDOMETRIOSIS

(71) Applicant: ObsEva S.A., Plan-les-Ouates (CH)

(72) Inventors: Jean-Pierre Gotteland, Geneva (CH); Ernest Loumaye, Cologny (CH)

(73) Assignee: Kissei Pharmaceutical Co., Ltd., Matsumoto (JP)

(*) Notice: Subject to any disclaimer, the term of this patent is extended or adjusted under 35 U.S.C. 154(b) by 766 days.

(21) Appl. No.: 17/289,418

(22) PCT Filed: Oct. 29, 2019

(86) PCT No.: PCT/EP2019/079448
§ 371 (c)(1),
(2) Date: Apr. 28, 2021

(87) PCT Pub. No.: WO2020/089190
PCT Pub. Date: May 7, 2020

(65) Prior Publication Data
US 2022/0117969 A1    Apr. 21, 2022

Related U.S. Application Data

(60) Provisional application No. 62/752,100, filed on Oct. 29, 2018.

(51) Int. Cl.
| A61K 31/519 | (2006.01) |
| A61K 31/4184 | (2006.01) |
| A61K 31/4439 | (2006.01) |
| A61K 31/513 | (2006.01) |
| A61K 31/55 | (2006.01) |
| A61K 31/565 | (2006.01) |
| A61K 31/567 | (2006.01) |
| A61K 31/57 | (2006.01) |
| A61K 31/573 | (2006.01) |
| A61K 31/585 | (2006.01) |
| A61K 47/54 | (2017.01) |
| A61P 15/00 | (2006.01) |

(52) U.S. Cl.
CPC ........ *A61K 31/519* (2013.01); *A61K 31/4184* (2013.01); *A61K 31/4439* (2013.01); *A61K 31/513* (2013.01); *A61K 31/55* (2013.01); *A61K 31/565* (2013.01); *A61K 31/567* (2013.01); *A61K 31/57* (2013.01); *A61K 31/573* (2013.01); *A61K 31/585* (2013.01); *A61K 47/541* (2017.08); *A61P 15/00* (2018.01)

(58) Field of Classification Search
CPC ................................................... A61K 31/519
See application file for complete search history.

(56) References Cited

U.S. PATENT DOCUMENTS

| 9,040,693 | B2 | 5/2015 | Ohno et al. |
| 9,169,266 | B2 | 10/2015 | Jo et al. |
| 9,737,539 | B2 | 8/2017 | Jo et al. |
| 10,016,433 | B2 | 7/2018 | Jo et al. |
| 11,759,464 | B2 | 9/2023 | Loumaye et al. |
| 11,980,621 | B2 | 5/2024 | Loumaye et al. |
| 2017/0056403 | A1 | 3/2017 | Goss et al. |
| 2019/0134038 | A1 | 5/2019 | Jo et al. |
| 2019/0175600 | A1 | 6/2019 | Dan et al. |
| 2019/0262346 | A1* | 8/2019 | Johnson ............... A61K 31/513 |
| 2020/0138819 | A1 | 5/2020 | Loumaye et al. |
| 2020/0179390 | A1 | 6/2020 | Loumaye et al. |

FOREIGN PATENT DOCUMENTS

| CA | 3025760 A1 | 2/2018 |
| EP | 2535342 A1 | 12/2012 |
| EP | 3498280 A1 | 6/2019 |
| JP | 2003-525249 A | 8/2003 |
| JP | 2016-513708 A | 5/2016 |
| WO | WO-2007/046392 A1 | 4/2007 |
| WO | WO-2011/099507 A1 | 8/2011 |
| WO | WO-2014/042176 A1 | 3/2014 |
| WO | WO-2014/143669 A1 | 9/2014 |

(Continued)

OTHER PUBLICATIONS

Kang et al, Efficacy of Gonadotropin-Releasing Hormone Agonist and an Extended-Interval Dosing Regimen in the Treatment of Patients with Adenomyosis and Endometriosis, 2010, Gynecologic and Obstetric Investigation, vol. 69, p. 73-77 (Year: 2010).*
Invitation to Pay Additional Fees for International Application No. PCT/EP2019/0749449, dated Feb. 12, 2020 (14 pages).
International Search Report and Written Opinion for International Application No. PCT/EP2019/079448, dated May 19, 2020 (20 pages).
ObsEva S.A., "Annual Report 2016," retrieved from <http://investors.obseva.com/phoenix.zhtml?c=254482&p=irol-reportsannual> (114 pages).

(Continued)

*Primary Examiner* — Kamal A Saeed
*Assistant Examiner* — Karen Cheng
(74) *Attorney, Agent, or Firm* — Clark & Elbing LLP

(57) ABSTRACT

The present disclosure provides compositions and methods for treating endometrial growth disorders in a patient, such as a human patient, and particularly pre-menopausal female human patients. Exemplary disorders that may be treated using the compounds and therapeutic regimens described herein include adenomyosis and rectovaginal endometriosis. The compounds described herein that may be used to treat such indications include gonadotropin-releasing hormone (GnRH) antagonists. Suitable GnRH antagonists useful in conjunction with the compositions and methods described herein include thieno[3,4d]pyrimidine derivatives, such as 3-[2-fluoro-5-(2,3-difluoro-6-methoxybenzyloxy)4-methoxyphenyl]-2,4-dioxo-1,2,3,4-tetrahydrothieno[3,4d]pyrimidine-5-carboxylic acid and the choline salt thereof, among others.

11 Claims, 6 Drawing Sheets

(56) References Cited

FOREIGN PATENT DOCUMENTS

| WO | WO-2018/030317 A1 | 2/2018 |
|----|----|----|
| WO | WO-2018/060501 A2 | 4/2018 |
| WO | WO-2018/0224497 A1 | 12/2018 |
| WO | WO-2018/224498 A1 | 12/2018 |
| WO | WO-2020/094698 A2 | 5/2020 |

OTHER PUBLICATIONS

Archer et al., "Elagolix for the management of heavy menstrual bleeding associated with uterine fibroids: results from a phase 2a proof-of-concept study," Fertil Steril. 108(1):152-160.e4 (includes supplemental content) (2017) (13 pages).

"ObsEva SA Announces the Completion of a Phase 1 PK/PD Clinical Trial Evaluating Different Doses of OBE2109 and Add-Back Therapy," ObsEva, retrieved from, <http://www.obseva.com/news/obseva-sa-announces-the-completion-of-a-phase-1-pk-pd-clinical-trial-evaluating-different-doses-of-obe2109-and-add-back-therapy> on Mar. 8, 2018 (2017) (7 pages).

"Building a Leader by Innovating Women's Reproductive Health and Pregnancy Therapeutics," ObsEva, Nov. 2017, <http://www.jefferies.com/CMSFiles/Jefferies.com/files/ObsEva.pdf> (35 pages).

International Search Report and Written Opinion for International Application No. PCT/EP2018/064767, mailed Aug. 24, 2018 (16 pages).

Donnez et al., "Partial suppression of estradiol: a new strategy in endometriosis management?," Fertil Steril. 107(3):568-70 (2017).

Hamdine et al., "Ovarian response prediction in GnRH antagonist treatment for IVF using anti-Müllerian hormone," Hum Reprod. 30(1):170-8 (2015).

International Search Report and Written Opinion for International Application No. PCT/EP2018/064768, mailed Oct. 17, 2018 (20 pages).

Signorile et al., "A tissue specific magnetic resonance contrast agent, Gd-AMH, for diagnosis of stromal endometriosis lesions: a phase I study," J Cell Physiol. 230(6):1270-5 (2015).

"AbbVie Announces Positive Topline Results from Phase 3 Extension Study Evaluating Investigational Elagolix in Women with Uterine Fibroids," Abbvie. published Aug. 22, 2018, retrieved on Oct. 1, 2020 (6 pages).

Donnez et al., "Partial suppression of estradiol: a new strategy in endometriosis management?" Fertil Steril. 107(3):568-569 (2017).

Lewis et al., "A Comprehensive Review of the Pharmacologic Management of Uterine Leiomyoma," Biomed Res Int. 2018:2414609 (2018) (11 pages).

International Search Report and Written Opinion for International Application No. PCT/EP2019/080362, mailed Jul. 7, 2020 (20 pages).

U.S. Appl. No. 17/291,192, filed May 4, 2021 (270 pages).

U.S. Appl. No. 17/291,192, Loumaye et al.

U.S. Appl. No. 17/289,418, Gotteland et al.

Communication pursuant to Article 94(3) for European Patent Application No. 18731976.9, dated May 17, 2021 (6 pages).

ObsEva, "ObsEva SA Announces the Completion of a Phase 1 PK/PD Clinical Trial Evaluating Different Doses of OBE2109 and Add-Back Therapy," dated Jun. 7, 2017, retrieved on Jul. 28, 2021 (5 pages).

Credit Suisse, "ObsEva SA: Late-Stage Women's Health Co. w/ Potentially Best-in-Class Lead Asset; Outperform, $27 TP," accessible at <https://research-doc.credit-suisse.com/docView?language=ENG&format=PDF&sourceid=csplusresearchcp&document_id=1071589801&serialid=w5tUz5ckZojLgop%2BFQZCZvq2JSqlpv%2FqYEO7ASCs3s0%3D>, dated Feb. 21, 2017 (44 pages).

WHO, "Proposed INN: List 118," WHO Drug Inf. 31(4):719-54 (2017).

"United States Securities Exchange Commission—Annual Report Pursuant to Section 13 or 15(d) of the Securities Exchange Act of 1934—Myovant Sciences Ltd.," Published Jun. 7, 2018, (40 pages).

ObsEva S.A., Informed Consent and Authorization Form, 15-OBE2109-001, accessible at <https://proslc.com/wp-content/uploads/2013/06/EDEWEISS-ENDO-ICF.pdf>, dated Aug. 11, 2016, (21 pages).

"Metrofibroma," Medical Dictionary, <https://medical-dictionary.thefreedictionary.com/metrofibroma>, retrieved on Nov. 3, 2021 (1 page).

"Fibroma," Medical Dictionary, <https://medical-dictionary.thefreedictionary.com/fibroma>, retrieved on Nov. 3, 2021 (2 pages).

PubChem, "Compound Summary for CID 5757, Estradiol," <https://pubchem.ncbi.nlm.nih.gov/compound/Estradiol>, retrieved on Nov. 3, 2021 (61 pages).

Pohl et al., "Gonadotropin-Releasing Hormone Receptor Antagonist Mono- and Combination Therapy With Estradiol/Norethindrone Acetate Add-Back: Pharmacodynamics and Safety of OBE2109," J Clin Endocrinol Metab. 103(2):497-504 (2018).

Taylor et al., "Treatment of Endometriosis-Associated Pain with Elagolix, an Oral GnRH Antagonist," N Engl J Med. 377(1): 28-40, S1-S41 (includes supplemental content) (May 2017) (55 pages).

Donnez et al., "Profile of Linzagolix in the Management of Endometriosis, Including Design, Development and Potential Place in Therapy: A Narrative Review," Drug Des Devel Ther. 17:369-380 (Feb. 2023).

Engel et al., "Presurgical short term treatment of uterine fibroids with different doses of cetrorelix acetate: A double-blind, placebo-controlled multicenter study," Eur J Obstet Gynecol Reprod Biol. 134(2):225-232 (Oct. 2007).

Küpker et al., "Use of GnRH antagonists in the treatment of endometriosis," Reprod Biomed Online. 5(1):12-16 (2002).

Donnez et al., "Linzagolix with and without hormonal add-back therapy for the treatment of symptomatic uterine fibroids: two randomised, placebo-controlled, phase 3 trials," Lancet. 400(10356):896-907 (Sep. 17, 2022).

Struthers et al., "Suppression of gonadotropins and estradiol in premenopausal women by oral administration of the nonpeptide gonadotropin-releasing hormone antagonist elagolix," J Clin Endocrinol Metab. 94(2):545-51 (2009) (14 pages).

Franke et al., "Gonadotropin-releasing hormone agonist plus 'add-back' hormone replacement therapy for treatment of endometriosis: a prospective, randomized, placebo-controlled, double-blind trial," Fertil Steril. 74(3):534-9 (2000).

Chen et al., "Discovery of sodium R-(+)-4-{2-[5-(2-fluoro-3-methoxyphenyl)-3-(2-fluoro-6-[trifluoromethyl]-benzyl)-4-methyl-2,6-dioxo-3,6-dihydro-2H-pyrimidin-1-yl]-1-phenylethylamino}butyrate (elagolix), a potent and orally available nonpeptide antagonist of the human gonadotropin-releasing hormone receptor," J Med Chem. 51(23):7478-85 (Dec. 2008).

Donnez et al., "Treatment of endometriosis-associated pain with linzagolix, an oral gonadotropin-releasing hormone-antagonist: a randomized clinical trial," Fertil Steril. 114(1):44-55 (Jul. 2020).

Rafique et al., "Medical Management of Endometriosis," Clin Obstet Gynecol. 60(3):485-496 (Sep. 2017).

ObsEva SA, "History of Changes for Study: NCT03070951. Efficacy and Safety of OBE2109 in Subjects With Heavy Menstrual Bleeding Associated With Uterine Fibroids (PRIMROSE 2)," U.S. National Library of Medicine, <<https://classic.clinicaltrials.gov/ct2/history/NCT03070951?V_11=View#StudyPageTop>>, retrieved on Sep. 27, 2023, latest version submitted Nov. 10, 2022 (21 pages).

* cited by examiner

FIG. 1

A. Dysmenorrhea
None      0 = No symptoms
Mild      1 = Some loss of ability to work or carry out normal activities
Moderate  2 = Unable to work or carry out normal daily activities for part of 1 or more days and/or moderately decreased work efficiency
Severe    3 = Unable to work or carry out normal daily activities for 1 or more full days and/or significantly decreased work efficiency B. Deep Dyspareunia
None      0 = No symptoms
Mild      1 = Tolerated discomfort during intercourse
Moderate  2 = Interference of usual frequency of sexual intercourse due to pain
Severe    3 = Avoids, or wishes to avoid, intercourse because of pain C. Non Menstrual Pelvic Pain
None      0 = No symptoms
Mild      1 = Occasional pelvic discomfort
Moderate  2 = Noticeable discomfort for most of cycle
Severe    3 = Pain persistent during cycle other than during menstruation

| Total Pelvic Pain Score (A + B + C) | |
|---|---|
| None | 0 |
| Mild | 1 - 3 |
| Moderate | 4 - 6 |
| Severe | 7 - 9 |

D. Pelvic Tenderness *(assessed by the physician)*
None      0 = No findings
Mild      1 = Minimal tenderness on palpation
Moderate  2 = Moderate tenderness on palpation
Severe    3 = Exam limited due to tenderness

| Total Physical Sign Score (D + E) | |
|---|---|
| None | 0 |
| Mild | 1 - 2 |
| Moderate | 3 - 4 |
| Severe | 5 - 6 |

E. Induration *(assessed by the physician)*
None      0 = No findings
Mild      1 = Uterus freely mobile, minimal induration in the cul-de-sac
Moderate  2 = Significant induration in the cul-de-sac, restricted uterine mobility
Severe    3 = Nodular adnexa and cul-de-sac, uterus fixed

| Composite Pelvic Pain and Physical Sign Score (A + B + C + D + E) | | | |
|---|---|---|---|
| None | 0 | Severe | 6 - 10 |
| Mild | 1 - 2 | Very Severe | 11 - 15 |
| Moderate | 3 - 5 | | |

FIG. 2A

PART 1: CORE QUESTIONNAIRE

During The Last 4 Weeks,
How Often, Because Of Your Endometriosis / Adenomyosis, Have You...

|   |   | Never | Rarely | Sometimes | Often | Always |
|---|---|---|---|---|---|---|
| 1. | Been unable to go to social events because of the pain? | ☐ | ☐ | ☐ | ☐ | ☐ |
| 2. | Been unable to do jobs around the home because of the pain? | ☐ | ☐ | ☐ | ☐ | ☐ |
| 3. | Found it difficult to stand because of the pain? | ☐ | ☐ | ☐ | ☐ | ☐ |
| 4. | Found it difficult to sit because of the pain? | ☐ | ☐ | ☐ | ☐ | ☐ |
| 5. | Found it difficult to walk because of the pain? | ☐ | ☐ | ☐ | ☐ | ☐ |
| 6. | Found it difficult to exercise or do the leisure activities you would like to do because of the pain? | ☐ | ☐ | ☐ | ☐ | ☐ |
| 7. | Lost your appetite and/or been unable to eat because of the pain? | ☐ | ☐ | ☐ | ☐ | ☐ |

FIG. 2B

During The Last 4 Weeks,
How Often, Because Of Your Endometriosis / Adenomyosis, Have You...

|     |     | Never | Rarely | Sometimes | Often | Always |
|-----|-----|-------|--------|-----------|-------|--------|
| 8.  | Been unable to sleep properly because of the pain? | ☐ | ☐ | ☐ | ☐ | ☐ |
| 9.  | Had to go to bed/lie down because of the pain? | ☐ | ☐ | ☐ | ☐ | ☐ |
| 10. | Been unable to do the things you want to do because of the pain? | ☐ | ☐ | ☐ | ☐ | ☐ |
| 11. | Felt unable to cope with the pain? | ☐ | ☐ | ☐ | ☐ | ☐ |
| 12. | Generally felt unwell? | ☐ | ☐ | ☐ | ☐ | ☐ |
| 13. | Felt frustrated because your symptoms are not getting better? | ☐ | ☐ | ☐ | ☐ | ☐ |
| 14. | Felt frustrated because you are not able to control your symptoms? | ☐ | ☐ | ☐ | ☐ | ☐ |

FIG. 2C

During The Last 4 Weeks,
How Often, Because Of Your Endometriosis / Adenomyosis, Have You...

|  |  | Never | Rarely | Sometimes | Often | Always |
|---|---|---|---|---|---|---|
| 15. | Felt unable to forget your symptoms? | ☐ | ☐ | ☐ | ☐ | ☐ |
| 16. | Felt as though your symptoms are ruling your life? | ☐ | ☐ | ☐ | ☐ | ☐ |
| 17. | Felt your symptoms are taking away your life? | ☐ | ☐ | ☐ | ☐ | ☐ |
| 18. | Felt depressed? | ☐ | ☐ | ☐ | ☐ | ☐ |
| 19. | Felt weepy/tearful? | ☐ | ☐ | ☐ | ☐ | ☐ |
| 20. | Felt miserable? | ☐ | ☐ | ☐ | ☐ | ☐ |
| 21. | Had mood swings? | ☐ | ☐ | ☐ | ☐ | ☐ |
| 22. | Felt bad tempered or short tempered? | ☐ | ☐ | ☐ | ☐ | ☐ |

FIG. 2D

During The Last 4 Weeks,
How Often, Because Of Your Endometriosis / Adenomyosis, Have You...

| | Never | Rarely | Sometimes | Often | Always |
|---|---|---|---|---|---|
| 23. Felt violent or aggressive? | ☐ | ☐ | ☐ | ☐ | ☐ |
| 24. Felt unable to tell people how you feel? | ☐ | ☐ | ☐ | ☐ | ☐ |
| 25. Felt others do not understand what you are going through? | ☐ | ☐ | ☐ | ☐ | ☐ |
| 26. Felt as though others think you are moaning? | ☐ | ☐ | ☐ | ☐ | ☐ |
| 27. Felt alone? | ☐ | ☐ | ☐ | ☐ | ☐ |
| 28. Felt frustrated as you cannot always wear the clothes you would choose? | ☐ | ☐ | ☐ | ☐ | ☐ |
| 29. Felt your appearance has been affected? | ☐ | ☐ | ☐ | ☐ | ☐ |
| 30. Lacked confidence? | ☐ | ☐ | ☐ | ☐ | ☐ |

FIG. 3

> Since the start of the study, my overall status is:
>
> 1 ☐ Very Much Improved
> 2 ☐ Much Improved
> 3 ☐ Minimally Improved
> 4 ☐ No Change
> 5 ☐ Minimally Worse
> 6 ☐ Much Worse
> 7 ☐ Very Much Worse

COMPOSITIONS AND METHODS FOR THE TREATMENT OF ADENOMYOSIS AND RECTOVAGINAL ENDOMETRIOSIS

FIELD OF THE INVENTION

The invention relates to the therapeutic treatment of disorders of the female reproductive system, including endometrial growth disorders, such as adenomyosis and rectovaginal endometriosis.

BACKGROUND OF THE INVENTION

Adenomyosis and rectovaginal endometriosis are particularly severe endometrial growth disorders characterized by the invasion of endometrial tissue into the uterine myometrium and rectovaginal zones, respectively. The term adenomyosis or uterine adenomyosis is used to describe the presence of both endometrial glands and stroma deep within the myometrium. This condition is associated with hypertrophy and hyperplasia of the subjacent muscle cells, which may ultimately result in an altered size and globulous morphology of the uterus. Due to the severity of this disorder, one of the key symptoms is strong menstrual and even non-menstrual pelvic pain with abnormal uterine bleeding. There is a paucity of treatment options for women with uterine adenomyosis, as existing medicinal interventions consist primarily of analgesic therapies or, in an off-label use, hormonal therapies. Few minimally invasive surgeries exist for uterine adenomyosis patients, and hysterectomy is often considered to be the only curative option for this disorder. There are currently no therapeutic drugs approved for the treatment of adenomyosis or its associated symptomology. Like adenomyosis, rectovaginal endometriosis patients present with a variety of pain symptoms including dysmenorrhea, dyspareunia, chronic pelvic pain, dysuria, and dyschezia. Treatment options for rectovaginal endometriosis are limited. Since medical therapies are either ineffective or have considerable side effects, rectovaginal endometriosis patients often undergo surgical procedures to reduce the endometrial node, and may even be subject to resection of the bowel if the node infiltrates the rectal or sigmoidal wall.

There exists a need for new, effective therapeutics for alleviating the symptoms associated with these disorders, as well as for treating their underlying pathology.

SUMMARY OF THE INVENTION

The present disclosure relates to compositions and methods for the treatment of adenomyosis and rectovaginal endometriosis in patients suffering from one or both of these conditions. The patient may be a mammalian patient, such as a human patient, and may be diagnosed with, and treated for, one or both of these diseases using the compositions and methods described herein. In some embodiments, the patient has previously been diagnosed as having one or both of these disorders, and the compositions and methods provided herein are used to treat the patient. Using the compositions and methods of the disclosure, a patient having adenomyosis and/or rectovaginal endometriosis may be administered a gonadotropin-releasing hormone (GnRH) receptor antagonist so as to alleviate one or more symptoms of these diseases, such as global pelvic pain, dysmenorrhea, dyspareunia, dyschezia, and uterine bleeding. Additionally or alternatively, a GnRH antagonist may be administered to the patient in accordance with the compositions and methods described herein so as to ameliorate the underlying biochemical etiology of one or both of these conditions, such as by reducing endogenous serum concentrations of β17-estradiol (E2), for example, to a level of from about 20 pg/m to about 50 μg/ml or less, follicle-stimulating hormone (FSH), and/or luteinizing hormone (LH) in the patient. Without being limited by mechanism, the compositions and methods of the disclosure may thus be used to reduce uterine volume in adenomyosis patients and diminish rectal and/or vaginal endometriosis lesions in patients suffering from rectovaginal endometriosis.

GnRH antagonists that may be used in conjunction with the compositions and methods described herein include optionally substituted thieno[3,4d]pyrimidine derivatives, such as 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylic acid or the choline salt thereof. In some embodiments, the GnRH antagonist is an optionally substituted 3-aminoalkyl pyrimidine-2,4(1H,3H)-dione derivative, such as sodium 4-({(1R)-2-[5-(2-fluoro-3-methoxyphenyl)-3-{[2-fluoro-6-(trifluoromethyl)phenyl] methyl}-4-methyl-2,6-dioxo-3,6-dihydropyrimidin-1(2H)-yl]-1-phenylethyl}amino)butanoate, also referred to as elagolix, or the carboxylic acid conjugate thereof. The GnRH antagonist may be, for example, an optionally substituted thieno[2,3d]pyrimidine derivative, such as N-(4-(1-(2,6-difluorobenzyl)-5-((dimethylamino)methyl)-3-(6-methoxy-3-pyridazinyl)-2,4-dioxo-1,2,3,4-tetrahydrothieno [2,3-d]pyrimidin-6-yl)phenyl)-N'-methoxyurea, also referred to as relugolix, or a pharmaceutically acceptable salt thereof. In some embodiments, the GnRH antagonist is an optionally substituted propane-1,3-dione derivative, such as (2R)—N-{5-[3-(2,5-difluorophenyl)-2-(1,3-dihydro-2H-benzimidazol-2-ylidene)-3-oxopropanoyl]-2-fluorobenzene-1-sulfonyl}-2-hydroxypropanimidamide, also referred to as opigolix or ASP-1707. Additional GnRH antagonists that may be used in conjunction with the compositions and methods described herein include SK12670 and BAY-784, as well as derivatives and variants thereof, among others.

The present disclosure is based, in part, on the surprising discovery that GnRH antagonists, such as those described above, may be used to effectively treat adenomyosis and rectovaginal endometriosis. These diseases are particularly severe endometrial growth disorders. Adenomyosis, for instance, is a pathology in which endometrial glands and stroma invade the uterine myometrium. This penetration of endometrial tissue into the patient's myometrium can cause myocyte hypertrophy and hyperplasia, which interferes with the structure and function of uterine muscle tissue. Due to the severity of the growth of endometrial structures into the myometrial tissue, adenomyosis patients generally suffer from substantial pain, including global pelvic pain, dysmenorrhea, dyspareunia, and dyschezia. Unlike traditional endometriosis, adenomyosis patients may also exhibit significant uterine blood loss. Like adenomyosis, rectovaginal endometriosis is another dangerous endometrial growth disorder in which endometrial tissue extends outside of the uterus and infiltrates rectal and/or vaginal tissue. Patients having rectovaginal endometriosis may present with, for example, endometriosis tissue that penetrates the cervix, as is the case in Type II rectovaginal endometriosis. In some embodiments, rectovaginal endometriosis patients exhibit endometriosis tissue that infiltrates the wall of the rectum or sigmoid, which is diagnostic of Type III rectovaginal endometriosis. Due to the location and invasive nature of the endometrial growth in rectovaginal endometriosis patients, this disease can induce particularly painful symptoms, including global pelvic pain, dysmenorrhea, dyspareunia, and dyschezia, and may further result in abnormal uterine bleeding.

The compositions and methods described herein provide a series of important clinical benefits, as the contents of the present disclosure may be used to effectuate the treatment of patients having severe endometrial growth disorders. To obtain these beneficial effects, a patient may be administered a GnRH antagonist, for example, on a periodic basis according to a dosing schedule described herein. A patient suffering from adenomyosis and/or rectovaginal endometriosis may be administered a GnRH antagonist one or more times per day, week, or month over the course of a defined treatment period. For example, a patient may be administered an optionally substituted thieno[3,4d]pyrimidine derivative, such as 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid or the choline salt thereof, in an amount of from about 50 mg per day to about 400 mg per day (e.g., in an amount of about 100 mg per day or about 200 mg per day) over the course of a treatment period, such as a treatment period lasting one or more months (e.g., from about 4 weeks to about 52 weeks, such as a treatment period of 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, or more). In some embodiments, the GnRH antagonist is an optionally substituted 3-aminoalkyl pyrimidine-2,4(1H,3H)-dione derivative, such as sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate (elagolix), or the carboxylic acid conjugate thereof, and is administered to the patient in an amount of from about 100 mg per day to about 600 mg per day (e.g., in an amount of about 150 mg per day, about 300 mg per day, about 400 mg per day, or about 600 mg per day) over the course of a treatment period, such as a treatment period lasting one or more months (e.g., from about 4 weeks to about 52 weeks, such as a treatment period of 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, or more). The GnRH antagonist may be, for example, an optionally substituted thieno[2,3d]pyrimidine derivative, such as N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea (relugolix), or a pharmaceutically acceptable salt thereof, and may be administered to the patient in an amount of from about 20 mg per day to about 50 mg per day (e.g., in an amount of about 40 mg per day) over the course of a treatment period, such as a treatment period lasting one or more months (e.g., from about 4 weeks to about 52 weeks, such as a treatment period of 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, or more). In some embodiments, the GnRH antagonist is an optionally substituted propane-1,3-dione derivative, such as (2R)—N-{5-[3-(2,5-difluorophenyl)-2-(1,3-dihydro-2H-benzimidazol-2-ylidene)-3-oxopropanoyl]-2-fluorobenzene-1-sulfonyl}-2-hydroxypropanimidamide (opigolix), or the GnRH antagonist is SK12670 or BAY-784, and the GnRH antagonist may be administered to the patient one or more times per day, week, or month over the course of a treatment period, such as a treatment period lasting one or more months (e.g., from about 4 weeks to about 52 weeks, such as a treatment period of 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, or more).

In a first aspect, the disclosure features a method of treating adenomyosis in a human patient in need thereof by administering to the patient a therapeutically effective amount of a GnRH antagonist. In an additional aspect, the disclosure features a method of treating adenomyosis in a human patient by:
 a) diagnosing the patient as having adenomyosis; and
 b) administering to the patient a therapeutically effective amount of a GnRH antagonist.

In a further aspect, the disclosure features a method of reducing uterine volume in a human patient diagnosed as having adenomyosis by administering to the patient a therapeutically effective amount of a GnRH antagonist. In another aspect, the disclosure features a method of reducing uterine volume in a human patient by:
 a) diagnosing the patient as having adenomyosis; and
 b) administering to the patient a therapeutically effective amount of a GnRH antagonist.

In an additional aspect, the disclosure features a method of reducing the thickness of the anterior and/or posterior region of the uterine myometrium in a human patient diagnosed as having adenomyosis by administering to the patient a therapeutically effective amount of a GnRH antagonist.

In yet another aspect, the disclosure features a method of reducing the thickness of the anterior and/or posterior region of the uterine myometrium in a human patient by:
 a) diagnosing the patient as having adenomyosis; and
 b) administering to the patient a therapeutically effective amount of a GnRH antagonist.

In another aspect, the disclosure features a method of reducing pelvic pain in a human patient diagnosed as having adenomyosis by administering to the patient a therapeutically effective amount of a GnRH antagonist. In a further aspect, the disclosure features a method of reducing pelvic pain in a human patient by:
 a) diagnosing the patient as having adenomyosis; and
 b) administering to the patient a therapeutically effective amount of a GnRH antagonist.

In an additional aspect, the disclosure features a method of reducing dysmenorrhea in a human patient diagnosed as having adenomyosis by administering to the patient a therapeutically effective amount of a GnRH antagonist. In a further aspect, the disclosure features a method of reducing dysmenorrhea in a human patient by:
 a) diagnosing the patient as having adenomyosis; and
 b) administering to the patient a therapeutically effective amount of a GnRH antagonist.

In yet another aspect, the disclosure features a method of reducing dyspareunia in a human patient diagnosed as having adenomyosis by administering to the patient a therapeutically effective amount of a GnRH antagonist. In a further aspect, the disclosure features a method of reducing dyspareunia in a human patient by:
 a) diagnosing the patient as having adenomyosis; and
 b) administering to the patient a therapeutically effective amount of a GnRH antagonist.

In another aspect, the disclosure features a method of reducing dyschezia in a human patient diagnosed as having adenomyosis by administering to the patient a therapeutically effective amount of a GnRH antagonist. In an additional aspect, the disclosure features a method of reducing dyschezia in a human patient by:

a) diagnosing the patient as having adenomyosis; and
b) administering to the patient a therapeutically effective amount of a GnRH antagonist.

In yet another aspect, the disclosure features a method of reducing uterine tenderness in a human patient diagnosed as having adenomyosis by administering to the patient a therapeutically effective amount of a GnRH antagonist. In a further aspect, the disclosure features a method of reducing uterine tenderness in a human patient by:
a) diagnosing the patient as having adenomyosis; and
b) administering to the patient a therapeutically effective amount of a GnRH antagonist.

In an additional aspect, the disclosure features a method of reducing uterine bleeding in a human patient diagnosed as having adenomyosis by administering to the patient a therapeutically effective amount of a GnRH antagonist. In yet another aspect, the disclosure features a method of reducing uterine bleeding in a human patient by:
a) diagnosing the patient as having adenomyosis; and
b) administering to the patient a therapeutically effective amount of a GnRH antagonist.

In another aspect, the disclosure features a method of inducing amenorrhea in a human patient diagnosed as having adenomyosis by administering to the patient a therapeutically effective amount of a GnRH antagonist. In an additional aspect, the disclosure features a method of inducing amenorrhea in a human patient by:
a) diagnosing the patient as having adenomyosis; and
b) administering to the patient a therapeutically effective amount of a GnRH antagonist.

In an additional aspect, the disclosure features a method of reducing serum concentration of E2, FSH, and/or LS in a human patient diagnosed as having adenomyosis by administering to the patient a therapeutically effective amount of a GnRH antagonist. In yet another aspect, the disclosure features a method of reducing serum concentration of E2, FSH, and/or LS in a human patient by:
a) diagnosing the patient as having adenomyosis; and
b) administering to the patient a therapeutically effective amount of a GnRH antagonist.

In some embodiments of any of the foregoing aspects of the disclosure, the GnRH antagonist is a compound represented by formula (I)

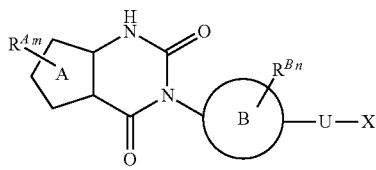

(I)

wherein ring A is a thiophene ring;
each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;
m is an integer from 0 to 3;
ring B is an aryl group or a monocyclic heteroaryl group;
each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;
n is an integer from 0 to 2;
U is a single bond;
X is a group represented by —S-L-Y, —O-L-Y, —CO-L-Y, or —SO$_2$-L-Y, wherein
L is an optionally substituted lower alkylene group;
Y is a group represented by Z or —NW$^7$W$^8$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^8$ may bind together with the neighboring nitrogen atom to form an optionally substituted cyclic amino group; and
Z is an optionally fused and optionally substituted cycloalkyl group, an optionally fused and optionally substituted heterocycloalkyl group, an optionally fused and optionally substituted aryl group, or an optionally fused and optionally substituted heteroaryl group;
or a pharmaceutically acceptable salt thereof.

In some embodiments of formula (I), the ring A is a thiophene ring represented by formula (IIa)

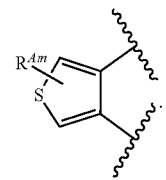

(IIa)

In some embodiments of formula (I) or (IIa), m is 1.
In some embodiments of formula (I) or (IIa), the ring A is an optionally substituted thiophene ring represented by formula (IIb)

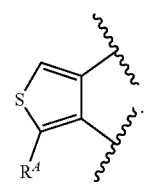

(IIb)

In some embodiments of formula (I), (IIa), or (IIb), each $R^A$ is independently a halogen atom, an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group.

In some embodiments of formula (I), (IIa), or (IIb), each $R^A$ is COOH or pharmaceutically acceptable salt thereof.

In some embodiments of formula (I), (IIa), or (IIb), the ring B is an optionally substituted benzene ring, pyridine ring, or thiophene ring.

In some embodiments of formula (I), (IIa), or (IIb), the ring B is represented by a formula selected from the group consisting of:

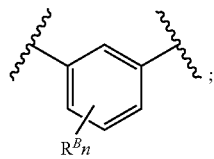

(IIIa)

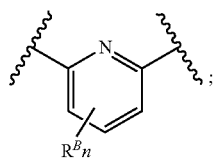

(IIIb)

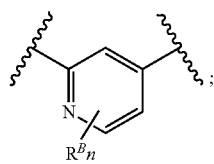

(IIIc)

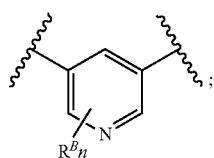

(IIId)

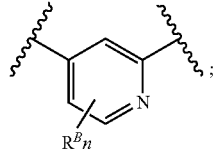

(IIIe)

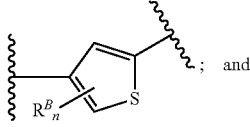

; and (IIIf)

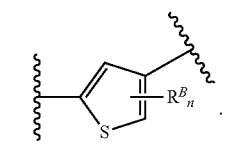

(IIIg)

In some embodiments of formula (I), (IIa), (IIb), or any one of (IIIa)-(IIIg), n is 2.

In some embodiments of formula (I), (IIa), (IIb), or any one of (IIIa)-(IIIg), the ring B is represented by a formula selected from the group consisting of:

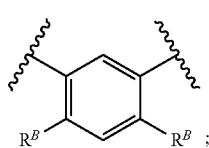

(IVa)

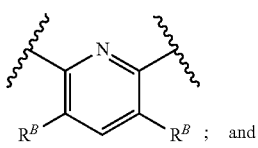

; and (IVb)

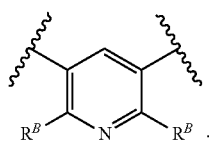

.

(IVc)

In some embodiments of formula (I), (IIa), (IIb), any one of (IIIa)-(IIIg), or any one of (IVa)-(IVc), each $R^B$ is independently a halogen atom, an optionally substituted lower alkyl group, or $OW^4$, wherein each $W^4$ is independently a hydrogen atom or an optionally substituted lower alkyl group.

In some embodiments of formula (I), (IIa), (IIb), any one of (IIIa)-(IIIg), or any one of (IVa)-(IVc), each $R^B$ is independently a fluorine atom, chlorine atom, bromine atom, methyl group, or methoxy group.

In some embodiments of formula (I), (IIa), (IIb), any one of (IIIa)-(IIIg), or any one of (IVa)-(IVc), U is a single bond.

In some embodiments of formula (I), (IIa), (IIb), any one of (IIIa)-(IIIg), or any one of (IVa)-(IVc), X is a group represented by —O-L-Y.

In some embodiments of formula (I), (IIa), (IIb), any one of (IIIa)-(IIIg), or any one of (IVa)-(IVc), L is a methylene group.

In some embodiments of formula (I), (IIa), (IIb), any one of (IIIa)-(IIIg), or any one of (IVa)-(IVc), Y is an optionally substituted benzene ring represented by formula (V)

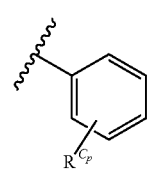

(V)

wherein each $R^C$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments of formula (I), (Ia), (IIb), any one of (IIIa)-(IIg), any one of (IVa)-(IVc), or (V), Y is a substituted benzene ring represented by formula (Va)

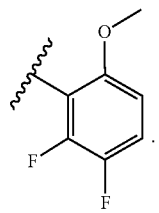

(Va)

In some embodiments, the compound is represented by formula (Ia)

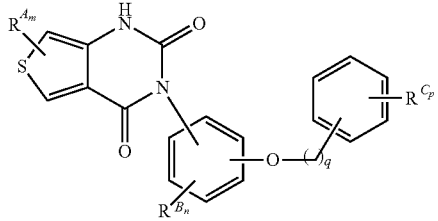

(Ia)

wherein each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

q is an integer from 0 to 3;

each $R^C$ is independently a halogen atom, an optionally substituted lower alkyl group, or $OW^9$, wherein each $W^9$ is independently a hydrogen atom or an optionally substituted lower alkyl group; and p is an integer from 0 to 3;

or a pharmaceutically acceptable salt thereof.

In some embodiments, the compound is represented by formula (Ib)

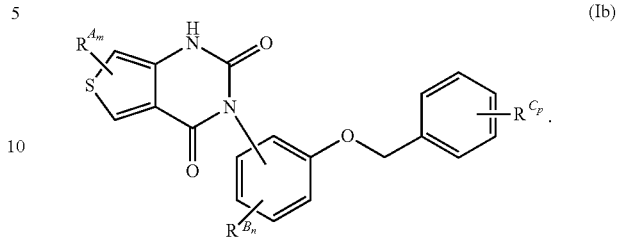

(Ib)

In some embodiments, the compound is represented by formula (Ic)

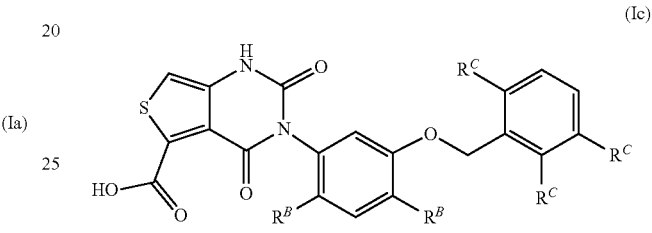

(Ic)

or a pharmaceutically acceptable salt thereof.

In some embodiments, the compound is 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid, represented by formula (VI)

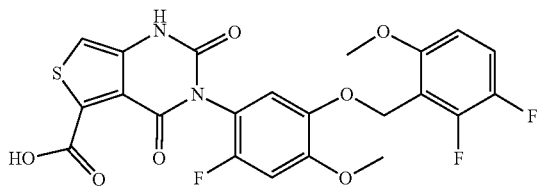

(VI)

or a pharmaceutically acceptable salt thereof. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of an electrostatically neutral carboxylic acid. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylic acid is administered to the patient in the form of a pharmaceutically acceptable salt. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of the choline salt, choline 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylate.

In some embodiments, the compound is the choline salt of the compound represented by formula (VI), choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate is in a crystalline state.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits characteristic X-ray powder diffraction (XRPD) peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{19}F$ solid-state NMR peaks centered at about −151.8 ppm, −145.2 ppm, and −131.6 ppm.

In some embodiments, the compound of any one of formulas (I), (Ia)-(Ic), (IIa), (IIb), (IIIa)-(IIIg), (IVa)-(IVc), (V), (Va), or (VI) is orally administered to the patient.

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 50 mg to about 400 mg per dose (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, or 400 mg of the compound of any one of formulas (I), (Ia)-(Ic), (IIa), (IIb), (IIIa)-(IIIg), (IVa)-(IVc), (V), (Va), or (VI) (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 35 mg to about 65 mg per dose (e.g., in the recited amount or in an equivalent amount of a pharmaceutically acceptable salt, such as a choline salt), such as an amount of about 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 50 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 60 mg to about 90 mg per dose (e.g., in the recited amount or in an equivalent amount of a pharmaceutically acceptable salt, such as a choline salt), such as an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 75 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 50 mg to about 150 mg per dose (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 100 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 150 mg to about 250 mg per dose (e.g., in the recited amount or in an equivalent amount of a pharmaceutically acceptable salt, such as a choline salt), such as an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa) (IVc), (V), (Va), or (VI) is administered to the patient in an amount of about 200 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIIb), (IIIa)-(IIIg), (IVa)-(IVc), (V), (Va), or (VI) is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (I), (Ia)-(Ic), (IIa), (IIb), (IIIa)-(IIIg), (IVa)-(IVc), (V), (Va), or (VI) may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (I), (Ia)-(Ic), (IIa), (IIb), (IIIa)-(IIIg), (IVa)-(IVc), (V), (Va), or (VI) is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

The compound of any one of formulas (I), (Ia)-(Ic), (IIa), (IIb), (IIIa)-(IIIg), (IVa)-(IVc), (V), (Va), or (VI) may be administered to the patient in one or more unit dosage forms that collectively constitute a single dose. For example, a patient may be administered a single dose of the compound of a specified amount, such as a single dose of 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, or more (e.g., in the recited amount or in an equivalent amount of a pharmaceutically acceptable salt, such as a choline salt), by administration of one or more unit dosage forms of the compound to the patient. As a non-limiting example, a single dose of 200 mg of the compound may be administered to the subject by way of two individual 100-mg unit dosage forms of the compound. The two 100-mg unit dosage forms collectively constitute a single 200-mg dose of the compound if administered to the patient at substantially the same time.

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 35 mg to about 65 mg per day (e.g., in the recited amount or in an equivalent amount of a pharmaceutically acceptable salt, such as a choline salt), such as an amount of about 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 50 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 60 mg to about 90 mg per day (e.g., in the recited amount or in an equivalent amount of a pharmaceutically acceptable salt, such as a choline salt), such as an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 75 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 50 mg to about 150 mg per day (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 100 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 150 mg to about 250 mg per day (e.g., in the recited amount or in an equivalent amount of a pharmaceutically acceptable salt, such as a choline salt), such as an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 200 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in a single dose per day. For example, the compound may be administered to the patient in an amount (e.g., a single dose) of from about 35 mg to about 65 mg per day (e.g., in the recited amount or in an equivalent amount of a pharmaceutically acceptable salt, such as a choline salt), such as an amount of about 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg per day (e.g., in the recited amount or in an equivalent amount of a pharmaceutically acceptable salt, such as a choline salt). In some embodiments, the compound is administered to the patient in an amount (e.g., a single dose) of about 50 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(Vc), (V), (Va), or (VI) is administered to the patient in a single dose per day. For example, the compound may be administered to the patient in an amount (e.g., a single dose) of from about 60 mg to about 90 mg per day (e.g., in the recited amount or in an equivalent amount of a pharmaceutically acceptable salt, such as a choline salt), such as an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg per day (e.g., in the recited amount or in an equivalent amount of a pharmaceutically acceptable salt, such as a choline salt). In some embodiments, the compound is administered to the patient in an amount (e.g., a single dose) of about 75 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in a single dose per day. For example, the compound may be administered to the patient in an amount (e.g., a single dose) of from about 50 mg to about 150 mg per day (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per day (e.g., in the recited amount or in an equivalent amount of a pharmaceutically acceptable salt, such as a choline salt). In some embodiments, the compound is administered to the patient in an amount (e.g., a single dose) of about 100 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in a single dose per day, and is administered to the patient in an amount (e.g., a single dose) of from about 150 mg to about 250 mg per day (e.g., in the recited amount or in an equivalent amount of a pharmaceutically acceptable salt, such as a choline salt), such as an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per day (e.g., in the recited amount or in an equivalent amount of a pharmaceutically acceptable salt, such as a choline salt). In some embodiments, the compound is administered to the patient in an amount (e.g., a single dose) of about 200 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period, such as a treatment period of one or more weeks, months, or years, for example, a treatment period of from about 1 week to about 48 months, or more (e.g., a treatment period of about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, 73 weeks, 74 weeks, 75 weeks, 76 weeks, 77 weeks, 78 weeks, 79 weeks, 80 weeks, 81 weeks, 82 weeks, 83 weeks, 84 weeks, 85 weeks, 86 weeks, 87 weeks, 88 weeks, 89 weeks, 90 weeks, 91 weeks, 92 weeks, 93 weeks, 94 weeks, 95 weeks, 96 weeks, 97 weeks, 98 weeks, 99 weeks, 100 weeks, 101 weeks, 102 weeks, 103 weeks, 104 weeks, 105 weeks, 106 weeks, 107 weeks, 108 weeks, 109 weeks, 110 weeks, 111 weeks, 112 weeks, 113 weeks, 114 weeks, 115 weeks, 116 weeks, 117 weeks, 118 weeks, 119 weeks, 120 weeks, 121 weeks, 122 weeks, 123 weeks, 124 weeks, 125 weeks, 126 weeks, 127 weeks, 128 weeks, 129 weeks, 130 weeks, 131 weeks, 132 weeks, 133 weeks, 134 weeks, 135 weeks, 136 weeks, 137 weeks, 138 weeks, 139 weeks, 140 weeks, 141 weeks, 142 weeks, 143 weeks, 144 weeks, 145 weeks, 146 weeks, 147 weeks, 148 weeks, 149 weeks, 150 weeks, 151 weeks, 152 weeks, 153 weeks, 154 weeks, 155 weeks, 156 weeks, 157 weeks, 158 weeks, 159 weeks, 160 weeks, 161 weeks, 162 weeks, 163 weeks, 164 weeks, 165 weeks, 166 weeks, 167 weeks, 168 weeks, 169 weeks, 170 weeks, 171 weeks, 172 weeks, 173 weeks, 174 weeks, 175 weeks, 176 weeks, 177 weeks, 178 weeks, 179 weeks, 180 weeks, 181 weeks, 182 weeks, 183 weeks, 184 weeks, 185 weeks, 186 weeks, 187 weeks, 188 weeks, 189 weeks, 190 weeks, 191 weeks, 192 weeks, 193 weeks, 194 weeks, 195 weeks, 196 weeks, 197 weeks, 198 weeks, 199 weeks, or 200 weeks, or more). The compound may be administered to the patient in the recited amount or in an equivalent amount of a pharmaceutically acceptable salt, such as a choline salt. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 1 month to about 48 months, or more, such as a treatment period of about 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 4 weeks, such as a treatment period of from about 4 weeks to about 12 months, or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 1 month to about 12 months, or more, such as a treatment period of about 1 month, 2 months, 3 months, 4 months, 5 months, 6 months, 7 months, 8 months, 9 months, 10 months, 11 months, or 12 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 8 weeks, such as a treatment period of from about 8 weeks to about 10 months, or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, or 40 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 2 months to about 10 months, or more, such as a treatment period of about 2 months, 3 months, 4 months, 5 months, 6 months, 7 months, 8 months, 9 months, or 10 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 12 weeks, such as a treatment period of from about 12 weeks to about 48 weeks (e.g., a treatment period of from about 16 weeks to about 48 weeks), or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 3 months to about 12 months, or more, such as a treatment period of about 3 months, 4 months, 5 months, 6 months, 7 months, 8 months, 9 months, 10 months, 11 months, or 12 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 24 weeks, such as a treatment period of from about 24 weeks to about 72 weeks, or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 6 months to about 18 months, or more, such as a treatment period of about 6 months, 7 months, 8 months, 9 months, 10 months, 11 months, 12 months, 13 months, 14 months, 15 months, 16 months, 17 months, or 18 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient at a particular dose (e.g., a particular daily dose) over the course of a first treatment period, and is subsequently periodically administered to the patient at a higher or lower dose (e.g., a higher or lower daily dose) over the course of a second treatment period. For example, in some embodiments, the compound is administered to the patient in one or more daily doses (e.g., from 1 to 10 doses, such as 1, 2, 3, 4, 5, 6, 7, 8, 9, or 10 doses, or more, such as a single daily dose) totaling from about 150 mg to about 250 mg per day over the course of a first treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling from about 50 mg to about 150 mg per day over the course of a second treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per day over the course of a second treatment period (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more, such as a single daily dose) totaling from about 175 mg to about 225 mg per day over the course of a first treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, or 225 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling from about 75 mg to about 125 mg per day over the course of a second treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, or 125 mg per day over the course of a second treatment period (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more, such as a single daily dose) totaling from about 185 mg to about 215 mg per day over the course of a first treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, or 215 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling from about 85 mg to about 115 mg per day over the course of a second treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, or 115 mg per day over the course of a second treatment period (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more, such as a single daily dose) totaling about 200 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling about 100 mg per day over the course of a second treatment period (e.g., in the recited amount or in an equivalent amount of a pharmaceutically acceptable salt, such as a choline salt).

In some embodiments, the first and second treatment periods collectively have a duration of one or more weeks, months, or years, for example, a combined treatment period of from about 1 week to about 48 months, or more (e.g., a combined treatment period of about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, 73 weeks, 74 weeks, 75 weeks, 76 weeks, 77 weeks, 78 weeks, 79 weeks, 80 weeks, 81 weeks, 82 weeks, 83 weeks, 84 weeks, 85 weeks, 86 weeks, 87 weeks, 88 weeks, 89 weeks, 90 weeks, 91 weeks, 92 weeks, 93 weeks, 94 weeks, 95 weeks, 96 weeks, 97 weeks, 98 weeks, 99 weeks, 100 weeks, 101 weeks, 102 weeks, 103 weeks, 104 weeks, 105 weeks, 106 weeks, 107 weeks, 108 weeks, 109 weeks, 110 weeks, 111 weeks, 112 weeks, 113 weeks, 114 weeks, 115 weeks, 116 weeks, 117 weeks, 118 weeks, 119 weeks, 120 weeks, 121 weeks, 122 weeks, 123 weeks, 124 weeks, 125 weeks, 126 weeks, 127 weeks, 128 weeks, 129 weeks, 130 weeks, 131 weeks, 132 weeks, 133 weeks, 134 weeks, 135 weeks, 136 weeks, 137 weeks, 138 weeks, 139 weeks, 140 weeks, 141 weeks, 142 weeks, 143 weeks, 144 weeks, 145 weeks, 146 weeks, 147 weeks, 148 weeks, 149 weeks, 150 weeks, 151 weeks, 152 weeks, 153 weeks, 154 weeks, 155 weeks, 156 weeks, 157 weeks, 158 weeks, 159 weeks, 160 weeks, 161 weeks, 162 weeks, 163 weeks, 164 weeks, 165 weeks, 166 weeks, 167 weeks, 168 weeks, 169 weeks, 170 weeks, 171 weeks, 172 weeks, 173 weeks, 174 weeks, 175 weeks, 176 weeks, 177 weeks, 178 weeks, 179 weeks, 180 weeks, 181 weeks, 182 weeks, 183 weeks, 184 weeks, 185 weeks, 186 weeks, 187 weeks, 188 weeks, 189 weeks, 190 weeks, 191 weeks, 192 weeks, 193 weeks, 194 weeks, 195 weeks, 196 weeks, 197 weeks, 198 weeks, 199 weeks, or 200 weeks, or more). In some embodiments, the first and second treatment periods collectively have a duration of from about 1 month to about 48 months, or more, such as a combined treatment period of about 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, or more.

In some embodiments, the first treatment period has a duration of at least 2 weeks, such as a duration of from about 2 weeks to about 6 months, or more. For example, the first treatment period may have a duration of about 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the first treatment period has a duration of from about 0.5 months to about 6 months, or more, such as a duration of about 0.5 months, 1 month, 2 months, 3 months, 4 months, 5 months, or 6 months, or more.

In some embodiments, the first treatment period has a duration of at least 4 weeks, such as a duration of from about 4 weeks to about 5 months, or more. For example, the first treatment period may have a duration of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks, or more. In some embodiments, the first treatment period has a duration of from about 1 month to about 5 months, or more, such as a treatment period of about 1 month, 2 months, 3 months, 4 months, or 5 months, or more.

In some embodiments, the first treatment period has a duration of at least 6 weeks, such as a duration of from about 6 weeks to about 24 weeks (e.g., a duration of from about 8 weeks to about 24 weeks), or more. For example, the first treatment period may have a duration of about 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the first treatment period has a duration of from about 1.5 months to about 6 months, or more, such as a duration of about 1.5 months, 2 months, 3 months, 4 months, 5 months, or 6 months, or more.

In some embodiments, the first treatment period has a duration of about 12 weeks.

In some embodiments, the second treatment period has a duration of at least 2 weeks, such as a duration of from about 2 weeks to about 6 months, or more. For example, the second treatment period may have a duration of about 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the second treatment period has a duration of from about 0.5 months to about 6 months, or more, such as a duration of about 0.5 months, 1 month, 2 months, 3 months, 4 months, 5 months, or 6 months, or more.

In some embodiments, the second treatment period has a duration of at least 4 weeks, such as a duration of from about 4 weeks to about 5 months, or more. For example, the second treatment period may have a duration of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks, or more. In some embodiments, the second treatment period has a duration of from about 1 month to about 5 months, or more, such as a treatment period of about 1 month, 2 months, 3 months, 4 months, or 5 months, or more.

In some embodiments, the second treatment period has a duration of at least 6 weeks, such as a duration of from about 6 weeks to about 24 weeks (e.g., a duration of from about 8 weeks to about 24 weeks), or more. For example, the second treatment period may have a duration of about 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the second treatment period has a duration of from about 1.5 months to about 6 months, or more, such as a duration of about 1.5 months, 2 months, 3 months, 4 months, 5 months, or 6 months, or more.

In some embodiments, the second treatment period has a duration of about 12 weeks.

In some embodiments of any of the foregoing aspects of the disclosure, the GnRH antagonist is a compound represented by any one of formulas (VII)-(XIV), below, such as elagolix, relugolix, or opigolix (ASP1707). In some embodiments, the GnRH antagonist is BAY-784 or SK-2706.

In some embodiments, the GnRH antagonist is a compound represented by formula (VII)

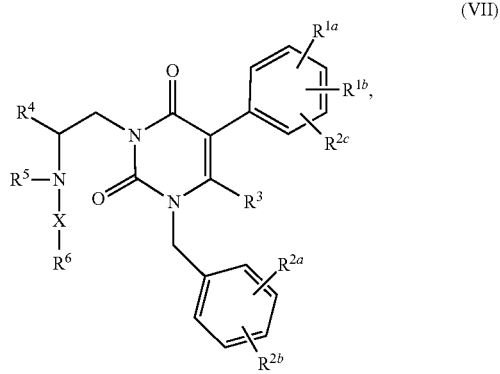

(VII)

wherein $R_{1a}$, $R_{1b}$ and $R_{1c}$ are the same or different and are each independently hydrogen, halogen, $C_{1-4}$alkyl, hydroxy or alkoxy, or $R_{1a}$ and $R_{1b}$ taken together form —OCH$_2$O— or —OCH$_2$CH$_2$—;

$R_{2a}$ and $R_{2b}$ are the same or different and are each independently hydrogen, halogen, trifluoromethyl, cyano or —SO$_2$CH$_3$;

$R_3$ is hydrogen or methyl;
$R_4$ is phenyl or $C_{3-7}$ alkyl;
$R_5$ is hydrogen or $C_{1-4}$alkyl;

$R_6$ is —COOH or an acid isostere; and
X is $C_{1-6}$alkanediyl optionally substituted with from 1 to 3 $C_{1-6}$alkyl groups;

or a pharmaceutically acceptable salt thereof.

In some embodiments, the GnRH antagonist is a compound represented by formula (VIII)

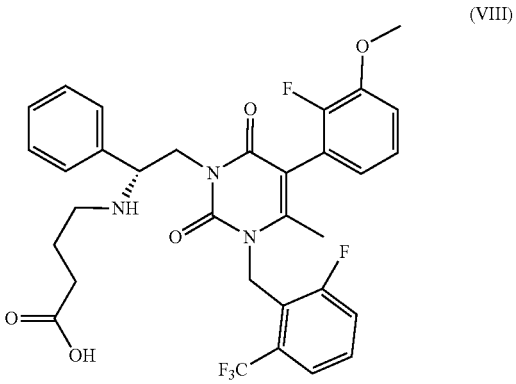 [SMILES: COc1cccc(-c2c(C)n(Cc3c(F)cccc3C(F)(F)F)c(=O)n(C[C@H](NCCCC(=O)O)c3ccccc3)c2=O)c1F]

(VIII)

or a pharmaceutically acceptable salt thereof. In some embodiments, the GnRH antagonist is the sodium salt of the compound represented by formula (VIII), which is represented by formula (IX), below.

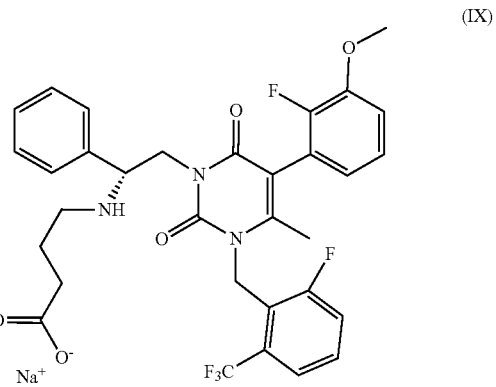

(IX)

In some embodiments, the compound of any one of formulas (VII)-(IX) is administered to the patient in an amount of from about 50 mg to about 650 mg per dose (e.g., in the recited amount or in an equivalent amount of a pharmaceutically acceptable salt, such as a sodium salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 633 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, or 650 mg per dose (e.g., in the recited amount or in an equivalent amount of a pharmaceutically acceptable salt, such as a sodium salt). In some embodiments, the compound of any one of formulas (VII)-(IX) is administered to the patient in an amount of about 150 mg per dose, 300 mg per dose, 400 mg per dose, or 600 mg per dose (e.g., in the recited amount or in an equivalent amount of a pharmaceutically acceptable salt, such as a sodium salt).

In some embodiments, the compound of any one of formulas (VII)-(IX) is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (VII)-(IX) may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (VII)-(IX) is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

The compound of any one of formulas (VII)-(IX) may be administered to the patient in one or more unit dosage forms that collectively constitute a single dose. For example, a patient may be administered a single dose of the compound of a specified amount, such as a single dose of 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, or more (e.g., in the recited amount or in an equivalent amount of a pharmaceutically acceptable salt, such as a sodium salt), by administration of one or more unit dosage forms of the compound to the patient. As a non-limiting example, a single dose of 300 mg of the compound may be administered to the subject by way of two individual 150-mg unit dosage forms of the compound. The two 150-mg unit dosage forms collectively constitute a single 300-mg dose of the compound if administered to the patient at substantially the same time.

In some embodiments, the compound of any one of formulas (VII)-(IX) is administered to the patient in one or more daily doses (e.g., from 1 to 10 doses, such as 1, 2, 3, 4, 5, 6, 7, 8, 9, or 10 doses, or more) totaling from about 50 mg to about 650 mg per day (e.g., in the recited amount or in an equivalent amount of a pharmaceutically acceptable salt, such as a sodium salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 633 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, or 650 mg per day (e.g., in the recited amount or in an equivalent amount of a pharmaceutically acceptable salt, such as a sodium salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 150 mg per day, 300 mg per day, 400 mg per day (e.g., 200 mg administered twice daily, or 600 mg per day (e.g., 300 mg administered twice daily) (e.g., in the recited amount or in an equivalent amount of a pharmaceutically acceptable salt, such as a sodium salt).-

In some embodiments, the GnRH antagonist is a compound represented by formula (X)

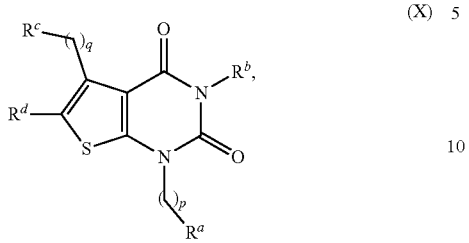

wherein $R^a$ is a hydrogen atom, an optionally substituted aryl group (such as an aryl group that may have 1 to 5 substituents selected from halogen, nitro, cyano, amino, a carboxyl group that may be esterified or amidated, an alkylenedioxy, alkyl, alkoxy, alkylthio, alkylsulfinyl, and alkylsulfonyl), an optionally substituted cycloalkyl group, or an optionally substituted heterocyclic group;

$R^b$ is an optionally substituted nitrogen-containing heterocyclic group;

$R^c$ is an optionally substituted amino group;

$R^d$ is an optionally substituted aryl group;

p is an integer from 0 to 3; and q is an integer from 0 to 3;

or a pharmaceutically acceptable salt thereof.

In some embodiments, the GnRH antagonist is a compound represented by formula (XI)

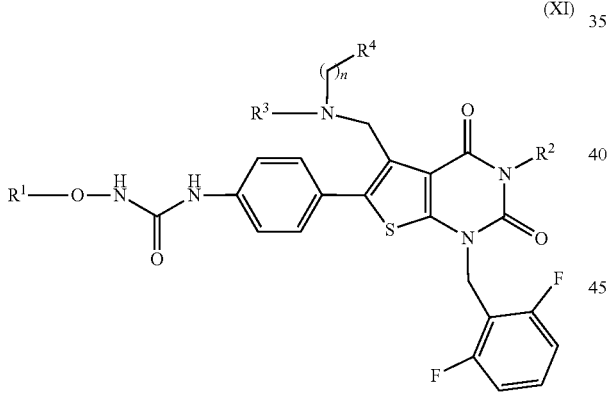

wherein $R^1$ is $C_{1-4}$alkyl;

$R^2$ is (1) a $C_{1-6}$alkyl which may have a substituent selected from the group consisting of (1') a hydroxy group, (2') a $C_{1-4}$alkoxy, (3') a $C_{1-4}$alkoxy-carbonyl, (4') a di-$C_{1-4}$alkyl-carbamoyl, (5') a 5- to 7-membered nitrogen-containing heterocyclic group, (6') a $C_{1-4}$alkyl-carbonyl and (7') a halogen, (2) a $C_{3-6}$ cycloalkyl which may have (1') a hydroxy group or (2') a mono-$C_{1-4}$alkyl-carbonylamino, (3) a 5- to 7-membered nitrogen-containing heterocyclic group which may have a substituent selected from the group consisting of (1') a halogen, (2') a hydroxy group, (3') a $C_{1-4}$alkyl and (4') a $C_{1-4}$alkoxy, (4) a phenyl which may have a substituent selected from the group consisting of (1') a halogen, (2') a $C_{1-4}$alkoxy-$C_{1-4}$alkyl, (3') a mono-$C_{1-4}$ alkyl-carbamoyl-$C_{1-4}$alkyl, (4') a $C_{1-4}$alkoxy and (5') a mono-$C_{1-4}$alkylcarbamoyl-$C_{1-4}$alkoxy, or (5) a $C_{1-4}$alkoxy;

$R^3$ is $C_{1-4}$alkyl;

$R^4$ is (1) hydrogen, (2) $C_{1-4}$alkoxy, (3) $C_{6-10}$aryl, (4) N—$C_{1-4}$alkyl-N—$C_{1-4}$alkylsulfonylamino, (5) hydroxyl, or (6) a 5- to 7-membered nitrogen-containing heterocyclic group which may have a substituent selected from the group consisting of (1') oxo, (2') a $C_{1-4}$alkyl, (3') a hydroxy-$C_{1-4}$alkyl, (4') a $C_{1-4}$alkoxy-carbonyl, (5') a mono-$C_{1-4}$alkyl-carbamoyl and (6') a $C_{1-4}$alkylsulfonyl; and n is an integer from 1 to 4;

optionally provided that when $R^2$ is a phenyl which may have a substituent, $R^4$ is a 5- to 7-membered nitrogen-containing heterocyclic group which may have a substituent selected from the group consisting of (1) oxo, (2) hydroxy-$C_{1-6}$alkyl, (3) $C_{1-4}$alkoxy-carbonyl, (4) mono-$C_{1-4}$alkyl-carbamoyl and (5) $C_{1-4}$alkylsulfonyl;

or a pharmaceutically acceptable salt thereof. In some embodiments, the GnRH antagonist is a compound represented by formula (XII), below.

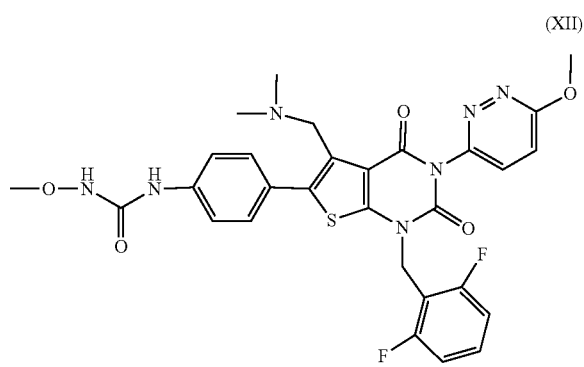

In some embodiments, the compound of any one of formulas (X)-(XII) is administered to the patient in an amount of from about 10 mg to about 60 mg per dose (e.g., in the recited amount or in an equivalent amount of a pharmaceutically acceptable salt, such as a chloride salt), such as an amount of about 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg per dose (e.g., in the recited amount or in an equivalent amount of a pharmaceutically acceptable salt, such as a chloride salt). In some embodiments, the compound of any one of formulas (X)-(XII) is administered to the patient in an amount of about 40 mg per dose (e.g., in the recited amount or in an equivalent amount of a pharmaceutically acceptable salt, such as a chloride salt).

In some embodiments, the compound of any one of formulas (X)-(XII) is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (X)-(XII) may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (X)-(XII) is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

The compound of any one of formulas (I)-(XII) may be administered to the patient in one or more unit dosage forms that collectively constitute a single dose. For example, a patient may be administered a single dose of the compound of a specified amount, such as a single dose of 25 mg, 50 mg, 75 mg, 100 mg, or more (e.g., in the recited amount or in an equivalent amount of a pharmaceutically acceptable salt, such as a chloride salt), by administration of one or more unit dosage forms of the compound to the patient. As a non-limiting example, a single dose of 40 mg of the compound may be administered to the subject by way of two individual 20-mg unit dosage forms of the compound. The two 20-mg unit dosage forms collectively constitute a single 40-mg dose of the compound if administered to the patient at substantially the same time.

In some embodiments, the compound of any one of formulas (X)-(XII) is administered to the patient in one or more daily doses (e.g., from 1 to 10 doses, such as 1, 2, 3, 4, 5, 6, 7, 8, 9, or 10 doses, or more) totaling from about 10 mg to about 60 mg per day (e.g., in the recited amount or in an equivalent amount of a pharmaceutically acceptable salt, such as a chloride salt), such as an amount of about 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg per day (e.g., in the recited amount or in an equivalent amount of a pharmaceutically acceptable salt, such as a chloride salt). In some embodiments, the compound is administered to the patient in one or more daily doses (e.g., from 1 to 10 doses, such as 1, 2, 3, 4, 5, 6, 7, 8, 9, or 10 doses, or more) totaling from about 20 mg to about 50 mg per day (e.g., in the recited amount or in an equivalent amount of a pharmaceutically acceptable salt, such as a chloride salt), such as an amount of about 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg per day (e.g., in the recited amount or in an equivalent amount of a pharmaceutically acceptable salt, such as a chloride salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 40 mg per day (e.g., in the recited amount or in an equivalent amount of a pharmaceutically acceptable salt, such as a chloride salt).

In some embodiments, the GnRH antagonist is a compound represented by formula (XIII)

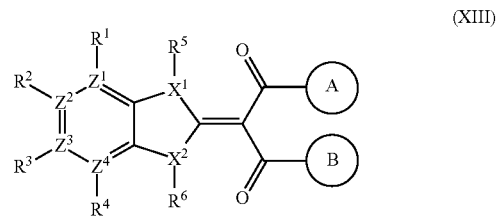

(XIII)

wherein $R^1$, $R^2$, $R^3$ and $R^4$ are the same or different, and are each independently selected from hydrogen, nitro, cyano, halogen, an optionally substituted hydrocarbon group, an optionally substituted heterocyclic group, hydroxy, alkoxy, carboxy, optionally substituted acyl-O—, optionally substituted acyl, a substituent —S(O)$n_{101}$- (wherein $n_{101}$ is an integer of 0 to 2), H—S(O)$n_{101}$-, optionally substituted carbamoyl, optionally substituted sulfamoyl, optionally substituted amino, and two adjacent groups selected from the group of $R^1$, $R^2$, $R^3$ and $R^4$ may combine to form an aryl or a carbocyclic (e.g., cycloalkenyl) group;

$R^5$ and $R^6$ are the same or different and are each independently selected from hydrogen, halogen, optionally substituted hydrocarbon, and optionally substituted amino, $X^1$ and $X^2$ are the same or different and are each independently selected from N, S and O;

A and B are the same or different and are each independently selected from optionally substituted aryl and optionally substituted heterocyclyl, and $Z^1$, $Z^2$, $Z^3$ and $Z^4$ are each independently selected from C and N; optionally provided that 1) when $X^1$ and $X^2$ each is S or O, one or both of the corresponding $R^5$ and $R^6$ are absent; and/or 2) when one to four of $Z^1$, $Z^2$, $Z^3$ and/or $Z^4$ are N, the corresponding $R^1$, $R^2$, $R^3$ and/or $R^4$ are absent;

or a pharmaceutically acceptable salt thereof. In some embodiments, the GnRH antagonist is a compound represented by formula (XIV), below.

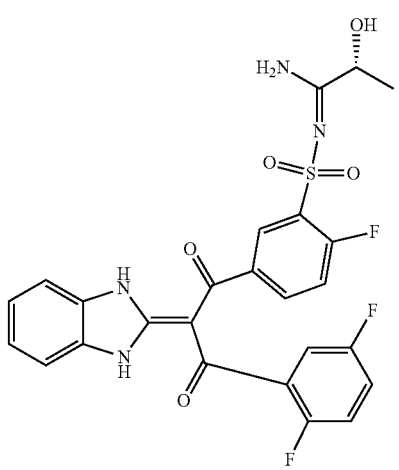

(XIV)

In some embodiments, the compound of any one of formulas (XIII) and (XIV), or SK12670 or BAY-784, is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (XIII) and (XIV), or SK12670 or BAY-784, may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (XIII) and (XIV), or SK12670 or BAY-784, is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

In some embodiments of any of the foregoing aspects of the disclosure, add-back therapy is administered (e.g., periodically administered) to the patient.

In some embodiments, the add-back therapy is administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of β17-estradiol, ethinyl estradiol, or a conjugated estrogen, such as a conjugated equine estrogen) and/or a progestin (e.g., norethindrone or a compound that is metabolized in vivo to produce norethindrone, such as an ester of norethindrone that is de-esterified in vivo to produce norethindrone, for instance, norethindrone acetate (also referred to herein as "NETA"), among other agents, such as progesterone, norgestimate, medroxyprogesterone, and drospirenone) in the form of a single pharmaceutical composition, such as a single tablet, capsule, gel cap, powder, liquid solution, or liquid suspension. In some embodiments, the add-back therapy is administered orally, transdermally, or intravaginally.

In some embodiments, the add-back therapy is administered to the patient in one or more doses per day, week, month, or year, such as daily, for example, from 1 to 10 times daily, or more (e.g., 1, 2, 3, 4, 5, 6, 7, 8, 9, 10, or more, times daily). In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described above and herein.

In some embodiments, the add-back therapy is administered to the patient once daily, following administration of the GnRH antagonist. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient once daily, prior to administration of the GnRH antagonist. For example, the GnRH antagonist may be administered to the patient orally, and prior to oral administration of the GnRH antagonist, the add-back therapy may be administered to the patient orally, transdermally, or intravaginally.

In some embodiments, the add-back therapy includes an estrogen. In some embodiments, the estrogen is selected from the group consisting of 17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The 17-estradiol may be administered to the patient, for example, in an amount of from about 0.1 mg/day to about 2.5 mg/day, such as in an amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient in an amount of 1.0 mg/day, for instance, by oral administration. In some embodiments, the β17-estradiol is administered to the patient in an amount of 0.5 mg/day, for instance, by oral administration.

In some embodiments, the estrogen is ethinyl estradiol. The ethinyl estradiol may be administered to the patient, for example, at a dose of from about 1.0 μg to about 6.0 μg, such as at a dose of about 1.0 μg, 1.1 μg, 1.2 μg, 1.3 μg, 1.4 μg, 1.5 μg, 1.6 μg, 1.7 μg, 1.8 μg, 1.9 μg, 2.0 μg, 2.1 μg, 2.2 μg, 2.3 μg, 2.4 μg, 2.5 μg, 2.6 μg, 2.7 μg, 2.8 μg, 2.9 μg, 3.0 μg, 3.1 μg, 3.2 μg, 3.3 μg, 3.4 μg, 3.5 μg, 3.6 μg, 3.7 μg, 3.8 μg, 3.9 μg, 4.0 μg, 4.1 μg, 4.2 μg, 4.2 μg, 4.3 μg, 4.4 μg, 4.5 μg, 4.6 μg, 4.7 μg, 4.8 μg, 4.9 μg, 5.0 μg, 5.1 μg, 5.2 μg, 5.3 μg, 5.4 μg, 5.5 μg, 5.6 μg, 5.7 μg, 5.8 μg, 5.9 μg, or 6.0 μg, for instance, by oral administration. In some embodiments, the ethinyl estradiol is administered to the patient at a dose of 5.0 μg, for instance, by oral administration. In some embodiments, the ethinyl estradiol is administered to the patient at a dose of 2.5 μg, for instance, by oral administration.

The ethinyl estradiol may be administered to the patient one or more times per day, week, or month. The ethinyl estradiol may be administered to the patient, for example, in an amount of about 1.0 μg/day to about 6.0 μg/day, such as in an amount of about 1.0 μg/day, 1.1 μg/day, 1.2 μg/day, 1.3 μg/day, 1.4 μg/day, 1.5 μg/day, 1.6 μg/day, 1.7 μg/day, 1.8 μg/day, 1.9 μg/day, 2.0 μg/day, 2.1 μg/day, 2.2 μg/day, 2.3 μg/day, 2.4 μg/day, 2.5 μg/day, 2.6 μg/day, 2.7 μg/day, 2.8 μg/day, 2.9 μg/day, 3.0 μg/day, 3.1 μg/day, 3.2 μg/day, 3.3 μg/day, 3.4 μg/day, 3.5 μg/day, 3.6 μg/day, 3.7 μg/day, 3.8 μg/day, 3.9 μg/day, 4.0 μg/day, 4.1 μg/day, 4.2 μg/day, 4.2 μg/day, 4.3 μg/day, 4.4 μg/day, 4.5 μg/day, 4.6 μg/day, 4.7 μg/day, 4.8 μg/day, 4.9 μg/day, 5.0 μg/day, 5.1 μg/day, 5.2 μg/day, 5.3 μg/day, 5.4 μg/day, 5.5 μg/day, 5.6 μg/day, 5.7 μg/day, 5.8 μg/day, 5.9 μg/day, or 6.0 μg/day, for instance, by oral administration. In some embodiments, the ethinyl estradiol is administered to the patient in an amount of 5.0 μg/day, for instance, by oral administration. In some embodiments, the ethinyl estradiol is administered to the patient in an amount of 2.5 μg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, in an amount of from about 0.1 mg/day to about 2.0 mg/day, such as in an amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient in an amount of 0.625 mg/day, for instance, by oral administration. In some embodiments, the conjugated estrogen is administered to the patient in an amount of 0.45 mg/day, for instance, by oral administration. In some embodiments, the conjugated estrogen is administered to the patient in an amount of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, in an amount of from about 0.05 mg/day to about 5.0 mg/day, such as in an amount of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient in an amount of 1.0 mg/day, for instance, by oral administration. In some embodiments, the norethindrone is administered to the patient in an amount of 0.5 mg/day, for instance, by oral administration. In some embodiments, the norethindrone is administered to the patient in an amount of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, in an amount of from about 0.05 mg/day to about 5.0 mg/day, such as in an amount of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient in an amount of 1.0 mg/day, for instance, by oral administration. In some embodiments, the norethindrone acetate is administered to the patient in an amount of 0.5 mg/day, for instance, by oral administration. In some embodiments, the norethindrone acetate is administered to the patient in an amount of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, in an amount of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient in an amount of 200 mg/day, for instance, by oral administration. In some embodiments, the progesterone is administered to the patient in an amount of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, in an amount of from about 0.01 mg/day to about 2.0 mg/day, such as in an amount of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient in an amount of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, in an amount of from about 0.5 mg/day to about 10.0 mg/day, such as in an amount of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient in an amount of 5.0 mg/day, for instance, by oral administration. In some embodiments, the medroxyprogesterone is administered to the patient in an amount of 2.5 mg/day, for instance, by oral administration. In some embodiments, the medroxyprogesterone is administered to the patient in an amount of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, in an amount of from about 0.1 mg/day to about 1.0 mg/day, such as in an amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient in an amount of 0.5 mg/day, for instance, by oral administration. In some embodiments, the drospirenone is administered to the patient in an amount of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the add-back therapy includes from about 0.75 mg to about 1.25 mg of β17-estradiol, e.g., administered orally, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in the same pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in a separate pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the GnRH antagonist is administered to the patient in a fixed-dose composition that contains the GnRH antagonist (e.g., in an amount of about 100 mg or about 200 mg of the compound of any one of formulas (I)-(VI)), from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the GnRH antagonist is administered to the patient in a fixed-dose composition that contains the GnRH antagonist (e.g., in an amount of about 100 mg or about 200 mg of the compound of any one of formulas (I)-(VI)), about 1.0 mg of β17-estradiol (e.g., 1.0 mg of β17-estradiol), and about 0.5 mg of norethindrone or a compound that is metabolized in vivo to produce norethindrone, such as an ester of norethindrone that is de-esterified in vivo to produce norethindrone, for instance, norethindrone acetate (e.g., 0.5 mg of norethindrone or a compound that is metabolized in vivo to produce norethindrone, such as an ester of norethindrone that is de-esterified in vivo to produce norethindrone, for instance, norethindrone acetate). In some embodiments, the GnRH antagonist is administered to the patient in a fixed-dose composition that contains the GnRH antagonist (e.g., in an amount of about 100 mg or about 200 mg of the compound of any one of formulas (I)-(VI)), 1.0 mg of β17-estradiol, and 0.5 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the above fixed-dose composition is administered to the patient once daily.

In some embodiments, the add-back therapy includes from about 0.25 mg to about 0.75 mg of β17-estradiol, e.g., administered orally, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of θ17-estradiol, e.g., administered orally, and 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in the same pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in a separate pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the GnRH antagonist is administered to the patient in a fixed-dose composition that contains the GnRH antagonist (e.g., in an amount of about 100 mg or about 200 mg of the compound of any one of formulas (I)-(VI)), from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the GnRH antagonist is administered to the patient in a fixed-dose composition that contains the GnRH antagonist (e.g., in an amount of about 100 mg or about 200 mg of the compound of any one of formulas (I)-(VI)), about 0.5 mg of β17-estradiol (e.g., 0.5 mg of β17-estradiol), and about 0.1 mg of norethindrone or a compound that is metabolized in vivo to produce norethindrone, such as an ester of norethindrone that is de-esterified in vivo to produce norethindrone, for instance, norethindrone acetate (e.g., 0.1 mg of norethindrone or a compound that is metabolized in vivo to produce norethindrone, such as an ester of norethindrone that is de-esterified in vivo to produce norethindrone, for instance, norethindrone acetate). In some embodiments, the GnRH antagonist is administered to the patient in a fixed-dose composition that contains the GnRH antagonist (e.g., in an amount of about 100 mg or about 200 mg of the compound of any one of formulas (I)-(VI)), 0.5 mg of β17-estradiol, and 0.1 mg of norethindrone acetate.

In some embodiments of any of the foregoing aspects of the disclosure, the patient is a pre-menopausal female of from about 18 to about 48 years of age, such as a patient of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 years of age.

In some embodiments, the patient exhibits a serum concentration of FSH of about 20 IU/L or less prior to administration of the GnRH antagonist to the patient, such as a serum concentration of FSH of from about 5 IU/L to about 20 IU/L (e.g., a serum concentration of FSH of about 5 IU/L, 6 IU/L, 7 IU/L, 8 IU/L, 9 IU/L, 10 IU/L, 11 IU/L, 12 IU/L, 13 IU/L, 14 IU/L, 15 IU/L, 16 IU/L, 17 IU/L, 18 IU/L, 19 IU/L, or 20 IU/L.

In some embodiments, the patient exhibits a junctional-zone width of about 12 mm or more prior to administration of the GnRH antagonist to the patient, such as a junctional zone width of from about 12 mm to about 20 mm, or more (e.g., a junctional zone width of from about 12 mm to about 20 mm, from about 12 mm to about 19 mm, from about 12 mm to about 18 mm, from about 12 mm to about 17 mm, from about 12 mm to about 16 mm, from about 12 mm to about 15 mm, from about 12 mm to about 14 mm, or more) prior to administration of the GnRH antagonist to the patient. The junctional zone width may be assessed, for example, by way of magnetic resonance imaging (MRI).

In some embodiments, the patient exhibits a reduction in serum concentration of FSH, LH, and/or E2 following administration of the GnRH antagonist to the patient. The reduction in serum concentration of LH, FSH, and/or E2 may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a reduction in uterine volume following administration of the GnRH antagonist to the patient. The reduction in uterine volume may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in uterine volume may be assessed, for example, by way of MRI or transvaginal ultrasound (TVUS).

In some embodiments, the patient exhibits a reduction in the thickness of the anterior and/or posterior region of the uterine myometrium following administration of the GnRH antagonist to the patient. The reduction in the thickness of the anterior and/or posterior region of the uterine myometrium may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a reduction in pelvic pain following administration of the GnRH antagonist to the patient. The reduction in pelvic pain may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in pelvic pain may be assessed by way of a modified Biberoglu & Behrman (mB&B) score, Numerical Rating Scale (NRS) score, or Verbal Rating Scale (VRS) score.

In some embodiments, the patient exhibits a reduction in dysmenorrhea following administration of the GnRH antagonist to the patient. The reduction in dysmenorrhea may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in dysmenorrhea may be assessed by way of an mB&B score, NRS score, or VRS score.

In some embodiments, the patient exhibits a reduction in dyspareunia following administration of the GnRH antagonist to the patient. The reduction in dyspareunia may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in dyspareunia may be assessed by way of an mB&B score, NRS score, or VRS score.

In some embodiments, the patient exhibits a reduction in dyschezia following administration of the GnRH antagonist to the patient. The reduction in dyschezia may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in dyschezia may be assessed by way of an mB&B score, NRS score, or VRS score.

In some embodiments, the patient exhibits a reduction in uterine tenderness following administration of the GnRH antagonist to the patient. The reduction in uterine tenderness may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a reduction in uterine bleeding following administration of the GnRH antagonist to the patient. The reduction in dyspareunia may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in uterine bleeding may be assessed by way of an alkaline hematin method.

In some embodiments, the patient exhibits amenorrhea following administration of the GnRH antagonist to the patient. The amenorrhea may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a reduction in the diameter of a junctional zone of adenomyosis following administration of the GnRH antagonist to the patient. The reduction in the diameter of a junctional zone of adenomyosis may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits an improvement in Endometriosis Health Profile questionnaire (EHP-30) score following administration of the GnRH antagonist to the patient. The improvement in the EHP-30 score may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a positive Patient Global Impression of Change (PGIC) score following administration of the GnRH antagonist to the patient. The positive PGIC score may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient does not exhibit a reduction in bone mineral density (BMD) of greater than 5% following administration of the GnRH antagonist to the patient. In some embodiments, the patient does not exhibit a reduction in BMD of greater than 1% following administration of the GnRH antagonist to the patient. BMBD may be assessed, for example, by dual energy X-ray absorptiometry, such as in the spine and/or femur of the patient. In some embodiments, the BMD is assessed by comparing the concentration of BAP in a sample isolated from the patient following the administration to the concentration of BAP in a sample isolated from the patient prior to the administration. In some embodiments, the BMD is assessed by comparing the concentration of DPD in a sample isolated from the patient following the administration to the concentration of DPD in a sample isolated from the patient prior to the administration. In some embodiments, the BMD is assessed by comparing the concentration of CTX in a sample isolated from the patient following the administration to the concentration of CTX in a sample isolated from the patient prior to the administration. In some embodiments, the BMD is assessed by comparing the concentration of P1NP in a sample isolated from the patient following the administration to the concentration of P1 NP in a sample isolated from the patient prior to the administration.

In another aspect, the disclosure features a kit containing a GnRH antagonist, such as a GnRH antagonist of any of the above aspects or embodiments of the disclosure. The kit may further contain a package insert, such as a package insert instructing a user of the kit to administer the GnRH antagonist to a patient having adenomyosis in accordance with the method of any one of the foregoing aspects or embodiments of the disclosure.

In some embodiments, the GnRH antagonist contained within the kit is a compound represented by formula (I)

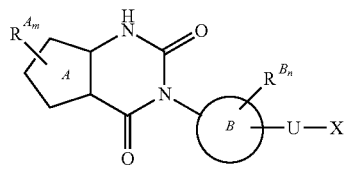

(I)

wherein ring A is a thiophene ring;
each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;
ring B is an aryl group or a monocyclic heteroaryl group;
each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;
U is a single bond;
X is a group represented by —S-L-Y, —O-L-Y, —CO-L-Y, or —SO$_2$-L-Y, wherein
L is an optionally substituted lower alkylene group;
Y is a group represented by Z or —NW$^7$W$^8$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^8$ may bind together with the neighboring nitrogen atom to form an optionally substituted cyclic amino group; and
Z is an optionally fused and optionally substituted cycloalkyl group, an optionally fused and optionally substituted heterocycloalkyl group, an optionally fused and optionally substituted aryl group, or an optionally fused and optionally substituted heteroaryl group;
or a pharmaceutically acceptable salt thereof.

In some embodiments of formula (I), the ring A is a thiophene ring represented by formula (IIa)

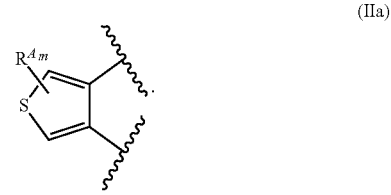

(IIa)

In some embodiments of formula (I) or (IIa), m is 1.
In some embodiments of formula (I) or (IIa), the ring A is an optionally substituted thiophene ring represented by formula (IIb)

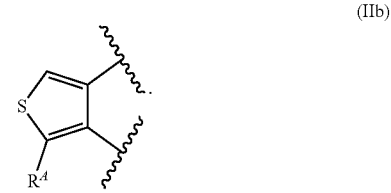

(IIb)

In some embodiments of formula (I), (IIa), or (IIb), each $R^A$ is independently a halogen atom, an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group.

In some embodiments of formula (I), (IIa), or (IIb), each $R^4$ is COOH or pharmaceutically acceptable salt thereof.

In some embodiments of formula (I), (IIa), or (IIb), the ring B is an optionally substituted benzene ring, pyridine ring, or thiophene ring.

In some embodiments of formula (I), (IIa), or (IIb), the ring B is represented by a formula selected from the group consisting of:

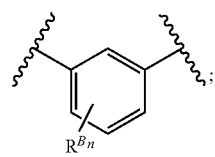
(IIIa)

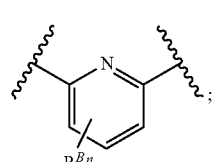
(IIIb)

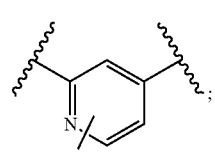
(IIIc)

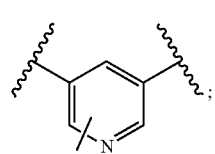
(IIId)

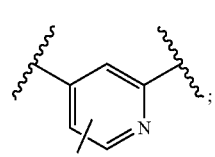
(IIIe)

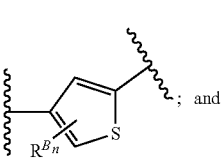
; and
(IIIf)

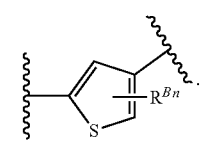
.
(IIIg)

In some embodiments of formula (I), (IIa), (IIb), or any one of (IIIa)-(IIIg), n is 2.

In some embodiments of formula (I), (IIa), (IIb), or any one of (IIIa)-(IIIg), the ring B is represented by a formula selected from the group consisting of:

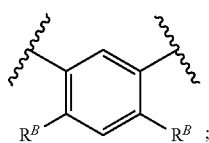
(IVa)

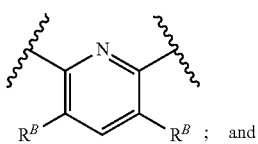
; and
(IVb)

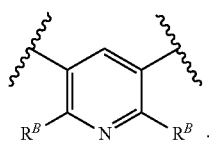
.
(IVc)

In some embodiments of formula (I), (IIa), (IIb), any one of (IIIa)-(IIIg), or any one of (IVa)-(IVc), each $R^B$ is independently a halogen atom, an optionally substituted lower alkyl group, or $OW^4$, wherein each $W^4$ is independently a hydrogen atom or an optionally substituted lower alkyl group.

In some embodiments of formula (I), (IIa), (IIb), any one of (IIIa)-(IIIg), or any one of (IVa)-(IVc), each $R^B$ is independently a fluorine atom, chlorine atom, bromine atom, methyl group, or methoxy group.

In some embodiments of formula (I), (IIa), (IIb), any one of (IIIa)-(IIIg), or any one of (IVa)-(IVc), U is a single bond.

In some embodiments of formula (I), (IIa), (IIb), any one of (IIIa)-(IIIg), or any one of (IVa)-(IVc), X is a group represented by —O-L-Y.

In some embodiments of formula (I), (IIa), (IIb), any one of (IIIa)-(IIIg), or any one of (IVa)-(IVc), L is a methylene group.

In some embodiments of formula (I), (IIa), (IIb), any one of (IIIa)-(IIIg), or any one of (IVa)-(IVc), Y is an optionally substituted benzene ring represented by formula (V)

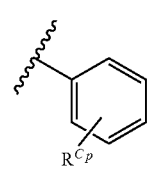
(V)

wherein each $R^c$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments of formula (I), (IIa), (IIb), any one of (IIIa)-(IIIg), any one of (IVa)-(IVc), or (V), Y is a substituted benzene ring represented by formula (Va)

(Va)

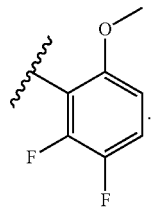

In some embodiments, the compound is represented by formula (Ia)

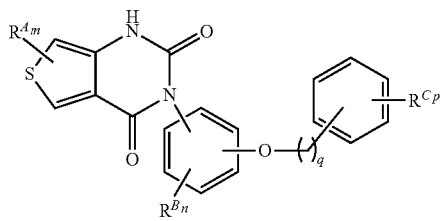

wherein each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

q is an integer from 0 to 3;

each $R^C$ is independently a halogen atom, an optionally substituted lower alkyl group, or $OW^9$, wherein each $W^9$ is independently a hydrogen atom or an optionally substituted lower alkyl group; and p is an integer from 0 to 3;

or a pharmaceutically acceptable salt thereof.

In some embodiments, the compound is represented by formula (Ib)

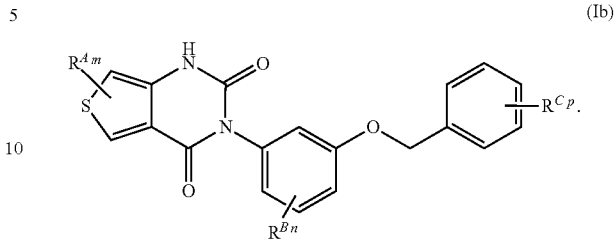

In some embodiments, the compound is represented by formula (Ic)

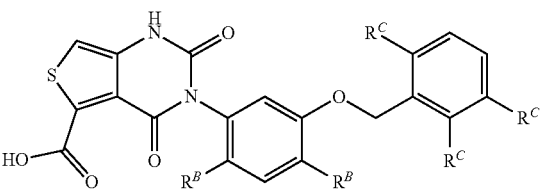

or a pharmaceutically acceptable salt thereof.

In some embodiments, the compound is 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid, represented by formula (VI)

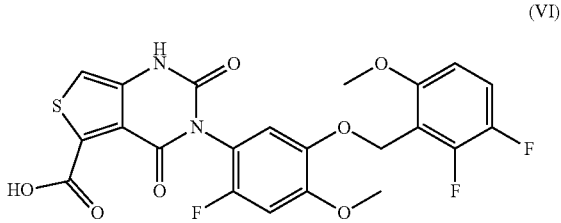 [SMILES: COc1cc(F)c(-n2c(=O)[nH]c3csc(C(=O)O)c3c2=O)cc1OCc1c(OC)ccc(F)c1F]

or a pharmaceutically acceptable salt thereof. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of an electrostatically neutral carboxylic acid, and the kit, accordingly, contains the carboxylic acid. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of a pharmaceutically acceptable salt, and the kit, accordingly, contains a pharmaceutically acceptable salt. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of the choline salt, choline 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylate, and the kit, accordingly, contains the choline salt.

In some embodiments, the compound is the choline salt of the compound represented by formula (VI), choline 3-[2- fluoro-5-(2,3-difluoro-6-methoxybenzyloxy)4-methoxyphenyl]-2,4-dioxo-1,2,3,4-tetrahydrothieno [3,4d]pyrimidine-5-carboxylate.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate is in a crystalline state.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits characteristic X-ray powder diffraction (XRPD) peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{19}F$ solid-state NMR peaks centered at about −151.8 ppm, −145.2 ppm, and −131.6 ppm.

In some embodiments, the GnRH antagonist contained within the kit is a compound represented by formula (VII)

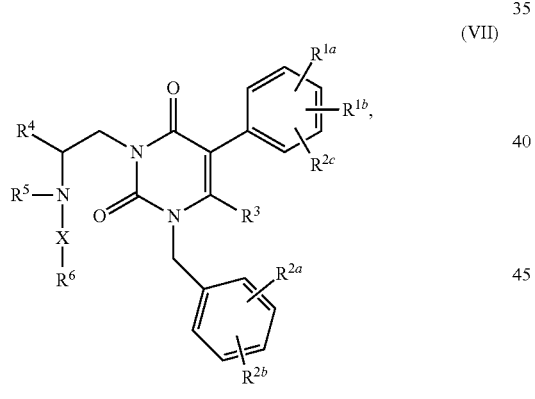

(VII)

wherein $R_{1a}$, $R_{1b}$ and $R_1$, are the same or different and are each independently hydrogen, halogen, $C_{1-4}$alkyl, hydroxy or alkoxy, or $R_{1a}$ and $R_{1b}$ taken together form —OCH$_2$O— or —OCH$_2$CH$_2$—;

$R_{2a}$ and $R_{2b}$ are the same or different and are each independently hydrogen, halogen, trifluoromethyl, cyano or —SO$_2$CH$_3$;

$R_3$ is hydrogen or methyl;

$R_4$ is phenyl or $C_{3-7}$alkyl;

$R_5$ is hydrogen or $C_{1-4}$alkyl;

$R_6$ is —COOH or an acid isostere; and

X is $C_{1-6}$alkanediyl optionally substituted with from 1 to 3 $C_{1-6}$alkyl groups;

or a pharmaceutically acceptable salt thereof.

In some embodiments, the GnRH antagonist is a compound represented by formula (VIII)

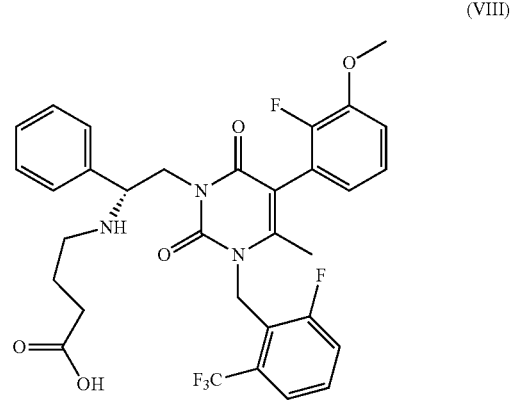 [SMILES: COc1cccc(-c2c(C)n(Cc3c(F)cccc3C(F)(F)F)c(=O)n(C[C@H](NCCCC(=O)O)c3ccccc3)c2=O)c1F]

(VIII)

or a pharmaceutically acceptable salt thereof. In some embodiments, the GnRH antagonist is the sodium salt of the compound represented by formula (VIII), which is represented by formula (IX), below.

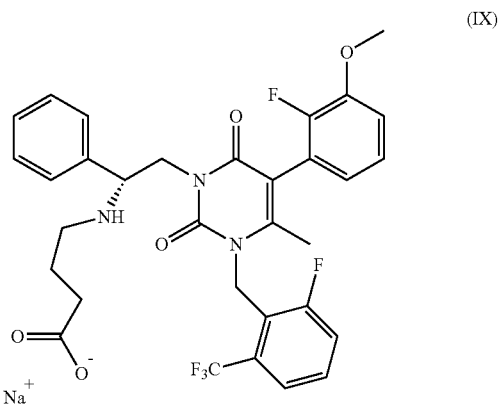

(IX)

In some embodiments, the GnRH antagonist contained within the kit is a compound represented by formula (X)

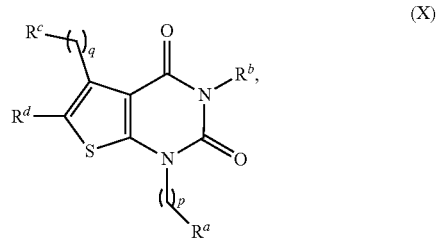

(X)

wherein $R^a$ is a hydrogen atom, an optionally substituted aryl group (such as an aryl group that may have 1 to 5 substituents selected from halogen, nitro, cyano, amino, a carboxyl group that may be esterified or amidated, an alkylenedioxy, alkyl, alkoxy, alkylthio, alkylsulfinyl, and alkylsulfonyl), an optionally substituted cycloalkyl group, or an optionally substituted heterocyclic group;

$R^b$ is an optionally substituted nitrogen-containing heterocyclic group;

$R^c$ is an optionally substituted amino group;

$R^d$ is an optionally substituted aryl group;

p is an integer from 0 to 3; and q is an integer from 0 to 3;

or a pharmaceutically acceptable salt thereof.

In some embodiments, the GnRH antagonist is a compound represented by formula (XI)

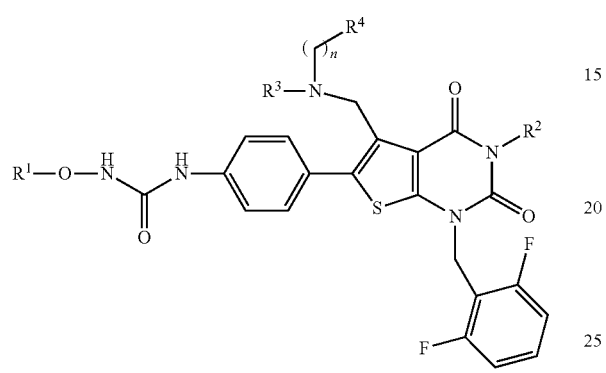

(XI)

wherein $R^1$ is $C_{1-4}$alkyl;

$R^2$ is (1) a $C_{1-6}$alkyl which may have a substituent selected from the group consisting of (1') a hydroxy group, (2') a $C_{1-4}$alkoxy, (3') a $C_{1-4}$alkoxy-carbonyl, (4') a di-$C_{1-4}$alkyl-carbamoyl, (5') a 5- to 7-membered nitrogen-containing heterocyclic group, (6') a $C_{1-4}$alkyl-carbonyl and (7') a halogen, (2) a $C_{3-8}$ cycloalkyl which may have (1') a hydroxy group or (2') a mono-$C_{1-4}$alkyl-carbonylamino, (3) a 5- to 7-membered nitrogen-containing heterocyclic group which may have a substituent selected from the group consisting of (1') a halogen, (2') a hydroxy group, (3') a $C_{1-4}$alkyl and (4') a $C_{1-4}$alkoxy, (4) a phenyl which may have a substituent selected from the group consisting of (1') a halogen, (2') a $C_{1-4}$alkoxy-$C_{1-4}$alkyl, (3') a mono-$C_{1-4}$alkyl-carbamoyl-$C_{1-4}$alkyl, (4') a $C_{1-4}$alkoxy and (5') a mono-$C_{1-4}$alkylcarbamoyl-$C_{1-4}$alkoxy, or (5) a $C_{1-4}$alkoxy;

$R^3$ is $C_{1-4}$alkyl;

$R^4$ is (1) hydrogen, (2) $C_{1-4}$alkoxy, (3) $C_{6-10}$aryl, (4) N-$C_4$alkyl-N—$C_{1-4}$alkylsulfonylamino, (5) hydroxyl, or (6) a 5- to 7-membered nitrogen-containing heterocyclic group which may have a substituent selected from the group consisting of (1') oxo, (2') a $C_{1-4}$alkyl, (3') a hydroxy-$C_{1-4}$alkyl, (4') a $C_{1-4}$alkoxy-carbonyl, (5') a mono-$C_{1-4}$alkyl-carbamoyl and (6') a $C_{1-4}$alkylsulfonyl; and n is an integer from 1 to 4;

optionally provided that when $R^2$ is a phenyl which may have a substituent, $R^4$ is a 5- to 7-membered nitrogen-containing heterocyclic group which may have a substituent selected from the group consisting of (1) oxo, (2) hydroxy-$C_{1-4}$alkyl, (3) $C_{1-4}$alkoxy-carbonyl, (4) mono-$C_{1-4}$alkyl-carbamoyl and (5) $C_{1-4}$alkylsulfonyl;

or a pharmaceutically acceptable salt thereof. In some embodiments, the GnRH antagonist is a compound represented by formula (XII), below.

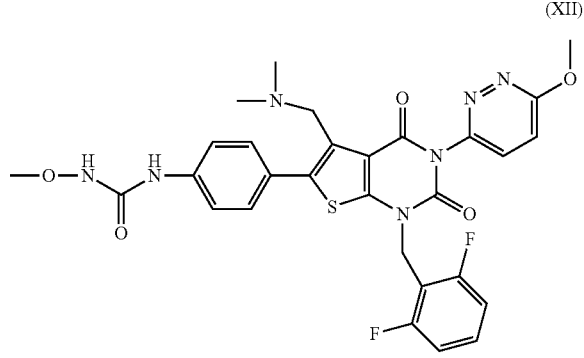

(XII)

In some embodiments, the GnRH antagonist contained within the kit is a compound represented by formula (XIII)

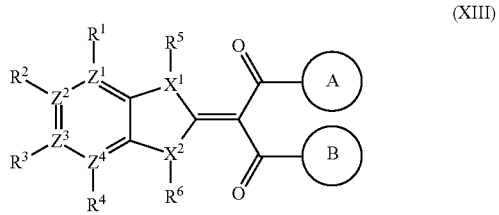

(XIII)

wherein $R^1$, $R^2$, $R^3$ and $R^4$ are the same or different, and are each independently selected from hydrogen, nitro, cyano, halogen, an optionally substituted hydrocarbon group, an optionally substituted heterocyclic group, hydroxy, alkoxy, carboxy, optionally substituted acyl-O—, optionally substituted acyl, a substituent —S(O)$_{n_{101}}$- (wherein $n_{101}$ is an integer of 0 to 2), H—S(O)$_{n_{101}}$-, optionally substituted carbamoyl, optionally substituted sulfamoyl, optionally substituted amino, and two adjacent groups selected from the group of $R^1$, $R^2$, $R^3$ and $R^4$ may combine to form an aryl or a carbocyclic (e.g., cycloalkenyl) group;

$R^5$ and $R^6$ are the same or different and are each independently selected from hydrogen, halogen, optionally substituted hydrocarbon, and optionally substituted amino, $X^1$ and $X^2$ are the same or different and are each independently selected from N, S and O;

A and B are the same or different and are each independently selected from optionally substituted aryl and optionally substituted heterocyclyl, and $Z^1$, $Z^2$, $Z^3$ and $Z^4$ are each independently selected from C and N; optionally provided that 1) when $X^1$ and $X^2$ each is S or O, one or both of the corresponding $R^5$ and $R^6$ are absent; and/or 2) when one to four of $Z^1$, $Z^2$, $Z^3$ and/or $Z^4$ are N, the corresponding $R^1$, $R^2$, $R^3$ and/or $R^4$ are absent;

or a pharmaceutically acceptable salt thereof. In some embodiments, the GnRH antagonist is a compound represented by formula (XIV), below.

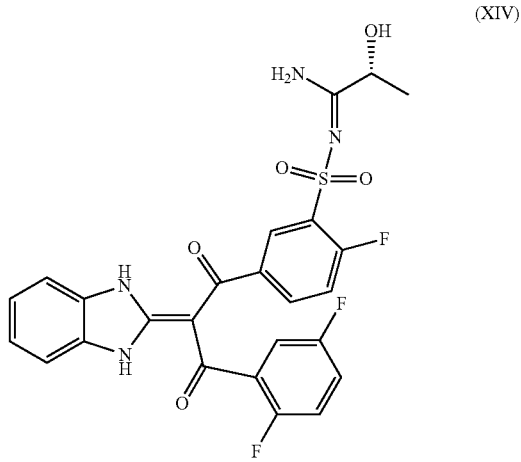 [SMILES: C[C@@H](O)/C(N)=N/S(=O)(=O)c1cc(C(=O)C(C(=O)c2cc(F)ccc2F)=C2Nc3ccccc3N2)ccc1F]

(XIV)

In some embodiments, the GnRH antagonist contained within the kit is SK12670 or BAY-784, or a variant or derivative thereof.

In a further aspect, the disclosure features a method of treating rectovaginal endometriosis in a human patient in need thereof by administering to the patient a therapeutically effective amount of a GnRH antagonist. In another aspect, the disclosure features a method of treating rectovaginal endometriosis in a human patient by:
a) diagnosing the patient as having rectovaginal endometriosis; and
b) administering to the patient a therapeutically effective amount of a GnRH antagonist.

In an additional aspect, the disclosure features a method of reducing the volume of one or more rectovaginal endometriosis nodes in a human patient diagnosed as having rectovaginal endometriosis by administering to the patient a therapeutically effective amount of a GnRH antagonist. In another aspect, the disclosure features a method of reducing the volume of one or more rectovaginal endometriosis nodes in a human patient by:
a) diagnosing the patient as having rectovaginal endometriosis; and
b) administering to the patient a therapeutically effective amount of a GnRH antagonist.

In a further aspect, the disclosure features a method of reducing pelvic pain in a human patient diagnosed as having rectovaginal endometriosis by administering to the patient a therapeutically effective amount of a GnRH antagonist. In yet another aspect, the disclosure features a method of reducing pelvic pain in a human patient by:
a) diagnosing the patient as having rectovaginal endometriosis; and
b) administering to the patient a therapeutically effective amount of a GnRH antagonist.

In an additional aspect, the disclosure features a method of reducing dysmenorrhea in a human patient diagnosed as having rectovaginal endometriosis by administering to the patient a therapeutically effective amount of a GnRH antagonist. In another aspect, the disclosure features a method of reducing dysmenorrhea in a human patient by:
a) diagnosing the patient as having rectovaginal endometriosis; and
b) administering to the patient a therapeutically effective amount of a GnRH antagonist.

In yet another aspect, the disclosure features a method of reducing dyspareunia in a human patient diagnosed as having rectovaginal endometriosis by administering to the patient a therapeutically effective amount of a GnRH antagonist. In another aspect, the disclosure features a method of reducing dyspareunia in a human patient by:
a) diagnosing the patient as having rectovaginal endometriosis; and
b) administering to the patient a therapeutically effective amount of a GnRH antagonist.

In a further aspect, the disclosure features a method of reducing dyschezia in a human patient diagnosed as having rectovaginal endometriosis by administering to the patient a therapeutically effective amount of a GnRH antagonist. In yet another aspect, the disclosure features a method of reducing dyschezia in a human patient by:
a) diagnosing the patient as having rectovaginal endometriosis; and
b) administering to the patient a therapeutically effective amount of a GnRH antagonist.

In a further aspect, the disclosure features a method of reducing uterine bleeding in a human patient diagnosed as having rectovaginal endometriosis by administering to the patient a therapeutically effective amount of a GnRH antagonist. In an additional aspect, the disclosure features a method of reducing uterine bleeding in a human patient by:
a) diagnosing the patient as having rectovaginal endometriosis; and
b) administering to the patient a therapeutically effective amount of a GnRH antagonist.

In another aspect, the disclosure features a method of inducing amenorrhea in a human patient diagnosed as having rectovaginal endometriosis by administering to the patient a therapeutically effective amount of a GnRH antagonist. In a further aspect, the disclosure features a method of inducing amenorrhea in a human patient by:
a) diagnosing the patient as having rectovaginal endometriosis; and
b) administering to the patient a therapeutically effective amount of a GnRH antagonist.

In some embodiments of any of the foregoing aspects of the disclosure, the GnRH antagonist is a compound represented by formula (I)

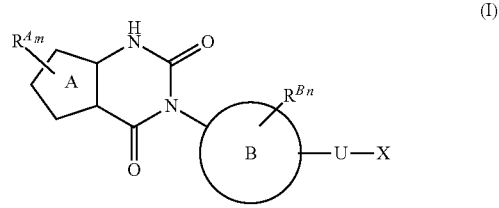

(I)

wherein ring A is a thiophene ring;
each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

ring B is an aryl group or a monocyclic heteroaryl group;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

U is a single bond;

X is a group represented by —S-L-Y, —O-L-Y, —CO-L-Y, or —SO$_2$-L-Y, wherein

L is an optionally substituted lower alkylene group;

Y is a group represented by Z or —NW$^7$W$^8$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^a$ may bind together with the neighboring nitrogen atom to form an optionally substituted cyclic amino group; and Z is an optionally fused and optionally substituted cycloalkyl group, an optionally fused and optionally substituted heterocycloalkyl group, an optionally fused and optionally substituted aryl group, or an optionally fused and optionally substituted heteroaryl group;

or a pharmaceutically acceptable salt thereof.

In some embodiments of formula (I), the ring A is a thiophene ring represented by formula (IIa)

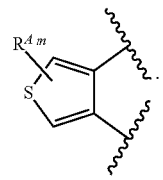
(IIa)

In some embodiments of formula (I) or (IIa), m is 1.

In some embodiments of formula (I) or (IIa), the ring A is an optionally substituted thiophene ring represented by formula (IIb)

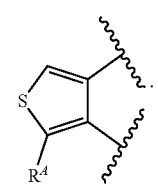
(IIb)

In some embodiments of formula (I), (IIa), or (IIb), each $R^A$ is independently a halogen atom, an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group.

In some embodiments of formula (I), (IIa), or (IIb), each $R^A$ is COOH or pharmaceutically acceptable salt thereof.

In some embodiments of formula (I), (IIa), or (IIb), the ring B is an optionally substituted benzene ring, pyridine ring, or thiophene ring.

In some embodiments of formula (I), (IIa), or (IIb), the ring B is represented by a formula selected from the group consisting of:

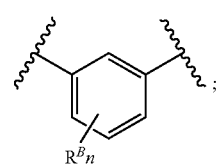
(IIIa)

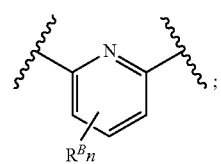
(IIIb)

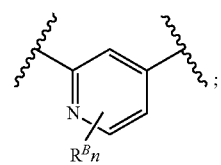
(IIIc)

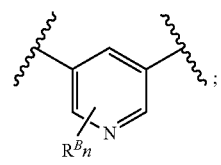
(IIId)

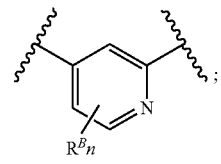
(IIIe)

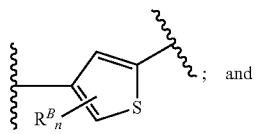
(IIIf)

and

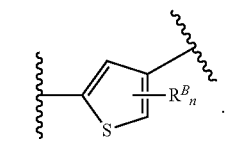
(IIIg)

In some embodiments of formula (I), (IIa), (IIb), or any one of (IIIa)-(IIIg), n is 2.

In some embodiments of formula (I), (IIa), (IIb), or any one of (IIIa)-(IIIg), the ring B is represented by a formula selected from the group consisting of:

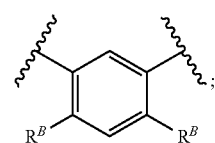
(IVa)

-continued

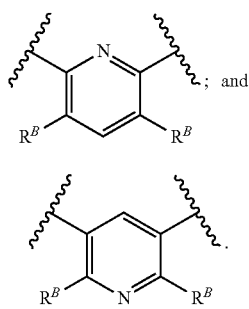

(IVb)

(IVc)

In some embodiments of formula (I), (IIa), (IIb), any one of (IIIa)-(IIIg), or any one of (IVa)-(IVc), each $R^B$ is independently a halogen atom, an optionally substituted lower alkyl group, or $OW^4$, wherein each $W^4$ is independently a hydrogen atom or an optionally substituted lower alkyl group.

In some embodiments of formula (I), (IIa), (IIb), any one of (IIIa)-(IIIg), or any one of (IVa)-(Vc), each $R^B$ is independently a fluorine atom, chlorine atom, bromine atom, methyl group, or methoxy group.

In some embodiments of formula (I), (IIa), (IIb), any one of (IIIa)-(IIIg), or any one of (IVa)-(IVc), U is a single bond.

In some embodiments of formula (I), (IIa), (IIb), any one of (IIIa)-(IIIg), or any one of (IVa)-(IVc), X is a group represented by —O-L-Y.

In some embodiments of formula (I), (IIa), (IIb), any one of (IIIa)-(IIIg), or any one of (IVa)-(IVc), L is a methylene group.

In some embodiments of formula (I), (IIa), (IIb), any one of (IIIa)-(IIIg), or any one of (IVa)-(IVc), Y is an optionally substituted benzene ring represented by formula (V)

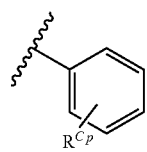

(V)

wherein each $R^c$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments of formula (I), (IIa), (IIb), any one of (IIIa)-(IIIg), any one of (IVa)-(IVc), or (V), Y is a substituted benzene ring represented by formula (Va)

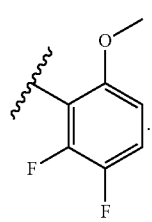

(Va)

In some embodiments, the compound is represented by formula (Ia)

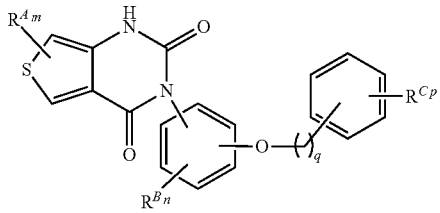

(Ia)

wherein each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

q is an integer from 0 to 3;

each $R^c$ is independently a halogen atom, an optionally substituted lower alkyl group, or $OW^9$, wherein each $W^9$ is independently a hydrogen atom or an optionally substituted lower alkyl group; and p is an integer from 0 to 3;

or a pharmaceutically acceptable salt thereof.

In some embodiments, the compound is represented by formula (Ib)

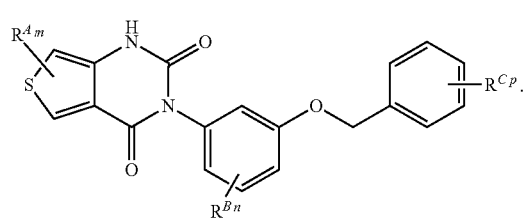

(Ib)

In some embodiments, the compound is represented by formula (Ic)

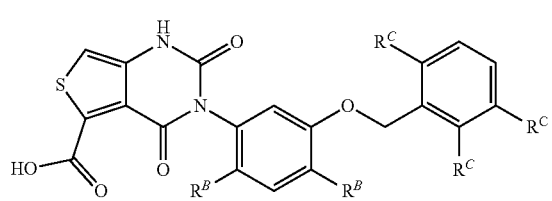

(Ic)

or a pharmaceutically acceptable salt thereof.

In some embodiments, the compound is 3-[2-fluoro-5-(2, 3-difluoro-6-methoxybenzyloxy)4-methoxyphenyl]-2,4-dioxo-1,2,3,4-tetrahydrothieno [3,4d]pyrimidine-5-carboxylic acid, represented by formula (VI)

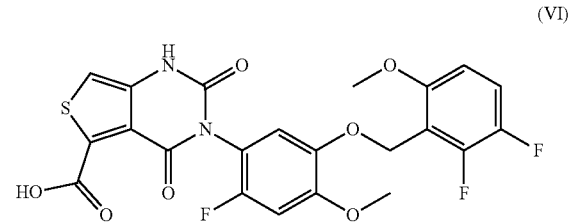 [SMILES: COc1cc(F)c(-n2c(=O)[nH]c3csc(C(=O)O)c3c2=O)cc1OCc1c(OC)ccc(F)c1F]

(VI)

or a pharmaceutically acceptable salt thereof. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of an electrostatically neutral carboxylic acid. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylic acid is administered to the patient in the form of a pharmaceutically acceptable salt. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of the choline salt, choline 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylate.

In some embodiments, the compound is the choline salt of the compound represented by formula (VI), choline 3-[$^2$-fluoro-5-(2,3-difluoro-6-methoxybenzyloxy)4-methoxyphenyl]-2,4-dioxo-1,2,3,4-tetrahydrothieno [3,4d]pyrimidine-5-carboxylate.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate is in a crystalline state.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits characteristic X-ray powder diffraction (XRPD) peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{13}$C solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{19}$F solid-state NMR peaks centered at about −151.8 ppm, −145.2 ppm, and −131.6 ppm.

In some embodiments, the compound of any one of formulas (I), (Ia)-(Ic), (IIa), (IIb), (IIIa)-(IIIg), (IVa)-(IVc), (V), (Va), or (VI) is orally administered to the patient.

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 50 mg to about 400 mg per dose (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, or 400 mg of the compound of any one of formulas (I), (Ia)-(Ic), (IIa), (IIb), (IIIa)-(IIIg), (IVa)-(IVc), (V), (Va), or (VI) (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 35 mg to about 65 mg per dose (e.g., in the recited amount or in an equivalent amount of a pharmaceutically acceptable salt, such as a choline salt), such as an amount of about 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 50 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIIb), (IIIa)-(IIIg), (IVa)-(IVc), (V), (Va), or (VI) is administered to the patient in an amount of from about 60 mg to about 90 mg per dose (e.g., in the recited amount or in an equivalent amount of a pharmaceutically acceptable salt, such as a choline salt), such as an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 75 mg per dose (e.g., in the recited amount or in an equivalent amount of a pharmaceutically acceptable salt, such as a choline salt).

In some embodiments, the compound of any one of formulas (I), (Ia)-(Ic), (IIa), (11b), (IIIa)-(IIIg), (IVa)-(IVc), (V), (Va), or (VI) is administered to the patient in an amount of from about 50 mg to about 150 mg per dose (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 100 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in an amount of from about 150 mg to about 250 mg per dose (e.g., in the recited amount or in an equivalent amount of a pharmaceutically acceptable salt, such as a choline salt), such as an amount of about 150 mg, 151 mg, 152 mg, 153 mg, 154 mg, 1.55 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per dose (e.g., in the recited amount or in an equivalent amount of a pharmaceutically acceptable salt, such as a choline salt). In some embodiments, the compound of any one of formulas (I), (Ia)-(Ic), (IIa), (IIb), (IIIa)-(IIIg), (IVa)-(IVc), (V), (Va), or (VI) is administered to the patient in an amount of about 200 mg per dose (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (I), (Ia)-(Ic), (IIa), (IIb), (IIIa)-(IIIg), (IVa)-(IVc), (V), (Va), or (VI) may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (I), (Ia)-(Ic), (IIa), (IIb), (IIIa)-(IIIg), (IVa)-(IVc), (V), (Va), or (VI) is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

The compound of any one of formulas (I), (Ia)-(Ic), (IIa), (IIb), (IIIa)-(IIIg), (IVa)-(IVc), (V), (Va), or (VI) may be administered to the patient in one or more unit dosage forms that collectively constitute a single dose. For example, a patient may be administered a single dose of the compound of a specified amount, such as a single dose of 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, or more (e.g., in the recited amount or in an equivalent amount of a pharmaceutically acceptable salt, such as a choline salt), by administration of one or more unit dosage forms of the compound to the patient. As a non-limiting example, a single dose of 200 mg of the compound may be administered to the subject by way of two individual 100-mg unit dosage forms of the compound. The two 100-mg unit dosage forms collectively constitute a single 200-mg dose of the compound if administered to the patient at substantially the same time.

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 35 mg to about 65 mg per day (e.g., in the recited amount or in an equivalent amount of a pharmaceutically acceptable salt, such as a choline salt), such as an amount of about 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 50 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 60 mg to about 90 mg per day (e.g., in the recited amount or in an equivalent amount of a pharmaceutically acceptable salt, such as a choline salt), such as an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 75 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 50 mg to about 150 mg per day (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 100 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more) totaling from about 150 mg to about 250 mg per day (e.g., in the recited amount or in an equivalent amount of a pharmaceutically acceptable salt, such as a choline salt), such as an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per day (e.g., in the recited amount or in an equivalent amount of a pharmaceutically acceptable salt, such as a choline salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 200 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in a single dose per day. For example, the compound may be administered to the patient in an amount (e.g., a single dose) of from about 35 mg to about 65 mg per day (e.g., in the recited amount or in an equivalent amount of a pharmaceutically acceptable salt, such as a choline salt), such as an amount of about 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg per day (e.g., in the recited amount or in an equivalent amount of a pharmaceutically acceptable salt, such as a choline salt). In some embodiments, the compound is administered to the patient in an amount (e.g., a single dose) of about 50 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in a single dose per day. For example, the compound may be administered to the patient in an amount (e.g., a single dose) of from about 60 mg to about 90 mg per day (e.g., in the recited amount or in an equivalent amount of a pharmaceutically acceptable salt, such as a choline salt), such as an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg per day (e.g., in the recited amount or in an equivalent amount of a pharmaceutically acceptable salt, such as a choline salt). In some embodiments, the compound is administered to the patient in an amount (e.g., a single dose) of about 75 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIa)-(IIIg), (IVa)-(IVc), (V), (Va), or (VI) is administered to the patient in a single dose per day. For example, the compound may be administered to the patient in an amount (e.g., a single dose) of from about 50 mg to about 150 mg per day (e.g., in the recited amount or in an equivalent amount of a pharmaceutically acceptable salt, such as a choline salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per day (e.g., in the recited amount or in an equivalent amount of a pharmaceutically acceptable salt, such as a choline salt). In some embodiments, the compound is administered to the patient in an amount (e.g., a single dose) of about 100 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in a single dose per day, and is administered to the patient in an amount (e.g., a single dose) of from about 150 mg to about 250 mg per day (e.g., in the recited amount or in an equivalent amount of a pharmaceutically acceptable salt, such as a choline salt), such as an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per day (e.g., in the recited amount or in an equivalent amount of a pharmaceutically acceptable salt, such as a choline salt). In some embodiments, the compound is administered to the patient in an amount (e.g., a single dose) of about 200 mg per day (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period, such as a treatment period of one or more weeks, months, or years, for example, a treatment period of from about 1 week to about 48 months, or more (e.g., a treatment period of about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, 73 weeks, 74 weeks, 75 weeks, 76 weeks, 77 weeks, 78 weeks, 79 weeks, 80 weeks, 81 weeks, 82 weeks, 83 weeks, 84 weeks, 85 weeks, 86 weeks, 87 weeks, 88 weeks, 89 weeks, 90 weeks, 91 weeks, 92 weeks, 93 weeks, 94 weeks, 95 weeks, 96 weeks, 97 weeks, 98 weeks, 99 weeks, 100 weeks, 101 weeks, 102 weeks, 103 weeks, 104 weeks, 105 weeks, 106 weeks, 107 weeks, 108 weeks, 109 weeks, 110 weeks, 111 weeks, 112 weeks, 113 weeks, 114 weeks, 115 weeks, 116 weeks, 117 weeks, 118 weeks, 119 weeks, 120 weeks, 121 weeks, 122 weeks, 123 weeks, 124 weeks, 125 weeks, 126 weeks, 127 weeks, 128 weeks, 129 weeks, 130 weeks, 131 weeks, 132 weeks, 133 weeks, 134 weeks, 135 weeks, 136 weeks, 137 weeks, 138 weeks, 139 weeks, 140 weeks, 141 weeks, 142 weeks, 143 weeks, 144 weeks, 145 weeks, 146 weeks, 147 weeks, 148 weeks, 149 weeks, 150 weeks, 151 weeks, 152 weeks, 153 weeks, 154 weeks, 155 weeks, 156 weeks, 157 weeks, 158 weeks, 159 weeks, 160 weeks, 161 weeks, 162 weeks, 163 weeks, 164 weeks, 165 weeks, 166 weeks, 167 weeks, 168 weeks, 169 weeks, 170 weeks, 171 weeks, 172 weeks, 173 weeks, 174 weeks, 175 weeks, 176 weeks, 177 weeks, 178 weeks, 179 weeks, 180 weeks, 181 weeks, 182 weeks, 183 weeks, 184 weeks, 185 weeks, 186 weeks, 187 weeks, 188 weeks, 189 weeks, 190 weeks, 191 weeks, 192 weeks, 193 weeks, 194 weeks, 195 weeks, 196 weeks, 197 weeks, 198 weeks, 199 weeks, or 200 weeks, or more). In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 1 month to about 48 months, or more, such as a treatment period of about 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 4 weeks, such as a treatment period of from about 4 weeks to about 12 months, or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 1 month to about 12 months, or more, such as a treatment period of about 1 month, 2 months, 3 months, 4 months, 5 months, 6 months, 7 months, 8 months, 9 months, 10 months, 11 months, or 12 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 8 weeks, such as a treatment period of from about 8 weeks to about 10 months, or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, or 40 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 2 months to about 10 months, or more, such as a treatment period of about 2 months, 3 months, 4 months, 5 months, 6 months, 7 months, 8 months, 9 months, or 10 months, or more.

In some embodiments, the compound of any one of formulas (I), (Ia)-(Ic), (IIa), (IIb), (IIIa)-(IIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 12 weeks, such as a treatment period of from about 12 weeks to about 48 weeks (e.g., a treatment period of from about 16 weeks to about 48 weeks), or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 3 months to about 12 months, or more, such as a treatment period of about 3 months, 4 months, 5 months, 6 months, 7 months, 8 months, 9 months, 10 months, 11 months, or 12 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of at least 24 weeks, such as a treatment period of from about 24 weeks to about 72 weeks, or more. The compound may be administered to the patient in the recited amount or in an equivalent amount of a pharmaceutically acceptable salt, such as a choline salt. For example, the compound may be periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of about 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, or more. In some embodiments, the compound is periodically administered to the patient (e.g., using a dosing schedule defined above, such as an in amount of from about 50 mg per day to about 150 mg per day (e.g., 100 mg per day) or in an amount of from about 150 mg per day to about 250 mg per day (e.g., 200 mg per day)) over the course of a treatment period of from about 6 months to about 18 months, or more, such as a treatment period of about 6 months, 7 months, 8 months, 9 months, 10 months, 11 months, 12 months, 13 months, 14 months, 15 months, 16 months, 17 months, or 18 months, or more.

In some embodiments, the compound of any one of formulas (I), (Ia)-(Ic), (IIa), (IIb), (IIIa)-(IIIg), (IVa)-(IVc), (V), (Va), or (VI) is periodically administered to the patient at a particular dose (e.g., a particular daily dose) over the course of a first treatment period, and is subsequently periodically administered to the patient at a higher or lower dose (e.g., a higher or lower daily dose) over the course of a second treatment period. For example, in some embodiments, the compound is administered to the patient in one or more daily doses (e.g., from 1 to 10 doses, such as 1, 2, 3, 4, 5, 6, 7, 8, 9, or 10 doses, or more, such as a single daily dose) totaling from about 150 mg to about 250 mg per day over the course of a first treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling from about 50 mg to about 150 mg per day over the course of a second treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg per day over the course of a second treatment period (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more, such as a single daily dose) totaling from about 175 mg to about 225 mg per day over the course of a first treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, or 225 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling from about 75 mg to about 125 mg per day over the course of a second treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, or 125 mg per day over the course of a second treatment period (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more, such as a single daily dose) totaling from about 185 mg to about 215 mg per day over the course of a first treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, or 215 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling from about 85 mg to about 115 mg per day over the course of a second treatment period (e.g., in the recited amount or in an equivalent amount of a pharmaceutically acceptable salt, such as a choline salt), such as in one or more daily doses (e.g., from 1 to 10 doses, such as 1, 2, 3, 4, 5, 6, 7, 8, 9, or 10 doses, or more, such as a single daily dose) totaling an amount of about 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, or 115 mg per day over the course of a second treatment period (e.g., in the recited amount or in an equivalent amount of a pharmaceutically acceptable salt, such as a choline salt).

In some embodiments, the compound of any one of formulas (I), (Ia)-(Ic), (IIa), (IIb), (IIIa)-(IIg), (IVa)-(IVc), (V), (Va), or (VI) is administered to the patient in one or more daily doses (e.g., from 1 to 10 doses, such as 1, 2, 3, 4, 5, 6, 7, 8, 9, or 10 doses, or more, such as a single daily dose) totaling about 200 mg per day over the course of a first treatment period (e.g., in the recited amount or in an equivalent amount of a pharmaceutically acceptable salt, such as a choline salt). In some embodiments, the compound is subsequently administered to the patient in one or more daily doses (e.g., from 1 to 10 doses, such as 1, 2, 3, 4, 5, 6, 7, 8, 9, or 10 doses, or more, such as a single daily dose) totaling about 100 mg per day over the course of a second treatment period (e.g., in the recited amount or in an equivalent amount of a pharmaceutically acceptable salt, such as a choline salt).

In some embodiments, the first and second treatment periods collectively have a duration of one or more weeks, months, or years, for example, a combined treatment period of from about 1 week to about 48 months, or more (e.g., a combined treatment period of about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, 73 weeks, 74 weeks, 75 weeks, 76 weeks, 77 weeks, 78 weeks, 79 weeks, 80 weeks, 81 weeks, 82 weeks, 83 weeks, 84 weeks, 85 weeks, 86 weeks, 87 weeks, 88 weeks, 89 weeks, 90 weeks, 91 weeks, 92 weeks, 93 weeks, 94 weeks, 95 weeks, 96 weeks, 97 weeks, 98 weeks, 99 weeks, 100 weeks, 101 weeks, 102 weeks, 103 weeks, 104 weeks, 105 weeks, 106 weeks, 107 weeks, 108 weeks, 109 weeks, 110 weeks, 111 weeks, 112 weeks, 113 weeks, 114 weeks, 115 weeks, 116 weeks, 117 weeks, 118 weeks, 119 weeks, 120 weeks, 121 weeks, 122 weeks, 123 weeks, 124 weeks, 125 weeks, 126 weeks, 127 weeks, 128 weeks, 129 weeks, 130 weeks, 131 weeks, 132 weeks, 133 weeks, 134 weeks, 135 weeks, 136 weeks, 137 weeks, 138 weeks, 139 weeks, 140 weeks, 141 weeks, 142 weeks, 143 weeks, 144 weeks, 145 weeks, 146 weeks, 147 weeks, 148 weeks, 149 weeks, 150 weeks, 151 weeks, 152 weeks, 153 weeks, 154 weeks, 155 weeks, 156 weeks, 157 weeks, 158 weeks, 159 weeks, 160 weeks, 161 weeks, 162 weeks, 163 weeks, 164 weeks, 165 weeks, 166 weeks, 167 weeks, 168 weeks, 169 weeks, 170 weeks, 171 weeks, 172 weeks, 173 weeks, 174 weeks, 175 weeks, 176 weeks, 177 weeks, 178 weeks, 179 weeks, 180 weeks, 181 weeks, 182 weeks, 183 weeks, 184 weeks, 185 weeks, 186 weeks, 187 weeks, 188 weeks, 189 weeks, 190 weeks, 191 weeks, 192 weeks, 193 weeks, 194 weeks, 195 weeks, 196 weeks, 197 weeks, 198 weeks, 199 weeks, or 200 weeks, or more). In some embodiments, the first and second treatment periods collectively have a duration of from about 1 month to about 48 months, or more, such as a combined treatment period of about 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, or more.

In some embodiments, the first treatment period has a duration of at least 2 weeks, such as a duration of from about 2 weeks to about 6 months, or more. For example, the first treatment period may have a duration of about 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the first treatment period has a duration of from about 0.5 months to about 6 months, or more, such as a duration of about 0.5 months, 1 month, 2 months, 3 months, 4 months, 5 months, or 6 months, or more.

In some embodiments, the first treatment period has a duration of at least 4 weeks, such as a duration of from about 4 weeks to about 5 months, or more. For example, the first treatment period may have a duration of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks, or more. In some embodiments, the first treatment period has a duration of from about 1 month to about 5 months, or more, such as a treatment period of about 1 month, 2 months, 3 months, 4 months, or 5 months, or more.

In some embodiments, the first treatment period has a duration of at least 6 weeks, such as a duration of from about 6 weeks to about 24 weeks (e.g., a duration of from about 8 weeks to about 24 weeks), or more. For example, the first treatment period may have a duration of about 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the first treatment period has a duration of from about 1.5 months to about 6 months, or more, such as a duration of about 1.5 months, 2 months, 3 months, 4 months, 5 months, or 6 months, or more.

In some embodiments, the first treatment period has a duration of about 12 weeks.

In some embodiments, the second treatment period has a duration of at least 2 weeks, such as a duration of from about 2 weeks to about 6 months, or more. For example, the second treatment period may have a duration of about 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the second treatment period has a duration of from about 0.5 months to about 6 months, or more, such as a duration of about 0.5 months, 1 month, 2 months, 3 months, 4 months, 5 months, or 6 months, or more.

In some embodiments, the second treatment period has a duration of at least 4 weeks, such as a duration of from about 4 weeks to about 5 months, or more. For example, the second treatment period may have a duration of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks, or more. In some embodiments, the second treatment period has a duration of from about 1 month to about 5 months, or more, such as a treatment period of about 1 month, 2 months, 3 months, 4 months, or 5 months, or more.

In some embodiments, the second treatment period has a duration of at least 6 weeks, such as a duration of from about 6 weeks to about 24 weeks (e.g., a duration of from about 8 weeks to about 24 weeks), or more. For example, the second treatment period may have a duration of about 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, or more. In some embodiments, the second treatment period has a duration of from about 1.5 months to about 6 months, or more, such as a duration of about 1.5 months, 2 months, 3 months, 4 months, 5 months, or 6 months, or more.

In some embodiments, the second treatment period has a duration of about 12 weeks.

In some embodiments of any of the foregoing aspects of the disclosure, the GnRH antagonist is a compound represented by any one of formulas (VII)-(XIV), below, such as elagolix, relugolix, or opigolix (ASP1707). In some embodiments, the GnRH antagonist is BAY-784 or SK-2706.

In some embodiments, the GnRH antagonist is a compound represented by formula (VII)

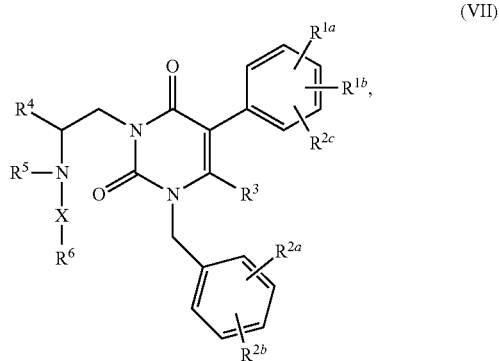

(VII)

wherein $R_{1a}$, $R_{1b}$ and $R_{1c}$ are the same or different and are each independently hydrogen, halogen, $C_{1-4}$alkyl, hydroxy or alkoxy, or $R_{1a}$ and $R_{1b}$ taken together form —OCH$_2$O— or —OCH$_2$CH$_2$—;

$R_{2a}$ and $R_{2b}$ are the same or different and are each independently hydrogen, halogen, trifluoromethyl, cyano or —SO$_2$CH$_3$;

$R_3$ is hydrogen or methyl;

$R_4$ is phenyl or $C_{3-7}$alkyl;

$R_5$ is hydrogen or $C_{1-4}$alkyl;

$R_6$ is —COOH or an acid isostere; and

X is $C_{1-6}$alkanediyl optionally substituted with from 1 to 3 $C_{1-6}$alkyl groups;

or a pharmaceutically acceptable salt thereof.

In some embodiments, the GnRH antagonist is a compound represented by formula (VIII)

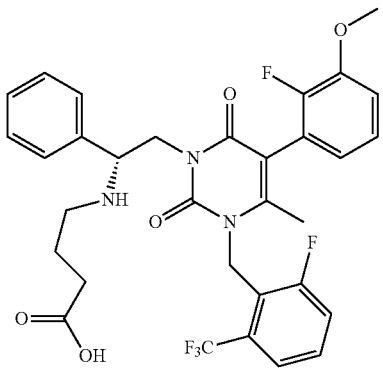

(VIII)

or a pharmaceutically acceptable salt thereof. In some embodiments, the GnRH antagonist is the sodium salt of the compound represented by formula (VIII), which is represented by formula (IX), below.

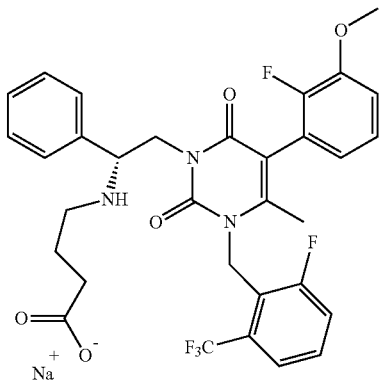

(IX)

In some embodiments, the compound of any one of formulas (VII)-(IX) is administered to the patient in an amount of from about 50 mg to about 650 mg per dose (e.g., in the recited amount or in an equivalent amount of a pharmaceutically acceptable salt, such as a sodium salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 633 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, or 650 mg per dose (e.g., in the recited amount or in an equivalent amount of a pharmaceutically acceptable salt, such as a sodium salt). In some embodiments, the compound of any one of formulas (VII)-(IX) is administered to the patient in an amount of about 150 mg per dose, 300 mg per dose, 400 mg per dose, or 600 mg per dose (e.g., in the recited amount or in an equivalent amount of a pharmaceutically acceptable salt, such as a sodium salt).

In some embodiments, the compound of any one of formulas (VII)-(IX) is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (VII)-(IX) may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (VII)-(IX) is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

The compound of any one of formulas (VII)-(IX) may be administered to the patient in one or more unit dosage forms that collectively constitute a single dose. For example, a patient may be administered a single dose of the compound of a specified amount, such as a single dose of 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, or more (e.g., in the recited amount or in an equivalent amount of a pharmaceutically acceptable salt, such as a sodium salt), by administration of one or more unit dosage forms of the compound to the patient. As a non-limiting example, a single dose of 300 mg of the compound may be administered to the subject by way of two individual 150-mg unit dosage forms of the compound. The two 150-mg unit dosage forms collectively constitute a single 300-mg dose of the compound if administered to the patient at substantially the same time.

In some embodiments, the compound of any one of formulas (VII)-(IX) is administered to the patient in one or more daily doses (e.g., from 1 to 10 doses, such as 1, 2, 3, 4, 5, 6, 7, 8, 9, or 10 doses, or more) totaling from about 50 mg to about 650 mg per day (e.g., in the recited amount or in an equivalent amount of a pharmaceutically acceptable salt, such as a sodium salt), such as an amount of about 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 633 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, or 650 mg per day (e.g., in the recited amount or in an equivalent amount of a pharmaceutically acceptable salt, such as a sodium salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 150 mg per day, 300 mg per day, 400 mg per day (e.g., 200 mg administered twice daily, or 600 mg per day (e.g., 300 mg administered twice daily) (e.g., in the recited amount or in an equivalent amount of a pharmaceutically acceptable salt, such as a sodium salt).

In some embodiments, the GnRH antagonist is a compound represented by formula (X)

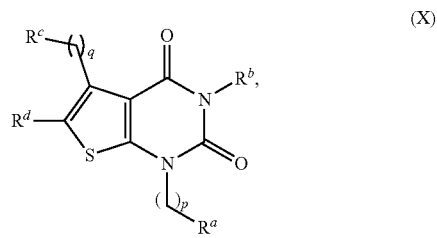

wherein $R^a$ is a hydrogen atom, an optionally substituted aryl group (such as an aryl group that may have 1 to 5 substituents selected from halogen, nitro, cyano, amino, a carboxyl group that may be esterified or amidated, an alkylenedioxy, alkyl, alkoxy, alkylthio, alkylsulfinyl, and alkylsulfonyl), an optionally substituted cycloalkyl group, or an optionally substituted heterocyclic group;

$R^b$ is an optionally substituted nitrogen-containing heterocyclic group;

$R^c$ is an optionally substituted amino group;

$R^d$ is an optionally substituted aryl group;

p is an integer from 0 to 3; and q is an integer from 0 to 3;

or a pharmaceutically acceptable salt thereof.

In some embodiments, the GnRH antagonist is a compound represented by formula (XI)

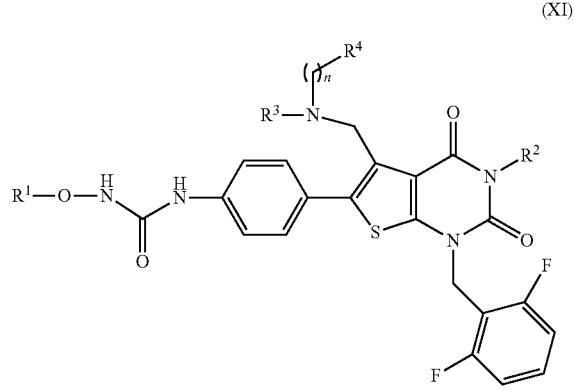

wherein $R_1$ is $C_{1-4}$alkyl;

$R^2$ is (1) a $C_{1-6}$alkyl which may have a substituent selected from the group consisting of (1') a hydroxy group, (2') a $C_{1-4}$alkoxy, (3') a $C_{1-4}$alkoxy-carbonyl, (4') a di-$C_{1-4}$alkyl-carbamoyl, (5') a 5- to 7-membered nitrogen-containing heterocyclic group, (6') a $C_{1-4}$alkyl-carbonyl and (7') a halogen, (2) a $C_{3-5}$ cycloalkyl which may have (1') a hydroxy group or (2') a mono-$C_{1-4}$alkyl-carbonylamino, (3) a 5- to 7-membered nitrogen-containing heterocyclic group which may have a substituent selected from the group consisting of (1') a halogen, (2') a hydroxy group, (3') a $C_{1-4}$alkyl and (4') a $C_{1-4}$alkoxy, (4) a phenyl which may have a substituent selected from the group consisting of (1') a halogen, (2') a $C_{1-4}$alkoxy-$C_{1-4}$alkyl, (3') a mono-$C_{1-4}$alkyl-carbamoyl-$C_{1-4}$alkyl, (4') a $C_{1-4}$alkoxy and (5') a mono-$C_{1-4}$alkylcarbamoyl-$C_{1-4}$alkoxy, or (5) a $C_{1-4}$alkoxy;

$R^3$ is $C_{1-4}$alkyl;

$R^4$ is (1) hydrogen, (2) $C_{1-4}$alkoxy, (3) $C_{6-10}$aryl, (4) N—$C_{1-4}$alkyl-N—$C_{1-4}$alkylsulfonylamino, (5) hydroxyl, or (6) a 5- to 7-membered nitrogen-containing heterocyclic group which may have a substituent selected from the group consisting of (1') oxo, (2') a $C_{1-4}$alkyl, (3') a hydroxy-$C_{1-4}$alkyl, (4') a $C_{1-4}$alkoxy-carbonyl, (5') a mono-$C_{1-4}$alkyl-carbamoyl and (6') a $C_{1-4}$alkylsulfonyl; and n is an integer from 1 to 4;

optionally provided that when $R^2$ is a phenyl which may have a substituent, $R^4$ is a 5- to 7-membered nitrogen-containing heterocyclic group which may have a substituent selected from the group consisting of (1) oxo, (2) hydroxy-$C_{1-4}$alkyl, (3) $C_{1-4}$alkoxy-carbonyl, (4) mono-$C_{1-4}$alkyl-carbamoyl and (5) $C_{1-4}$alkylsulfonyl;

or a pharmaceutically acceptable salt thereof. In some embodiments, the GnRH antagonist is a compound represented by formula (XII), below.

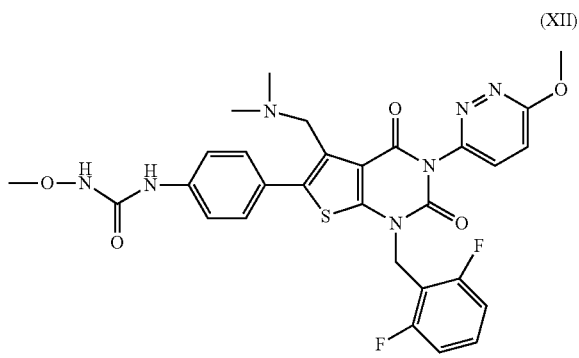

(XII)

In some embodiments, the compound of any one of formulas (X)-(XII) is administered to the patient in an amount of from about 10 mg to about 60 mg per dose (e.g., in the recited amount or in an equivalent amount of a pharmaceutically acceptable salt, such as a chloride salt), such as an amount of about 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg per dose (e.g., in the recited amount or in an equivalent amount of a pharmaceutically acceptable salt, such as a chloride salt). In some embodiments, the compound of any one of formulas (X)-(XII) is administered to the patient in an amount of about 40 mg per dose (e.g., in the recited amount or in an equivalent amount of a pharmaceutically acceptable salt, such as a chloride salt).

In some embodiments, the compound of any one of formulas (X)-(XII) is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (X)-(XII) may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (X)-(XII) is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

The compound of any one of formulas (I)-(XII) may be administered to the patient in one or more unit dosage forms that collectively constitute a single dose. For example, a patient may be administered a single dose of the compound of a specified amount, such as a single dose of 25 mg, 50 mg, 75 mg, 100 mg, or more (e.g., in the recited amount or in an equivalent amount of a pharmaceutically acceptable salt, such as a chloride salt), by administration of one or more unit dosage forms of the compound to the patient. As a non-limiting example, a single dose of 40 mg of the compound may be administered to the subject by way of two individual 20-mg unit dosage forms of the compound. The two 20-mg unit dosage forms collectively constitute a single 40-mg dose of the compound if administered to the patient at substantially the same time.

In some embodiments, the compound of any one of formulas (X)-(XII) is administered to the patient in one or more daily doses (e.g., from 1 to 10 doses, such as 1, 2, 3, 4, 5, 6, 7, 8, 9, or 10 doses, or more) totaling from about 10 mg to about 60 mg per day (e.g., in the recited amount or in an equivalent amount of a pharmaceutically acceptable salt, such as a chloride salt), such as an amount of about 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg per day (e.g., in the recited amount or in an equivalent amount of a pharmaceutically acceptable salt, such as a chloride salt). In some embodiments, the compound is administered to the patient in one or more daily doses (e.g., from 1 to 10 doses, such as 1, 2, 3, 4, 5, 6, 7, 8, 9, or 10 doses, or more) totaling from about 20 mg to about 50 mg per day (e.g., in the recited amount or in an equivalent amount of a pharmaceutically acceptable salt, such as a chloride salt), such as an amount of about 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg per day (e.g., in the recited amount or in an equivalent amount of a pharmaceutically acceptable salt, such as a chloride salt). In some embodiments, the compound is administered to the patient in one or more daily doses (e.g., from 1 to 10 doses, such as 1, 2, 3, 4, 5, 6, 7, 8, 9, or 10 doses, or more) totaling an amount of about 40 mg per day (e.g., in the recited amount or in an equivalent amount of a pharmaceutically acceptable salt, such as a chloride salt).

In some embodiments, the GnRH antagonist is a compound represented by formula (XIII)

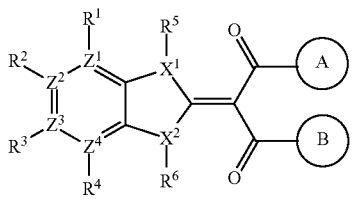

(XIII)

wherein $R^1$, $R^2$, $R^3$ and $R^4$ are the same or different, and are each independently selected from hydrogen, nitro, cyano, halogen, an optionally substituted hydrocarbon group, an optionally substituted heterocyclic group, hydroxy, alkoxy, carboxy, optionally substituted acyl-O—, optionally substituted acyl, a substituent —S(O)$n_{101}$- (wherein $n_{101}$ is an integer of 0 to 2), H—S(O)$n_{101}$-, optionally substituted carbamoyl, optionally substituted sulfamoyl, optionally substituted amino, and two adjacent groups selected from the group of $R^1$, $R^2$, $R^3$ and $R^4$ may combine to form an aryl or a carbocyclic (e.g., cycloalkenyl) group;

$R^5$ and $R^6$ are the same or different and are each independently selected from hydrogen, halogen, optionally substituted hydrocarbon, and optionally substituted amino, $X^1$ and $X^2$ are the same or different and are each independently selected from N, S and O;

A and B are the same or different and are each independently selected from optionally substituted aryl and optionally substituted heterocyclyl, and $Z^1$, $Z^2$, $Z^3$ and $Z^4$ are each independently selected from C and N; optionally provided that 1) when $X^1$ and $X^2$ each is S or O, one or both of the corresponding $R^5$ and $R^6$ are absent; and/or 2) when one to four of $Z^1$, $Z^2$, $Z^3$ and/or $Z^4$ are N, the corresponding $R^1$, $R^2$, $R^3$ and/or $R^4$ are absent;

or a pharmaceutically acceptable salt thereof. In some embodiments, the GnRH antagonist is a compound represented by formula (XIV), below.

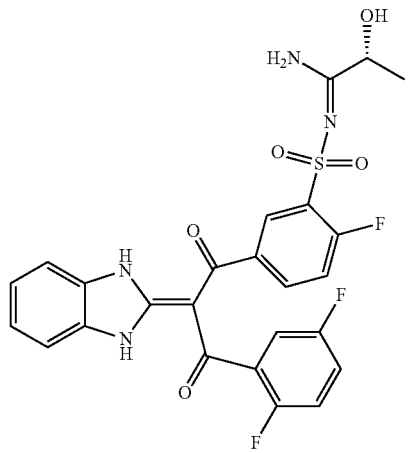

(XIV)

In some embodiments, the compound of any one of formulas (XIII) and (XIV), or SK12670 or BAY-784, is administered to the patient in one or more doses (i.e., one or more times) per day, week, or month, such as from 1 to 10 times per day (e.g., 1 time, 2 times, 3 times, 4 times, 5 times, 6 times, 7 times, 8 times, 9 times, or 10 times per day, such as 1 time or 2 times per day), 1 to 100 times per week (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times 40 times, 45 times, 50 times, 55 times, 60 times, 65 times, 70 times, 75 times, 80 times, 85 times, 90 times, 95 times, or 100 times per week, such as 7 times, 8 times, 9 times, 10 times, 11 times, 12 times, 13 times, 14 times per week), or 1 to 500 times per month (e.g., 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, 90 times, 91 times, 92 times, 93 times, 94 times, 95 times, 96 times, 97 times, 98 times, 99 times, 100 times, 200 times, 300 times, 400 times, or 500 times per month, such as 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, or 60 times per month), or more.

For example, the compound of any one of formulas (XIII) and (XIV), or SK12670 or BAY-784, may be administered to the patient in one or more doses every 4 hours, 6 hours, 8 hours, 10 hours, 12 hours, 14 hours, 16 hours, 18 hours, 20 hours, 22 hours, 24 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours, 74 hours, 76 hours, 78 hours, 80 hours, 82 hours, 84 hours, 86 hours, 88 hours, 90 hours, 92 hours, 94 hours, 96 hours, 98 hours, 100 hour, 102 hours, 104 hours, 105 hours, 106 hours, 108 hours, 110 hours, 112 hours, 114 hours, 116 hours, 118 hours, 120 hours, 122 hours, 124 hours, 126 hours, 128 hours, 130 hours, 132 hours, 134 hours, 136 hours, 138 hours, 140 hours, 142 hours, 144 hours, 146 hours, 148 hours, 150 hours, 152 hours, 154 hours, 156 hours, 158 hours, 160 hours, 162 hours, 164 hours, 166 hours, 168 hours, or more. In some embodiments, the compound of any one of formulas (XIII) and (XIV), or SK12670 or BAY-784, is administered to the patient in one or more doses per day, such as from 1 to 10 doses per 12 hours (e.g., 1 dose, 2 doses, 3 doses, 4 doses, 5 doses, 6 doses, 7 doses, 8 doses, 9 doses, 10 doses per 12 hours), from 1 to 10 doses per 24 hours (e.g., 1 dose, 2 doses, 3 doses, 4 doses, 5 doses, 6 doses, 7 doses, 8 doses, 9 doses, 10 doses per 24 hours), or from 1 to 10 doses per 48 hours (e.g., 1 dose, 2 doses, 3 doses, 4 doses, 5 doses, 6 doses, 7 doses, 8 doses, 9 doses, 10 doses per 48 hours), among others.

In some embodiments of any of the foregoing aspects of the disclosure, add-back therapy is administered (e.g., periodically administered) to the patient.

In some embodiments, the add-back therapy is administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of β17-estradiol, ethinyl estradiol, or a conjugated estrogen, such as a conjugated equine estrogen) and/or a progestin (e.g., norethindrone or a compound that is metabolized in vivo to produce norethindrone, such as an ester of norethindrone that is de-esterified in vivo to produce norethindrone, for instance, norethindrone acetate (also referred to herein as "NETA"), among other agents, such as progesterone, norgestimate, medroxyprogesterone, and drospirenone) in the form of a single pharmaceutical composition, such as a single tablet, capsule, gel cap, powder, liquid solution, or liquid suspension. In some embodiments, the add-back therapy is administered orally, transdermally, or intravaginally.

In some embodiments, the add-back therapy is administered to the patient in one or more doses per day, week, month, or year, such as daily, for example, from 1 to 10 times daily, or more (e.g., 1, 2, 3, 4, 5, 6, 7, 8, 9, 10, or more, times daily). In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described above and herein.

In some embodiments, the add-back therapy is administered to the patient once daily, following administration of the GnRH antagonist. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient once daily, prior to administration of the GnRH antagonist. For example, the GnRH antagonist may be administered to the patient orally, and prior to oral administration of the GnRH antagonist, the add-back therapy may be administered to the patient orally, transdermally, or intravaginally.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The 17-estradiol may be administered to the patient one or more times per day, week, or month. The β17-estradiol may be administered to the patient, for example, in an amount of from about 0.1 mg/day to about 2.5 mg/day, such as in an amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient in an amount of 1.0 mg/day, for instance, by oral administration. In some embodiments, the β17-estradiol is administered to the patient in an amount of 0.5 mg/day, for instance, by oral administration.

In some embodiments, the estrogen is ethinyl estradiol. The ethinyl estradiol may be administered to the patient, for example, at a dose of from about 1.0 µg to about 6.0 µg, such as at a dose of about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg, for instance, by oral administration. In some embodiments, the ethinyl estradiol is administered to the patient at a dose of 5.0 µg, for instance, by oral administration. In some embodiments, the ethinyl estradiol is administered to the patient at a dose of 2.5 µg, for instance, by oral administration.

The ethinyl estradiol may be administered to the patient one or more times per day, week, or month. The ethinyl estradiol may be administered to the patient, for example, in an amount of about 1.0 µg/day to about 6.0 µg/day, such as in an amount of about 1.0 µg/day, 1.1 µg/day, 1.2 µg/day, 1.3 µg/day, 1.4 µg/day, 1.5 µg/day, 1.6 µg/day, 1.7 µg/day, 1.8 µg/day, 1.9 µg/day, 2.0 µg/day, 2.1 µg/day, 2.2 µg/day, 2.3 µg/day, 2.4 µg/day, 2.5 µg/day, 2.6 µg/day, 2.7 µg/day, 2.8 µg/day, 2.9 µg/day, 3.0 µg/day, 3.1 µg/day, 3.2 µg/day, 3.3 µg/day, 3.4 µg/day, 3.5 µg/day, 3.6 µg/day, 3.7 µg/day, 3.8 µg/day, 3.9 µg/day, 4.0 µg/day, 4.1 µg/day, 4.2 µg/day, 4.2 µg/day, 4.3 µg/day, 4.4 µg/day, 4.5 µg/day, 4.6 µg/day, 4.7 µg/day, 4.8 µg/day, 4.9 µg/day, 5.0 µg/day, 5.1 µg/day, 5.2 µg/day, 5.3 µg/day, 5.4 µg/day, 5.5 µg/day, 5.6 µg/day, 5.7 µg/day, 5.8 µg/day, 5.9 µg/day, or 6.0 µg/day, for instance, by oral administration. In some embodiments, the ethinyl estradiol is administered to the patient in an amount of 5.0 µg/day, for instance, by oral administration. In some embodiments, the ethinyl estradiol is administered to the patient in an amount of 2.5 µg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, in an amount of from about 0.1 mg/day to about 2.0 mg/day, such as in an amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient in an amount of 0.625 mg/day, for instance, by oral administration. In some embodiments, the conjugated estrogen is administered to the patient in an amount of 0.45 mg/day, for instance, by oral administration. In some embodiments, the conjugated estrogen is administered to the patient in an amount of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, in an amount of from about 0.05 mg/day to about 5.0 mg/day, such as in an amount of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient in an amount of 1.0 mg/day, for instance, by oral administration. In some embodiments, the norethindrone is administered to the patient in an amount of 0.5 mg/day, for instance, by oral administration. In some embodiments, the norethindrone is administered to the patient in an amount of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, in an amount of from about 0.05 mg/day to about 5.0 mg/day, such as in an amount of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient in an amount of 1.0 mg/day, for instance, by oral administration. In some embodiments, the norethindrone acetate is administered to the patient in an amount of 0.5 mg/day, for instance, by oral administration. In some embodiments, the norethindrone acetate is administered to the patient in an amount of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, in an amount of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient in an amount of 200 mg/day, for instance, by oral administration. In some embodiments, the progesterone is administered to the patient in an amount of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, in an amount of from about 0.01 mg/day to about 2.0 mg/day, such as in an amount of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient in an amount of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, in an amount of from about 0.5 mg/day to about 10.0 mg/day, such as in an amount of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient in an amount of 5.0 mg/day, for instance, by oral administration. In some embodiments, the medroxyprogesterone is administered to the patient in an amount of 2.5 mg/day, for instance, by oral administration. In some embodiments, the medroxyprogesterone is administered to the patient in an amount of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, in an amount of from about 0.1 mg/day to about 1.0 mg/day, such as in an amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient in an amount of 0.5 mg/day, for instance, by oral administration. In some embodiments, the drospirenone is administered to the patient in an amount of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the add-back therapy includes from about 0.75 mg to about 1.25 mg of β17-estradiol, e.g., administered orally, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of $317-estradiol, e.g., administered orally, and, in the same pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of $317-estradiol, e.g., administered orally, and, in a separate pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the GnRH antagonist is administered to the patient in a fixed-dose composition that contains the GnRH antagonist (e.g., in an amount of about 100 mg or about 200 mg of the compound of any one of formulas (I)-(VI)), from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the GnRH antagonist is administered to the patient in a fixed-dose composition that contains the GnRH antagonist (e.g., in an amount of about 100 mg or about 200 mg of the compound of any one of formulas (I)-(VI)), about 1.0 mg of β17-estradiol (e.g., 1.0 mg of β17-estradiol), and about 0.5 mg of norethindrone or a compound that is metabolized in vivo to produce norethindrone, such as an ester of norethindrone that is de-esterified in vivo to produce norethindrone, for instance, norethindrone acetate (e.g., 0.5 mg of norethindrone or a compound that is metabolized in vivo to produce norethindrone, such as an ester of norethindrone that is de-esterified in vivo to produce norethindrone, for instance, norethindrone acetate). In some embodiments, the GnRH antagonist is administered to the patient in a fixed-dose composition that contains the GnRH antagonist (e.g., in an amount of about 100 mg or about 200 mg of the compound of any one of formulas (I)-(VI)), 1.0 mg of β17-estradiol, and 0.5 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the above fixed-dose composition is administered to the patient once daily.

In some embodiments, the add-back therapy includes from about 0.25 mg to about 0.75 mg of β17-estradiol, e.g., administered orally, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of (17-estradiol, e.g., administered orally, and 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in the same pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in a separate pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the GnRH antagonist is administered to the patient in a fixed-dose composition that contains the GnRH antagonist (e.g., in an amount of about 100 mg or about 200 mg of the compound of any one of formulas (I)-(VI)), from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the GnRH antagonist is administered to the patient in a fixed-dose composition that contains the GnRH antagonist (e.g., in an amount of about 100 mg or about 200 mg of the compound of any one of formulas (I)-(VI)), about 0.5 mg of (17-estradiol (e.g., 0.5 mg of β17-estradiol), and about 0.1 mg of norethindrone or a compound that is metabolized in vivo to produce norethindrone, such as an ester of norethindrone that is de-esterified in vivo to produce norethindrone, for instance, norethindrone acetate (e.g., 0.1 mg of norethindrone or a compound that is metabolized in vivo to produce norethindrone, such as an ester of norethindrone that is de-esterified in vivo to produce norethindrone, for instance, norethindrone acetate). In some embodiments, the GnRH antagonist is administered to the patient in a fixed-dose composition that contains the GnRH antagonist (e.g., in an amount of about 100 mg or about 200 mg of the compound of any one of formulas (I)-(VI)), 0.5 mg of (17-estradiol, and 0.1 mg of norethindrone acetate.

In some embodiments of any of the foregoing aspects of the disclosure, the patient is a pre-menopausal female of from about 18 to about 48 years of age, such as a patient of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 years of age.

In some embodiments, the patient exhibits a serum concentration of FSH of about 20 IU/L or less prior to administration of the GnRH antagonist to the patient, such as a serum concentration of FSH of from about 5 IU/L to about 20 IU/L (e.g., a serum concentration of FSH of about 5 IU/L, 6 IU/L, 7 IU/L, 8 IU/L, 9 IU/L, 10 IU/L, 11 IU/L, 12 IU/L, 13 IU/L, 14 IU/L, 15 IU/L, 16 IU/L, 17 IU/L, 18 IU/L, 19 IU/L, or 20 IU/L.

In some embodiments, the patient exhibits a rectal (type II) and/or vaginal (type Ill) endometriosis node of at least 2 cm prior to administration of the GnRH antagonist to the patient, such as a rectal (type II) and/or vaginal (type Ill) endometriosis node of from about 2 cm to about 10 cm, or more (e.g., a rectal (type II) and/or vaginal (type Ill) endometriosis node of from about 2 cm to about 9 cm, from about 2 cm to about 8 cm, from about 2 cm to about 7 cm, from about 2 cm to about 6 cm, from about 2 cm to about 5 cm, or from about 2 cm to about 4 cm, or more) prior to administration of the GnRH antagonist to the patient. The length of the rectal (type II) and/or vaginal (type Ill) endometriosis node may be assessed, for example, by way of MRI and/or TVUS.

In some embodiments, the patient exhibits a reduction in serum concentration of FSH, LH, and/or E2 following administration of the GnRH antagonist to the patient. The reduction in serum concentration of LH, FSH, and/or E2 may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a reduction in the volume of one or more rectovaginal endometriosis nodes following administration of the GnRH antagonist to the patient. The reduction in the volume of the one or more rectovaginal endometriosis nodes may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in the volume of the one or more rectovaginal endometriosis nodes may be assessed, for example, by way of MRI and/or TVUS.

In some embodiments, the patient exhibits a reduction in bowel involvement of one or more type III endometriosis nodes following administration of the GnRH antagonist to the patient. The reduction in bowel involvement of one or more type III endometriosis nodes may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in bowel involvement of one or more type Ill endometriosis nodes may be assessed, for example, by way of MRI.

In some embodiments, the patient exhibits a reduction in pelvic pain following administration of the GnRH antagonist to the patient. The reduction in pelvic pain may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in pelvic pain may be assessed by way of an mB&B score, NRS score, or VRS score.

In some embodiments, the patient exhibits a reduction in dysmenorrhea following administration of the GnRH antagonist to the patient. The reduction in dysmenorrhea may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in dysmenorrhea may be assessed by way of an mB&B score, NRS score, or VRS score.

In some embodiments, the patient exhibits a reduction in dyspareunia following administration of the GnRH antagonist to the patient. The reduction in dyspareunia may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in dyspareunia may be assessed by way of an mB&B score, NRS score, or VRS score.

In some embodiments, the patient exhibits a reduction in dyschezia following administration of the GnRH antagonist to the patient. The reduction in dyschezia may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in dyschezia may be assessed by way of an mB&B score, NRS score, or VRS score.

In some embodiments, the patient exhibits a reduction in uterine bleeding following administration of the GnRH antagonist to the patient. The reduction in dyspareunia may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient). The reduction in uterine bleeding may be assessed by way of an alkaline hematin method.

In some embodiments, the patient exhibits amenorrhea following administration of the GnRH antagonist to the patient. The amenorrhea may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits an improvement in EHP-30 score following administration of the GnRH antagonist to the patient. The improvement in the EHP-30 score may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient exhibits a positive PGIC score following administration of the GnRH antagonist to the patient. The positive PGIC score may be effectuated within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient (e.g., within from about 12 weeks to about 24 weeks of the first administration of the GnRH antagonist to the patient, such as within about 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks of the first administration of the GnRH antagonist to the patient).

In some embodiments, the patient does not exhibit a reduction in bone mineral density (BMD) of greater than 5% following administration of the GnRH antagonist to the patient. In some embodiments, the patient does not exhibit a reduction in BMD of greater than 1% following administration of the GnRH antagonist to the patient. BMBD may be assessed, for example, by dual energy X-ray absorptiometry, such as in the spine and/or femur of the patient. In some embodiments, the BMD is assessed by comparing the concentration of BAP in a sample isolated from the patient following the administration to the concentration of BAP in a sample isolated from the patient prior to the administration. In some embodiments, the BMD is assessed by comparing the concentration of DPD in a sample isolated from the patient following the administration to the concentration of DPD in a sample isolated from the patient prior to the administration. In some embodiments, the BMD is assessed by comparing the concentration of CTX in a sample isolated from the patient following the administration to the concentration of CTX in a sample isolated from the patient prior to the administration. In some embodiments, the BMD is assessed by comparing the concentration of P1NP in a sample isolated from the patient following the administration to the concentration of P1 NP in a sample isolated from the patient prior to the administration.

In another aspect, the disclosure features a kit containing a GnRH antagonist, such as a GnRH antagonist of any of the above aspects or embodiments of the disclosure. The kit may further contain a package insert, such as a package insert instructing a user of the kit to administer the GnRH antagonist to a patient having adenomyosis in accordance with the method of any one of the foregoing aspects or embodiments of the disclosure.

In some embodiments, the GnRH antagonist contained within the kit is a compound represented by formula (I)

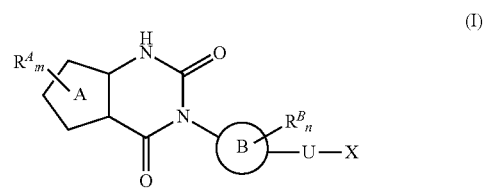

(I)

wherein ring A is a thiophene ring;

each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

ring B is an aryl group or a monocyclic heteroaryl group;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

U is a single bond;

X is a group represented by —S-L-Y, —O-L-Y, —CO-L-Y, or —SO$_2$-L-Y, wherein L is an optionally substituted lower alkylene group;

Y is a group represented by Z or —NW$^7$W$^1$, wherein W$^7$ and W$^8$ independently are a hydrogen atom, an optionally substituted lower alkyl group, or Z with the proviso that W$^7$ and W$^8$ are not simultaneously hydrogen atoms, or W$^7$ and W$^8$ may bind together with the neighboring nitrogen atom to form an optionally substituted cyclic amino group; and Z is an optionally fused and optionally substituted cycloalkyl group, an optionally fused and optionally substituted heterocycloalkyl group, an optionally fused and optionally substituted aryl group, or an optionally fused and optionally substituted heteroaryl group;

or a pharmaceutically acceptable salt thereof.

In some embodiments of formula (I), the ring A is a thiophene ring represented by formula (IIa)

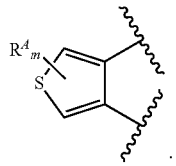
(IIa)

In some embodiments of formula (I) or (IIa), m is 1.

In some embodiments of formula (I) or (IIa), the ring A is an optionally substituted thiophene ring represented by formula (IIb)

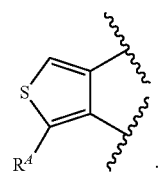
(IIb)

In some embodiments of formula (I), (IIa), or (IIb), each $R^A$ is independently a halogen atom, an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group.

In some embodiments of formula (I), (IIa), or (IIb), each $R^A$ is COOH or pharmaceutically acceptable salt thereof.

In some embodiments of formula (I), (IIa), or (IIb), the ring B is an optionally substituted benzene ring, pyridine ring, or thiophene ring.

In some embodiments of formula (I), (IIa), or (IIb), the ring B is represented by a formula selected from the group consisting of:

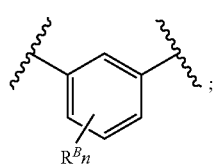
(IIIa)

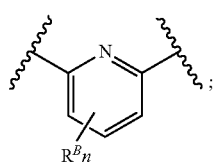
(IIIb)

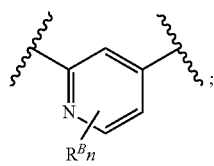
(IIIc)

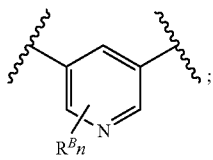
(IIId)

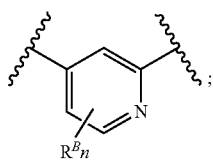
(IIIe)

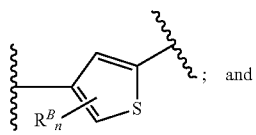
(IIIf); and

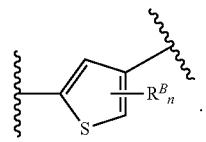
(IIIg)

In some embodiments of formula (I), (IIa), (IIb), or any one of (IIIa)-(IIIg), n is 2.

In some embodiments of formula (I), (IIa), (IIb), or any one of (IIIa)-(IIIg), the ring B is represented by a formula selected from the group consisting of:

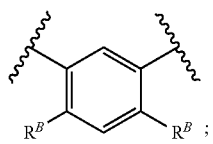
(IVa)

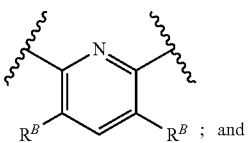
(IVb); and

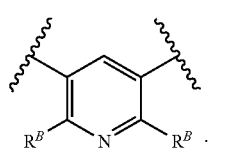
(IVc)

In some embodiments of formula (I), (IIa), (IIIb), any one of (IIIa)-(IIIg), or any one of (IVa)-(IVc), each $R^B$ is independently a halogen atom, an optionally substituted lower alkyl group, or $OW^4$, wherein each $W^4$ is independently a hydrogen atom or an optionally substituted lower alkyl group.

In some embodiments of formula (I), (IIa), (IIb), any one of (IIIa)-(IIIg), or any one of (IVa)-(IVc), each $R^B$ is independently a fluorine atom, chlorine atom, bromine atom, methyl group, or methoxy group.

In some embodiments of formula (I), (IIa), (IIb), any one of (IIIa)-(IIIg), or any one of (IVa)-(Vc), U is a single bond.

In some embodiments of formula (I), (IIa), (IIb), any one of (IIIa)-(IIIg), or any one of (IVa)-(IVc), X is a group represented by —O-L-Y.

In some embodiments of formula (I), (IIa), (IIb), any one of (IIIa)-(IIIg), or any one of (IVa)-(IVc), L is a methylene group.

In some embodiments of formula (I), (IIa), (IIb), any one of (IIIa)-(IIIg), or any one of (IVa)-(IVc), Y is an optionally substituted benzene ring represented by formula (V)

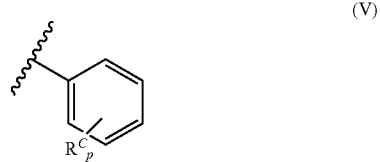

wherein each $R^c$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments of formula (I), (IIa), (IIb), any one of (IIIa)-(IIIg), any one of (IVa)-(IVc), or (V), Y is a substituted benzene ring represented by formula (Va)

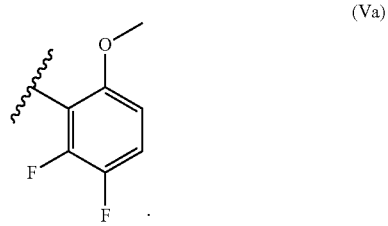 [SMILES: *c1c(OC)ccc(F)c1F]

In some embodiments, the compound is represented by formula (Ia)

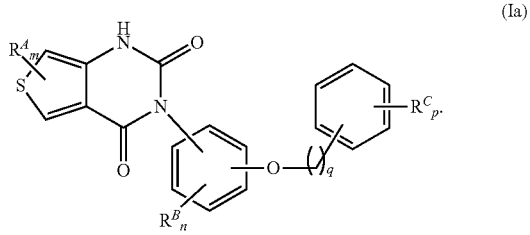

wherein each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer from 0 to 3;

each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer from 0 to 2;

q is an integer from 0 to 3;

each $R^c$ is independently a halogen atom, an optionally substituted lower alkyl group, or $OW^9$, wherein each $W^9$ is independently a hydrogen atom or an optionally substituted lower alkyl group; and p is an integer from 0 to 3;

or a pharmaceutically acceptable salt thereof.

In some embodiments, the compound is represented by formula (Ib)

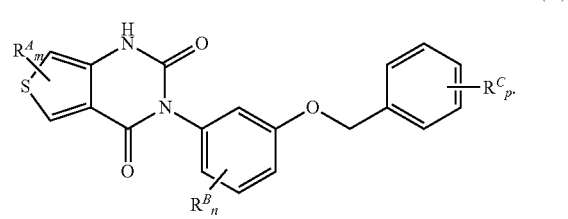

In some embodiments, the compound is represented by formula (Ic)

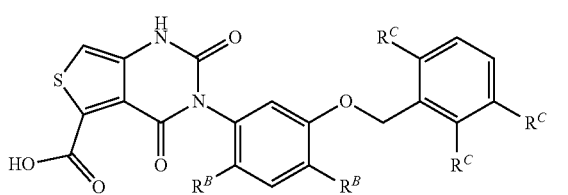

or a pharmaceutically acceptable salt thereof.

In some embodiments, the compound is 3-[2-fluoro-5-(2, 3-difluoro-6-methoxybenzyloxy)4-methoxyphenyl]-2,4-dioxo-1,2,3,4-tetrahydrothieno [3,4d]pyrimidine-5-carboxylic acid, represented by formula (VI)

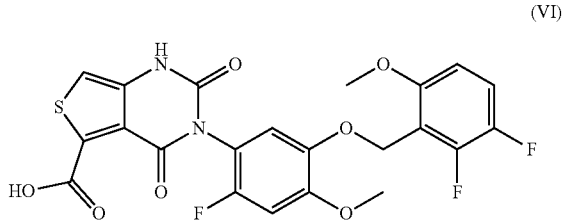 [SMILES: COc1cc(F)c(-n2c(=O)[nH]c3csc(C(=O)O)c3c2=O)cc1OCc1c(OC)ccc(F)c1F]

or a pharmaceutically acceptable salt thereof. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of an electrostatically neutral carboxylic acid. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylic acid is administered to the patient in the form of a pharmaceutically acceptable salt. In some embodiments, the compound 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid is administered to the patient in the form of the choline salt, choline 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylate.

In some embodiments, the compound is the choline salt of the compound represented by formula (VI), choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate is in a crystalline state.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits characteristic X-ray powder diffraction (XRPD) peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm.

In some embodiments, the choline 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate exhibits $^{19}F$ solid-state NMR peaks centered at about −151.8 ppm, −145.2 ppm, and −131.6 ppm.

In some embodiments, the GnRH antagonist contained within the kit is a compound represented by formula (VII)

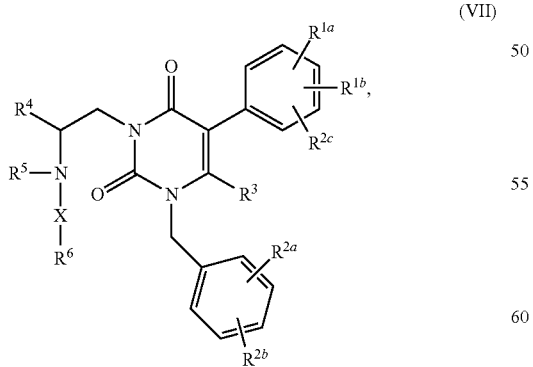

(VII)

wherein $R_{1a}$, $R_{1b}$ and $R_{1c}$ are the same or different and are each independently hydrogen, halogen, $C_{1-4}$ alkyl, hydroxy or alkoxy, or $R_{1a}$ and $R_{1b}$ taken together form —OCH$_2$O— or —OCH$_2$CH$_2$—;

$R_{2a}$ and $R_{2b}$ are the same or different and are each independently hydrogen, halogen, trifluoromethyl, cyano or —SO$_2$CH$_3$;
$R_3$ is hydrogen or methyl;
$R_4$ is phenyl or $C_{3-7}$alkyl;
$R_5$ is hydrogen or $C_{1-4}$alkyl;
$R_6$ is —COOH or an acid isostere; and
X is $C_{1-6}$alkanediyl optionally substituted with from 1 to 3 $C_{1-6}$alkyl groups;
or a pharmaceutically acceptable salt thereof.

In some embodiments, the GnRH antagonist is a compound represented by formula (VIII)

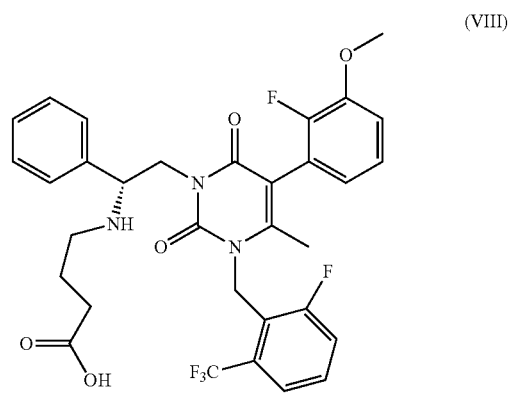 [SMILES: COc1cccc(-c2c(C)n(Cc3c(F)cccc3C(F)(F)F)c(=O)n(C[C@H](NCCCC(=O)O)c3ccccc3)c2=O)c1F]

(VIII)

or a pharmaceutically acceptable salt thereof. In some embodiments, the GnRH antagonist is the sodium salt of the compound represented by formula (VIII), which is represented by formula (IX), below.

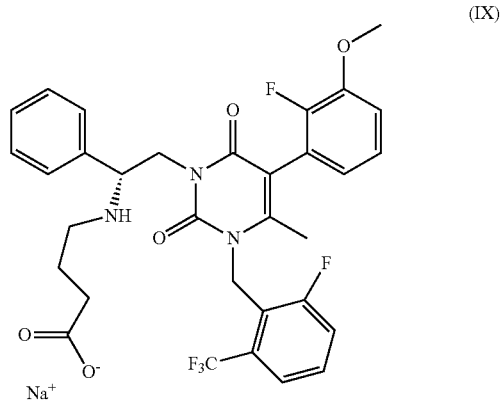 [SMILES: COc1cccc(-c2c(C)n(Cc3c(F)cccc3C(F)(F)F)c(=O)n(C[C@H](NCCCC(=O)[O-])c3ccccc3)c2=O)c1F ; [Na+]]

(IX)

In some embodiments, the GnRH antagonist contained within the kit is a compound represented by formula (X)

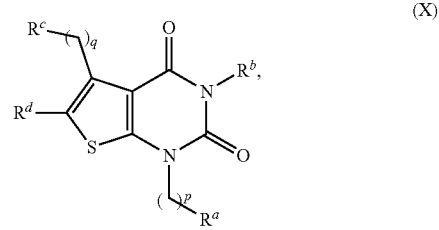

(X)

wherein R$^a$ is a hydrogen atom, an optionally substituted aryl group (such as an aryl group that may have 1 to 5 substituents selected from halogen, nitro, cyano, amino, a carboxyl group that may be esterified or amidated, an alkylenedioxy, alkyl, alkoxy, alkylthio, alkylsulfinyl, and alkylsulfonyl), an optionally substituted cycloalkyl group, or an optionally substituted heterocyclic group;

R$^b$ is an optionally substituted nitrogen-containing heterocyclic group;

R$^c$ is an optionally substituted amino group;

R$^d$ is an optionally substituted aryl group;

p is an integer from 0 to 3; and q is an integer from 0 to 3;

or a pharmaceutically acceptable salt thereof.

In some embodiments, the GnRH antagonist is a compound represented by formula (XI)

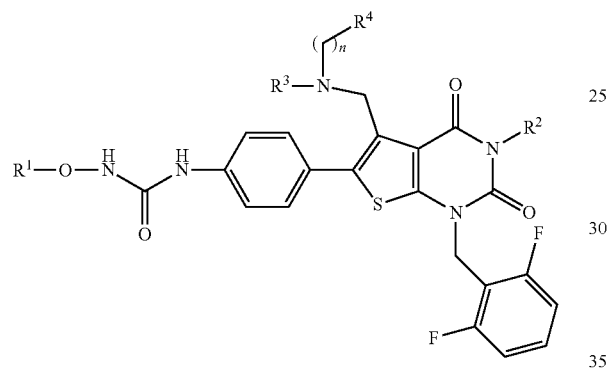

(XI)

wherein R$^1$ is C$_{1-4}$alkyl;

R$^2$ is (1) a C$_{1-6}$alkyl which may have a substituent selected from the group consisting of (1') a hydroxy group, (2') a C$_{1-4}$alkoxy, (3') a C$_{1-4}$alkoxy-carbonyl, (4') a di-C$_{1-4}$alkyl-carbamoyl, (5') a 5- to 7-membered nitrogen-containing heterocyclic group, (6') a C$_{1-4}$alkyl-carbonyl and (7') a halogen, (2) a C$_{3-6}$ cycloalkyl which may have (1') a hydroxy group or (2') a mono-C$_{1-4}$alkyl-carbonylamino, (3) a 5- to 7-membered nitrogen-containing heterocyclic group which may have a substituent selected from the group consisting of (1') a halogen, (2') a hydroxy group, (3') a C$_{1-4}$alkyl and (4') a C$_{1-4}$alkoxy, (4) a phenyl which may have a substituent selected from the group consisting of (1') a halogen, (2') a C$_{1-4}$alkoxy-C$_{1-4}$alkyl, (3') a mono-C$_{1-4}$alkyl-carbamoyl-C$_{1-4}$alkyl, (4') a C$_{1-4}$alkoxy and (5') a mono-C$_{1-4}$alkylcarbamoyl-C$_{1-4}$alkoxy, or (5) a C$_{1-4}$alkoxy;

R$^3$ is C$_{1-4}$alkyl;

R$^4$ is (1) hydrogen, (2) C$_{1-4}$alkoxy, (3) C$_{6-10}$aryl, (4) N—C$_{1-4}$alkyl-N—C$_{1-4}$alkylsulfonylamino, (5) hydroxyl, or (6) a 5- to 7-membered nitrogen-containing heterocyclic group which may have a substituent selected from the group consisting of (1') oxo, (2') a C$_{1-4}$alkyl, (3') a hydroxy-C$_{1-4}$alkyl, (4') a C$_{1-4}$alkoxy-carbonyl, (5') a mono-C$_{1-4}$alkyl-carbamoyl and (6') a C$_{1-4}$alkylsulfonyl; and n is an integer from 1 to 4;

optionally provided that when R$^2$ is a phenyl which may have a substituent, R$^4$ is a 5- to 7-membered nitrogen-containing heterocyclic group which may have a substituent selected from the group consisting of (1) oxo, (2) hydroxy-C$_{1-4}$alkyl, (3) C$_{1-4}$alkoxy-carbonyl, (4) mono-C$_{1-4}$alkyl-carbamoyl and (5) C$_{1-4}$alkylsulfonyl;

or a pharmaceutically acceptable salt thereof. In some embodiments, the GnRH antagonist is a compound represented by formula (XII), below.

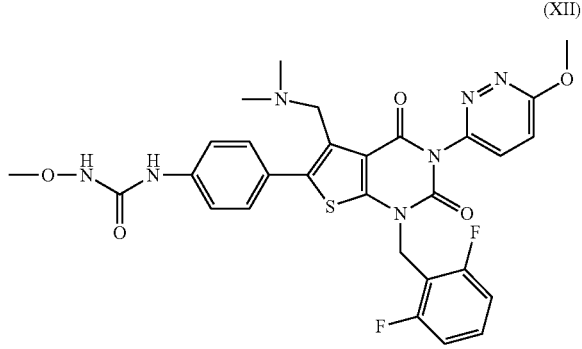

(XII)

In some embodiments, the GnRH antagonist contained within the kit is a compound represented by formula (XIII)

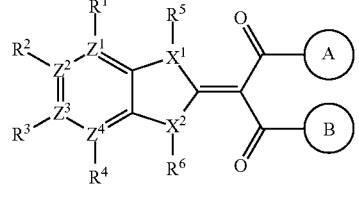

(XIII)

wherein R$^1$, R$^2$, R$^3$ and R$^4$ are the same or different, and are each independently selected from hydrogen, nitro, cyano, halogen, an optionally substituted hydrocarbon group, an optionally substituted heterocyclic group, hydroxy, alkoxy, carboxy, optionally substituted acyl-O—, optionally substituted acyl, a substituent —S(O)$_{n_{101}}$- (wherein $n_{101}$ is an integer of 0 to 2), H—S(O)$_{n_{101}}$-, optionally substituted carbamoyl, optionally substituted sulfamoyl, optionally substituted amino, and two adjacent groups selected from the group of R$^1$, R$^2$, R$^3$ and R$^4$ may combine to form an aryl or a carbocyclic (e.g., cycloalkenyl) group;

R$^5$ and R$^6$ are the same or different and are each independently selected from hydrogen, halogen, optionally substituted hydrocarbon, and optionally substituted amino, X$^1$ and X$^2$ are the same or different and are each independently selected from N, S and O;

A and B are the same or different and are each independently selected from optionally substituted aryl and optionally substituted heterocyclyl, and Z$^1$, Z$^2$, Z$^3$ and Z$^4$ are each independently selected from C and N; optionally provided that 1) when X$^1$ and X$^2$ each is S or O, one or both of the corresponding R$^5$ and R$^6$ are absent; and/or 2) when one to four of Z$^1$, Z$^2$, Z$^3$ and/or Z$^4$ are N, the corresponding R$^1$, R$^2$, R$^3$ and/or R$^4$ are absent;

or a pharmaceutically acceptable salt thereof. In some embodiments, the GnRH antagonist is a compound represented by formula (XIV), below.

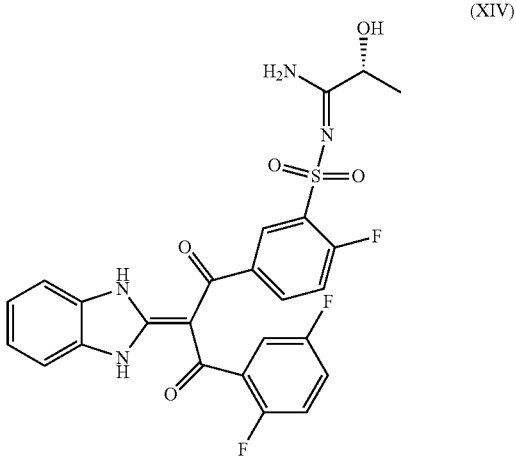 [SMILES: C[C@@H](O)/C(N)=N/S(=O)(=O)c1cc(C(=O)C(C(=O)c2cc(F)ccc2F)=C2Nc3ccccc3N2)ccc1F]
(XIV)

In some embodiments, the GnRH antagonist contained within the kit is SK12670 or BAY-784, or a variant or derivative thereof.

In a further aspect, the disclosure provides a GnRH antagonist, such as a GnRH antagonist described herein, for use in the treatment of any of the above-described conditions.

In another aspect, the disclosure provides uses of a GnRH antagonist, such as a GnRH antagonist described herein, in the manufacture of a medicament for the treatment of any of the above-described conditions.

BRIEF DESCRIPTION OF THE FIGURES

FIG. 1 is an exemplary mB&B questionnaire for assessing patient response to GnRH antagonist therapy.

FIGS. 2A-2D contain an exemplary EHP-30 questionnaire for assessing patient response to GnRH antagonist therapy.

FIG. 3 is an exemplary PGIC scale for assessing patient response to GnRH antagonist therapy.

DEFINITIONS

As used herein, the term "about" refers to a value that is within 10% above or below the value being described. For instance, a value of "about 5 mg" refers to a quantity that is from 4.5 mg to 5.5 mg.

As used herein, the term "abnormal uterine bleeding" refers to uterine blood loss that occurs either at an inappropriate time during a patient's menstrual cycle or in an amount that exceeds typical menstrual blood loss, such as "heavy menstrual blood loss" and "menorrhagia," which refer to menstrual blood loss of 80 ml or more (e.g., 80 ml, 90 ml, 100 ml, 110 ml, 120 ml, 130 ml, 140 ml, 150 ml, 160 ml, 170 ml, 180 ml, 190 ml, 200 ml, or more) per menstrual cycle (The Menorrhagia Research Group. Quantification of menstrual blood loss. The Obstetrician & Gynaecologist 6:88-92 (2004)).

As used herein, the term "add-back therapy" refers to the administration of estrogen during a treatment regimen, such as treatment with a GnRH antagonist (e.g., 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, as described herein), so as to counteract side effects that may otherwise be associated with excessive suppression of estradiol. Such side effects may include, for example, a reduction in bone mineral density (BMD). A patient's BMD may be assessed by dual energy X-ray absorptiometry, for instance, in the spine or femur of the patient. Add-back therapy may be administered to a patient according to the methods described herein so as to mitigate a reduction in BMD caused by the administration of a GnRH antagonist. Add-back therapy may include estrogen in the form of β17-estradiol, ethinyl estrogen, or a conjugated estrogen, such as a conjugated equine estrogen, and may further include one or more additional agents, such as a progestin (e.g., norethindrone or a compound that is metabolized in vivo to produce norethindrone, such as an ester of norethindrone that is de-esterified in vivo to produce norethindrone, for instance, norethindrone acetate, among other progestins such as progesterone, norgestimate, medroxyprogesterone, and drospirenone). Add-back therapy may be formulated for oral administration, such as in the form of a tablet, capsule, gel cap, powder, liquid solution, or liquid suspension. Add-back therapy may feature a co-formulation containing estrogen (e.g., in the form of β17-estradiol) and an additional agent such as a progestin (e.g., norethindrone or a compound that is metabolized in vivo to produce norethindrone, such as an ester of norethindrone that is de-esterified in vivo to produce norethindrone, for instance, norethindrone acetate). For instance, add-back therapy may be administered to a patient in the form of a single tablet, capsule, gel cap, powder, liquid solution, or liquid suspension that contains both estrogen (e.g., in the form of β17-estradiol) and a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

As used herein, a compound, such as a GnRH antagonist, estrogen, or progestin, among others, that is "administered" to a patient, such as a patient having an estrogen-dependent disease described herein, may be administered in an electrostatically neutral and/or nonionized form (e.g., in the form of a neutral carboxylic acid, a neutral amine, and the like) and/or in the form of a pharmaceutically acceptable salt, particularly if the compound contains a substituent that readily ionizes at physiological pH. For example, a compound containing a carboxylic acid substituent may be administered to a patient (e.g., a patient suffering from an estrogen-dependent disease described herein) in the form of the neutral, uncharged carboxylic acid and/or in the form of a carboxylate salt containing a pharmaceutically acceptable cation. Similarly, a compound containing an amine substituent may be administered to the patient in the form of the neutral, uncharged amine and/or in the form of an ammonium salt containing a pharmaceutically acceptable anion.

For example, as used herein, a GnRH antagonist of the disclosure, such as an optionally substituted thieno[3,4d]pyrimidine compound containing a carboxylic acid substituent, may be "administered" to a patient in the form of the neutral, uncharged carboxylic acid and/or in the form of a pharmaceutically acceptable salt (e.g., a salt containing the corresponding carboxylate anion and a pharmaceutically acceptable cation). Accordingly, as used herein, a GnRH antagonist of the formula 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid may be "administered" to a patient in the form of the neutral, uncharged carboxylic acid and/or in the form of a pharmaceutically acceptable salt (e.g., a salt containing the corresponding 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate anion and a pharmaceutically acceptable cation). For example, a GnRH antagonist of the formula 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid may be "administered" to a patient in the form of the neutral, uncharged carboxylic acid and/or in the form of a choline salt (i.e., a salt containing the corresponding 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate anion and a choline cation).

For example, as used herein, a GnRH antagonist of the disclosure, such as an optionally substituted 3-aminoalkyl pyrimidine-2,4(1H,3H)-dione compound containing a carboxylic acid substituent, may be "administered" to a patient in the form of the neutral, uncharged carboxylic acid and/or in the form of a pharmaceutically acceptable salt (e.g., a salt containing the corresponding carboxylate anion and a pharmaceutically acceptable cation). Accordingly, as used herein, a GnRH antagonist of the formula 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoic acid may be "administered" to a patient in the form of the neutral, uncharged carboxylic acid and/or in the form of a pharmaceutically acceptable salt (e.g., a salt containing the corresponding 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate anion and a pharmaceutically acceptable cation). For example, a GnRH antagonist of the formula 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoic acid may be "administered" to a patient in the form of the neutral, uncharged carboxylic acid and/or in the form of a sodium salt (i.e., a salt containing the corresponding 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate anion and a sodium cation).

For example, as used herein, a GnRH antagonist of the disclosure, such as an optionally substituted thieno[2,3d] pyrimidine compound containing an amine substituent, may be "administered" to a patient in the form of the neutral, uncharged amine and/or in the form of a pharmaceutically acceptable salt (e.g., a salt containing the corresponding ammonium cation and a pharmaceutically acceptable anion). Accordingly, as used herein, a GnRH antagonist of the formula N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea may be "administered" to a patient in the form of the neutral, uncharged amine and/or in the form of a pharmaceutically acceptable salt (e.g., a salt containing the corresponding, protonated N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea cation and a pharmaceutically acceptable anion). For example, a GnRH antagonist of the formula N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea may be "administered" to a patient in the form of the neutral, uncharged amine and/or in the form of a chloride salt (i.e., a salt containing the corresponding, protonated N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea cation and a chloride anion).

As used herein, a compound, such as a GnRH antagonist, estrogen, or progestin, among others, that is "administered" to a patient (e.g., a patient having an estrogen-dependent disease described herein) in a recited amount (e.g., per dose, per day, per week, per month, etc.) may be administered to the patient in the recited amount of an electrostatically neutral and/or nonionized form of the compound or in an equivalent amount of a pharmaceutically acceptable salt of the compound. As used herein, an amount of a pharmaceutically acceptable salt of a compound that is "equivalent" to a recited amount of the compound is an amount of the pharmaceutically acceptable salt that contains the same molar quantity of the compound as that contained by the recited amount of the compound. One can readily calculate the amount of a pharmaceutically acceptable salt of a compound that is "equivalent" to a recited amount of the compound using standard stoichiometry calculations known in the art.

Accordingly, as used herein, a GnRH antagonist of the disclosure, such as an optionally substituted thieno[3,4d] pyrimidine compound containing a carboxylic acid substituent, that is "administered" to a patient in a recited amount (e.g., per dose, per day, per week, per month, etc.) may be administered to the patient in the recited amount of an electrostatically neutral and/or nonionized of the compound or in an equivalent amount of a pharmaceutically acceptable salt of the compound. For example, as an optionally substituted thieno[3,4d]pyrimidine compound containing a carboxylic acid substituent, such as 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid, that is "administered" to a patient in a recited amount may be administered to the patient in the recited amount of the neutral, uncharged form of the compound or in an equivalent amount of a pharmaceutically acceptable salt of the compound (e.g., a salt containing the corresponding 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate anion and a pharmaceutically acceptable cation, such as a choline cation). Accordingly, an optionally substituted thieno[3,4d]pyrimidine compound containing a carboxylic acid substituent, such as 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid, that is "administered" to a patient in a recited amount, such as a recited amount of from 25 mg to 400 mg (e.g., 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, or 400 mg), may be administered to the patient in the recited amount of the neutral, uncharged form of the compound or in an equivalent amount of a pharmaceutically acceptable salt of the compound (e.g., a salt containing the corresponding 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylate anion and a pharmaceutically acceptable cation, such as a choline cation).

Accordingly, as used herein, a GnRH antagonist of the disclosure, such as an optionally substituted 3-aminoalkyl pyrimidine-2,4(1H,3H)-dione compound containing a carboxylic acid substituent, that is "administered" to a patient in a recited amount (e.g., per dose, per day, per week, per month, etc.) may be administered to the patient in the recited amount of an electrostatically neutral and/or nonionized form of the compound or in an equivalent amount of a pharmaceutically acceptable salt of the compound. For example, as an optionally substituted 3-aminoalkyl pyrimidine-2,4(1H,3H)-dione compound containing a carboxylic acid substituent, such as 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoic acid, that is "administered" to a patient in a recited amount may be administered to the patient in the recited amount of the neutral, uncharged form of the compound or in an equivalent amount of a pharmaceutically acceptable salt of the compound (e.g., a salt containing the corresponding 4-({(1R)-2-[5-(2-fluoro-3-methoxyphenyl)-3-{[$^2$-fluoro-6-(trifluoromethyl)phenyl]methyl}-4-methyl-2,6-dioxo-3,6-dihydropyrimidin-1(2H)-yl]-1-phenylethyl}amino) butanoate anion and a pharmaceutically acceptable cation, such as a sodium cation). Accordingly, an optionally substituted 3-aminoalkyl pyrimidine-2,4(1H,3H)-dione compound containing a carboxylic acid substituent, such as 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoic acid, that is "administered" to a patient in a recited amount, such as a recited amount of from 50 mg to 650 mg (e.g., 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 491 mg, 492 mg, 493 mg, 494 mg, 495 mg, 496 mg, 497 mg, 498 mg, 499 mg, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 591 mg, 592 mg, 593 mg, 594 mg, 595 mg, 596 mg, 597 mg, 598 mg, 599 mg, 600 mg, 601 mg, 602 mg, 603 mg, 604 mg, 605 mg, 606 mg, 607 mg, 608 mg, 609 mg, 610 mg, 611 mg, 612 mg, 613 mg, 614 mg, 615 mg, 616 mg, 617 mg, 618 mg, 619 mg, 620 mg, 621 mg, 622 mg, 623 mg, 624 mg, 625 mg, 626 mg, 627 mg, 628 mg, 629 mg, 630 mg, 631 mg, 632 mg, 633 mg, 634 mg, 635 mg, 636 mg, 637 mg, 638 mg, 639 mg, 640 mg, 641 mg, 642 mg, 643 mg, 644 mg, 645 mg, 646 mg, 647 mg, 648 mg, 649 mg, or 650 mg), may be administered to the patient in the recited amount of the neutral, uncharged form of the compound or in an equivalent amount of a pharmaceutically acceptable salt of the compound (e.g., a salt containing the corresponding 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate anion and a pharmaceutically acceptable cation, such as a sodium cation).

Accordingly, as used herein, a GnRH antagonist of the disclosure, such as an optionally substituted thieno[2,3d]pyrimidine compound containing an amine substituent, that is "administered" to a patient in a recited amount (e.g., per dose, per day, per week, per month, etc.) may be administered to the patient in the recited amount of an electrostatically neutral and/or nonionized form of the compound or in an equivalent amount of a pharmaceutically acceptable salt of the compound. For example, as an optionally substituted thieno[2,3d]pyrimidine compound containing an amine substituent, such as N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, that is "administered" to a patient in a recited amount may be administered to the patient in the recited amount of the neutral, uncharged form of the compound or in an equivalent amount of a pharmaceutically acceptable salt of the compound (e.g., a salt containing the corresponding, protonated N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea cation and a pharmaceutically acceptable anion, such as a chloride anion). Accordingly, an optionally substituted thieno[2,3d]pyrimidine compound containing an amine substituent, such as N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, that is "administered" to a patient in a recited amount, such as a recited amount of from 10 mg to 60 mg (e.g., 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, or 60 mg), may be administered to the patient in the recited amount of the neutral, uncharged form of the compound or in an equivalent amount of a pharmaceutically acceptable salt of the compound (e.g., a salt containing the corresponding, protonated N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea cation and a pharmaceutically acceptable anion, such as a chloride anion).

As used herein, the term "affinity" refers to the strength of a binding interaction between two molecules, such as a ligand and a receptor. The term "K", as used herein, is intended to refer to the inhibition constant of an antagonist for a particular molecule of interest, and can be expressed as a molar concentration (M). $K_i$ values for antagonist-target interactions can be determined, e.g., using methods established in the art. Methods that can be used to determine the $K_i$ of an antagonist for a molecular target include competitive binding experiments, e.g., as described in U.S. Pat. No. 9,040,693. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the terms "benefit" and "response" are used interchangeably in the context of a subject undergoing therapy for the treatment of an endometrial growth disorder described herein. These terms refers to any clinical improvement in the subject's condition. Exemplary benefits in the context of a subject administered a gonadotropin-releasing hormone (GnRH) antagonist for the treatment of adenomyosis include, without limitation, (i) a reduction in serum concentration of FSH, LH, and/or E2 following administration of the GnRH antagonist to the patient, (ii) a reduction in uterine volume following administration of the GnRH antagonist to the patient, (iii) a reduction in the thickness of the anterior and/or posterior region of the uterine myometrium following administration of the GnRH antagonist to the patient, (iv) a reduction in pelvic pain following administration of the GnRH antagonist to the patient; (v) a reduction in dysmenorrhea following administration of the GnRH antagonist to the patient; (vi) a reduction in dyspareunia following administration of the GnRH antagonist to the patient; (vii) a reduction in dyschezia following administration of the GnRH antagonist to the patient; (viii) a reduction in uterine tenderness following administration of the GnRH antagonist to the patient; (ix) a reduction in uterine bleeding following administration of the GnRH antagonist to the patient; (x) achievement of amenorrhea following administration of the GnRH antagonist to the patient; (xi) a reduction in the diameter of a junctional zone of adenomyosis following administration of the GnRH antagonist to the patient; and (xii) an improvement in the patient's overall well-being as determined by an improvement in the patients Endometriosis Health Profile questionnaire (EHP-30) score following administration of the GnRH antagonist to the patient and/or by way of a positive Patient Global Impression of Change (PGIC) score following administration of the GnRH antagonist to the patient.

Similarly, exemplary benefits in the context of a subject administered a GnRH antagonist for the treatment of rectovaginal endometriosis include, without limitation, (i) a reduction in serum concentration of FSH, LH, and/or E2 following administration of the GnRH antagonist to the patient, (ii) a reduction in the volume of one or more rectovaginal endometriosis nodes following administration of the GnRH antagonist to the patient, (iii) a reduction in bowel involvement of one or more type III endometriosis nodes following administration of the GnRH antagonist to the patient, (iv) a reduction in pelvic pain following administration of the GnRH antagonist to the patient; (v) a reduction in dysmenorrhea following administration of the GnRH antagonist to the patient; (vi) a reduction in dyspareunia following administration of the GnRH antagonist to the patient; (vii) a reduction in dyschezia following administration of the GnRH antagonist to the patient; (viii) a reduction in uterine bleeding following administration of the GnRH antagonist to the patient; (ix) achievement of amenorrhea following administration of the GnRH antagonist to the patient; and (x) an improvement in the patient's overall well-being as determined by an improvement in the patients EHP-30 score following administration of the GnRH antagonist to the patient and/or by way of a positive PGIC score following administration of the GnRH antagonist to the patient.

As used herein, the term "Biberoglu and Behrman scale" or "B&B scale" or a modification thereof, such as a "modified Biberoglu and Behrman scale" refers to a multi-point scale that can be used to indicate the severity of one or more symptoms experienced by patient suffering from endometriosis. A B&B score can be assessed by verbally prompting the patient to indicate the degree of function or quality of life being experienced. A B&B score can be used, e.g., to assess the severity of such symptoms as dysmenorrhea, dyspareunia, chronic pelvic pain, pelvic tenderness, and induration, among others. Methods of determining a B&B score are described in detail, e.g., in Biberoglu and Behrman, Am. J. Obstet. Gynecol. 139:645 (1981).

As used herein, the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein, the term "dose" refers to the quantity of a therapeutic agent, such as a GnRH antagonist described herein, that is administered to a subject for the treatment of a disorder or condition, such as to treat or ameliorate one or more symptoms of adenomyosis and/or rectovaginal endometriosis. A therapeutic agent as described herein may be administered in a single dose or in multiple doses. In each case, the therapeutic agent may be administered using one or more "unit dosage forms" of the therapeutic agent, a term that refers to a one or more discrete compositions containing a therapeutic agent that collectively constitute a single dose of the agent. For instance, a single dose of 200 mg of a therapeutic agent may be administered using, e.g., two 100 mg unit dosage forms of the therapeutic agent. The unit dosage forms may be, for example, solid unit dosage forms, such as tablets or capsules, among others.

As used herein, the term "dual energy X-ray absorptiometry" (DEXA) refers to a spectroscopic method of measuring bone mineral density in a patient (e.g., a human patient) in which X-ray radiation of two distinct frequencies are transmitted towards a target bone of the patient. The absorption of the transmitted radiation can subsequently be correlated with a measure of the bone mineral density within the target bone. Methods of determining bone mineral density using DEXA are described in detail, e.g., in Mazess et al., American Journal of Clinical Nutrition 51:1106-1112 (1990).

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "Endometriosis Health Profile-30" or "EHP-30" refers to a questionnaire that can be used to evaluate quality of life in patient suffering from endometriosis. A score obtained from this questionnaire (i.e., an "EHP-30 score") may provide an indication of the patient's degree of pain, feeling of control and powerlessness, emotional well-being, social support, and/or self-image. Exemplary methods that can be used to perform an EHP-30 questionnaire and procedures for interpreting the scores obtained therefrom are known in the art are described, e.g., in Renouvel et al., Journal de Gynécologie Obstétrique et Biologie de la Reproduction 38:404-410 (2009), the disclosure of which is incorporated herein by reference as it pertains to methods for conducting and evaluating an EHP-30 questionnaire.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "gonadotropin-releasing hormone antagonist" or "GnRH antagonist" refers to a compound that specifically binds the GnRH receptor and is capable of inhibiting receptor signalling, e.g., such that release of one or more gonadotropins (such as follicle-stimulating hormone and luteinizing hormone) is inhibited. GnRH antagonists for use with the compositions and methods described herein include thieno[3,4d]pyrimidine derivatives and variants, such as those described in U.S. Pat. No. 9,040,693, the disclosure of which is incorporated herein by reference in its entirety. Exemplary GnRH antagonists include 3-[2-fluoro-5-(2,3-difluoro-6-methoxybenzyloxy)4-methoxyphenyl]-2,4-dioxo-1,2,3,4-tetrahydrothieno [3,4d] pyrimidine-5-carboxylic acid or a pharmaceutically acceptable salt thereof, such as the choline salt thereof, e.g., as described in U.S. Pat. No. 9,169,266, the disclosure of which is incorporated herein by reference in its entirety. Additional examples of GnRH antagonists that may be used in conjunction with the compositions and methods described herein include optionally substituted 3-aminoalkyl pyrimidine-2,4(1H,3H)-dione derivatives, such as sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino) butanoate, also referred to as elagolix, or the carboxylic acid conjugate thereof, and related compounds described in U.S. Pat. No. 7,056,927, the disclosure of which is incorporated herein by reference in its entirety. Further examples of GnRH antagonists that may be used in conjunction with the compositions and methods described herein include optionally substituted thieno[2,3d]pyrimidine derivatives, such as N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, also referred to as relugolix, or a pharmaceutically acceptable salt thereof, and related compounds described in U.S. Pat. No. 7,300,935, the disclosure of which is incorporated herein by reference in its entirety. Additional examples of GnRH antagonists that may be used in conjunction with the compositions and methods described herein include optionally substituted propane-1,3-dione derivatives, such as (2R)—N-{5-[3-(2,5-difluorophenyl)-2-(1,3-dihydro-2H-benzimidazol-2-ylidene)-3-oxopropanoyl]-2-fluorobenzene-1-sulfonyl}-2-hydroxypropanimidamide, also referred to as opigolix or ASP-1707, and related compounds described in U.S. Pat. No. 6,960,591, the disclosure of which is incorporated herein by reference in its entirety.

As used herein, the term "$IC_{50}$" refers to the concentration of a substance (antagonist) that reduces the efficacy of a reference agonist or the constitutive activity of a biological target by 50%, e.g., as measured in a competitive ligand binding assay. Exemplary competitive ligand binding assays include competitive radioligand binding assays, competitive enzyme-linked immunosorbant assays (ELISA), and fluorescence anisotropy-based assays, among others known in the art.

As used herein, the term "menstrual cycle" refers to a recurring cycle of physiological changes in females, such as human females, that is associated with reproductive fertility. While the cycle length may vary from woman to woman, 28 days is generally taken as representative of the average ovulatory cycle in human females.

As used herein, the term "Numerical Rating Score" (NRS) refers to a score within an 11-point numerical scale of 0-10 that indicates the degree of pain experienced by a patient. For instance, a score of 0 may indicate the patient is experiencing no pain, while scores from 1-3 may indicate that the patient is experiencing mild pain. A score of from 4-6 may indicate that the patient is experiencing moderate pain, and a score of from 7-10 may indicate that the patient is experiencing severe pain. Typically, to determine a NRS score, the patient is asked to indicate the level of pain currently being experienced, as well as the pain experienced at its most intense and least intense occurrences. Methods for determining a NRS are described in detail, e.g., in McCaffery et al., Pain: Clinical Manual for Nursing Practice. Baltimore (1993), the disclosure of which is incorporated herein by reference as it pertains to methods for obtaining and evaluating an NRS.

As used herein, the term "pharmaceutical composition" means a mixture containing a therapeutic compound to be administered to a patient, such as a mammal, e.g., a human, in order to prevent, treat or control a particular disease or condition affecting the mammal, such as preterm labor or dysmenorrhea.

As used herein, the term "pharmaceutically acceptable" refers to those compounds, materials, compositions and/or dosage forms, which are suitable for contact with the tissues of a patient, such as a mammal (e.g., a human) without excessive toxicity, irritation, allergic response and other problem complications commensurate with a reasonable benefit/risk ratio.

As used herein in the context of administration of a therapeutic agent, the term "periodically" refers to administration of the agent two or more times over the course of a treatment period (e.g., two or more times daily, weekly, monthly, or yearly).

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a patient.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 μM and 100 nM). A ligand that does not exhibit specific binding to a protein or a domain thereof may exhibit a $K_D$ of greater than 100 nM (e.g., greater than 200 nM, 300 nM, 400 nM, 500 nM, 600 nm, 700 nM, 800 nM, 900 nM, 1 μM, 100 μM, 500 μM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are used interchangeably and refer to an organism, such as a mammal (e.g., a human) that receives treatment for adenomyosis and/or rectovaginal endometriosis using the compositions and methods described herein and/or that is diagnosed as having adenomyosis and/or rectovaginal endometriosis in accordance with the methods described herein. Examples of patients include pre-menopausal female human patients receiving treatment for adenomyosis and/or rectovaginal endometriosis. For instance, adenomyosis patients in need of treatment using a GnRH antagonist according to the methods described herein include, e.g., adenomyosis patients diagnosed as having a junctional-zone width of about 12 mm or more prior to administration of the GnRH antagonist to the patient (e.g., a junctional zone width of from about 12 mm to about 20 mm, from about 12 mm to about 19 mm, from about 12 mm to about 18 mm, from about 12 mm to about 17 mm, from about 12 mm to about 16 mm, from about 12 mm to about 15 mm, from about 12 mm to about 14 mm, or more, prior to administration of the GnRH antagonist to the patient). Examples of rectovaginal endometriosis patients in need of treatment using a GnRH antagonist according to the methods described herein include, e.g., rectovaginal endometriosis patients exhibiting a rectal (type II) and/or vaginal (type III) endometriosis node of at least 2 cm prior to administration of the GnRH antagonist to the patient, such as a rectal (type II) and/or vaginal (type Ill) endometriosis node of from about 2 cm to about 10 cm, or more (e.g., a rectal (type II) and/or vaginal (type Ill) endometriosis node of from about 2 cm to about 9 cm, from about 2 cm to about 8 cm, from about 2 cm to about 7 cm, from about 2 cm to about 6 cm, from about 2 cm to about 5 cm, or from about 2 cm to about 4 cm, or more) prior to administration of the GnRH antagonist to the patient.

As used herein, the terms "treat" or "treatment" refer to therapeutic treatment, in which the object is to prevent or slow down (lessen) an undesired physiological change or disorder, such as the progression of adenomyosis and/or rectovaginal endometriosis in a human patient. Beneficial or desired clinical results include, but are not limited to, alleviation of symptoms, such as a reduction in pelvic pain, a reduction in dysmenorrhea, a reduction in dyspareunia, a reduction in dyschezia, and a reduction in uterine bleeding, among other desired benefits described herein. As a non-limiting example, a patient, such as a human female patient, suffering from adenomyosis may be considered to be treated using a GnRH antagonist described herein if the patient exhibits: (i) a reduction in uterine volume following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (ii) a reduction in the thickness of the anterior and/or posterior region of the uterine myometrium following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (iii) a reduction in pelvic pain following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (iv) a reduction in dysmenorrhea following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (v) a reduction in dyspareunia following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (vi) a reduction in dyschezia following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (vii) a reduction in uterine tenderness following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (viii) a reduction in uterine bleeding following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (ix) achievement of amenorrhea following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (x) a reduction in the diameter of a junctional zone of adenomyosis following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); and/or (xi) an improvement in the patient's overall well-being as determined by an improvement in the patients EHP-30 score following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient) and/or the observation of a positive PGIC score following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient).

As an example of treatment of a patient having rectovaginal endometriosis, the patient may be considered to be treated using a GnRH antagonist described herein if the patient exhibits: (i) a reduction in the volume of one or more rectovaginal endometriosis nodes following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (ii) a reduction in bowel involvement of one or more type Ill endometriosis nodes following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (iii) a reduction in pelvic pain following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (iv) a reduction in dysmenorrhea following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (v) a reduction in dyspareunia following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (vi) a reduction in dyschezia following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (vii) a reduction in uterine tenderness following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (viii) a reduction in uterine bleeding following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); (ix) achievement of amenorrhea following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient); and/or (x) an improvement in the patient's overall well-being as determined by an improvement in the patients EHP-30 score following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient) and/or the observation of a positive PGIC score following administration of the GnRH antagonist to the patient (e.g., within from about one day to about 36 weeks of the first administration of the GnRH antagonist to the patient, such as within about 1 day, 2 days, 3 days, 4 days, 4 days, 6 days, 7 days, 2 weeks, 3 weeks, 4 weeks, 5 weeks, 6 weeks, 7 weeks, 8 weeks, 9 weeks, 10 weeks, 11 week, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, or 36 weeks, of the first administration of the GnRH antagonist to the patient).

As used herein, the term "treatment period" refers to a duration of time over which a patient may be periodically administered a therapeutic agent, such as a GnRH antagonist described herein.

Treatment periods as described herein may have a duration of several days, weeks, months, or years. For instance, a treatment period for administration of a thieno[3,4d] pyrimidine derivative, such as 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, may last for from about four weeks to about six months (e.g., from about 28 days to about 180 days, about 30 days to about 175 days, about 35 days to about 170 days, about 40 days to about 165 days, about 45 days to about 160 days, about 50 days to about 155 days, about 55 days to about 150 days, about 60 days to about 145 days, about 65 days to about 140 days, about 70 days to about 135 days, about 75 days, to about 130 days, about 80 days to about 125 days, about 85 days, to about 120 days, or about 90 days to about 115 days). In some embodiments, the GnRH antagonist is periodically administered to the patient over a treatment period of from about eight weeks to about sixteen weeks (e.g., from about 60 days to about 110 days, about 65 days to about 105 days, about 70 days to about 100 days, about 75 days to about 95 days, or about 80 days, to about 90 days). In some embodiments, the GnRH antagonist is periodically administered to the patient over a treatment period of about twelve weeks. In some embodiments, the GnRH antagonist is periodically administered to the patient over a treatment period of from about 20 weeks to about 30 weeks (e.g., from about 140 days to about 210 days, about 150 days to about 100 days, about 60 days to about 90 days, about 65 days to about 85 days, or about 68 days). In some embodiments, the GnRH antagonist is periodically administered to the patient over a treatment period of about 24 weeks.

As used herein, the term "Verbal Rating Score" (VRS) refers to a subjective multi-point scale used to indicate the level of pain being experienced by a patient undergoing therapy or that has previously undergone therapy for a disease or condition, such as endometriosis. The VRS may be a five-point scale and can be assessed by prompting the patient with one or more questions in order to determine the level of pain currently being experienced by the patient. Methods for assessing a VRS are described in detail, e.g., in Jensen et al., Journal of Pain and Symptom Management 41:1073-1093 (2011), the disclosure of which is incorporated herein by reference as it pertains to methods for obtaining and evaluating a VRS.

As used herein, the term "aryl" refers to an unsaturated aromatic carbocyclic group of from 6 to 14 carbon atoms having a single ring (e.g., optionally substituted phenyl) or multiple condensed rings (e.g., optionally substituted naphthyl). Exemplary aryl groups include phenyl, naphthyl, phenanthrenyl, and the like.

As used herein, the term "cycloalkyl" refers to a monocyclic cycloalkyl group having from 3 to 8 carbon atoms, such as cyclopropyl, cyclobutyl, cyclopentyl, cyclohexyl, cycloheptyl, cyclooctyl, and the like.

As used herein, the term "halogen atom" refers to a fluorine atom, a chlorine atom, a bromine atom, or an iodine atom.

As used herein, the term "heteroaryl" refers to a monocyclic heteroaromatic, or a bicyclic or a tricyclic fused-ring heteroaromatic group. Exemplary heteroaryl groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heterocycloalkyl" refers to a 3 to 8-membered heterocycloalkyl group having 1 or more heteroatoms, such as a nitrogen atom, an oxygen atom, a sulfur atom, and the like, and optionally having 1 or 2 oxo groups such as pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl, and the like.

As used herein, the terms "lower alkyl" and "$C_{1-6}$ alkyl" refer to an optionally branched alkyl moiety having from 1 to 6 carbon atoms, such as methyl, ethyl, propyl, isopropyl, butyl, isobutyl, sec-butyl, tert-butyl, pentyl, isopentyl, neopentyl, tert-pentyl, hexyl, and the like.

As used herein, the term "lower alkylene" refers to an optionally branched alkylene group having from 1 to 6 carbon atoms, such as methylene, ethylene, methylmethylene, trimethylene, dimethylmethylene, ethylmethylene, methylethylene, propylmethylene, isopropylmethylene, dimethylethylene, butylmethylene, ethylmethylmethylene, pentamethylene, diethylmethylene, dimethyltrimethylene, hexamethylene, diethylethylene and the like.

As used herein, the term "lower alkenyl" refers to an optionally branched alkenyl moiety having from 2 to 6 carbon atoms, such as vinyl, allyl, 1-propenyl, isopropenyl, 1-butenyl, 2-butenyl, 2-methylallyl, and the like.

As used herein, the term "lower alkynyl" refers to an optionally branched alkynyl moiety having from 2 to 6 carbon atoms, such as ethynyl, 2-propynyl, and the like.

As used herein, the term "optionally fused" refers to a cyclic chemical group that may be fused with a ring system, such as cycloalkyl, heterocycloalkyl, aryl, or heteroaryl. Exemplary ring systems that may be fused to an optionally fused chemical group include, e.g., indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, naphtyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl, and the like.

As used herein, the term "optionally substituted" refers to a chemical moiety that may have one or more (e.g., 1, 2, 3, 4, 5, 6, 7, 8, 9, 10, or more chemical substituents, such as lower alkyl, lower alkenyl, lower alkynyl, cycloalkyl, heterocyclolalkyl, aryl, alkylaryl, heteroaryl, alkylheteroaryl, amino, ammonium, acyl, acyloxy, acylamino, aminocarbonyl, alkoxycarbonyl, ureido, carbamate, sulfinyl, sulfonyl, alkoxy, sulfanyl, halogen, carboxy, trihalomethyl, cyano, hydroxy, mercapto, nitro, and the like. An optionally substituted chemical moiety may contain, e.g., neighboring substituents that have undergone ring closure, such as ring closure of vicinal functional substituents, thus forming, e.g., lactams, lactones, cyclic anhydrides, acetals, thioacetals, or aminals formed by ring closure, for instance, in order to generate protecting group.

As used herein, the term "sulfinyl" refers to the chemical moiety "—S(O)—R" in which R represents, e.g., hydrogen, aryl, heteroaryl, optionally substituted alkyl, optionally substituted alkenyl, or optionally substituted alkynyl.

As used herein, the term "sulfonyl" refers to the chemical moiety "—$SO_2$—R" in which R represents, e.g., hydrogen, aryl, heteroaryl, optionally substituted alkyl, optionally substituted alkenyl, or optionally substituted alkynyl.

DETAILED DESCRIPTION

The present disclosure features compositions and methods for treating adenomyosis and/or rectovaginal endometriosis in a patient, such as a pre-menopausal female human patient. For example, the patient may be presenting with or diagnosed as having adenomyosis, as assessed on the basis of the patient having a junctional-zone width of about 12 mm or more, such as a junctional zone width of from about 12 mm to about 20 mm, as assessed by magnetic resonance imaging (MRI) and/or transvaginal ultrasound (TVUS). In an exemplary case of a patient suffering from rectovaginal endometriosis, the patient may be diagnosed as having this disorder based on a finding that the patient exhibits a rectal (type II) and/or vaginal (type III) endometriosis node of at least 2 cm, such as a rectal (type II) and/or vaginal (type III) endometriosis node of from about 2 cm to about 10 cm, or more. Exemplary qualitative and quantitative scores that can be used to evaluate a patient and determine whether or not the patient is responding to treatment include, without limitation, the patient's Endometriosis Health Profile questionnaire (EHP-30) score, Patient Global Impression of Change (PGIC) score, modified Biberoglu & Behrman (mB&B) score, Numerical Rating Scale (NRS) score, and Verbal Rating Scale (VRS) score.

The compounds described herein as useful for the treatment of adenomyosis and rectovaginal endometriosis include gonadotropin-releasing hormone (GnRH) antagonists. GnRH antagonists that may be used in conjunction with the compositions and methods described herein include thieno[3,4d]pyrimidine derivatives, such as 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid or a pharmaceutically acceptable salt thereof. Particularly, the GnRH antagonist may be the choline salt thereof. Additional examples of GnRH antagonists that may be used in conjunction with the compositions and methods described herein include optionally substituted 3-aminoalkyl pyrimidine-2,4(1H,3H)-dione derivatives, such as sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate, also referred to as elagolix, or the carboxylic acid conjugate thereof, and related compounds described in U.S. Pat. No. 7,056,927, the disclosure of which is incorporated herein by reference in its entirety. Further examples of GnRH antagonists that may be used in conjunction with the compositions and methods described herein include optionally substituted thieno[2,3d]pyrimidine derivatives, such as N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, also referred to as relugolix, or a pharmaceutically acceptable salt thereof, and related compounds described in U.S. Pat. No. 7,300,935, the disclosure of which is incorporated herein by reference in its entirety. Additional examples of GnRH antagonists that may be used in conjunction with the compositions and methods described herein include optionally substituted propane-1,3-dione derivatives, such as (2R)—N-{5-[3-(2,5-difluorophenyl)-2-(1,3-dihydro-2H-benzimidazol-2-ylidene)-3-oxopropanoyl]-2-fluorobenzene-1-sulfonyl}-2-hydroxypropanimidamide, also referred to as opigolix or ASP-1707, and related compounds described in U.S. Pat. No. 6,960,591, the disclosure of which is incorporated herein by reference in its entirety.

The GnRH antagonists described herein can provide a variety of therapeutic benefits, including a suppression of endogenous levels of β-17 estradiol (E2), follicle-stimulating hormone (FSH), and/or luteinizing hormone (LH) in a patient exhibiting an elevated serum concentration of one or more of these hormones, as well as a reduction in myometrial invasion by endometrial tissue in patients suffering from adenomyosis and a reduction in endometrial lesion size in patients having rectovaginal endometriosis.

In addition to treating the underlying causes of adenomyosis and rectovaginal endometriosis, the GnRH antagonists described herein also provide the advantageous therapeutic property of being able to rapidly alleviate the symptoms of these disorders. Adenomyosis and rectovaginal endometriosis are particularly severe endometrial growth pathologies. Adenomyosis, for instance, is a disease in which endometrial glands and stroma invade the uterine myometrium. This penetration of endometrial tissue into the patient's myometrium can cause substantial pain, including global pelvic pain, dysmenorrhea, dyspareunia, and dyschezia. Unlike traditional endometriosis, adenomyosis patients may also exhibit significant uterine blood loss. Rectovaginal endometriosis is another particularly severe endometrial growth disorder in which endometrial tissue extends outside of the uterus and infiltrates rectal and/or vaginal tissue. Patients having rectovaginal endometriosis may experience, for example, endometriosis tissue that penetrates the cervix, as is the case in Type II rectovaginal endometriosis, or may have endometriosis tissue that infiltrates the wall of the rectum or sigmoid, which is diagnostic of Type III rectovaginal endometriosis. The invasion of endometrial tissue into the rectal and vaginal zones causes significant pain, including global pelvic pain, dysmenorrhea, dyspareunia, and dyschezia, and may further result in abnormal uterine bleeding. The GnRH antagonists described herein provide the beneficial feature of being able to suppress these symptoms and enhance the patient's overall quality of life.

The sections that follow provide a description of the GnRH antagonists that may be used in conjunction with the compositions and methods described herein, as well as a description of diseases that may be treated using these agents.

GnRH Antagonists
Thieno[3,4d]pyrimidines

GnRH antagonists for use with the compositions and methods described herein include thieno[3,4d]pyrimidine derivatives and variants, such as those described in U.S. Pat. No. 9,040,693, the disclosure of which is incorporated herein by reference in its entirety. Exemplary GnRH antagonists include those represented by formula (I)

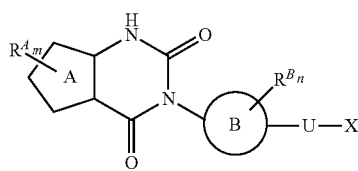

(I)

wherein ring A is a thiophene ring;
each $R^A$ is independently a halogen atom, a cyano group, a nitro group, an optionally substituted lower alkyl group, an optionally substituted lower alkenyl group, an optionally substituted lower alkynyl group, a hydroxyiminomethyl group, an optionally substituted sulfonyl group, an optionally substituted sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$, or $SO_2NW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group;
m is an integer from 0 to 3;
ring B is an aryl group or a monocyclic heteroaryl group;
each $R^B$ is independently a halogen atom, a cyano group, an optionally substituted lower alkyl group, $OW^4$, $COW^4$, $COOW^4$, or $CONW^5W^6$, wherein $W^4$ to $W^6$ independently are a hydrogen atom or an optionally substituted lower alkyl group, or $W^5$ and $W^6$ may bind together with the neighboring nitrogen atom to form an optionally substituted cyclic amino group;
n is an integer from 0 to 2;
U is a single bond;
X is a group represented by —S-L-Y, —O-L-Y, —CO-L-Y, or —SO$_2$-L-Y, wherein L is an optionally substituted lower alkylene group;
Y is a group represented by Z or —NW$^7$We, wherein $W^7$ and $W^8$ independently are a hydrogen atom, an optionally substituted lower alkyl group, or Z with the proviso that $W^7$ and $W^8$ are not simultaneously hydrogen atoms, or $W^7$ and $W^8$ may bind together with the neighboring nitrogen atom to form an optionally substituted cyclic amino group;
Z is an optionally fused and optionally substituted cycloalkyl group, an optionally fused and optionally substituted heterocycloalkyl group, an optionally fused and optionally substituted aryl group, or an optionally fused and optionally substituted heteroaryl group;
or a pharmaceutically acceptable salt thereof.

In some embodiments, the ring A is a thiophene ring represented by formula (IIa)

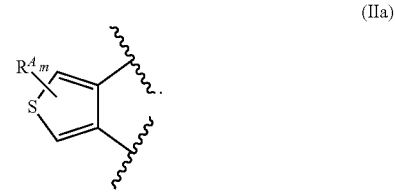

(IIa)

In some embodiments, m is 1 or 2. In some embodiments, m is 1. For instance, the ring A may be an optionally substituted thiophene ring represented by formula (IIb)

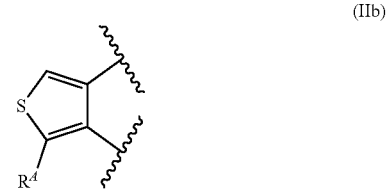

(IIb)

Each $R^A$ may independently be, for example, a halogen atom (e.g., fluorine, chlorine, bromine, or iodine), an optionally substituted lower alkyl group, $COOW^1$, or $CONW^2W^3$, wherein $W^1$ to $W^3$ independently are a hydrogen atom or an optionally substituted lower alkyl group, or $W^2$ and $W^3$ may bind together with the neighboring nitrogen atom to form an optionally substituted cyclic amino group. In some embodiments, each $R^A$ is COOH or pharmaceutically acceptable salt thereof.

In some embodiments, ring B is an optionally substituted benzene ring, pyridine ring, or thiophene ring. For instance, ring B may be represented by a formula selected from the group consisting of:

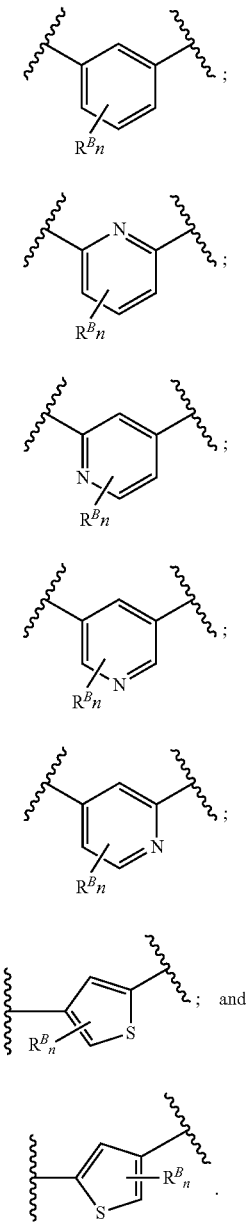

In some embodiments, n is 1 or 2. For instance, in some embodiments, n is 1. Ring B may be, for example, represented by a formula selected from the group consisting of:

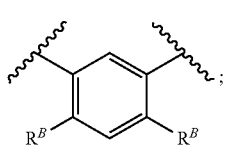

(IVa)

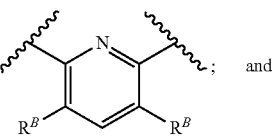

(IVb)

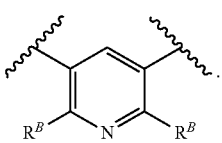

(IVc)

In some embodiments, each $R^B$ is independently a halogen atom, an optionally substituted lower alkyl group, or $OW^4$, wherein each $W^4$ is independently a hydrogen atom or an optionally substituted lower alkyl group. For instance, each $R^B$ may be independently a fluorine atom, chlorine atom, bromine atom, methyl group, or methoxy group.

In some embodiments, U is a single bond. X may be, for example, a group represented by —O-L-Y. L may be, for example, a methylene group. In some embodiments, Y is an optionally substituted benzene ring represented by formula (V)

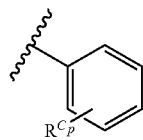

(V)

wherein each $R^c$ is independently a halogen atom, an optionally substituted lower alkyl group, or $OW^9$, wherein each $W^9$ is independently a hydrogen atom or an optionally substituted lower alkyl group; and p is an integer from 0 to 3.

In some embodiments, Y is a substituted benzene ring represented by formula (Va)

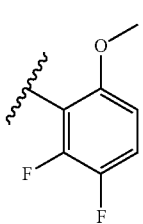

(Va)

For example, GnRH antagonists that may be used for the treatment of the endometrial growth disorders described herein include those thieno[3,4d]pyrimidine compounds described in Table 1, below. The synthesis and characterization of these compounds is reported, for instance, in U.S. Pat. No. 9,040,693, incorporated herein by reference.

Table 1. Exemplary Thieno[3,4d]pyrimidine GnRH Antagonists Useful for the Treatment of Adenomyosis and Rectovaginal Endometriosis

TABLE 1

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 1 | | (CDCl$_3$) 1.6-1.75 (2H, m), 2.45-2.6 (2H, m), 3.7-3.85 (2H, m), 3.94 (3H, s), 6.82 (1H, s), 7.0-7.15 (2H, m), 7.15-7.25 (1H, m), 7.49 (1H, dd, J = 8.4 Hz, 2.0 Hz), 7.54 (1H, d, J = 8.4 Hz), 7.6 (1H, d, J = 2.0 Hz), 7.7-7.8 (1H, m), 9.47 (1H, s) |
| 2 | | (CDCl$_3$) 1.6-1.75 (2H, m), 2.4-2.6 (2H, m), 3.7-3.8 (1H, m), 3.8-3.9 (1H, m), 6.82 (1H, d, J = 5.2 Hz), 7.0-7.15 (2H, m), 7.15-7.25 (1H, m), 7.46 (1H, dd, J = 8.3 Hz, 2.1 Hz), 7.54 (1H, d, J = 8.3 Hz), 7.65 (1H, d, J = 2.1 Hz), 7.7-7.8 (2H, m), 9.65 (1H, s) |
| 3 | | (CDCl$_3$) 1.6-1.75 (2H, m), 2.4-2.6 (2H, m), 3.7-3.9 (2H, m), 6.89 (1H, d, J = 5.8 Hz), 7.0- 7.15 (2H, m), 7.15-7.25 (1H, m), 7.32 (1H, d, J = 5.8 Hz), 7.46 (1H, dd, J = 8.4 Hz, 2.1 Hz), 7.55 (1H, d, J = 8.4 Hz), 7.64 (1H, d, J = 2.1 Hz), 7.75-7.8 (1H, m), 9.54 (1H, brs) |
| 4 | | (CDCl$_3$) 1.6-1.8 (2H, m), 2.4-2.6 (2H, m), 3.65-3.8 (4H, m), 3.8-3.9 (1H, m), 7.0-7.15 (2H, m), 7.15-7.25 (1H, m), 7.49 (1H, dd, J = 8.4 Hz, 1.9 Hz), 7.55 (1H, d, J = 8.4 Hz), 7.59 (1H, d, J = 1.9 Hz), 7.75 (1H, d, J = 7.5 Hz), 7.91 (1H, s) |
| 5 | | (CDCl$_3$) 1.95-2.05 (2H, m), 2.75-2.85 (2H, m), 3.3-3.35 (2H, m), 4.48 (2H, s), 6.5 (1H, d, J = 8.4 Hz), 6.55-6.65 (1H, m), 6.81 (1H, d, J = 5.6 Hz), 6.9-7.0 (2H, m), 7.2-7.35 (3H, m), 7.51 (1H, d, J = 9.94 (1H, brs) |
| 6 | | (CDCl$_3$) 1.38 (3H, t, J = 7.1 Hz), 1.6-1.75 (2H, m), 2.4-2.6 (2H, m), 3.7-3.85 (2H, m), 4.41 (2H, q, J = 7.1 Hz), 6.82 (1H, s), 7.0-7.15 (2H, m), 7.15-7.25 (1H, m), 7.47 (1H, dd, J = 8.5 Hz, 2.2 Hz), 7.53 (1H, d, J = 8.5 Hz), 7.6 (1H, d, J = 2.2 Hz), 7.7-7.8 (1H, m), 9.11 (1H, s) |
| 7 | | (CDCl$_3$) 1.2-1.35 (2H, m), 1.75-1.9 (2H, m), 2.4-2.55 (2H, m), 3.2-4.3 (2H, br), 6.87 (1H, d, J = 5.3 Hz), 7.1-7.2 (3H, m), 7.25-7.35 (2H, m), 7.63 (1H, d, J = 8.5 Hz), 7.69 (1H, dd, J = 8.5 Hz, 1.9 Hz), 7.78 (1H, d, J = 1.9 Hz), 9.5-10.2 (1H, br) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 8 | | (CDCl$_3$) 3.2 (3H, s), 6.87 (1H, d, J = 5.4 Hz), 7.1-7.15 (2H, m), 7.2-7.35 (4H, m), 7.54 (1H, dd, J = 8.4 Hz, 2.0 Hz), 7.6 (1H, d, J = 2.0 Hz), 7.64 (1H, d, J = 8.4 Hz), 9.5-11.0 (1H, br) |
| 9 | | (CDCl$_3$) 0.9-1.8 (10H, m), 2.77 (3H, s), 3.7-3.8 (1H, m), 6.87 (1H, d, J = 5.7 Hz), 7.3 (1H, d, J = 5.7 Hz), 7.69 (1H, d, J = 8.1 Hz), 7.8-7.9 (2H, m), 9.5-10.5 (1H, br) |
| 10 | | (DMSO-d$_6$) 3.26 (3H, s), 7.19 (1H, d, J = 5.7 Hz), 7.22 (1H, d, J =5.7 Hz), 7.25-7.3 (1H, m), 7.45-7.55 (1H, m), 7.62 (1H, dd, J = 8.5 Hz, 2.1 Hz), 7.8-7.9 (2H, m), 8.04 (1H, d, J = 2.1 Hz), 8.3-8.4 (1H, m), 12.54 (1H, s) |
| 11 | | (DMSO-d$_6$) 3.16, (3H, s), 7.05 (1H, d, J = 7.8 Hz), 7.15-7.45 (4H, m), 7.5-7.6 (1H, m), 7.75-8.1 (3H, m), 12.55 (1H, s) |
| 12 | | (DMSO-d$_6$) 0.8-0.9 (6H, m), 1.75-1.95 (1H, m), 2.6-2.8 (5H, m), 7.15-7.25 (2H, m), 7.8- 7.95 (2H, m), 8.0-8.1 (1H, m), 12.53 (1H, s) |
| 13 | | (DMSO-d$_6$) 1.6-1.75 (2H, m), 2.4-2.55 (2H, m), 3.7-3.85 (2H, m), 6.95 (1H, d, J = 3.1 Hz), 7.05-7.25 (3H, m), 7.52 (1H, dd, J = 8.5 Hz, 2.0 Hz), 7.56 (1H, d, J = 8.1 Hz), 7.78 (1H, d, J = 8.5 Hz), 8.04 (1H, d, J = 2.0 Hz), 8.52 (1H, d, J = 3.1 Hz), 11.53 (1H, s) |
| 14 | | (CDCl$_3$) 1.75-1.9 (2H, m), 2.55-2.7 (2H, m), 3.75-3.95 (2H, m), 6.9 (1H, d, J = 5.5 Hz), 7.05-7.25 (4H, m), 7.29 (1H, d, J = 5.5 Hz), 7.74 (1H, d, J = 8.2 Hz), 10.17 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 15 | 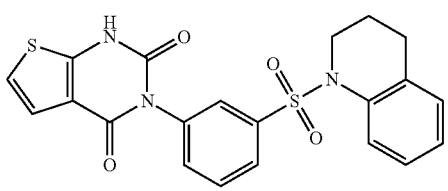 [SMILES: O=c1[nH]c2sccc2c(=O)n1-c1cccc(S(=O)(=O)N2CCCc3ccccc32)c1] | (DMSO-$d_6$) 1.6-1.7 (2H, m), 2.4-2.5 (2H, m), 3.7-3.8 (2H, m), 7.05-7.1 (2H, m), 7.1-7.25 (3H, m), 7.45-7.65 (4H, m), 7.74 (1H, d, J = 1.0 Hz), 12.37 (1H, s) |
| 16 | 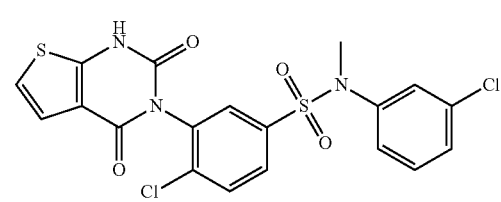 [SMILES: CN(c1cccc(Cl)c1)S(=O)(=O)c1ccc(Cl)c(-n2c(=O)[nH]c3sccc3c2=O)c1] | (DMSO-$d_6$) 3.18 (3H, s), 7.0-7.1 (1H, m), 7.15-7.25 (3H, m), 7.35-7.4 (2H, m), 7.6 (1H, dd, J = 8.5 Hz, 2.3 Hz), 7.87 (1H, d, J = 8.5 Hz), 7.96 (1H, d, J = 2.3 Hz), 12.54 (1H, s) |
| 17 | 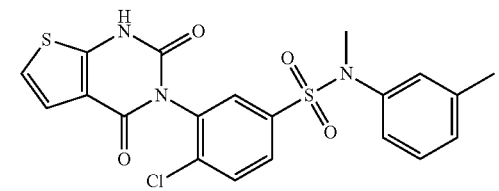 [SMILES: Cc1cccc(N(C)S(=O)(=O)c2ccc(Cl)c(-n3c(=O)[nH]c4sccc4c3=O)c2)c1] | (DMSO-$d_6$) 2.26 (3H, s), 3.15 (3H, s), 6.8-6.95 (2H, m), 7.05-7.25 (4H, m), 7.6 (1H, dd, J = 8.4 Hz, 2.3 Hz), 7.8-7.9 (2H, m), 12.54 (1H, s) |
| 18 | 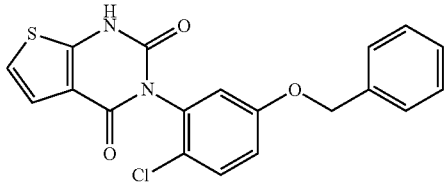 [SMILES: O=c1[nH]c2sccc2c(=O)n1-c1cc(OCc2ccccc2)ccc1Cl] | (DMSO-$d_6$) 5.1 (2H, s), 7.14 (1H, dd, J = 9.0 Hz, 2.9 Hz), 7.18 (1H, d, J = 5.6 Hz), 7.22 (1H, d, J = 5.6 Hz), 7.25 (1H, d, J = 2.9 Hz), 7.3-7.5 (5H, m), 7.53 (1H, d, J = 9.0 Hz), 12.48 (1H, s) |
| 19 | 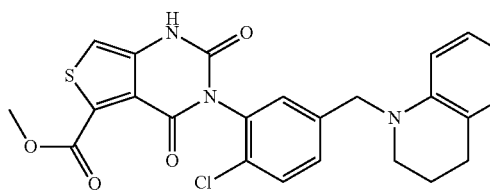 | (DMSO-$d_6$) 1.85-2.0 (2H, m), 2.7-2.8 (2H, m), 3.3-3.4 (2H, m), 3.81 (3H, s), 4.5 (2H, s), 6.4-6.5 (2H, m), 6.85-6.95 (2H, m), 7.2 (1H, s), 7.31 (1H, dd, J = 8.2 Hz, 2.1 Hz), 7.4 (1H, d, J = 2.1 Hz), 7.56 (1H, d, J = 8.2 Hz), 11.61 (1H, s) |
| 20 | 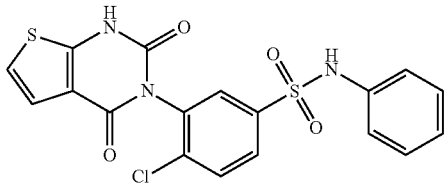 [SMILES: O=c1[nH]c2sccc2c(=O)n1-c1cc(S(=O)(=O)Nc2ccccc2)ccc1Cl] | (DMSO-$d_6$) 7.05-7.3 (7H, m), 7.75-7.9 (2H, m), 7.95-8.05 (1H, m), 10.48 (1H, s), 12.56 (1H, s) |
| 21 | 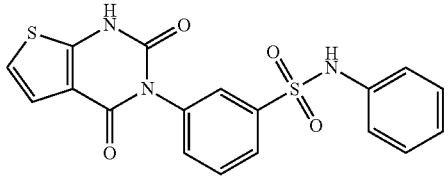 [SMILES: O=c1[nH]c2sccc2c(=O)n1-c1cccc(S(=O)(=O)Nc2ccccc2)c1] | (DMSO-$d_6$) 7.0-7.3 (7H, m), 7.55-7.7 (2H, m), 7.75-7.85 (2H, m), 10.4 (1H, s), 12.4 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 22 | | (DMSO-$d_6$) 1.6-1.7 (2H, m), 2.4-2.55 (2H, m), 3.7-3.8 (2H, m), 7.05-7.25 (3H, m), 7.39 (1H, s), 7.55 (1H, d, J = 8.2 Hz), 7.6 (1H, dd, J = 8.5 Hz, 2.4 Hz), 7.83 (1H, d, J = 8.5 Hz), 8.09 (1H, d, J = 2.4 Hz), 12.03. (1H, s), 14.23 (1H, s) |
| 23 | | (DMSO-$d_6$) 5.11 (2H, s), 7.19 (1H, dd, J = 9.0 Hz, 2.9 Hz), 7.3-7.45 (5H, m), 7.45-7.5 (2H, m), 7.57 (1H, d, J = 9.0 Hz), 12.04 (1H, s), 14.45 (1H, brs) |
| 24 | | (DMSO-$d_6$) 1.85-2.0 (2H, m), 2.7-2.8 (2H, m), 3.3-3.4 (2H, m), 4.52 (2H, s), 6.44 (1H, d, J = 8.2 Hz), 6.45-6.5 (1H, m), 6.85-6.95 (2H, m), 7.36 (1H, d, J = 8.2 Hz), 7.38 (1H, s), 7.48 (1H, d, J = 2.1 Hz), 7.61 (1H, d, J = 8.2 Hz), 12.0 (1H, s), 14.45 (1H, brs) |
| 25 | | (DMSO-$d_6$) 2.33 (3H, s), 5.09 (2H, s), 7.15-7.3 (4H, m), 7.35 (1H, d, J = 2.7 Hz), 7.41 (1H, s), 7.43 (1H, d, J = 7.7 Hz), 7.58 (1H, d, J = 9.0 Hz), 12.04 (1H, s), 14.44 (1H, s) |
| 26 | | (DMSO-$d_6$) 2.32 (3H, s), 5.07 (2H, s), 7.1-7.35 (6H, m), 7.41 (1H, s), 7.57 (1H, d, J = 8.7 Hz), 12.04 (1H, s), 14.45 (1H, brs) |
| 27 | | (DMSO-$d_6$) 5.24 (2H, s), 7.2 (1H, dd, J = 8.8 Hz, 3.0 Hz), 7.35 (1H, d, J = 3.0 Hz), 7.41 (1H, s), 7.59 (1H, d, J = 8.8 Hz), 7.69 (2H, d, J = 8.2 Hz), 7.78 (2H, d, J = 8.2 Hz), 12.04 (1H, s), 14.43 (1H, s) |
| 28 | | (DMSO-$d_6$) 1.5-1.6 (3H, m), 5.45-5.55 (1H, m), 7.0-7.1 (1H, m), 7.23 (1H, dd, J = 6.1 Hz, 2.9 Hz), 7.25-7.5 (7H, m), 11.95-12.1 (1H, m), 14.42 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 29 | | (DMSO-d$_6$) 2.85-3.0 (4H, m), 7.15-7.35 (8H, m), 7.38 (1H, s), 7.41 (1H, t, J = 7.7 Hz), 11.92 (1H, s), 14.94 (1H, brs) |
| 30 | | DMSO-d$_6$) 1.6-1.7 (2H, m), 2.4-2.55 (2H, m), 3.7-3.85 (2H, m), 7.0-7.2 (3H, m), 7.24 (1H, s), 7.56 (1H, d, J = 8.3 Hz), 7.59 (1H, dd, J = 8.5 Hz, 2.1 Hz), 7.81 (1H, d, J = 8.5 Hz), 8.05-8.15 (2H, m), 9.55 (1H, s), 11.81 (1H, s) |
| 31 | | (CDCl$_3$) 1.65-1.75 (2H, m), 2.4-2.6 (2H, m), 2.99 (3H, d, J = 4.7 Hz), 3.7-3.9 (2H, m), 6.91 (1H, s), 6.95-7.15 (2H, m), 7.15-7.25 (1H, m), 7.5-7.65 (3H, m), 7.7-7.8 (1H, m), 8.91 (1H, s), 10.05-10.15 (1H, m) |
| 32 | | (CDCl$_3$) 1.55 (6H, s), 1.6-1.75 (2H, m), 2.4-2.55 (2H, m), 3.7-3.9 (2H, m), 6.04 (1H, s), 6.49 (1H, s), 7.0-7.15 (2H, m), 7.15-7.25 (2H, m), 7.5-7.55 (1H, m), 7.55-7.6 (2H, m), 7.76 (1H, d, J = 8.3 Hz), 8.41 (1H, s) |
| 33 | | (DMSO-d$_6$) 1.6-1.75 (2H, m), 2.45-2.55 (2H, m), 3.7-3.85 (2H, m), 4.95-5.05 (2H, m), 5.99 (1H, t, J = 5.5 Hz), 6.73 (1H, s), 7.05-7.15 (2H, m), 7.15-7.25 (1H, m), 7.5-7.6 (2H, m), 7.78 (1H, d, J = 8.5 Hz), 7.97 (1H, d, J = 2.3 Hz), 11.41 (1H, s) |
| 34 | | (DMSO-d$_6$) 1.6-1.75 (2H, m), 2.45-2.55 (2H, m), 3.7-3.8 (2H, m), 7.05-7.15 (2H, m), 7.15-7.25 (1H, m), 7.5-7.6 (3H, m), 7.82 (1H, d, J = 8.5 Hz), 8.09 (1H, d, J = 2.1 Hz), 10.5-10.55 (1H, m), 11.88 (1H, s) |
| 35 | | (DMSO-d$_6$) 1.64 (3H, d, J = 6.5 Hz), 3.8-3.9 (6H, m), 5.79 (1H, q, J = 6.5 Hz), 6.7-6.8 (1H, m), 6.85-6.95 (2H, m), 6.95-7.05 (1H, m), 7.15-7.25 (2H, m), 7.25-7.35 (1H, m), 11.63 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 36 | | (DMSO-$d_6$) 3.83 (3H, s), 3.85 (3H, s), 4.99 (2H, s), 6.85-7.0 (2H, m), 7.1-7.2 (2H, m), 7.21 (1H, s), 7.25-7.35 (1H, m), 7.4-7.5 (1H, m), 11.68 (1H, s) |
| 37 | | (DMSO-$d_6$) 3.75 (3H, s), 3.85 (3H, s), 4.99 (2H, s), 6.85-7.0 (2H, m), 7.1-7.2 (2H, m), 7.25-7.35 (1H, m), 7.4-7.5 (1H, m), 7.65 (1H, s), 12.64 (1H, s) |
| 38 | | (DMSO-$d_6$) 1.54 (3H, d, J = 6.3 Hz), 3.8-3.85 (3H, m), 5.46 (1H, q, J = 6.3 Hz), 6.9-7.0 (1H, m), 7.05-7.1 (1H, m), 7.15-7.45 (7H, m), 11.63 (1H, s) |
| 39 | | (DMSO-$d_6$) 1.7 (3H, d, J = 6.8 Hz), 3.8-3.85 (3H, m), 5.7-5.8 (1H, m), 6.9-7.0 (1H, m), 7.05-7.15 (3H, m), 7.15-7.3 (2H, m), 7.35-7.5 (1H, m), 11.63 (1H, s) |
| 40 | | (DMSO-$d_6$) 1.71 (3H, d, J = 6.6 Hz), 3.82 (3H, s), 5.95-6.05 (1H, m), 6.8-6.9 (1H, m), 7.0-7.05 (1H, m), 7.15-7.3 (2H, m), 7.3-7.4 (1H, m), 7.45-7.5 (2H, m), 11.63 (1H, s) |
| 41 | | (DMSO-$d_6$) 1.58 (3H, d, J = 6.3 Hz), 3.8-3.85 (3H, m), 5.66 (1H, q, J = 6.3 Hz), 6.9-7.0 (1H, m), 7.05-7.15 (1H, m), 7.15-7.3 (4H, m), 7.3-7.4 (1H, m), 7.45-7.55 (1H, m), 11.63 (1H, s) |
| 42 | | (DMSO-$d_6$) 1.69 (3H, d, J = 6.4 Hz), 3.7-3.75 (3H, m), 5.7-5.8 (1H, m), 6.9-7.0 (1H, m), 7.05-7.15 (3H, m), 7.2-7.3 (1H, m), 7.35-7.5 (1H, m), 7.6-7.65 (1H, m), 12.59 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 43 | | (DMSO-$d_6$) 1.71 (3H, d, J = 6.6 Hz), 3.74 (3H, s), 5.95-6.05 (1H, m), 6.8-6.9 (1H, m), 6.95-7.05 (1H, m), 7.2-7.3 (1H, m), 7.3-7.4 (1H, m), 7.4-7.5 (2H, m), 7.6-7.65 (1H, m), 12.59 (1H, s) |
| 44 | | (DMSO-$d_6$) 1.64 (3H, d, J = 6.7 Hz), 3.7-3.8 (3H, m), 3.8-3.9 (3H, m), 5.75-5.85 (1H, m), 6.7-6.8 (1H, m), 6.85-6.95 (2H, m), 6.95-7.05 (1H, m), 7.15-7.25 (1H, m), 7.25-7.35 (1H, m), 7.63 (1H, s), 12.58 (1H, s) |
| 45 | | (DMSO-$d_6$) 1.51 (3H, d, J = 6.3 Hz), 3.8-3.9 (6H, m), 5.6-5.7 (1H, m), 6.8-6.9 (1H, m), 6.9- 7.0 (1H, m), 7.0-7.1 (2H, m), 7.15-7.3 (3H, m), 7.3-7.4 (1H, m), 11.6 (1H, s) |
| 46 | | (DMSO-$d_6$) 1.57 (3H, d, J = 6.3 Hz), 3.8-3.85 3H, m), 5.6-5.7 (1H, m), 6.8-6.9 (1H, m), 7.05-7.1 (1H, m), 7.15-7.3 (2H, m), 7.3-7.4 m), 7.45-7.5 (1H, m), 7.5-7.6 (1H, m), 11.61 (1H, s) |
| 47 | | (DMSO-$d_6$) 1.54 (3H, d, J = 6.2 Hz), 3.75-3.85 (3H, m), 5.45-5.55 (1H, m), 6.95-7.05 (1H, m), 7.05-7.15 (1H, m), 7.15-7.25 (2H, m), 7.3-7.45 (3H, m), 7.49 (1H, s), 11.61 (1H, s) |
| 48 | | (DMSO-$d_6$) 1.65 (3H, d, J = 6.5 Hz), 3.8-3.9 3H, m), 5.75-5.85 (1H, m), 6.7-6.8 (1H, m), 6.85-7.0 (2H, m), 7.05-7.1 (1H, m), 7.2-7.35 (2H, m), 7.37 (1H, d, J = 3.6 Hz), 12.01 (1H, s), 14.43(1H, s) |
| 49 | | (DMSO-$d_6$) 3.85 (3H, s), 5.0 (2H, s), 6.88 (1H, t, J = 8.7 Hz), 6.95 (1H, d, J = 8.7 Hz), 7.15-7.25 (2H, m), 7.3-7.5 (3H, m), 12.06 (1H, s), 14.43 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 50 | 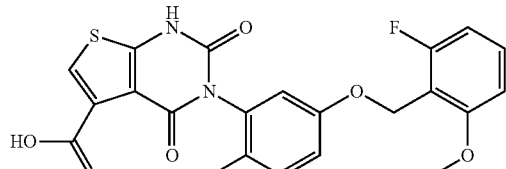 | (DMSO-$d_6$) 3.85 (3H, s), 5.0 (2H, s), 6.88 (1H, t, J = 8.6 Hz), 6.95 (1H, d, J = 8.6 Hz), 7.1-7.2 (1H, m), 7.2-7.25 (1H, m), 7.3-7.4 (1H, m), 7.4-7.5 (1H, m), 7.94 (1H, s), 13.04 (1H, s), 13.93 (1H s) |
| 51 | 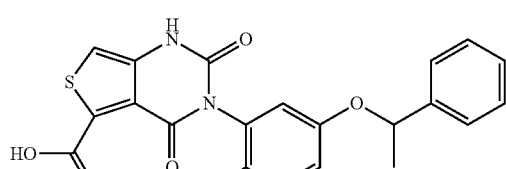 | (DMSO-$d_6$) 1.5-1.6 (3H, m), 5.4-5.5 (1H, m), 6.95-7.05 (1H, m), 7.1-7.2 (1H, m), 7.2-7.4 (5H, m), 7.4-7.45 (2H, m), 11.95-12.05 (1H, m), 14.42 (1H, s) |
| 52 | 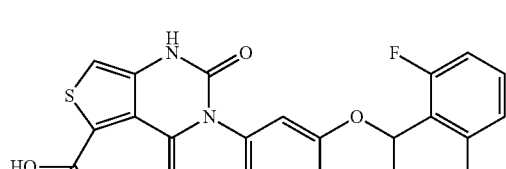 | (DMSO-$d_6$) 1.7 (3H, d, J = 6.6 Hz), 5.76 (1H, q, J = 6.6 Hz), 7.0-7.2 (4H, m), 7.25-7.35 (1H, m), 7.35-7.5 (2H, m), 11.95-12.05 (1H, m), 14.42 (1H, s) |
| 53 | 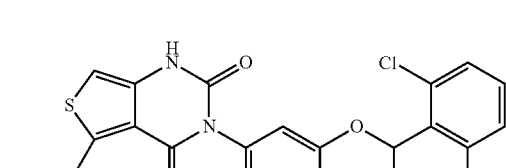 | (DMSO-$d_6$) 1.65-1.75 (3H, m), 6.03 (1H, q, J = 6.6 Hz), 6.85-6.95 (1H, m), 7.05-7.15 (1H, m), 7.25-7.4 (3H, m), 7.4-7.5 (2H, m), 11.95-12.05 (1H, m), 14.4 (1H, s) |
| 54 | 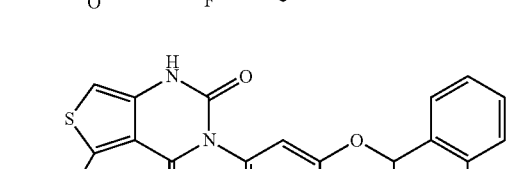 | (DMSO-$d_6$) 1.55-1.65 (3H, m), 5.65 (1H, q, J = 6.5 Hz), 7.0-7.05 (1H, m), 7.15-7.25 (3H, m), 7.25-7.4 (3H, m), 7.45-7.55 (1H, m), 11.95-12.05. (1H, m), 14.42 (1H, s) |
| 55 | 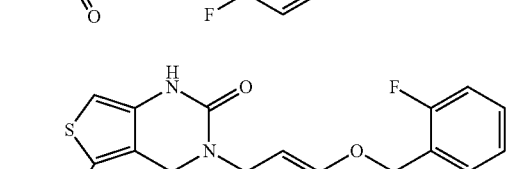 | (DMSO-$d_6$) 1.65-1.75 (3H, m), 5.7-5.8 (1H, m), 6.95-7.2 (4H, m), 7.2-7.5 (2H, m), 7.93 (1H, d, J = 7.2 Hz), 12.98 (1H, s), 13.85-14.0 (1H, m) |
| 56 | 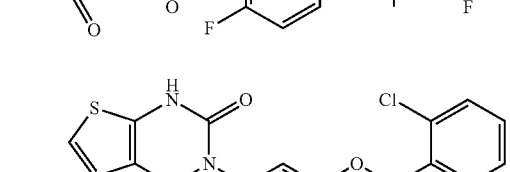 | (DMSO-$d_6$) 1.72 (3H, d, J = 6.6 Hz), 6.0-6.1 (1H, m), 6.85-6.95 (1H, m), 7.05-7.1 (1H, m), 7.25-7.4 (2H, m), 7.45-7.5 (2H, m), 7.92 (1H, d, J = 11.1 Hz), 12.98 (1H, brs), 13.85-14.0 (1H, m) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 57 | | (DMSO-$d_6$) 1.65 (3H, d, J = 6.6 Hz), 3.8-3.9 (3H, m), 5.79 (1H, q, J = 6.6 Hz), 6.7-6.8 (1H, m), 6.85-6.95 (2H, m), 7.0-7.1 (1H, m), 7.2-7.35 (2H, m), 7.85-8.0 (1H, m), 12.98 (1H, brs), 13.85-14.05 (1H, m) |
| 58 | | (DMSO-$d_6$) 1.52 (3H, d, J = 6.3 Hz), 3.8-3.9 (3H, m), 5.64 (1H, q, J = 6.3 Hz), 6.85-7.0 (2H, m), 7.0-7.15 (2H, m), 7.2-7.4 (4H, m), 11.95-12.0 (1H, m), 14.41 (1H, s) |
| 59 | | (DMSO-$d_6$) 1.45-1.65 (3H, m), 5.55-5.8 (1H, m), 6.8-7.7 (8H, m), 11.98 (1H, s), 14.39 (1H, s) |
| 60 | | (DMSO-$d_6$) 1.45-1.65 (3H, m), 5.4-5.6 (1H, m), 6.95-7.6 (8H, m), 11.99 (1H, s), 14.39 (1H, s) |
| 61 | | (DMSO-$d_6$) 1.56 (3H, s), 1.57 (3H, s), 3.82 (3H, s), 7.15-7.45 (8H, m), 7.8-7.9 (1H, m), 11.68 (1H, s) |
| 62 | | (DMSO-$d_6$) 1.5-1.6 (6H, m), 3.34 (3H, s), 3.82 (3H, s), 6.84 (1H, d, J = 8.2 Hz), 7.0-7.1 (1H, m), 7.1-7.3 (3H, m), 7.3-7.4 (1H, m), 7.5-7.6 (1H, m), 7.8-7.9 (1H, m), 11.63 (1H, s) |
| 63 | | (DMSO-$d_6$) 1.59 (3H, s), 1.6 (3H, s), 3.82 (3H, s), 7.05-7.15 (1H, m), 7.19 (1H, s), 7.2-7.4 (3H, m), 7.4-7.5 (1H, m), 7.65-7.75 (1H, m), 7.9-8.0 (1H, m), 11.7 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 64 | 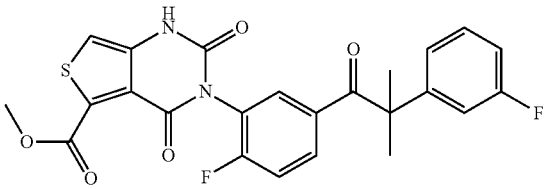 [SMILES: COC(=O)c1scc2[nH]c(=O)n(-c3cc(C(=O)C(C)(C)c4cccc(F)c4)ccc3F)c(=O)c12] | (DMSO-$d_6$) 1.57 (3H, s), 1.58 (3H, s), 3.82 (3H, s), 7.06 (1H, d, J = 8.4 Hz), 7.1-7.25 (3H, m), 7.25-7.35 (1H, m), 7.35-7.45 (2H, m), 7.8-7.9 (1H, m), 11.68 (1H, s) |
| 65 | 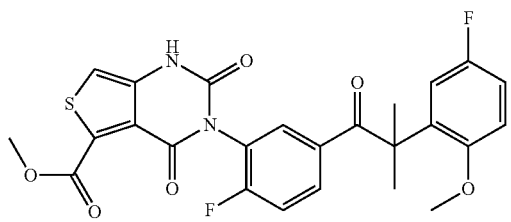 [SMILES: COC(=O)c1scc2[nH]c(=O)n(-c3cc(C(=O)C(C)(C)c4cc(F)ccc4OC)ccc3F)c(=O)c12] | (DMSO-$d_6$) 1.54 (6H, s), 3.31 (3H, s), 3.82 (3H, s), 6.8-6.9 (1H, m), 7.0-7.1 (1H, m), 7.15-7.25 (2H, m), 7.3-7.45 (2H, m), 7.8-7.9 (1H, m), 11.63 (1H, s) |
| 66 | 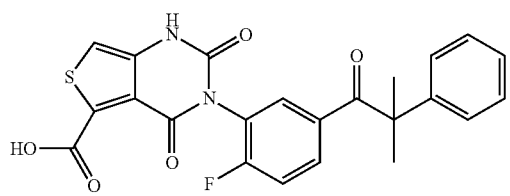 [SMILES: CC(C)(C(=O)c1ccc(F)c(-n2c(=O)[nH]c3csc(C(=O)O)c3c2=O)c1)c1ccccc1] | (DMSO-$d_6$) 1.55-1.6 (6H, m), 7.25-7.45 (8H, m), 7.9-8.0 (1H, m), 12.0 (1H, s), 14.29 (1H, s) |
| 67 | 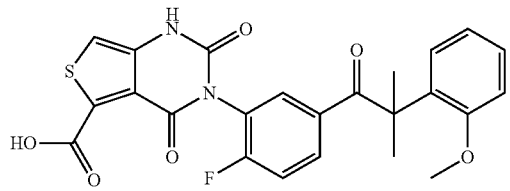 [SMILES: COc1ccccc1C(C)(C)C(=O)c1ccc(F)c(-n2c(=O)[nH]c3csc(C(=O)O)c3c2=O)c1] | (DMSO-$d_6$) 1.55 (3H, s), 1.56 (3H, s), 3.33 (3H, s), 6.84 (1H, d, J = 8.2 Hz), 7.0-7.1 (1H, m), 7.15-7.3 (2H, m), 7.37 (1H, s), 7.4-7.5 (1H, m), 7.5-7.55 (1H, m), 7.9-7.95 (1H, m), 11.99 (1H, s), 14.35 (1H, s) |
| 68 | 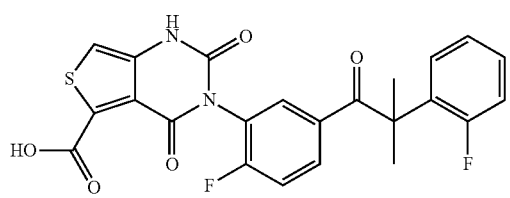 [SMILES: CC(C)(C(=O)c1ccc(F)c(-n2c(=O)[nH]c3csc(C(=O)O)c3c2=O)c1)c1ccccc1F] | (DMSO-$d_6$) 1.59 (3H, s), 1.62 (3H, s), 7.0-7.1 (1H, m), 7.25-7.4 (4H, m), 7.5-7.6 (1H, m), 7.65-7.75 (1H, m), 7.95-8.05 (1H, m), 12.01 (1H, s), 14.29 (1H, s) |
| 69 | 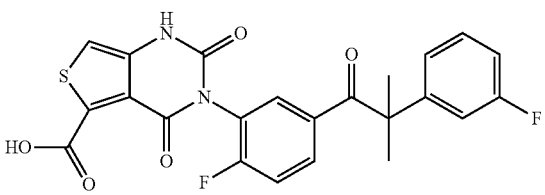 [SMILES: CC(C)(C(=O)c1ccc(F)c(-n2c(=O)[nH]c3csc(C(=O)O)c3c2=O)c1)c1cccc(F)c1] | (DMSO-$d_6$) 1.58 (3H, s), 1.59 (3H, s), 7.0-7.25 (3H, m), 7.3-7.45 (3H, m), 7.45-7.55 (1H, m), 7.9-7.95 (1H, m), 12.02 (1H, s), 14.29 (1H, s) |
| 70 | 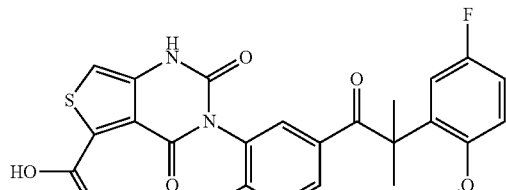 | (DMSO-$d_6$) 1.54 (3H, s), 3.31 (3H, s), 6.8-6.9 (1H, m), 7.0-7.1 (1H, m), 7.26 (1H, t, J = 9.2 Mz), 7.3-7.4 (2H, m), 7.5-7.6 (1H, m), 7.85-7.95 (1H, m), 11.99 (1H, s), 14.36 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 71 | 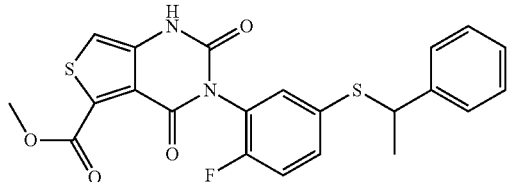 | (DMSO-$d_6$) 1.55-1.6 (3H, m), 3.82 (3H, s), 4.6-4.7 (1H, m), 7.1-7.2 (2H, m), 7.2-7.45 (8H, m), 11.49 (1H, s) |
| 72 | 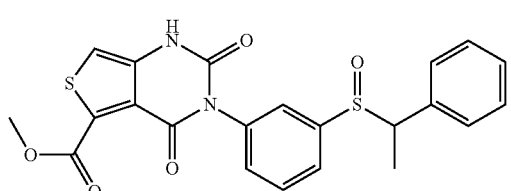 | (DMSO-$d_6$) 1.36 (3H, d, J = 7.2 Hz), 3.82 (3H, s), 4.05-4.15 (1H, m), 7.15-7.65 (10H, m), 11.54 (1H, s) |
| 73 | 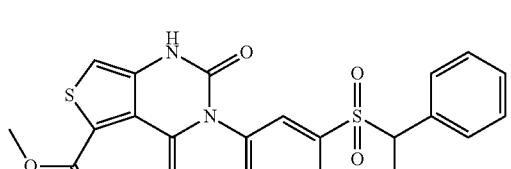 | (DMSO-$d_6$) 1.56 (3H, d, J = 7.1 Hz), 3.83 (3H, s), 4.71 (1H, q, J = 7.1 Hz), 7.18 (1H, s), 7.2- 7.35 (5H, m), 7.6-7.7 (3H, m), 7.75-7.8 (1H, m), 11.56 (1H, s) |
| 74 | 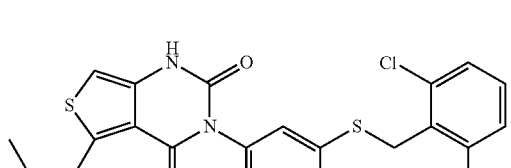 | (DMSO-$d_6$) 3.82 (3H, s), 4.44 (2H, s), 7.1-7.25 (2H, m), 7.3-7.4 (1H, m), 7.4-7.45 (3H, m), 7.45-7.55 (2H, m), 11.5 (1H, s) |
| 75 | 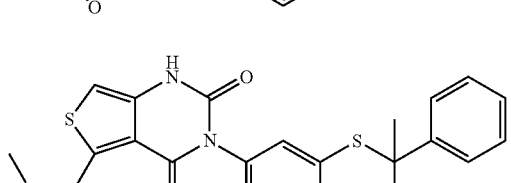 | (DMSO-$d_6$) 1.64 (6H, s), 3.82 (3H, s), 7.05-7.25 (4H, m), 7.25-7.4 (4H, m), 7.4-7.5 (2H, m), 11.45 (1H, s) |
| 76 | 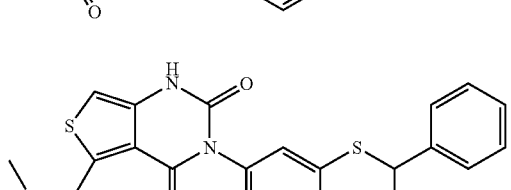 | (DMSO-$d_6$) 1.57 (3H, d, J = 6.9 Hz), 3.74 (3H, s), 4.66 (1H, q, J = 6.9 Hz), 7.1-7.15 (1H, m), 7.2-7.45 (8H, m), 7.59 (1H, s), 12.44 (1H, s) |
| 77 | 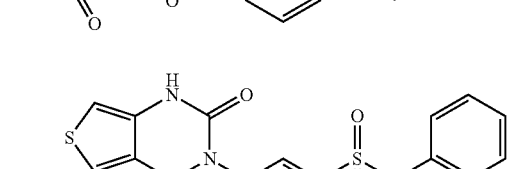 | (DMSO-$d_6$) 1.56 (3H, d, J = 6.8 Hz), 3.76 (3H, s), 4.65-4.75 (1H, m), 7.2-7.35 (5H, m), 7.6-7.75 (4H, m), 7.78 (1H, s), 12.52 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 78 | | (DMSO-$d_6$) 3.74 (3H, s), 4.44 (2H, s), 7.15-7.25 (1H, m), 7.3-7.55 (6H, m), 7.59 (1H, s), 12.45 (1H, s) |
| 79 | | (DMSO-$d_6$) 1.58 (3H, d, J = 6.9 Hz), 4.65 (1H, q, J = 6.9 Hz), 7.25-7.5 (10H), m), 11.93 (1H, s), 14.87 (1H, s) |
| 80 | | (DMSO-$d_6$) 1.39 (3H, d, J = 7.3 Hz), 4.05-4.15 (1H, m), 7.2-7.8 (10H, m), 11.95 (1H, s), 14.8 (1H, s) |
| 81 | | (DMSO-$d_6$) 1.59 (3H, d, J = 7.7 Hz), 4.72 (1H, q, J = 7.7 Hz), 7.2-7.35 (5H, m), 7.39 (1H, s), 7.65-7.9 (4H, m), 11.96 (1H, s), 14.73 (1H, s) |
| 82 | | (DMSO-$d_6$) 4.44 (2H, s), 7.25-7.45 (3H, m), 7.45-7.55 (5H, m), 11.93 (1H, s), 14.87 (1H, s) |
| 83 | | (DMSO-$d_6$) 4.94 (2H, s), 7.35-7.55 (4H, m), 7.75-7.85 (3H, m), 7.95-8.0 (1H, m), 11.96 (1H, s), 14.75 (1H, s) |
| 84 | | (DMSO-$d_6$) 1.65 (6H, s), 7.1-7.5 (10H, m), 11.88 (1H, s), 14.84 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 85 | | (DMSO-$d_6$) 1.58 (3H, d, J = 7.0 Hz), 4.66 (1H, q, J = 7.0 Hz), 7.15-7.45 (9H, m), 8.0 (1H, s), 12.94 (1H, s), 14.43 (1H, s) |
| 86 | | (DMSO-$d_6$) 1.58 (3H, d, J = 7.0 Hz), 4.72 (1H,q, J = 7.0 Hz), 7.2-7.35 (5H, m), 7.65-7.8 (3H, m), 7.84 (1H, s), 7.98 (1H, s), 12.96 (1H, s), 14.26 (1H, s) |
| 87 | | (DMSO-$d_6$) 4.45 (2H, s), 7.25-7.3 (1H, m), 7.3-7.4 (1H, m), 7.45-7.55 (5H, m), 8.0 (1H, s), 12.94 (1H, s), 14.42 (1H, s) |
| 88 | | (DMSO-$d_6$) 4.94 (2H, s), 7.35-7.45 (1H, m), 7.45-7.55 (2H, m), 7.7-7.85 (3H, m), 7.95-8.0 (2H, m), 12.96 (1H, s), 14.3 (1H, s) |
| 89 | | (DMSO-$d_6$) 3.37 (3H, s), 3.83 (3H, s), 7.15-7.25 (5H, m), 7.25-7.35 (2H, m), 7.44 (1H, d, J = 8.1 Hz), 7.56 (1H, d, J = 1.9 Hz), 11.63 (1H, s) |
| 90 | | (DMSO-$d_6$) 3.37 (3H, s), 3.83 (3H, s), 7.15-7.35 (8H, m), 7.53 (1H,dd, J = 7.3 Hz, 1.9 Hz), 11.63 (1H, s) |
| 91 | | (DMSO-$d_6$) 3.37 (3H, s), 3.82 (3H, s), 7.1-7.4 10H, m), 11.46 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 92 | | (DMSO-$d_6$) 3.37 (3H, s), 3.74 (3H, s), 7.1-7.4 (9H, m), 7.58 (1H, s), 12.42 (1H, s) |
| 93 | | (DMSO-$d_6$) 3.38 (3H, s), 7.15-7.4 (8H, m), 7.5-7.6 (1H, m), 11.96 (1H, s), 14.34 (1H, s) |
| 94 | | (DMSO-$d_6$) 3.37 (3H, s), 7.15-7.4 (7H, m), 7.44 (1H, d, J = 8.7 Hz), 7.72 (1H, s) |
| 95 | | (DMSO-$d_6$) 3.38 (3H, s), 7.15-7.25 (3H, m), 7.25-7.35 (3H, m), 7.38 (1H, s), 7.5 (1H, d, J = 7.5 Hz), 7.58 (1H, d, J = 1.9 Hz), 11.98 (1H, s), 14.33 (1H, s) |
| 96 | | (DMSO-$d_6$) 3.37 (3H, s), 7.15-7.4 (10H m), 11.89 (1H, s), 14.81 (1H, s) |
| 97 | | (DMSO-$d_6$) 3.37 (3H, s), 7.15-7.4 (9H, m), 7.99 (1H, s), 12.9 (1H, s), 14.37 (1H, s) |
| 98 | | (DMSO-$d_6$) 3.75-3.85 (3H, m), 6.3-6.4 (1H, m), 7.05-7.15 (1H, m), 7.2 (1H, s), 7.32 (1H, dd, J = 7.6 Hz, 2.9 Hz), 7.45-7.55 (4H, m), 7.55-7.65 (2H, m), 11.66 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 99 | | (DMSO-d$_6$) 3.75-3.95 (6H, m), 6.2-6.35 (1H, m), 6.9-7.0 (1H, m), 7.0-7.1 (1H, m), 7.17 (1H, d, J = 8.0 Hz), 7.21 (1H, s), 7.31 (1H, dd, J = 6.4 Hz, 3.0 Hz), 7.4-7.55 (3H, m), 11.64 (1H, s) |
| 100 | | (DMSO-d$_6$) 3.7-3.75 (3H, m), 3.85-3.95 (3H, m), 6.2-6.35 (1H, m), 6.9-7.0 (1H, m), 7.04 (1H, t, J = 7.6 Hz), 7.15-7.2 (1H, m), 7.25-7.35 (1H, m), 7.4-7.55 (3H, m), 7.64 (1H, s), 12.6 (1H, s) |
| 101 | | (DMSO-d$_6$) 6.3-6.4 (1H, m), 7.1-7.2 (1H, m), 7.35-7.4 (2H, m), 7.45-7.55 (3H, m), 7.55-7.65 (3H, m), 11.95-12.1 (1H, m), 14.32 (1H, s) |
| 102 | | (DMSO-d$_6$) 3.85-3.95 (3H, m), 6.25-6.35 (1H, m), 6.95-7.1 (2H, m), 7.15-7.2 (1H, m), 7.35-7.5 (4H, m), 7.56 (1H, d, J = 8.9 Hz), 12.0-12.1 (1H, m), 14.34 (1H, s) |
| 103 | | (DMSO-d$_6$) 3.85-3.95 (3H, m), 6.25-6.35 (1H, m), 6.95-7.1 (2H, m), 7.15-7.2 (1H, m), 7.3-7.4 (1H, m), 7.4-7.5 (2H, m), 7.55 (1H, d, J = 9.0 Hz), 7.92 (1H, d, J = 4.5 Hz), 13.0 (1H, brs), 13.8-13.95 (1H, m) |
| 104 | | (CDCl$_3$) 3.89 (3H, s), 6.84 (1H, d, J = 5.8 Hz), 7.05-7.1 (1H, m), 7.28 (1H, d, J = 5.8 Hz), 7.45-7.55 (1H, m), 7.59 (1H, d, J = 8.5 Hz), 7.65-7.75 (1H, m), 7.8-7.85 (1H, m), 7.85-8.0 (2H, m), 10.06 (1H, s), 10.75 (1H, s) |
| 105 | | (CDCl$_3$) 1.6-1.75 (2H, m), 2.45-2.55 (2H, m), 3.45-3.6 (1H, m), 3.7-3.85 (2H, m), 6.45 (1H, d, J = 0.5 Hz), 7.01 (1H, d, J = 7.0 Hz), 7.05-7.25 (2H, m), 7.5-7.6 (3H, m), 7.76 (1H, d, J = 7.7 Hz), 10.68 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 106 | | (DMSO-d6) 3.74 (3H, s), 3.83 (3H, s), 4.15-4.2 (2H, m), 6.75-6.85 (1H, m), 7.21 (1H, s), 7.25-7.4 (2H, m), 7.4-7.5 (1H, m), 7.5-7.55 (1H, m), 11.65 (1H, s) |
| 107 | | (DMSO-d6) 3.77 (3H, s), 3.83 (3H, s), 4.15 (2H, s), 6.75-6.9 (2H, m), 7.15-7.55 (5H, m), 11.65 (1H, s) |
| 108 | | (CDCl$_3$) 3.16 (3H, s), 6.88 (1H, d, J = 5.8 Hz), 7.0-7.1 (2H, m), 7.25-7.35 (3H, m), 7.5-7.6 (2H, m), 7.6-7.7 (1H, m), 9.5-11.0 (1H, br) |
| 109 | | (DMSO-d$_6$) 7.1-7.25 (3H, m), 7.44 (1H, d, J = 8.5 Hz), 7.5-7.6 (1H, m), 7.87 (1H, d, J = 8.5 Hz), 7.9-8.0 (2H, m), 8.18 (1H, d, J = 2.2 Hz), 11.0-12.0 (1H, br), 12.52 (1H, s) |
| 110 | | (CDCl$_3$) 3.22 (3H, s), 7.05-7.15 (3H, m), 7.25-7.35 (3H, m), 7.45-7.55 (1H, m), 7.71 (1H, s), 9.22 (1H, s), 14.14 (1H, s) |
| 111 | | (CDCl$_3$) 1.11 (3H, t, J = 7.1 Hz), 3.5-3.6 (1H, m), 3.65-3.8 (1H, m), 7.05-7.1 (2H, m), 7.13 (1H, s), 7.25-7.35 (3H, m), 7.55 (1H, d, J = 2.2 Hz), 7.7 (1H, d, J = 8.4 Hz), 7.77 (1H, dd, J = 8.4 Hz, 2.2 Hz), 9.22 (1H, s), 14.17 (1H, s) |
| 112 | | (CDCl$_3$) 3.33 (3H, s), 7.1 (1H, s), 7.15-7.2 (1H, m), 7.57 (1H, d, J = 8.2 Hz), 7.6-7.75 (4H, m), 8.3-8.4 (1H, m), 9.05 (1H, s), 14.09 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 113 | | (DMSO-d6) 1.6-1.75 (2H, m), 2.45-2.55 (2H, m), 3.7-3.85 (2H, m), 6.9-7.0 (1H, m), 7.05-7.25 (3H, m), 7.5-7.6 (2H, m), 7.78 (1H, d, J = 8.5 Hz), 8.0-8.05 (1H, m), 8.5-8.55 (1H, m), 11.52 (1H, s) |
| 114 | | (DMSO-d6) 3.17 (3H, s), 7.05-7.15 (2H, m), 7.25-7.4 (3H, m), 7.63 (1H, dd, J = 8.6 Hz, 2.2 Hz), 7.85-7.95 (3H, m), 12.5-13.5 (1H, br), 13.79 (1H, s) |
| 115 | | (DMSO-d6) 3.26 (3H, s), 7.25-7.3 (1H, m), 7.45-7.55 (1H, m), 7.65-7.75 (1H, m), 7.8-7.95 (3H, m), 8.05-8.1 (1H, m), 8.3-8.4 (1H, m) |
| 116 | | (CDCl$_3$) 3.17 (3H, s), 6.9-7.0 (1H, m), 7.13 (1H, s), 7.29 (1H, d, J = 2.5 Hz), 7.39 (1H, d, J = 8.4 Hz), 7.51 (1H, d, J = 1.2 Hz), 7.7-7.8 (2H, m), 9.12 (1H, s), 14.05 (1H, s) |
| 117 | | (CDCl$_3$) 3.25 (3H, s), 6.75-6.9 (2H, m), 7.13 (1H, s), 7.2-7.3 (1H, m), 7.63 (1H, d, J = 2.1 Hz), 7.75 (1H, d, J = 8.6 Hz), 7.8-7.85 (1H, m), 9.03 (1H, s), 14.11 (1H, s) |
| 118 | | (CDCl$_3$) 3.22 (3H, s), 7.08 (1H, s), 7.15-7.25 (2H, m), 7.38 (1H, d, J = 1.7 Hz), 7.7-7.8 (2H, m), 8.55-8.65 (2H, m) |
| 119 | | (DMSO-d6) 3.23 (3H, s), 3.8 (3H, s), 6.9-6.95 (1H, m), 7.35-7.55 (3H, m), 7.7-7.85 (2H, m), 7.9-8.0 (2H, m), 12.03 (1H, s), 14.29 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 120 | 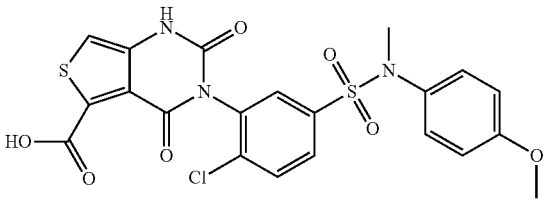 [SMILES: COc1ccc(N(C)S(=O)(=O)c2ccc(Cl)c(-n3c(=O)[nH]c4csc(C(=O)O)c4c3=O)c2)cc1] | (DMSO-d6) 3.12 (3H, s), 3.73 (3H, s), 6.85-6.9 (2H, m), 6.95-7.0 (2H, m), 7.39 (1H, s), 7.68 (1H, dd, J = 8.4 Hz), 2.3 Hz), 7.85-7.95 (2H, m), 12.03 (1H, s), 14.3 (1H, s) |
| 121 | 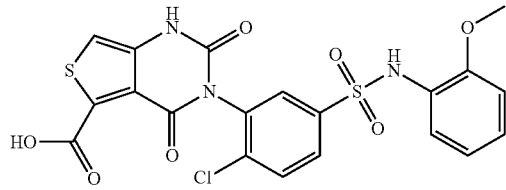 [SMILES: COc1ccccc1NS(=O)(=O)c1ccc(Cl)c(-n2c(=O)[nH]c3csc(C(=O)O)c3c2=O)c1] | (DMSO-d6) 3.51 (3H, s), 6.85-6.95 (2H, m), 7.15-7.25 (2H, m), 7.38 (1H, s), 7.7-7.8 (1H, m), 7.85-7.95 (1H, m), 7.95-8.0 (1H, m), 9.74 (1H, s), 12.02 (1H, s), 13.5-15.0 (1H, br) |
| 122 | 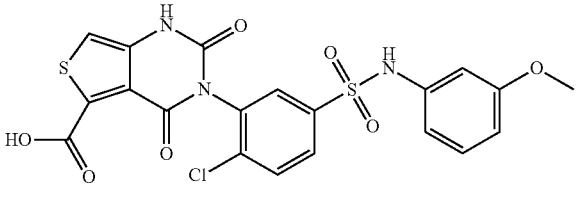 [SMILES: COc1cccc(NS(=O)(=O)c2ccc(Cl)c(-n3c(=O)[nH]c4csc(C(=O)O)c4c3=O)c2)c1] | (DMSO-d6) 3.67 (3H, s), 6.6-6.75 (3H, m), 7.1-7.2 (1H, m), 7.38 (1H, s), 7.84 (1H, dd, J = 8.5 Hz, 2.2 Hz), 7.89 (1H, d, J = 8.5 Hz), 8.13(1H, d, J = 2.2 Hz), 10.49 (1H, s), 12.04 (1H, s), 14.22 (1H, s) |
| 123 | 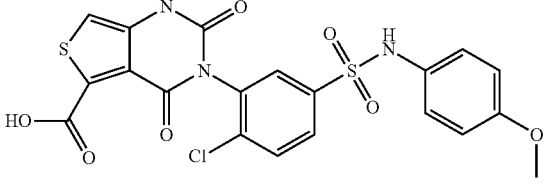 | (DMSO-d6) 3.69 (3H, s), 6.83 (2H, d, J = 8.9 Hz), 6.99 (2H, d, J = 8.9 Hz), 7.38 (1H, s), 7.75 (1H, dd, J = 8.5 Hz, 2.0 Hz), 7.88 (1H, d, J = 8.5 Hz), 7.99 (1H, d, J = 2.0 Hz), 10.08 (1H, s), 12.03 (1H, s), 14.24 (1H, s) |
| 124 | 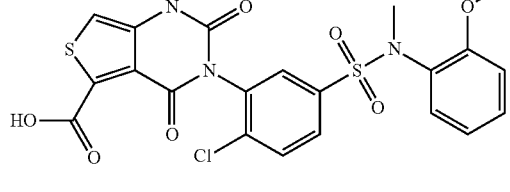 | (DMSO-d6) 3.17 (3H, s), 3.47 (3H, s), 6.9-7.0 (2H, m), 7.15-7.2 (1H, m), 7.25-7.35 (1H, m), 7.39 (1H, s), 7.71 (1H, dd, J = 8.6 Hz, 2.2 Hz), 7.9 (1H, d, J = 8.6 Hz), 8.02 (1H, d, J = 2.2 Hz), 12.02 (1H, s), 14.31 (1H, s) |
| 125 | 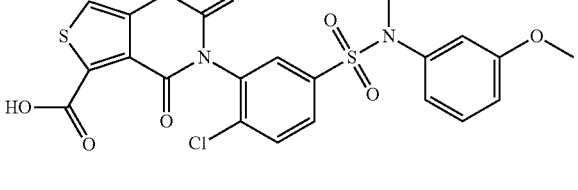 | (DMSO-d6) 3.18 (3H, s), 3.69 (3H, s), 6.55-6.7 (2H, m), 6.8-6.9 (1H, m), 7.2-7.3 (1H, m), 7.35-7.4 (1H, m), 7.6-7.7 (1H, m), 7.85-8.05 (2H, m), 12.04 (1H, s), 14.26 (1H, s) |
| 126 | 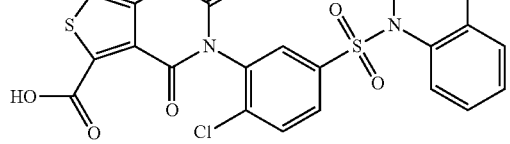 | (DMSO-d6) 3.18 (3H, s), 7.1-7.35 (3H, m), 7.35-7.45 (2H, m), 7.81 (1H, d, J =2.3 Hz), 7.95 (1H, d, J = 8.5 Hz), 8.03 (1H, d, J = 2.3 Hz), 12.03 (1H, s), 14.29 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 127 | | (DMSO-d6) 3.19 (3H, s), 6.95-7.05 (2H, m), 7.1-7.2 (1H, m), 7.35-7.45 (2H, m), 7.7-7.75 (1H, m), 7.9-8.0 (2H, m), 12.04 (1H, s), 14.27 (1H, s) |
| 128 | | (DMSO-d6) 3.15 (3H, s), 7.05-7.25 (4H, m), 7.38 (1H, s), 7.69 (1H, dd, J = 8.5 (1H, d, J = 8.5 Hz), 12.05 (1H, s), 14.29 (1H, s) |
| 129 | | (DMSO-d6) 3.15 (3H, s), 7.1-7.15 (2H, m), 7.35-7.45 (3H, m), 7.7 (1H, dd, J = 8.6 Hz, 2.1 Hz), 7.9-7.95 (2H, m), 12.05 (1H, s), 14.28 (1H, s) |
| 130 | | (DMSO-d6) 3.19 (3H, s), 7.05-7.1 (1H, m), 7.2-7.25 (1H, m), 7.35-7.45 (3H, m), 7.72 (1H, dd, J = 8.5 Hz, 2.1 Hz), 7.9-8.0 (2H, m), 12.06 (1H, s), 14.3 (1H, s) |
| 131 | | (DMSO-d6) 3.16 (3H, s), 7.0-7.1 (1H, m), 7.25-7.45 (3H, m), 7.55-7.6 (1H, m), 7.85-7.9 (1H, m), 7.97 (1H, d, J = 8.5 Hz), 8.1 (1H, s), 12.06 (1H, s), 14.31 (1H, s) |
| 132 | | (DMSO-d6) 3.13 (3H, s), 7.0-7.1 (1H, m), 7.3-7.4 (2H, m), 7.45-7.55 (2H, m), 7.86 (1H, dd, J = 8.5 Hz, 2.4 Hz), 7.98 (1H, d, J = 8.5 Hz), 8.02 (1H, d, J = 2.4 Hz), 12.03 (1H, s), 14.3 (1H, s) |
| 133 | | (DMSO-d6) 3.17 (3H, s), 7.2-7.3 (2H, m), 7.3-7.4 (3H, m), 7.71 (1H, dd, J = 8.5 Hz, 2.1 Hz), 7.9 (1H, d, J = 2.1 Hz), 7.93 (1H, d, J = 8.5 Hz), 12.0 (1H, s), 14.25 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 134 | 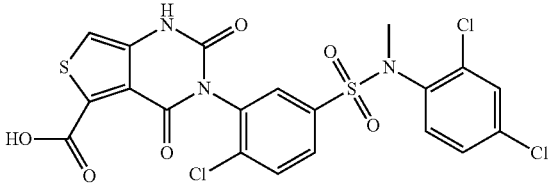 [SMILES: CN(c1ccc(Cl)cc1Cl)S(=O)(=O)c1ccc(Cl)c(-n2c(=O)[nH]c3csc(C(=O)O)c3c2=O)c1] | (DMSO-d6) 3.15 (3H, s), 7.06 (1H, d, J = 8.5 Hz), 7.35-7.45 (2H, m), 7.76 (1H, d, J = 2.4 Hz), 7.85-7.9 (1H, m), 7.97 (1H, d, J = 8.54 Hz), 8.07 (1H, d, J = 2.2 Hz), 12.03 (1H, s), 14.27 (1H, s) |
| 135 | 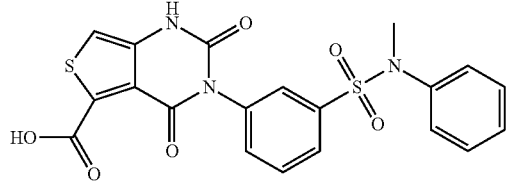 [SMILES: CN(c1ccccc1)S(=O)(=O)c1cccc(-n2c(=O)[nH]c3csc(C(=O)O)c3c2=O)c1] | (DMSO-d6) 3.16 (3H, s), 7.05-7.1 (2H, m), 7.25-7.4 (4H, m), 7.55-7.65 (1H, m), 7.7-7.8 (3H, m), 11.95 (1H, s), 14.77 (1H, s) |
| 136 | 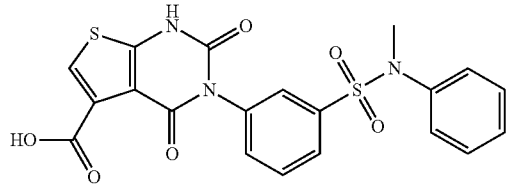 [SMILES: CN(c1ccccc1)S(=O)(=O)c1cccc(-n2c(=O)[nH]c3scc(C(=O)O)c3c2=O)c1] | (DMSO-d6) 3.16 (3H, s), 7.05-7.1 (2H, m), 7.25-7.4 (3H, m), 7.55-7.65 (1H, m), 7.7-7.8 (3H, m), 7.98 (1H, s), 12.95 (1H, s), 14.31 (1H, s) |
| 137 | 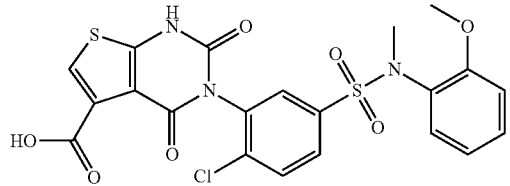 [SMILES: COc1ccccc1N(C)S(=O)(=O)c1ccc(Cl)c(-n2c(=O)[nH]c3scc(C(=O)O)c3c2=O)c1] | (DMSO-d6) 3.16 (3H, s), 3.47 (3H, s), 6.85-7.0 (2H, m), 7.1-7.2 (1H, m), 7.25-7.35 (1H, m), 7.69 (1H, dd, J = 8.4 Hz, 2.1 Hz), 7.85-7.95 (2H, m), 7.99 (1H, d, J = 2.1 Hz), 12.5-13.5 (1H, br), 13.83 (1H, brs) |
| 138 | 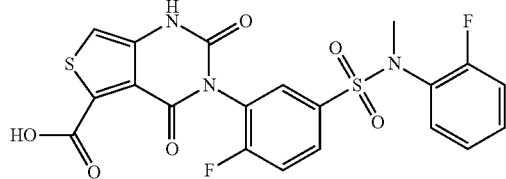 [SMILES: CN(c1ccccc1F)S(=O)(=O)c1ccc(F)c(-n2c(=O)[nH]c3csc(C(=O)O)c3c2=O)c1] | (DMSO-d6) 3.17 (3H, s), 7.1-7.25 (2H, m), 7.25-7.35 (1H, m), 7.35-7.45 (2H, m), 7.65-7.75 (1H, m), 7.8-7.9 (1H, m), 8.02 (1H, dd, J = 6.6 Hz, 2.3 Hz), 12.03 (1H, s), 14.31 (1H, s) |
| 139 | 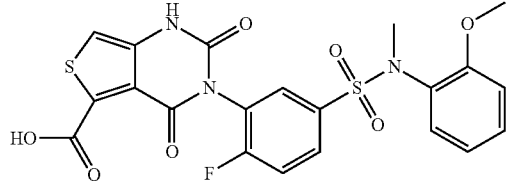 [SMILES: COc1ccccc1N(C)S(=O)(=O)c1ccc(F)c(-n2c(=O)[nH]c3csc(C(=O)O)c3c2=O)c1] | (DMSO-d6) 3.16 (3H, s), 3.47 (3H, s), 6.9-7.0 (2H, m), 7.19 (1H, dd, J = 8.0 Hz, 1.5 Hz), 7.3-7.35 (1H, m), 7.37 (1H, s), 7.6-7.7 (1H, m), 7.7-7.8 (1H, m), 8.0 (1H, dd, J = 6.6 Hz, 2.5 Hz), 12.02 (1H, s), 14.32 (1H, s) |
| 140 | 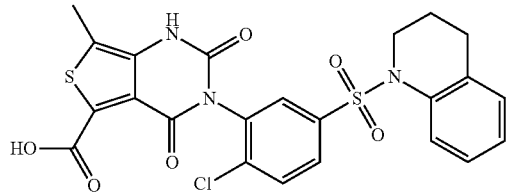 [SMILES: Cc1sc(C(=O)O)c2c(=O)n(-c3cc(S(=O)(=O)N4CCCc5ccccc54)ccc3Cl)c(=O)[nH]c12] | (DMSO-d6) 1.6-1.7 (2H, m), 2.45-2.55 (5H, m), 3.7-3.8 (2H, m), 7.05-7.25 (3H, m), 7.56 (1H, d, J = 8.5 Hz), 7.6-7.65 (1H, m), 7.84 (1H, d, J = 8.5 Hz), 8.1 (1H, d, J = 2.4 Hz), 11.94 (1H, s), 14.22 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported ¹H NMR spectral properties |
|---|---|---|
| 141 | | (CD3OD) 3.36 (3H, s), 3.54 (3H, s), 4.01 (3H, s), 6.85-6.95 (2H, m), 7.15-7.35 (4H, m), 7.69 (1H, d, J = 8.4 Hz) |
| 142 | | (DMSO-d6) 3.3 (3H, s), 3.87 (3H, s), 7.15-7.4 (6H, m), 7.42 (1H, d, J = 11.7 Hz), 7.92 (1H, d, J = 8.3 Hz), 11.95 (1H, s), 14.39 (1H, s) |
| 143 | | (DMSO-d6) 3.17 (3H, s), 7.05-7.15 (2H, m), 7.25-7.4 (4H, m), 7.6-7.75 (2H, m), 7.9-8.0 (1H, m), 12.02 (1H, s), 14.29 (1H, s) |
| 144 | | (DMSO-d6) 4.42 (2H, s), 7.2-7.45 (6H, m), 7.86 (1H, d, J = 8.5 Hz), 8.2 (1H, dd, J = 8.5 Hz, 2.2 Hz), 8.29 (1H, d, J = 2.2 Hz), 12.06 (1H, brs), 14.32 (1H, brs) |
| 145 | | (DMSO-d6) 1.4-1.5 (3H, m), 4.9-5.0 (1H, m), 7.15-7.45 (6H, m), 7.7-7.8 (1H, m), 8.1-8.15 (1H, m), 8.2-8.3 (1H, m), 12.0-12.1 (1H, m), 14.2-14.35 (1H, m) |
| 146 | | (DMSO-d6) 1.57 (6H, s), 7.25-7.45 (7H, m), 7.5-7.6 (1H, m), 7.9-8.0 (1H, m), 11.9-12.1 (1H, br), 14.2-14.4 (1H, br) |
| 147 | | (DMSO-d6) 1.55 (3H, s), 1.57 (3H, s), 3.33 (3H, s), 6.8-6.85 (1H, m), 7.0-7.1 (1H, m), 7.2-7.3 (1H, m), 7.3-7.5 (3H, m), 7.5-7.55 (1H, m), 7.94 (1H, d, J = 2.4 Hz), 12.0 (1H, s), 14.37 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 148 | | (DMSO-d6) 1.6 (3H, s), 1.62 (3H, s), 7.0-7.15 (1H, m), 7.25-7.4 (3H, m), 7.47 (1H, dd, J = 8.7 Hz, 2.0 Hz), 7.57 (1H, d, J = 8.7 Hz), 7.65- 7.75 (1H, m), 8.01 (1H, d, J = 2.0 Hz), 12.03 (1H, s), 14.3 (1H, brs) |
| 149 | | (DMSO-d6) 4.42 (2H, s), 7.2-7.35 (5H, m), 7.86 (1H, d, J = 8.5 Hz), 7.94 (1H, s), 8.15-8.3 (2H, m), 13.84 (1H, s) |
| 150 | | (DMSO-d6) 1.55 (6H, s), 7.25-7.55 (8H, m), 7.6-7.65 (1H, m), 11.99 (1H, s), 14.46 (1H, brs) |
| 151 | | (DMSO-d6) 1.49 (3H, s), 1.5 (3H, s), 3.66 (3H, s), 6.55-6.65 (1H, m), 6.75-6.85 (1H, m), 6.95-7.05 (1H, m), 7.25-7.5 (4H, m), 7.5-7.6 (1H, m), 11.99 (1H, s), 14.5 (1H, s) |
| 152 | | (DMSO-d6) 1.536 (3H, s), 1.543 (3H, s), 3.61 (3H, s), 6.75-6.85 (2H, m), 7.3-7.4 (3H, m), 7.45-7.6 (2H, m), 11.98 (1H, s), 14.5 (1H, s) |
| 153 | | (DMSO-d6) 1.49 (3H, s), 1.5 (3H, s), 3.66 (3H, s), 6.55-6.65 (1H, m), 6.75-6.85 (1H, m), 6.95-7.05 (1H, m), 7.25-7.55 (4H, m), 7.94 (1H, s), 12.8-13.1 (1H, br), 14.01 (1H, s) |
| 154 | | (DMSO-d6) 5.15 (2H, s), 6.9-7.1 (3H, m), 7.25-7.35 (2H, m), 7.4 (1H, s), 7.55-7.65 (1H, m), 7.65-7.75 (2H, m), 12.05 (1H, s), 14.42 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported ¹H NMR spectral properties |
|---|---|---|
| 155 | | (DMSO-d6) 2.85-2.95 (4H, m), 7.1-7.6 (9H, m), 12.04 (1H, s), 14.46 (1H, s) |
| 156 | | (DMSO-d6) 2.8-3.0 (4H, m), 7.15-7.45 (9H, m), 12.03 (1H, s), 14.46 (1H, brs) |
| 157 | | (DMSO-d6) 2.8-2.9 (4H, m), 3.79 (3H, s), 6.8-6.9 (1H, m), 6.9-7.0 (1H, m), 7.1-7.25 (2H, m), 7.25-7.45 (4H, m), 12.02 (1H, s), 14.48 (1H, brs) |
| 158 | | (DMSO-d6) 2.85-3.0 (4H, m), 7.05-7.2 (2H, m), 7.2-7.45 (6H, m), 12.03 (1H, s), 14.46 (1H, brs) |
| 159 | | (DMSO-d6) 2.8-2.95 (4H, m), 3.72 (3H, s), 6.7-6.85 (3H, m), 7.15-7.25 (1H, m), 7.25-7.45 (4H, m), 11.95-12.1 (1H, br), 14.35-14.55 (1H, br) |
| 160 | | (DMSO-d6) 2.75-2.95 (4H, m), 3.71 (3H, s), 6.8-6.9 (2H, m), 7.1-7.2 (2H, m), 7.25-7.45(4H, m), 12.01 (1H, brs), 14.4-14.55 (1H, br) |
| 161 | | (DMSO-d6) 2.85-3.0 (4H, m), 6.95-7.05 (1H, m), 7.05-7.15 (2H, m), 7.25-7.45 (5H, m), 12.03 (1H, brs), 14.3-14.6 (1H, br) |

TABLE 1-continued

Exemplary Thieno[3,4d]pyrimidine GnRH Antagonists Useful for the Treatment of Adenomyosis and Rectovaginal Endometriosis

| No. | Compound | Reported ¹H NMR spectral properties |
|---|---|---|
| 162 | | (DMSO-d6) 2.8-2.95 (4H, m), 7.05-7.15 (2H, m), 7.2-7.45 (6H, m), 12.03 (1H, brs), 14.3-14.6 (1H, br) |
| 163 | | (DMSO-d6) 2.28 (3H, s), 2.8-2.9 (4H, m), 7.05-7.25 (4H, m), 7.25-7.5 (4H, m), 12.04 (1H, brs), 14.47 (1H, brs) |
| 164 | | (DMSO-d6) 2.27 (3H, s), 2.8-2.95 (4H, m), 6.95-7.1 (3H, m), 7.1-7.2 (1H, m), 7.25-7.45 (4H, m), 12.03 (1H, brs), 14.47 (1H, brs) |
| 165 | | (DMSO-d6) 2.25 (3H, s), 2.8-2.95 (4H, m), 7.05-7.15 (4H, m), 7.25-7.45 (4H, m), 12.03 (1H, brs), 14.35-14.6 (1H, br) |
| 166 | | (DMSO-d6) 1.23 (3H, s), 1.25 (3H, s), 2.85 (2H, s), 3.67 (3H, s), 6.7-6.8 (2H, m), 6.85-6.95 (1H, m), 7.1-7.2 (1H, m), 7.25-7.35 (1H, m), 7.35-7.45 (2H, m), 7.5-7.6 (1H, m), 12.0 (1H, s), 14.55 (1H, s) |
| 167 | | (DMSO-d6) 2.65-2.75 (2H, m), 2.8-2.9 (2H, m), 3.75 (6H, s), 6.55-6.7 (2H, m), 7.1-7.2 (1H, m), 7.25-7.45 (4H, m), 12.0 (1H, s), 14.48 (1H, brs) |
| 168 | | (DMSO-d6) 2.8-2.95 (4H, m), 3.77 (3H, s), 6.9-7.1 (3H, m), 7.25-7.45 (4H, m), brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 169 | 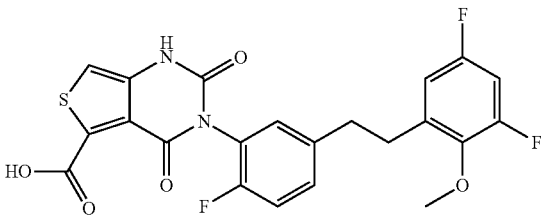 | (DMSO-d6) 2.85-2.95 (4H, m), 3.75 (3H, s), 6.9-7.05 (1H, m), 7.05-7.2 (1H, m), 7.3-7.45 (4H, m), 12.01 (1H, s), 14.45 (1H, brs) |
| 170 | 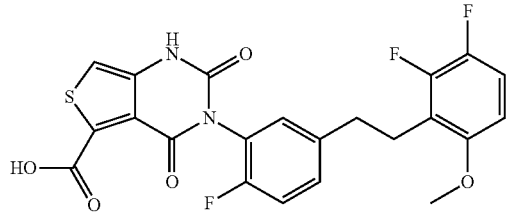 [SMILES: COc1ccc(F)c(F)c1CCc1ccc(F)c(-n2c(=O)[nH]c3csc(C(=O)O)c3c2=O)c1] | (DMSO-d6) 2.75-2.85 (2H, m), 2.85-2.95 (2H, m), 3.77 (3H, s), 6.75-6.85 (1H, m), 7.15-7.35 (4H, m), 7.37 (1H, s), 11.99 (1H, s), 14.46 (1H, brs) |
| 171 | 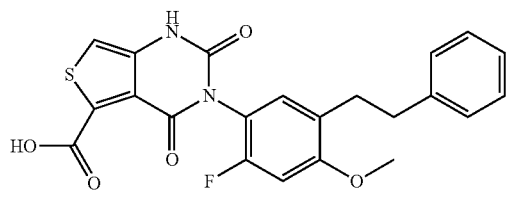 [SMILES: COc1cc(F)c(-n2c(=O)[nH]c3csc(C(=O)O)c3c2=O)cc1CCc1ccccc1] | (DMSO-d6) 2.75-2.9 (4H, m), 3.86 (3H, s), 7.08 (1H, d, J = 12.2 Hz), 7.15-7.35 (6H, m), 7.38 (1H, s), 11.97 (1H, s), 14.55 (1H, brs) |
| 172 | 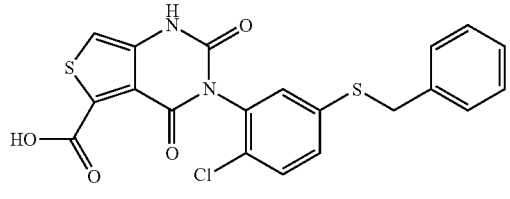 [SMILES: O=C(O)c1scc2[nH]c(=O)n(-c3cc(SCc4ccccc4)ccc3Cl)c(=O)c12] | (DMSO-d6) 4.28 (2H, s), 7.2-7.35 (3H, m), 7.35-7.5 (4H, m), 7.58 (1H, d, J = 8.5 Hz), 7.66 (1H, d, J = 2.2 Hz), 12.06 (1H, s), 14.41 (1H, s) |
| 173 | 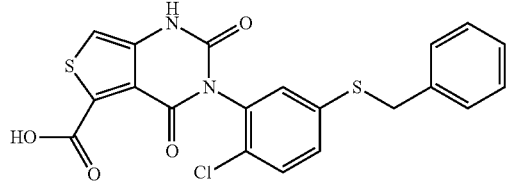 | (DMSO-d6) 4.29 (2H, s), 7.2-7.45 (6H, m), 7.57 (1H, d, J = 8.5 Hz), 7.64 (1H, d, J = 2.3 Hz), 7.94 (1H, s), 13.03 (1H, s), 13.94 (1H, s) |
| 174 | 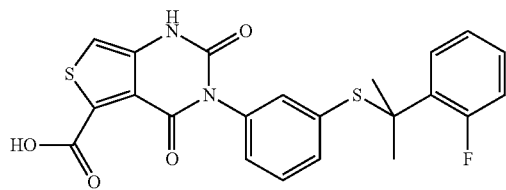 [SMILES: CC(C)(Sc1cccc(-n2c(=O)[nH]c3csc(C(=O)O)c3c2=O)c1)c1ccccc1F] | (DMSO-d6) 1.69 (6H, s), 7.0-7.2 (4H, m), 7.25-7.4 (5H, m), 11.89 (1H, s), 14.86 (1H, s) |
| 175 | 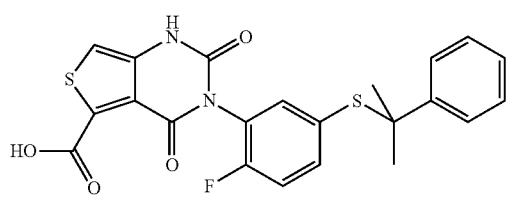 [SMILES: CC(C)(Sc1ccc(F)c(-n2c(=O)[nH]c3csc(C(=O)O)c3c2=O)c1)c1ccccc1] | (DMSO-d6) 4.24 (2H, s), 7.2-7.5 (8H, m), 7.62 (1H, dd, J = 6.7 Hz, 2.2 Hz), 12.05 (1H, s), 14.41 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 176 | 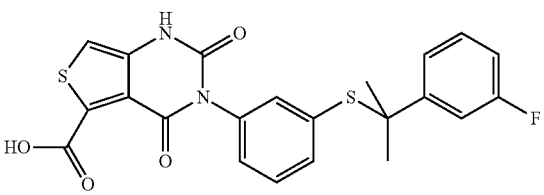 [SMILES: CC(C)(Sc1cccc(-n2c(=O)[nH]c3csc(C(=O)O)c3c2=O)c1)c1cccc(F)c1] | (DMSO-d6) 1.65 (6H, s), 7.0-7.1 (1H, m), 7.1-7.45 (8H, m), 11.88 (1H, s), 14.83 (1H, s) |
| 177 | 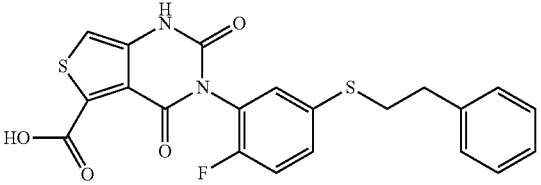 [SMILES: O=C(O)c1scc2[nH]c(=O)n(-c3cc(SCCc4ccccc4)ccc3F)c(=O)c12] | (DMSO-d6) 2.8-2.9 (2H, m), 3.15-3.25 (2H, m), 7.15-7.55 (8H, m), 7.58 (1H, dd, J = 6.8 Hz, 2.3 Hz) |
| 178 | 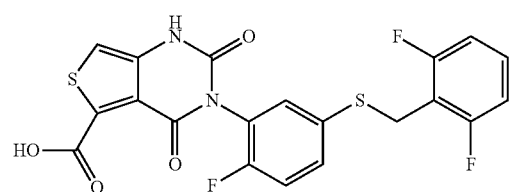 | (DMSO-d6) 4.21 (2H, s), 7.0-7.15 (2H, m), 7.3-7.45 (3H, m), 7.5-7.65 (2H, m), 12.0 (1H, s), 14.37 (1H, s) |
| 179 | 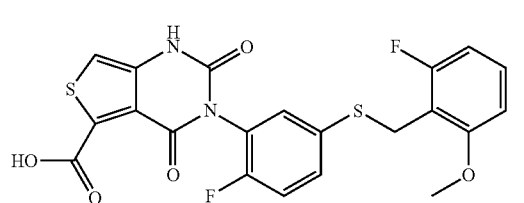 | (DMSO-d6) 3.76 (3H, s), 4.15 (2H, s), 6.75-6.9 (2H, m), 7.25-7.35 (2H, m), 7.35-7.45 (1H, m), 7.45-7.6 (2H, m) |
| 180 | 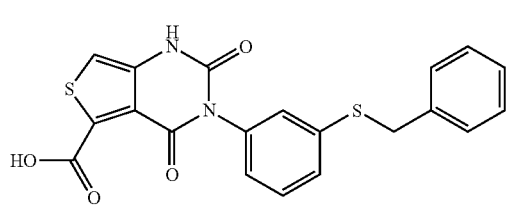 [SMILES: O=C(O)c1scc2[nH]c(=O)n(-c3cccc(SCc4ccccc4)c3)c(=O)c12] | (DMSO-d6) 4.27 (2H, s), 7.15-7.5 (10H, m), 11.93 (1H, s), 14.88 (1H, s) |
| 181 | 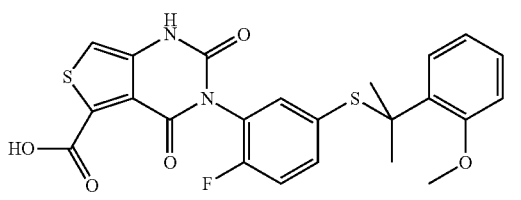 [SMILES: COc1ccccc1C(C)(C)Sc1ccc(F)c(-n2c(=O)[nH]c3csc(C(=O)O)c3c2=O)c1] | (DMSO-d6) 1.65-1.7 (6H, m), 3.86 (3H, s) 6.75-6.85 (1H, m), 7.0-7.15 (3H, m), 7.2-7.3 (2H, m), 7.37 (1H, s), 7.42 (1H, dd, J = 6.9 Hz, 2.2 Hz), 11.98 (1H, s), 14.38 (1H, s) |
| 182 | 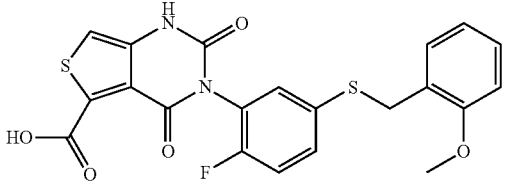 | (DMSO-d6) 3.79 (3H, s), 4.16 (2H, s), 6.8-6.9 (1H, m), 6.95-7.05 (1H, m), 7.2-7.3 (2H, m), 7.3-7.5 (3H, m), 7.59 (1H, dd, J = 7.0 hz, 2.2 Hz), 12.02 (1H, s), 14.39 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 183 | 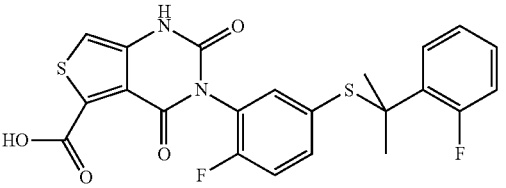 [SMILES: CC(C)(Sc1ccc(F)c(-n2c(=O)[nH]c3csc(C(=O)O)c3c2=O)c1)c1ccccc1F] | (DMSO-d6) 1.69 (6H, s), 7.0-7.35 (6H, m), 7.37 (1H, s), 7.46 (1H, dd, J = 6.7 Hz, 2.2 Hz), 11.98 (1H, s), 14.37 (1H, brs) |
| 184 | 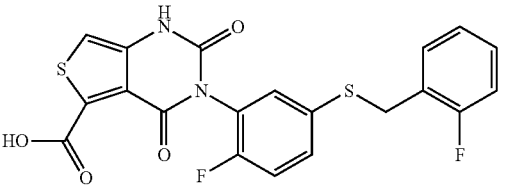 [SMILES: O=C(O)c1scc2[nH]c(=O)n(-c3cc(SCc4ccccc4F)ccc3F)c(=O)c12] | (DMSO-d6) 4.24 (2H, s), 7.05-7.25 (2H, m), 7.25-7.45 (4H, m), 7.45-7.55 (1H, m), 7.63 (1H, dd, J = 6.8 Hz, 2.5 Hz), 12.03 (1H, s), 14.38 (1H, s) |
| 185 | 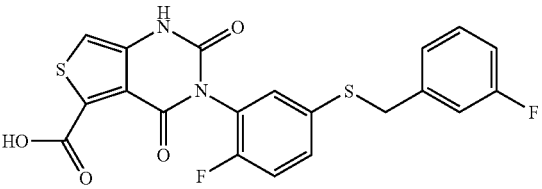 [SMILES: O=C(O)c1scc2[nH]c(=O)n(-c3cc(SCc4cccc(F)c4)ccc3F)c(=O)c12] | (DMSO-d6) 4.25 (2H, s), 7.0-7.1 (1H, m), 7.15-7.2 (2H, m), 7.25-7.5 (4H, m), 7.62 (1H, dd, J = 6.7 Hz, 2.3 Hz), 12.03 (1H, s), 14.37 (1H, s) |
| 186 | 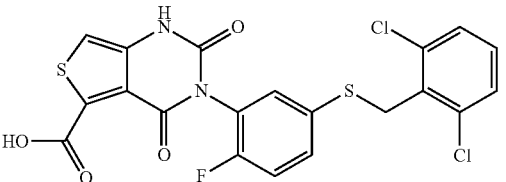 | (DMSO-d6) 4.4 (2H, s), 7.3-7.6 (6H, m), 7.65-7.75 (1H, m), 12.01 (1H, s), 14.37 (1H, s) |
| 187 | 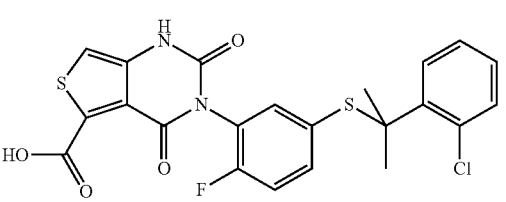 [SMILES: CC(C)(Sc1ccc(F)c(-n2c(=O)[nH]c3csc(C(=O)O)c3c2=O)c1)c1ccccc1Cl] | (DMSO-d6) 1.75-1.8 (6H, m), 7.05-7.15 (1H, m), 7.15-7.3 (4H, m), 7.37 (1H, s), 7.4-7.5 (2H, m), 11.97 (1H, s), 14.37 (1H, s) |
| 188 | 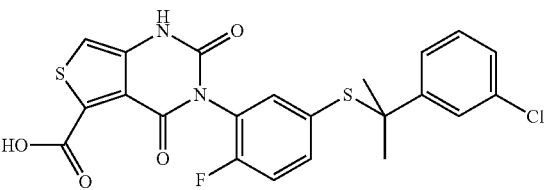 [SMILES: CC(C)(Sc1ccc(F)c(-n2c(=O)[nH]c3csc(C(=O)O)c3c2=O)c1)c1cccc(Cl)c1] | (DMSO-d6) 1.65 (6H, s), 7.15-7.25 (1H, m), 7.25-7.45 (6H, m), 7.5-7.6 (1H, m), 12.0 (1H, s), 14.38 (1H, s) |
| 189 | 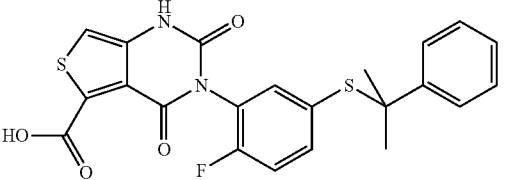 [SMILES: CC(C)(Sc1ccc(F)c(-n2c(=O)[nH]c3csc(C(=O)O)c3c2=O)c1)c1ccccc1] | (DMSO-d6) 1.64 (6H, s), 7.15-7.35 (5H, m), 7.37 (1H, s), 7.4-7.45 (2H, m), 7.52 (1H, dd, J = 7.3 Hz, 2.3 Hz), 11.99 (1H, s), 14.37 (1H, brs) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 190 | | (DMSO-d6) 1.75-1.85 (6H, m), 3.77 (3H, s), 6.6-6.7 (1H, m), 6.85 (1H, d, J = 8.1 Hz), 7.05-7.15 (1H, m), 7.2-7.35 (2H, m), 7.37 (1H, s), 7.4-7.45 (1H, m), 11.97 (1H, s), 14.4 (1H, brs) |
| 191 | | (DMSO-d6) 1.65-1.7 (6H, m), 3.85 (3H, s), 6.75-6.8 (1H, m), 7.0-7.1 (2H, m), 7.1-7.2 (1H, m), 7.25-7.35 (1H, m), 7.37 (1H, s), 7.4 (1H, dd, J = 7.3 Hz, 2.2 hz), 11.98 (1H, s), 14.39 (1H, brs) |
| 192 | | (DMSO-d6) 1.81 (6H, s), 6.9-7.05 (2H, m), 7.1-7.2 (1H, m), 7.25-7.4 (3H, m), 7.45-7.5 (1H, m), 11.97 (1H, s), 14.38 (1H, brs) |
| 193 | | (DMSO-d6) 1.8-1.85 (6H, m), 3.76 (3H, s), 6.75-6.85 (1H, m), 7.15-7.45 (5H, m), 11.98 (1H, s), 14.38 (1H, brs) |
| 194 | | (DMSO-d6) 4.29 (2H, s), 7.2-7.35 (2H, m), 7.35-7.55 (5H, m), 7.6-7.7 (1H, m), 12.02 (1H, s), 14.38 (1H, brs) |
| 195 | | (DMSO-d6) 4.24 (2H, s), 7.25-7.5 (7H, m), 7.6-7.65 (1H, m), 12.03 (1H, s), 14.38 (1H, brs) |
| 196 | | (DMSO-d6) 3.73 (3H, s), 4.16 (2H, s), 6.75-6.85 (1H, m), 7.1-7.6 (5H, m) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 197 | | (DMSO-d6) 3.77 (3H, s), 4.15 (2H, s), 6.95-7.15 (3H, m), 7.35-7.5 (3H, m), 7.6-7.65 (1H, m), 1.26 (1H, s), 14.41 (1H, s) |
| 198 | | (DMSO-d6) 1.6-1.7 (6H, m), 7.0-7.1 (1H, m), 7.15-7.25 (3H, m), 7.3-7.4 (3H, m), 7.5-7.55 (1H, m), 12.01 (1H, s), 14.4 (1H, s) |
| 199 | | (DMSO-d6) 1.66 (3H, s), 1.67 (3H, s), 3.86 (3H, s), 7.0 (1H, d, J = 2.5 Hz), 7.06 (1H, d, J = 8.8 Hz), 7.1-7.2 (1H, m), 7.25-7.35 (2H, m), 7.38 (1H, s), 7.4-7.5 (1H, m), 12.01 (1H, s), 14.41 (1H, brs) |
| 200 | | (DMSO-d6) 1.75-1.9 (1H, m), 2.15-2.3 (1H, m), 2.4-2.65 (4H, m), 7.0-7.2 (4H, m), 7.2- 7.35 (3H, m), 7.37 (1H, s), 7.45-7.5 (1H, m), 11.98 (1H, s), 14.41 (1H, brs) |
| 201 | | (DMSO-d6) 2.05-2.25 (4H, m), 3.5-3.65 (2H, m), 3.85-3.95 (2H, m), 6.85-6.95 (1H, m), 7.15-7.4 (8H, m), 11.98(1H, s), 14.38 (1H, brs) |
| 202 | | (DMSO-d6) 1.73 (6H, s), 7.3-7.4 (7H, m), 7.5-7.6 (1H, m), 7.95 (1H, dd, J = 6.7 Hz, 2.2 Hz), 12.01 (1H, s), 14.25 (1H, s) |
| 203 | | (DMSO-d6) 1.7 (6H, s), 6.89 (1H, s), 7.2-7.4 (6H, m), 7.5-7.7 (3H, m) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 204 | 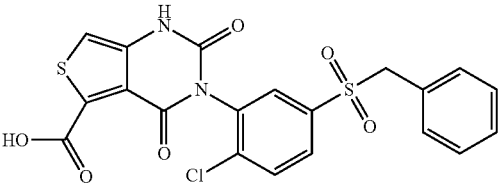 [SMILES: O=C(O)c1scc2[nH]c(=O)n(-c3cc(S(=O)(=O)Cc4ccccc4)ccc3Cl)c(=O)c12] | (DMSO-d6) 4.77 (2H, s), 7.15-7.25 (2H, m), 7.25-7.35 (3H, m), 7.39 (1H, s), 7.87 (1H, dd, J = 8.6 Hz, 2.2 Hz), 7.95 (1H, d, J = 8.6 Hz), 8.09 (1H, d, J = 2.2 Hz), 12.08 (1H, s), 14.26 (1H, s) |
| 205 | 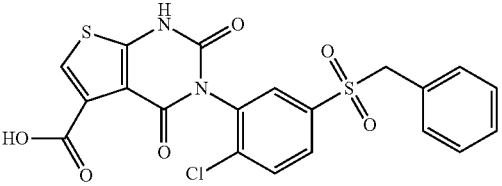 [SMILES: O=C(O)c1csc2[nH]c(=O)n(-c3cc(S(=O)(=O)Cc4ccccc4)ccc3Cl)c(=O)c12] | (DMSO-d6) 4.77 (2H, s), 7.15-7.25 (2H, m), 7.25-7.35 (3H, m), 7.8-8.0 (3H, m), 8.08 (1H, d, J = 2.3 Hz), 13.78 (1H, s) |
| 206 | 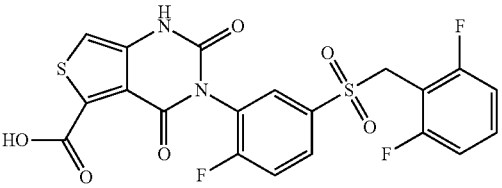 [SMILES: O=C(O)c1scc2[nH]c(=O)n(-c3cc(S(=O)(=O)Cc4c(F)cccc4F)ccc3F)c(=O)c12] | (DMSO-d6) 4.76 (2H, s), 7.05-7.15 (2H, m), 7.36 (1H, s), 7.4-7.55 (1H, m), 7.7-7.8 (1H, m), 7.95-8.1 (2H, m), 12.02 (1H, s), 14.26 (1H, s) |
| 207 | 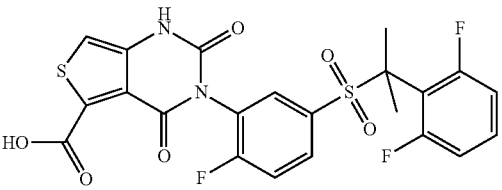 [SMILES: CC(C)(c1c(F)cccc1F)S(=O)(=O)c1ccc(F)c(-n2c(=O)[nH]c3csc(C(=O)O)c3c2=O)c1] | (DMSO-d6) 1.89 (6H, s), 7.0-7.1 (2H, m), 7.36 (1H, s), 7.4-7.5 (1H, m), 7.6-7.7 (2H, m), 8.0- 8.1 (1H, m), 12.0 (1H, s), 14.28 (1H, s) |
| 208 | 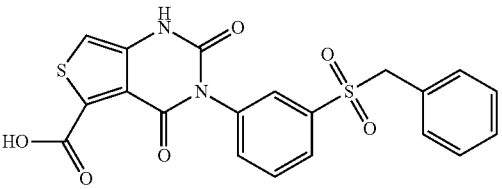 [SMILES: O=C(O)c1scc2[nH]c(=O)n(-c3cccc(S(=O)(=O)Cc4ccccc4)c3)c(=O)c12] | (DMSO-d6) 4.72 (2H, s), 7.15-7.25 (2H, m), 7.25-7.35 (3H, m), 7.39 (1H, s), 7.7-7.95 (4H, m), 11.97 (1H, s), 14.72 (1H, s) |
| 209 | 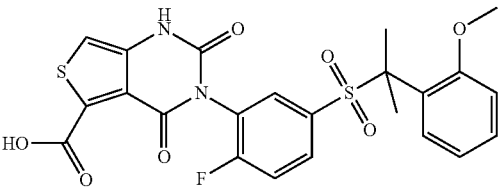 [SMILES: COc1ccccc1C(C)(C)S(=O)(=O)c1ccc(F)c(-n2c(=O)[nH]c3csc(C(=O)O)c3c2=O)c1] | (DMSO-d6) 1.86 (6H, s), 3.35 (3H, s), 6.83 (1H, d, J = 8.6 Hz), 6.9-7.0 (1H, m), 7.25-7.35 (2H, m), 7.37 (1H, s), 7.4-7.45 (1H, m), 7.5-7.6 (1H, m), 7.85-7.95 (1H, m), 12.0 (1H, s), 14.29 (1H, s) |
| 210 | 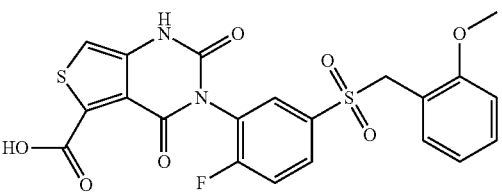 [SMILES: COc1ccccc1CS(=O)(=O)c1ccc(F)c(-n2c(=O)[nH]c3csc(C(=O)O)c3c2=O)c1] | (DMSO-d6) 3.46 (3H, s), 4.63 (2H, s), 6.85-6.95 (2H, m), 7.2-7.35 (2H, m), 7.37 (1H, s), 7.6-7.75 (2H, m), 7.9-8.0 (1H, m), 12.02 (1H, s), 14.26 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 211 | | (DMSO-d6) 1.81 (6H, s), 7.05-7.2 (2H, m), 7.3-7.45 (3H, m), 7.5-7.65 (2H, m), 7.98 (1H, dd, J =6.7 Hz, 2.3 Hz), 12.01 (1H, s), 14.27 (1H, s) |
| 212 | | (DMSO-d6) 4.81 (2H, s), 6.95-7.05 (2H, m), 7.1-7.2 (1H, m), 7.3-7.4 (2H, m), 7.7-7.75 (1H, m), 7.9-8.0 (1H, m), 8.04 (1H, dd, J = 6.8 Hz, 2.6 Hz), 12.05 (1H, s), 14.24 (1H, s) |
| 213 | | (DMSO-d6) 4.7-4.8 (2H, m), 7.1-7.3 (3H, m), 7.35-7.45 (2H, m), 7.65-7.75 (1H, m), 7.9-8.0 (1H, m), 8.05 (1H, dd, J = 6.8 Hz, 2.5 Hz), 12.03 (1H, s), 14.25 (1H, s) |
| 214 | | (DMSO-d6) 1.75-1.85 (6H, m), 7.05-7.2 (2H, m), 7.3-7.5 (4H, m), 7.6-7.8 (3H, m), 11.91 (1H, s), 14.72 (1H, s) |
| 215 | | (DMSO-d6) 4.74 (2H, s), 7.15-7.2 (2H, m), 7.25-7.35 (3H, m), 7.37 (1H, s), 7.65-7.75 (1H, m), 7.85-7.95 (1H, m), 8.07 (1H, dd, J = 6.6 Hz, 2.5 Hz), 12.04 (1H, s), 14.24 (1H, s) |
| 216 | | (DMSO-d6) 1.72 (6H, s), 7.1-7.25 (3H, m), 7.3-7.45 (3H, m), 7.6-7.7 (1H, m), 7.7-7.8 (2H, m), 11.92 (1H, s), 14.7 (1H, s) |
| 217 | | (DMSO-d6) 2.85-2.95 (2H, m), 3.65-3.75 (2H, m), 7.15-7.3 (5H, m), 7.37 (1H, s), 7.7-7.8 (1H, m), 8.1-8.15 (1H, m), 8.27 (1H, dd, J = 6.6 Hz, 2.6 Hz), 12.05 (1H, s), 14.23 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 218 | 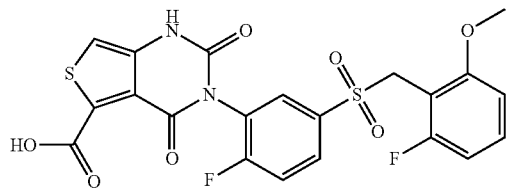 [SMILES: COc1cccc(F)c1CS(=O)(=O)c1ccc(F)c(-n2c(=O)[nH]c3csc(C(=O)O)c3c2=O)c1] | (DMSO-d6) 3.47 (3H, s), 4.62 (2H, s), 6.75 (1H, d, J = 8,4 Hz), 6.8-6.9 (1H, m), 7.3-7.4 (2H, m), 7.65-7.75 (1H, m), 7.8-7.9 (1H, m), 7.95-8.05(1H, m), 12.0 (1H, s), 14.27 (1H, brs) |
| 219 | 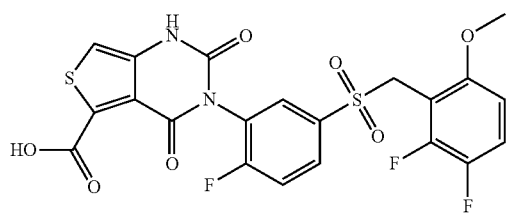 [SMILES: COc1ccc(F)c(F)c1CS(=O)(=O)c1ccc(F)c(-n2c(=O)[nH]c3csc(C(=O)O)c3c2=O)c1] | (DMSO-d6) 3.45 (3H, s), 4.68 (2H, s), 6.7-6.75 (1H, m), 7.35-7.45 (2H, m), 7.65-7.75 (1H, m), 7.85-8.0 (2H, m), 12.01 (1H, s), 14.25 (1H, brs) |
| 220 | 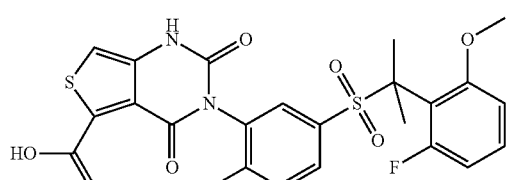 | (DMSO-d6) 1.9-2.0 (6H, m), 3.38 (3H, s), 6.65-6.8 (2H, m), 7.3-7.4 (2H, m), 7.4-7.5 (1H, m), 7.55-7.6 (1H, m), 7.95-8.0 (1H, m), 12.0 (1H, s), 14.28 (1H, brs) |
| 221 | 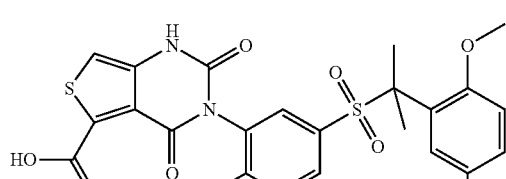 | (DMSO-d6) 1.85 (6H, s), 3.34 (3H, s), 6.84 (1H, dd, J = 9.1 Hz, 5.2 Hz), 7.1-7.25 (2H, m), 7.37 (1H, s), 7.4-7.45 (1H, m), 7.55-7.65 (1H, m), 7.9-8.0 (1H, m), 12.0 (1H, s), 14.29 (1H, brs) |
| 222 | 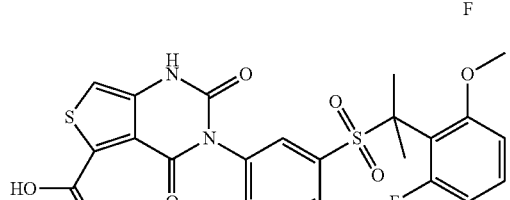 | (DMSO-d6) 1.9-2.0 (6H, m), 3.36 (3H, s), 6.65-6.7 (1H, m), 7.35-7.45 (2H, m), 7.5-7.65 (2H, m), 7.95-8.0 (1H, m), 12.0 (1H, s), 14.28 (1H, brs) |
| 223 | 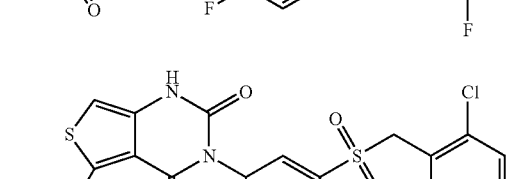 | (DMSO-d6) 4.85 (2H, s), 7.3-7.45 (5H, m), 7.65-7.75 (1H, m), 7.8-7.9 (1H, m), 8.05-8.1 (1H, m), 12.03 (1H, s), 14.25 (1H, brs) |
| 224 | 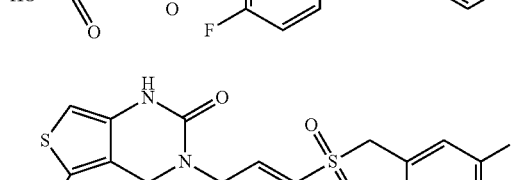 | (DMSO-d6) 4.81 (2H, s), 7.05-7.15 (1H, m), 7.25-7.45 (4H, m), 7.7-7.8 (1H, m), 7.9-8.0 (1H, m), 8.05-8.1 (1H, m), 12.05 (1H, s), 14.24 (1H, brs) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 225 | | (DMSO-d6) 1.95 (6H, s), 7.25-7.45 (5H, m), 7.5-7.65 (2H, m), 8.03 (1H, dd, J = 6.8 Hz, 2.4 Hz), 12.0 (1H, s), 14.28 (1H, s) |
| 226 | | (DMSO-d6) 1.72 (6H, s), 7.3-7.5 (6H, m), 7.55-7.65 (1H, m), 8.01 (1H, dd, J = 6.7 Hz, 2.3 Hz), 1202. (1H, s), 14.25 (1H, s) |
| 227 | | (DMSO-d6) 4.96 (2H, s), 7.35-7.45 (2H, m), 7.45-7.55 (2H, m), 7.65-7.75 (1H, m), 7.85- 7.95 (1H, m), 8.15-8.2 (1H, m), 12.05 (1H, s), 14.28 (1H, s) |
| 228 | | (DMSO-d6) 3.43 (3H, s), 4.6-4.7 (2H, m), 6.85-6.9 (1H, m), 7.1-7.2 (2H, m), 7.37 (1H, s), 7.65-7.7 (1H, m), 7.75-7.85 (1H, m), 7.9-8.0 (1H, m), 12.04 (1H, s), 14.29 (1H, s) |
| 229 | | (DMSO-d6) 1.72 (3H, s), 1.73 (3H, s), 7.15-7.25 (3H, m), 7.35-7.45 (2H, m), 7.45-7.55 (1H, m), 7.6 (1H, t, J = 9.1 Hz), 7.9-8.0 (1H, m), 1204. (1H, s), 14.28 (1H, brs) |
| 230 | | (DMSO-d6) 1.86 (6H, s), 6.87 (1H, d, J = 8.8 Hz), 7.35-7.45 (4H, m), 7.55-7.65 (1H, m), 7.95-8.0 (1H, m), 12.03 (1H, s), 14.3 (1H, brs) |
| 231 | | (DMSO-d6) 1.8-1.95 (1H, m), 2.0-2.15 (1H, m), 2.55-2.7 (2H, m), 3.0-3.15 (2H, m), 6.95-7.05 (2H, m), 7.2-7.35 (4H, m), 7.37 (1H, s), 7.45-7.55 (1H, m), 7.9-8.0 (1H, m), 12.0 (1H, s), 14.28 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 232 | 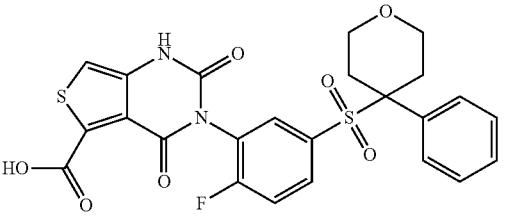 [SMILES: O=C(O)c1scc2[nH]c(=O)n(-c3cc(S(=O)(=O)C4(c5ccccc5)CCOCC4)ccc3F)c(=O)c12] | (DMSO-d6) 2.2-2.35 (2H, m), 3.05-3.2 (2H, m), 3.8-3.9 (2H, m), 7.2-7.4 (7H, m), 7.45-7.55 (1H, m), 7.8-7.9 (1H, m), 12.02 (1H, s), 14.25 (1H, brs) |
| 233 | 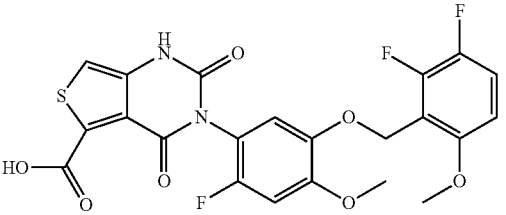 | (DMSO-d6) 3.75-3.85 (6H, m), 4.96 (2H, s), 6.85-6.95 (1H, m), 7.13 (1H, d, J = 11.3 Hz), 7.26 (1H, d, J = 7.2 Hz), 7.39 (1H, s), 7.4-7.55 (1H, m), 12.0 (1H, s), 14.53 (1H, s) |
| 234 | 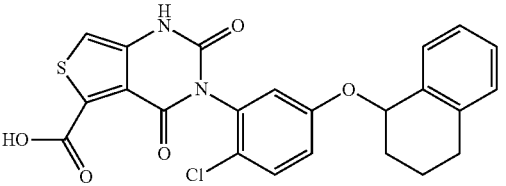 [SMILES: O=C(O)c1scc2[nH]c(=O)n(-c3cc(OC4CCCc5ccccc54)ccc3Cl)c(=O)c12] | (DMSO-d6) 1.7-2.1 (4H, m), 2.65-2.9 (2H, m), 5.45-5.5 (1H, m), 7.1-7.45 (7H, m), 7.57 (1H, d, J = 9.0 Hz), 12.0-12.1 (1H, m), 14.45 (1H, s) |
| 235 | 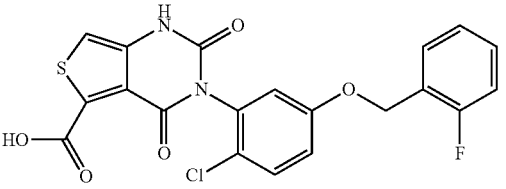 | (DMSO-d6) 5.14 (2H, s), 7.15-7.5 (6H, m), 7.55-7.65 (2H, m), 12.05 (1H, s), 14.43 (1H, s) |
| 236 | 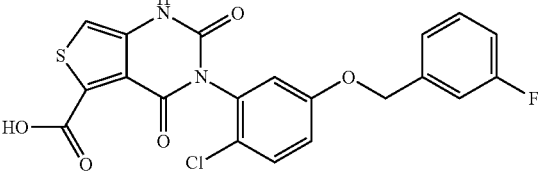 | (DMSO-d6) 5.14 (2H, s), 7.15-7.25 (2H, m), 7.25-7.5 (5H, m), 7.58 (1H, d, J = 9.1 Hz), 12.05 (1H, s), 14.43 (1H, s) |
| 237 | 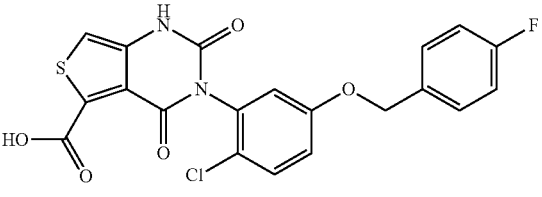 [SMILES: O=C(O)c1scc2[nH]c(=O)n(-c3cc(OCc4ccc(F)cc4)ccc3Cl)c(=O)c12] | (DMSO-d6) 5.09 (2H, s), 7.15-7.3 (3H, m), 7.32 (1H, d, J = 2.9 Hz), 7.41 (1H, s), 7.5-7.6 (3H, m), 12.04 (1H, s), 14.44 (1H, s) |
| 238 | 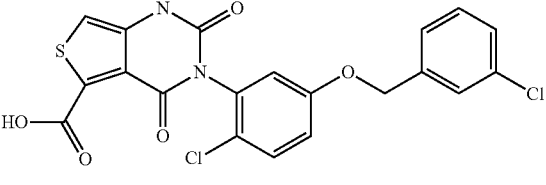 | (DMSO-d6) 5.13 (2H, s), 7.19 (1H, dd, J = 9.0 Hz, 3.0 Hz), 7.3-7.5 (5H, m), 7.5-7.6 (2H, m), 12.05 (1H, s), 14.44 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported ¹H NMR spectral properties |
|---|---|---|
| 239 | | (DMSO-d6) 3.76 (3H, s), 5.08 (2H, s), 6.85-6.95 (1H, m), 7.0-7.05 (2H, m), 7.18 (1H, dd, J = 9.1 Hz, 3.1 Hz), 7.25-7.35 (2H, m), 7.41 (1H, s), 7.57 (1H, d, J = 9.1 Hz), 12.04 (1H, s), 14.44 (1H, s) |
| 240 | | (DMSO-d6) 1.5-1.6 (3H, m), 5.45-5.55 (1H, m), 7.0-7.1 (1H, m), 7.23 (1H, dd, J = 6.1 Hz, 2.9 Hz), 7.25-7.5 (7H, m), 11.95-12.1 (1H, m), 14.42 (1H, s) |
| 241 | | (DMSO-d6) 1.5-1.6 (3H, m), 5.45-5.55 (1H, m), 7.0-7.1 (1H, m), 7.23 (1H, dd, J = 6.1 Hz, 2.9 Hz), 7.25-7.5 (7H, m), 11.95-12.1 (1H, m), 14.42 (1H, s) |
| 242 | | (DMSO-d6) 3.82 (3H, s), 5.04 (2H, s), 6.95-7.0 (1H, m), 7.06 (1H, d, J = 7.9 Hz), 7.17 (1H, dd, J = 9.1 Hz, 2.9 Hz), 7.3-7.45 (4H, m), 7.56 (1H, d, J = 9.1 Hz), 12.04 (1H, s), 14.46 (1H, s) |
| 243 | | (DMSO-d6) 3.76 (3H, s), 5.02 (2H, s), 6.9-7.0 (2H, m), 7.15-7.2 (1H, m), 7.3 (1H, d, J = 3.3 Hz), 7.35-7.45 (3H, m), 7.56 (1H, d, J = 9.0 Hz), 12.04 (1H, s), 14.46 (1H, s) |
| 244 | | (DMSO-d6) 5.18 (2H, s), 7.02 (1H, s), 7.16 (1H, dd, J = 9.0 Hz, 2.7 Hz), 7.25-7.4 (2H, m), 7.5-7.6 (2H, m), 7.8-7.9 (1H, m), 8.58 (1H, d, J = 4.5 Hz), 11.0-12.5 (1H, br) |
| 245 | | (DMSO-d6) 5.11 (2H, s), 7.15-7.2 (1H, m), 7.32 (1H, d, J = 2.9 Hz), 7.41 (1H, s), 7.45-7.55 (4H, m), 7.57 (1H, d, J = 8.6 Hz), 12.06 (1H, s), 14.43 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported ¹H NMR spectral properties |
|---|---|---|
| 246 | | (DMSO-d6) 5.16 (2H, s), 7.1-7.25 (2H, m), 7.31 (1H, d, J = 2.9 Hz), 7.4-7.5 (1H, m), 7.56 (1H, d, J = 9.0 Hz), 7.85-7.95 (1H, m), 8.5-8.6 (1H, m), 8.69 (1H, s), 11.0-13.0 (1H, br) |
| 247 | | (DMSO-d6) 2.1-2.25 (2H, m), 4.1-4.2 (1H, m), 4.25-4.35 (1H, m), 5.45-5.55 (1H, m), 6.8-6.95 (2H, m), 7.2-7.35 (3H, m), 7.35-7.45 (2H, m), 7.59 (1H, d, J = 8.7 Hz), 12.0-12.05 (1H, m), 14.42 (1H, s) |
| 248 | | (DMSO-d6) 5.2 (2H, s), 7.1-7.2 (2H, m), 7.3 (1H, d, J = 2.9 Hz) 7.4-7.5 (2H, m), 7.56 (1H, d, J = 8.8 Hz), 8.55-8.65 (2H, m), 11.0-13.0 (1H, br) |
| 249 | | (DMSO-d6) 1.6 (3H, d, J = 6.3 Hz), 5.65-5.75 (1H, m), 7.0-7.1 (1H, m), 7.15-7.3 (3H, m), 7.3-7.45 (2H, m), 7.45-7.55 (2H, m), 11.95-12.1 (1H, m), 14.42 (1H, s) |
| 250 | | (DMSO-d6) 1.5-1.6 (3H, m), 5.5-5.6 (1H, m), 7.0-7.15 (2H, m), 7.2-7.3 (3H, m), 7.35-7.55 (3H, m), 11.95-12.0 (1H, m), 14.41 (1H, s) |
| 251 | | (DMSO-d6) 1.5-1.6 (3H, m), 5.45-5.6 (1H, m), 7.0-7.1 (1H, m), 7.15-7.25 (3H, m), 7.4 (1H, d, J = 4.1 Hz), 7.45-7.55 (3H, m), 11.95-12.05 (1H, m), 14.42 (1H, s) |
| 252 | | (DMSO-d6) 1.35-1.5 (1H, m), 1.65-2.05 (5H, m), 2.8-3.0 (2H, m), 5.45-5.6 (1H, m), 7.05-7.2 (4H, m), 7.25-7.35 (2H, m), 8.8 Hz), 12.02 (1H, s), 14.43 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 253 | | (DMSO-d6) 1.73 (3H, d, J = 6.6 Hz), 6.07 (1H, q, J = 6.6 Hz), 6.89 (1H, dd, J = 9.0 Hz, 3.0 Hz), 7.15-7.2 (1H, m), 7.3-7.4 (2H, m), 7.45-7.55 (3H, m), 12.0 (1H, s), 14.4 (1H, s) |
| 254 | | (DMSO-d6) 1.53 (3H, d, J = 6.2 Hz), 5.68 (1H, q, J = 6.2 Hz), 6.85-7.0 (2H, m), 7.05 (1H, d, J = 8.4 Hz), 7.2 (1H, t, J = 3.2 Hz), 7.25-7.4 (3H, m), 7.47 (1H, d, J = 9.3 Hz), 12.01 (1H, s), 14.45 (1H, s) |
| 255 | | (DMSO-d6) 1.5-1.6 (3H, m), 3.7-3.75 (3H, m), 5.4-5.5 (1H, m), 6.8-6.9 (1H, m), 6.95-7.1 (3H, m), 7.2-7.3 (2H, m), 7.4 (1H, d, J = 3.4 Hz), 7.47 (1H, dd, J = 9.0 Hz, 1.6 Hz), 11.95-12.05 (1H m), 14.43 (1H, s) |
| 256 | | (DMSO-d6) 1.5-1.6 (3H, m), 3.73 (3H, s), 5.4-5.5 (1H, m), 6.85-6.95 (2H, m), 7.0-7.05 (1H, m), 7.15-7.25 (1H, m), 7.3-7.5 (4H, m), 11.95-12.05 (1H, m), 14.44 (1H, s) |
| 257 | | (DMSO-d6) 0.93 (3H, t, J = 7.5 Hz), 1.9-2.05 (1H, m), 2.1-2.25 (1H, m), 5.55 (1H, t, J = 7.3 Hz), 6.95-7.25 (4H, m), 7.35-7.5 (2H, m), 7.52 (1H, d, J = 8.7 Hz), 11.95-12.05 (1H, m), 14.4 (1H, s) |
| 258 | | (DMSO-d6) 0.93 (3H, t, J = 7.4 Hz), 1.9-2.05 (1H, m), 2.1-2.25 (1H, m), 5.5-5.6 (1H, m), 6.95-7.25 (4H, m), 7.35-7.5 (1H, m), 7.52 (1H, d, J = 9.2 Hz), 7.95 (1H, d, J = 6.7 Hz), 12.99 (1H, s), 13.8-14.0 (1H, m) |
| 259 | | (DMSO-d6) 1.55-1.65 (3H, m), 5.65-5.8 (1H, m), 6.9-7.0 (1H, m), 7.2-7.3 (1H, m), 7.35-7.45 (1H, m), 7.45-7.6 (2H, m), 7.7-7.85 (3H, m), 12.03 (1H, s), 14.41 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 260 | 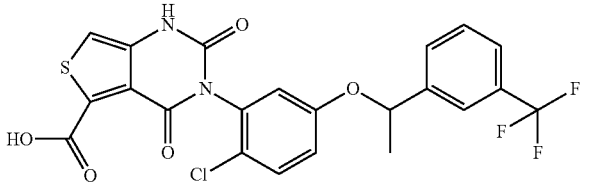 [SMILES: CC(Oc1ccc(Cl)c(-n2c(=O)[nH]c3csc(C(=O)O)c3c2=O)c1)c1cccc(C(F)(F)F)c1] | (DMSO-d6) 1.55-1.65 (3H, m), 5.6-5.7 (1H, m), 7.05-7.15 (1H, m), 7.25-7.3 (1H, m), 7.4 (1H, d, J = 5.6 Hz), 7.45-7.55 (1H, m), 7.55-7.85 (4H, m), 11.95-12.1 (1H, m), 14.4 (1H, s) |
| 261 | 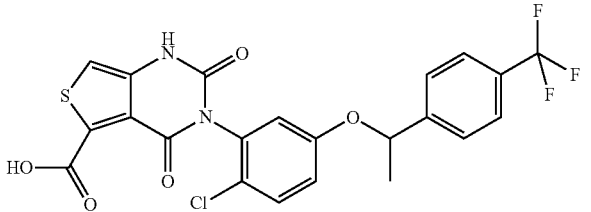 | (DMSO-d6) 1.55-1.65 (3H, m), 5.6-5.7 (1H, m), 7.0-7.1 (1H, m), 7.25 (1H, dd, J = 6.6 Hz, 3.0 Hz), 7.4 (1H, d, J = 5.3 Hz), 7.45-7.55 (1H, m), 7.6-7.7 (2H, m), 7.7-7.8 (2H, m), 11.95-12.1 (1H, m), 14.4 (1H, s) |
| 262 | 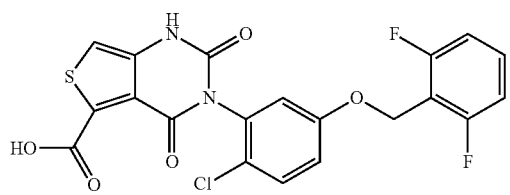 | (DMSO-d6) 5.13 (2H, s), 7.15-7.3 (3H, m), 7.34 (1H, d, J = 2.9 Hz), 7.4 (1H, s), 7.5-7.65 (2H, m), 12.03 (1H, s), 14.4 (1H, s) |
| 263 | 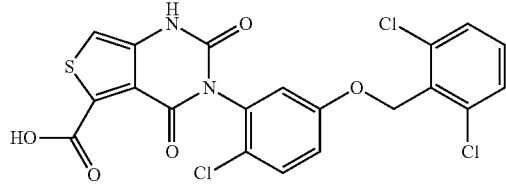 [SMILES: O=C(O)c1scc2[nH]c(=O)n(-c3cc(OCc4c(Cl)cccc4Cl)ccc3Cl)c(=O)c12] | (DMSO-d6) 5.24 (2H, s), 7.2-7.65 (7H, m), 12.02 (1H, s), 14.39 (1H, s) |
| 264 | 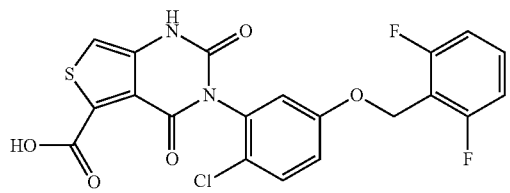 [SMILES: O=C(O)c1scc2[nH]c(=O)n(-c3cc(OCc4c(F)cccc4F)ccc3Cl)c(=O)c12] | (DMSO-d6) 5.12 (2H, s), 7.15-7.25 (3H, m), 7.32 (1H, d, J = 3.1 Hz), 7.5-7.65 (2H, m), 7.94 (1H, s), 12.8-13.2 (1H, br), 13.93 (1H, s) |
| 265 | 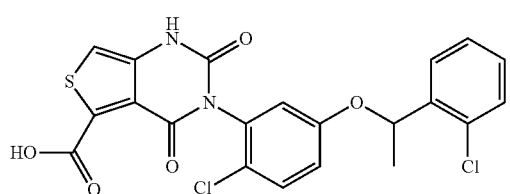 | (DMSO-d6) 1.59 (3H, d, J = 6.3 Hz), 5.71 (1H, q, J = 6.3 Hz), 6.85-6.95 (1H, m), 7.2-7.25 (1H, m), 7.3-7.45 (3H, m), 7.45-7.55 (3H, m), 11.95-12.05 (1H, m), 14.39 (1H, s) |
| 266 | 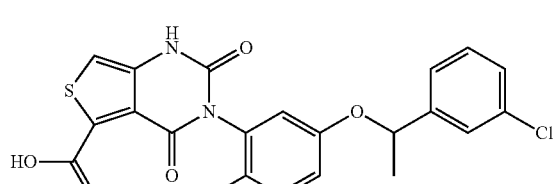 | (DMSO-d6) 1.56 (3H, d, J = 6.2 Hz), 5.45-5.6 (1H, m), 7.0-7.1 (1H, m), 7.2-7.55 (7H, m), 11.95-12.05 (1H, m), 14.39 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 267 | 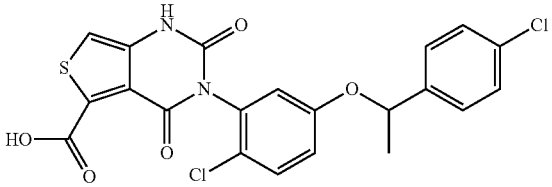 [SMILES: CC(Oc1ccc(Cl)c(-n2c(=O)[nH]c3csc(C(=O)O)c3c2=O)c1)c1ccc(Cl)cc1] | (DMSO-d6) 1.5-1.6 (3H, m), 5.45-5.6 (1H, m), 7.0-7.05 (1H, m), 7.22 (1H, dd, J = 8.9 Hz, 3.0 Hz), 7.35-7.5 (6H, m), 11.9-12.05 (1H, m), 14.39 (1H, s) |
| 268 | 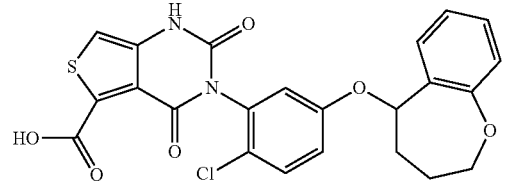 [SMILES: O=C(O)c1scc2[nH]c(=O)n(-c3cc(OC4CCCOc5ccccc54)ccc3Cl)c(=O)c12] | (DMSO-d6) 1.9-2.15 (4H, m), 3.75-3.85 (1H, m), 4.1-4.25 (1H, m), 5.45-5.55 (1H, m), 6.95-7.45 (7H, m), 7.53 (1H, d, J = 8.9 Hz), 11.95-12.05 (1H, m), 14.42 (1H, s) |
| 269 | 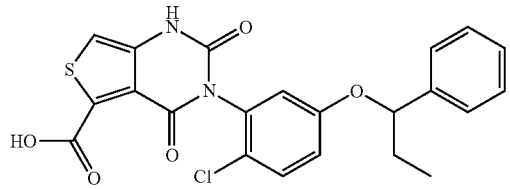 [SMILES: CCC(Oc1ccc(Cl)c(-n2c(=O)[nH]c3csc(C(=O)O)c3c2=O)c1)c1ccccc1] | (DMSO-d6) 0.91 (3H, t, J = 7.5 Hz), 1.75-2.0 (2H, m), 5.2-5.3 (1H, m), 6.95-7.05 (1H, m), 7.15-7.5 (8H, m), 11.95-12.05 (1H, m), 14.39 (1H, s) |
| 270 | 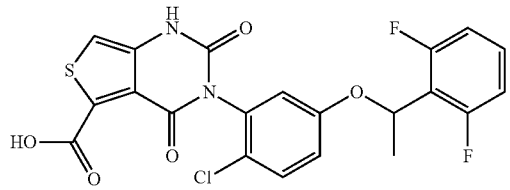 | (DMSO-d6) 1.71 (3H, d, J = 6.5 Hz), 5.81 (1H, q, J = 6.5 Hz), 7.0-7.15 (3H, m), 7.2-7.25 (1H, m), 7.35-7.5 (2H, m), 7.53 (1H, d, J = 9.2 Hz), 11.95-12.05 (1H, m), 14.41 (1H, s) |
| 271 | 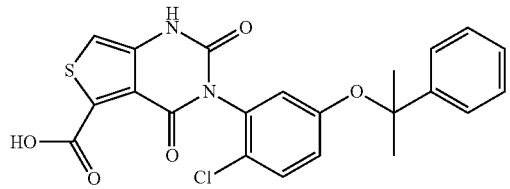 [SMILES: CC(C)(Oc1ccc(Cl)c(-n2c(=O)[nH]c3csc(C(=O)O)c3c2=O)c1)c1ccccc1] | (DMSO-d6) 1.65-1.75 (6H, m), 6.64 (1H, dd, J = 8.7 Hz, 2.8 Hz), 7.07 (1H, d, J = 2.8 Hz), 7.25-7.5 (7H, m), 11.97 (1H, s), 14.42 (1H, s) |
| 272 | 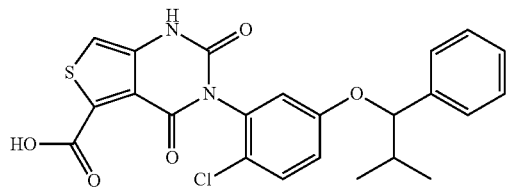 [SMILES: CC(C)C(Oc1ccc(Cl)c(-n2c(=O)[nH]c3csc(C(=O)O)c3c2=O)c1)c1ccccc1] | (DMSO-d6) 0.82 (3H, d, J = 6.4 Hz), 0.95-1.05 (3H, m), 2.05-2.15 (1H, m), 5.0-5.1 (1H, m), 6.95-7.05 (1H, m), 7.15-7.5 (8H, m), 11.95-12.05 (1H, m), 14.4 (1H, s) |
| 273 | 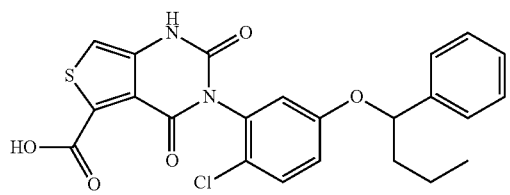 [SMILES: CCCC(Oc1ccc(Cl)c(-n2c(=O)[nH]c3csc(C(=O)O)c3c2=O)c1)c1ccccc1] | (DMSO-d6) 0.91 (3H, t, J = 7.4 Hz), 1.25-1.5 (2H, m), 1.7-1.8 (1H, m), 1.85-2.0 (1H, m), 5.3-5.35 (1H, m), 6.95-7.05 (1H, m), 7.15-7.5 (8H, m), 11.95-12.05 (1H, m), 14.41 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 274 | 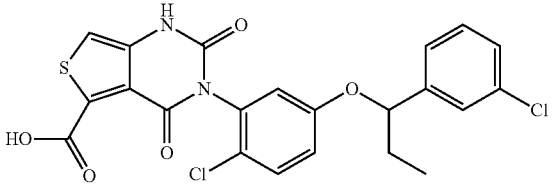 [SMILES: CCC(Oc1ccc(Cl)c(-n2c(=O)[nH]c3csc(C(=O)O)c3c2=O)c1)c1cccc(Cl)c1] | (DMSO-d6) 0.91 (3H, t, J = 7.4 Hz), 1.75-2.0 (2H, m), 5.25-5.35 (1H, m), 7.0-7.1 (1H, m), 7.2-7.25 (1H, m), 7.3-7.55 (6H, m), 11.95-12.05 (1H, m), 14.4 (1H, s) |
| 275 | 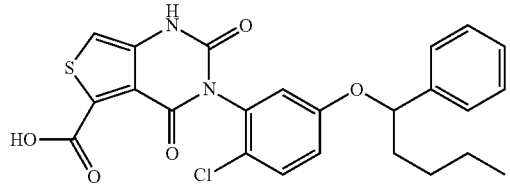 [SMILES: CCCCC(Oc1ccc(Cl)c(-n2c(=O)[nH]c3csc(C(=O)O)c3c2=O)c1)c1ccccc1] | (DMSO-d6) 0.85 (3H, t, J = 7.1 Hz), 1.2-1.45 (4H, m), 1.7-1.85 (1H, m), 1.9-2.0 (1H, m), 5.25-5.35 (1H, m), 6.95-7.05 (1H, m), 7.15-7.5 (8H, m), 11.95-12.05 (1H, m), 14.41 (1H, s) |
| 276 | 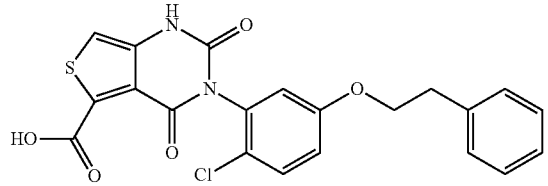 [SMILES: O=C(O)c1scc2[nH]c(=O)n(-c3cc(OCCc4ccccc4)ccc3Cl)c(=O)c12] | (DMSO-d6) 3.05 (2H, t, J = 7.0 Hz), 4.19 (2H, t, J = 7.0 Hz), 7.05-7.15 (1H, (1H, d, J = 9.2 Hz), 12.03 (1H, s), 14.45 (1H, s) |
| 277 | 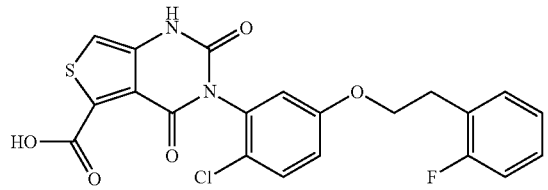 [SMILES: O=C(O)c1scc2[nH]c(=O)n(-c3cc(OCCc4ccccc4F)ccc3Cl)c(=O)c12] | (DMSO-d6) 3.09 (2H, t, J = 6.8 Hz), 4.19 (2H, t, J = 6.8 Hz), 7.05-7.35 (5H, m), 7.35-7.45 (2H, m), 7.54 (1H, d, J = 8.9 Hz), 12.03 (1H, s), 14.45 (1H, s) |
| 278 | 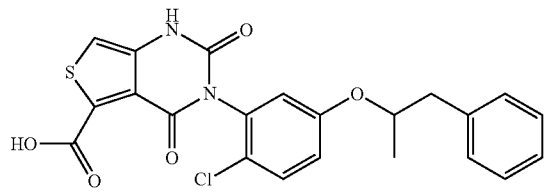 [SMILES: CC(Cc1ccccc1)Oc1ccc(Cl)c(-n2c(=O)[nH]c3csc(C(=O)O)c3c2=O)c1] | (DMSO-d6) 1.22 (3H, d, J = 6.0 Hz), 2.8-2.9 (1H, m), 2.95-3.05 (1H, m), 4.6-4.75 (1H, m), 7.09 (1H, dd, J = 9.0 Hz, 3.0 Hz), 7.15-7.35 (6H, m), 7.35-7.45 (1H, m), 7.52 (1H, d, J = 9.2 Hz), 12.02 (1H, s), 14.46 (1H, s) |
| 279 | 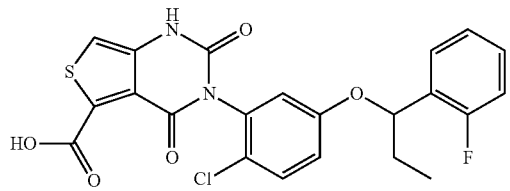 [SMILES: CCC(Oc1ccc(Cl)c(-n2c(=O)[nH]c3csc(C(=O)O)c3c2=O)c1)c1ccccc1F] | (DMSO-d6) 0.93 (3H, t, J = 7.5 Hz), 1.8-2.05 (2H, m), 5.47 (1H, t, J = 6.1 Hz), 6.95-7.05 (1H, m), 7.15-7.25 (3H, m), 7.3-7.55 (4H, m), 11.95-12.05 (1H, m), 14.35-14.45 (1H, m) |
| 280 | 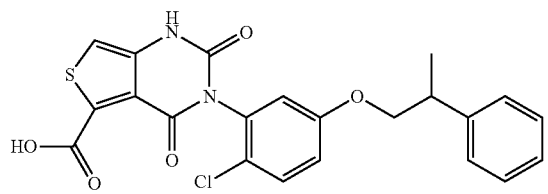 [SMILES: CC(COc1ccc(Cl)c(-n2c(=O)[nH]c3csc(C(=O)O)c3c2=O)c1)c1ccccc1] | (DMSO-d6) 1.32 (3H, d, J = 6.9 Hz), 3.15-3.3 (1H, m), 4.0-4.15 (2H, m), 7.09 (1H, dd, J = 8.9 Hz, 3.1 Hz), 7.15-7.45 (7H, m), 7.52 (1H, d, J = 8.9 Hz), 12.02 (1H, s), 14.45 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 281 | | (DMSO-d6) 0.93 (3H, t, J = 7.5 Hz), 1.8-2.05 (2H, m), 5.48 (1H, t, J = 6.5 Hz), 6.95-7.05 (1H, m), 7.15-7.25 (3H, m), 7.3-7.4 (1H, m), 7.4-7.55 (2H, m), 7.94 (1H, d, J = 3.4 Hz), 12.98 (1H, s), 13.93 (1H, s) |
| 282 | | (DMSO-d6) 1.32 (3H, d, J = 6.9 Hz), 3.15-3.3 (1H, m), 4.0-4.15 (2H, m), 7.05-7.1 (1H, m), 7.15-7.4 (6H, m), 7.52 (1H, d, J = 9.0 Hz), 7.95 (1H, s), 13.0 (1H, s), 13.98 (1H, s) |
| 283 | | (DMSO-d6) 5.15 (2H, s), 7.15-7.3 (4H, m), 7.35 (1H, d, J = 2.8 Hz), 7.46 (1H, s), 7.59 (1H, d, J = 8.8 Hz), 12.19 (1H, s) |
| 284 | | (DMSO-d6) 5.14 (2H, s), 7.2-7.5 (6H, m), 7.6 (1H, d, J = 8.7 Hz), 12.11 (1H, s), 14.44 (1H, s) |
| 285 | | (DMSO-d6) 1.4 (6H, s), 4.01 (2H, s), 7.05- 7.15 (1H, m), 7.15-7.25 (2H, m), 7.3-7.35 (2H, m), 7.39 (1H, s), 7.4-7.5 (2H, m), 7.52 (1H, d, J = 9.2 Hz), 12.0 (1H, s), 14.44 (1H, s) |
| 286 | | (DMSO-d6) 1.52 (3H, d, J = 6.3 Hz), 3.67 (3H, s), 3.75-3.85 (3H, m), 5.65 (1H, q, J = 6.3 Hz), 6.8-7.0 (4H, m), 7.15-7.25 (1H, m), 7.39 (1H, d, J = 1.9 Hz), 7.48 (1H, d, J = 8.9 Hz), 11.99 (1H, s), 14.42 (1H, s) |
| 287 | | (DMSO-d6) 1.55 (3H, d, J = 6.3 Hz), 3.31 (3H, s), 3.7-3.75 (3H, m), 5.35-5.45 (1H, m), 6.35-6.45 (1H, m), 6.5-6.6 (2H, m), 7.0-7.1 (1H, m), 7.2-7.3 (1H, m), 7.39 (1H, d, J = 2.0 Hz), 7.45-7.5 (1H, m), 11.95-12.05 (1H, m), 14.41 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported ¹H NMR spectral properties |
|---|---|---|
| 288 | | (DMSO-d6) 1.5-1.6 (3H, m), 3.81 (3H, s), 5.4-5.5 (1H, m), 7.0-7.3 (5H, m), 7.4 (1H, d, J = 3.9 Hz), 7.48 (1H, dd, J = 8.9 Hz, 1.6 Hz), 11.95-12.05 (1H, m), 14.41 (1H, s) |
| 289 | | (DMSO-d6) 1.58 (3H, d, J = 6.4 Hz), 3.75 (3H, s), 5.55-5.7 (1H, m), 6.75-6.9 (4H, m), 11.95-12.05 (1H, m), 14.42 (1H, s) |
| 290 | | (DMSO-d6) 1.75 (6H, s), 6.78 (1H, dd, J = 9.0 Hz, 3.0 Hz), 7.0-7.55 (7H, m), 11.91 (1H, brs), 14.0-14.8 (1H, br) |
| 291 | | (DMSO-d6) 0.8 (3H, t, J = 7.3 Hz), 1.65-1.7 (3H, m), 1.85-2.05 (2H, m), 6.55-6.65 (1H, m), 7.08 (1H, dd, J = 6.6 Hz, 3.0 Hz), 7.25-7.45 (7H, m), 11.97 (1H, s), 14.43 (1H, s) |
| 292 | | (DMSO-d6) 1.83 (6H, s), 6.69 (1H, dd, J = 9.1 Hz, 3.1 Hz), 7.06 (1H, d, J = 3.1 Hz), 7.3-7.5 (5H, m), 7.61 (1H, dd, J = 7.7 Hz, 1.8 Hz), 11.96 (1H, s), 14.42 (1H, s) |
| 293 | | (DMSO-d6) 5.15 (2H, s), 7.15-7.75 (7H, m), 12.03 (1H, s), 14.41 (1H, s) |
| 294 | | (DMSO-d6) 5.14 (2H, s), 7.23 (1H, dd, J = 8.8 Hz, 3.2 Hz), 7.3-7.45 (3H, m), 7.45-7.55 (1H, m), 7.59 (1H, d, J ? 9.1 Hz), 7.65-7.7 (1H, m), 12.03 (1H, s), 14.41 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 295 | 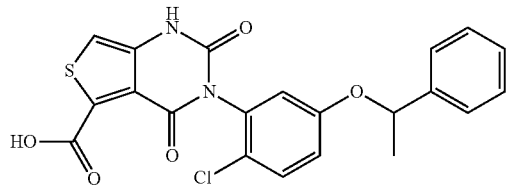 | (DMSO-d6) 1.56 (3H, d, J = 6.3 Hz), 5.45-5.55 (1H, m), 6.85-6.9 (1H, m), 6.95-7.05 (2H, m), 7.25-7.45 (7H, m), 11.9 (1H, s) |
| 296 | 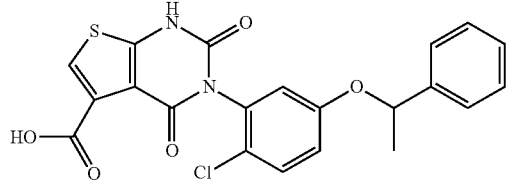 [SMILES: CC(Oc1ccc(Cl)c(-n2c(=O)[nH]c3scc(C(=O)O)c3c2=O)c1)c1ccccc1] | (DMSO-d6) 1.56 (3H, d, J = 6.4 Hz), 5.5 (1H, q, J = 6.4 Hz), 6.85-6.9 (1H, m), 6.9-7.05 (2H, m), 7.25-7.4 (4H, m), 7.4-7.45 (2H, m), 7.99 (1H, s), 12.86 (1H, s), 14.43 (1H, s) |
| 297 | 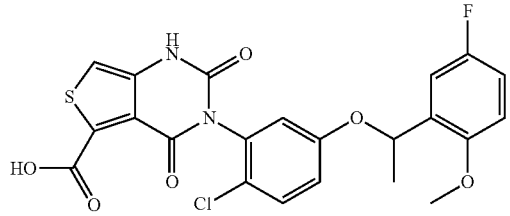 [SMILES: COc1ccc(F)cc1C(C)Oc1ccc(Cl)c(-n2c(=O)[nH]c3csc(C(=O)O)c3c2=O)c1] | (DMSO-d6) 1.52 (3H, d, J = 6.0 Hz), 3.84 (3H, s), 5.6-5.7 (1H, m), 6.85-7.55 (7H, m), 11.99 (1H, s), 14.42 (1H, s) |
| 298 | 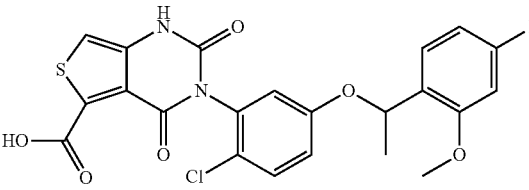 | (DMSO-d6) 1.52 (3H, d, J = 6.4 Hz), 3.85-3.9 (3H, m), 5.6-5.7 (1H, m), 6.75-6.8 (1H, m), 6.85-7.0 (2H, m), 7.15-7.25 (1H, m), 7.3-7.45 (2H, m), 7.48 (1H, d, J = 9.2 Hz), 12.0 (1H, s), 14.44 (1H, s) |
| 299 | 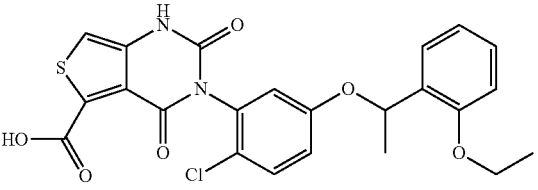 [SMILES: CCOc1ccccc1C(C)Oc1ccc(Cl)c(-n2c(=O)[nH]c3csc(C(=O)O)c3c2=O)c1] | (DMSO-d6) 1.3-1.4 (3H, m), 1.54 (3H, d, J = 6.3 Hz), 4.05-4.2 (2H, m), 5.65-5.75 (1H, m), 6.85-7.0 (2H, m), 7.0-7.05 (1H, m), 7.15-7.35 (3H, m), 7.39 (1H, d, J = 4.2 Hz), 7.48 (1H, d, J = 9.1 Hz), 11.95-12.05 (1H, m), 14.42 (1H, s) |
| 300 | 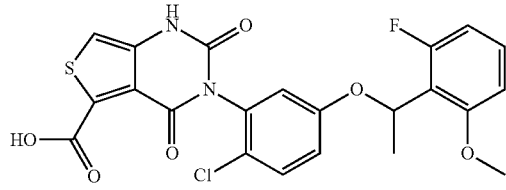 [SMILES: COc1cccc(F)c1C(C)Oc1ccc(Cl)c(-n2c(=O)[nH]c3csc(C(=O)O)c3c2=O)c1] | (DMSO-d6) 1.66 (3H, d, J = 6.6 Hz), 3.85-3.9 (3H, m), 5.8-5.9 (1H, m), 6.75-6.85 (1H, m), 6.85-7.0 (2H, m), 7.17 (1H, d, J = 2.6 Hz), 7.25-7.4 (2H, m), 7.48 (1H, d, J = 8.6 Hz), 12.0 (1H, s), 14.42 (1H, s) |
| 301 | 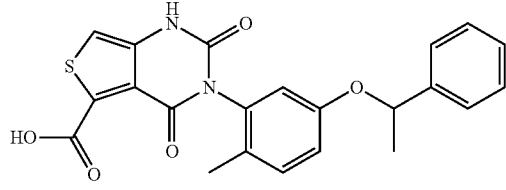 [SMILES: Cc1ccc(OC(C)c2ccccc2)cc1-n1c(=O)[nH]c2csc(C(=O)O)c2c1=O] | (DMSO-d6) 1.5-1.6 (3H, m), 1.95 (3H, s), 5.4-5.5 (1H, m), 6.85-6.95 (1H, m), 6.98 (1H, dd, J = 5.8 Hz, 2.6 Hz), 7.15-7.45 (7H, m), 11.85-11.95 (1H, m), 14.76 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported ¹H NMR spectral properties |
|---|---|---|
| 302 | | (DMSO-d6) 1.56 (3H, d, J = 6.3 Hz), 5.52 (1H, q, J = 6.3 Hz), 7.03 (1H, dd, J = 9.0 Hz, 3.0 Hz), 7.15-7.5 (7H, m), 7.9-8.0 (1H, m), 12.99 (1H, brs), 13.95 (1H, s) |
| 303 | | (DMSO-d6) 3.85 (3H, s), 5.03 (2H, s), 6.85- 7.0 (2H, m), 7.21 (1H, dd, J = 8.9 Hz, 3.1 Hz), 7.32 (1H, d, J = 3.1 Hz), 7.4-7.5 (2H, m), 7.58 (1H, d, J = 8.9 Hz), 12.06 (1H, s), 14.43 (1H, s) |
| 304 | | (DMSO-d6) 1.73 (3H, d, J = 6.7 Hz), 6.0-6.1 (1H, m), 6.8-6.85 (1H, m),6.9-7.0 (2H, m), 7.3-7.4 (3H, m), 7.45-7.5 (2H, m), 11.89 (1H, s), 14.86 (1H, s) |
| 305 | | (DMSO-d6) 1.73 (3H, d, J = 6.7 Hz), 6.05 (1H, q, J = 6.7 Hz), 6.8-7.0 (3H, m), 7.3-7.4 (2H, m), 7.45-7.5 (2H, m), 7.99 (1H, s), 12.92 (1H, s), 14.43 (1H, s) |
| 306 | | (DMSO-d6) 1.56 (3H, d, J = 5.7 Hz), 5.45-5.55 (1H, m), 7.0-7.5 (8H, m), 11.95-12.05 (1H, m), 14.4 (1H, brs) |
| 307 | | (DMSO-d6) 1.52 (3H, d, J = 3.84 (3H, s), 5.55-5.65 (1H, m), 6.9-7.0 (1H, m), 7.0-7.15 (4H, m), 7.2-7.3 (1H, m), 7.35-7.4 (1H, m), 11.98 (1H, s), 14.4 (1H, s) |
| 308 | | (DMSO-d6) 5.2-5.35 (2H, m), 7.25 (1H, dd, J = 9.1 Hz, 3.0 Hz), 7.38 (1H, d, J = 3.0 Hz), 7.41 (1H, s), 7.55-7.65 (2H, m), 7.75-7.8 (2H, m), 7.94 (1H, d, J = 7.7 Hz), 12.05 (1H, s), 14.43 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 309 | | (DMSO-d6) 3.26 (3H, s), 3.6-3.7 (2H, m), 4.1-4.2 (2H, m), 5.07 (2H, s), 6.95-7.0 (1H, m), 7.07 (1H, d, J = 8.0 Hz), 7.15-7.2 (1H, m), 7.3-7.4 (2H, m), 7.4-7.45 (2H, m), 7.55 (1H, d, J = 9.3 Hz), 12.04 (1H, s), 14.46 (1H, s) |
| 310 | | (DMSO-d6) 3.83 (3H, s), 5.0-5.1 (2H, m), 6.9-6.95 (1H, m), 7.15-7.25 (2H, m), 7.3-7.4 (2H, m), 7.45-7.55 (1H, m), 12.02 (1H, s), 14.4 (1H, s) |
| 311 | | (DMSO-d6) 1.66 (3H, d, J = 6.5 Hz), 3.8-3.9 (3H, m), 5.75-5.85 (1H, m), 6.8-7.0 (2H, m), 7.05-7.15 (1H, m), 7.2-7.4 (3H, m), 11.95-12.05 (1H, m), 14.39 (1H, s) |
| 312 | | (DMSO-d6) 2.48 (3H, s), 5.09 (2H, s), 7.15-7.25 (2H, m), 7.34 (1H, d, J = 2.9 Hz), 7.35-7.45 (3H, m), 7.49 (1H, d, J = 7.2 Hz), 7.58 (1H, d, J = 9.0 Hz), 12.04 (1H, s), 14.45 (1H, s) |
| 313 | | (DMSO-d6) 5.1 (2H, s), 6.95-7.0 (1H, m), 7.05-7.15 (2H, m), 7.3-7.5 (7H, m), 11.88 (1H, s), 14.89 (1H, s) |
| 314 | | (DMSO-d6) 5.14 (2H, s), 7.2-7.3 (3H, m), 7.35-7.45 (2H, m), 7.55-7.65 (1H, m), 12.02 (1H, s), 14.38 (1H, s) |
| 315 | | (DMSO-d6) 5.08 (2H, s), 7.15-7.25 (1H, m), 7.25-7.3 (1H, m), 7.35-7.4 (2H, m), 7.55-7.7 (1H, m), 7.7-7.8 (1H, m), 12.0 (1H, s), 14.4 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 316 | | (DMSO-d6) 5.2 (2H, s), 7.2-7.3 (2H, m), 7.35-7.45 (2H, m), 7.95-8.05 (1H, m), 12.02 (1H, s), 14.38 (1H, s) |
| 317 | | (DMSO-d6) 3.82 (3H, s), 5.02 (2H, s), 6.95-7.0 (1H, m), 7.06 (1H, d, J = 8.2 Hz), 7.1-7.2 (1H, m), 7.24 (1H, dd, J = 6.0 Hz, 3.2 Hz), 7.3-7.45 (4H, m), 12.01 (1H, s), 14.44 (1H, s) |
| 318 | | (DMSO-d6) 1.31 (3H, t, J = 6.9 Hz), 4.09 (2H, q, J = 6.9 Hz), 5.03 (2H, s), 6.9-7.0 (1H, m), 7.04 (1H, d, J = 8.2 Hz), 7.1-7.2 (1H, m), 7.2-7.25 (1H, m), 7.3-7.45 (4H, m), 12.01 (1H, s), 14.43 (1H, s) |
| 319 | | (DMSO-d6) 5.08 (2H, s), 7.05-7.5 (7H, m), 7.55-7.65 (1H, m), 12.01 (1H, s), 14.42 (1H, s) |
| 320 | | (DMSO-d6) 2.34 (6H, s), 5.03 (2H, s), 7.0-7.45 (7H, m), 12.0 (1H, s), 14.4 (1H, s) |
| 321 | | (DMSO-d6) 5.17 (2H, s), 7.2-7.3 (2H, m), 7.35-7.45 (2H, m), 7.74 (1H, d, J = 8.2 Hz), 7.9-8.0 (1H, m), 12.02 (1H, s), 14.38 (1H, s) |
| 322 | | (DMSO-d6) 2.2-2.3 (3H, m), 5.05-5.15 (2H, m), 7.2-7.3 (2H, m), 7.32 (1H, d, J = 8.6 Hz), 7.35-7.45 (3H, m), 12.02 (1H, s), 14/39 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported ¹H NMR spectral properties |
|---|---|---|
| 323 | | (DMSO-d6) 3.85-3.95 (3H, m), 5.07 (2H, s), 7.1-7.4 (7H, m), 12.01 (1H, s), 14.42 (1H, s) |
| 324 | | (DMSO-d6) 5.18 (2H, s), 7.15-7.25 (1H, m), 7.25-7.35 (1H, m), 7.35-7.5 (3H, m), 7.55-7.7 (2H, m), 12.01 (1H, s), 14.41 (1H, s) |
| 325 | | (DMSO-d6) 3.81 (3H, s), 5.02 (2H, s), 7.0-7.1 (1H, m), 7.1-7.2 (2H, m), 7.2-7.4 (4H, m), 12.01 (1H, s), 14.42 (1H, s) |
| 326 | | (DMSO-d6) 3.75 (3H, s), 5.08 (2H, s), 6.9-7.0 (1H, m), 7.1-7.25 (3H, m), 7.27 (1H, dd, J = 6.1 Hz, 3.2 Hz), 7.3-7.4 (2H, m), 12.02 (1H, s), 14.41 (1H, s) |
| 327 | | (DMSO-d6) 5.14 (2H, s), 7.15-7.35 (3H, m), 7.35-7.45 (2H, m), 7.7-7.8 (1H, m), 12.02 (1H, s), 14.39 (1H, s) |
| 328 | | (DMSO-d6) 3.83 (3H, s), 5.01 (2H, s), 7.09 (1H, d, J = 8.8 Hz), 7.15-7.2 (1H, m), 7.25-7.35 (1H, m), 7.3-7.45 (3H, m), 7.48 (1H, d, J = 2.6 Hz), 12.02 (1H, s), 14.43 (1H, s) |
| 329 | | (DMSO-d6) 5.12 (2H, s), 7.15-7.25 (1H, m), 7.27 (1H, dd, J = 6.0 Hz, 3.2 Hz), 7.3-7.4 (2H, m), 7.4-7.5 (2H, m), 7.5-7.6 (1H, m), 7.7 (1H, dd, J = 7.4 Hz, 1.6 Hz), 12.01 (1H, s), 14.41 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 330 | | (DMSO-d6) 3.85 (3H, s), 5.1 (2H, s), 7.2-7.35 (2H, m), 7.35-7.45 (3H, m), 7.63 (1H, d, J = 8.7 Hz), 12.01 (1H, s), 14.38 (1H, s) |
| 331 | | (DMSO-d6) 5.21 (2H, s), 7.2-7.35 (2H, m), 7.35-7.45 (2H, m), 7.53 (1H, t, J = 9.2 Hz), 7.8-7.9 (1H, m), 8.02 (1H, d, J = 6.1 Hz), 12.02 (1H, s), 14.4 (1H, s) |
| 332 | | (DMSO-d6) 5.21 (2H, s), 7.15-7.25 (1H, m), 7.3 (1H, dd, J = 5.8 Hz, 3.0 Hz), 7.35-7.5 (3H, m), 7.65-7.75 (1H, m), 7.89 (1H, dd, J = 8.7 Hz, 5.4 Hz), 12.01 (1H, s), 14.4 (1H, s) |
| 333 | | (DMSO-d6) 2.24 (3H, s), 5.08 (2H, s), 7.05-7.15 (1H, m), 7.15-7.3 (2H, m), 7.35-7.45 (3H, m), 12.02 (1H, s), 14.4 (1H, s) |
| 334 | | (DMSO-d6 2.13 (3H, s), 3.82 (3H, s), 5.0 (2H, s), 6.85-6.95 (1H, m), 7.25 (1H, d, J = 10.0 Hz), 7.32 (1H, d, J = 6.4 Hz), 7.39 (1H, s), 7.4-7.55 (1H, m), 12.01 (1H, s), 14.47 (1H, s) |
| 335 | | (DMSO-d6) 2.12 (3H, s), 3.84 (3H, s), 4.96 (2H, s), 6.8-7.0 (2H, m), 7.24 (1H, d, J = 10.2 Hz), 7.32 (1H, d, J = 6.3 Hz), 7.35-7.5 (2H, m), 12.04 (1H, s), 14.48 (1H, s) |
| 336 | | (DMSO-d6) 2.36 (3H, s), 5.1-5.15 (2H, m), 7.2-7.3 (3H, m), 7.35-7.45 (2H, m), 7.5 (1H, dd, J = 8.7 Hz, 6.2 Hz), 12.03 (1H, s), 14.4 (1H, s) |

US 12,280,052 B2

233                                                                                    234

TABLE 1-continued

Exemplary Thieno[3,4d]pyrimidine GnRH Antagonists Useful for the Treatment of
Adenomyosis and Rectovaginal Endometriosis

| No. | Compound | Reported ¹H NMR spectral properties |
|---|---|---|
| 337 | 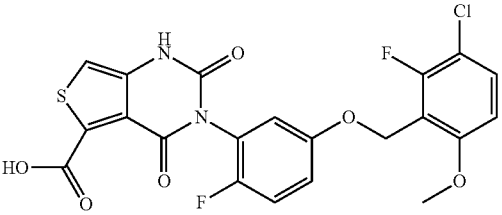 | (DMSO-d6) 3.86 (3H, s), 5.04 (2H, s), 7.0 (1H, d, J = 9.3 Hz), 7.15-7.25 (2H, m), 7.3-7.4 (2H, m), 7.55-7.65 (1H, m), 12.03 (1H, s), 14.41 (1H, s) |
| 338 | 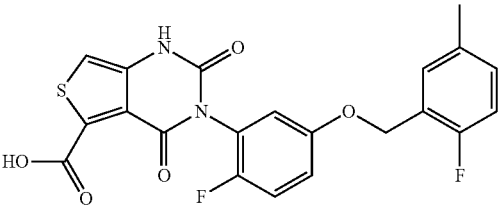 [SMILES: Cc1ccc(F)c(COc2ccc(F)c(-n3c(=O)[nH]c4csc(C(=O)O)c4c3=O)c2)c1] | (DMSO-d6) 2.3 (3H, s), 5.06 (2H, s), 7.1-7.45 (7H, m), 12.03 (1H, s), 14.43 (1H, s) |
| 339 | 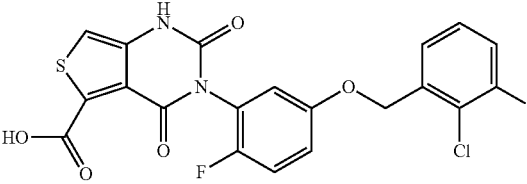 | (DMSO-d6) 3.88 (3H, s), 5.13(2H, s), 7.15-7.25 (3H, m), 7.27 (1H, dd, J = 6.0 Hz, 3.2 Hz), 7.3-7.4 (3H, m), 12.02 (1H, s), 14.42 (1H, s) |
| 340 | 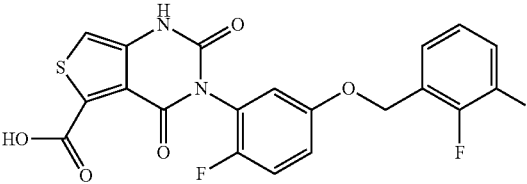 | (DMSO-d6) 3.85 (3H, s), 5.11 (2H, s), 7.05-7.3 (5H, m), 7.3-7.4 (2H, m), 12.02 (1H, s), 14.42 (1H, s) |
| 341 | 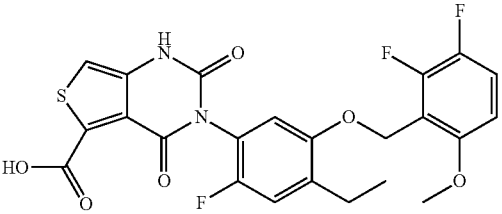 | (DMSO-d6) 1.1 (3H, t, J = 7.5 Hz), 2.45-2.6 (2H, m), 3.82 (3H, s), 5.0 (2H, s), 6.9-6.95 (1H, m), 7.23 (1H, d, J = 10.3 Hz), 7.34 (1H, d, J = 6.3 Hz), 7.39 (1H, s), 7.4-7.55 (1H, m), 12.03 (1H, s), 14.47 (1H, s) |
| 342 | 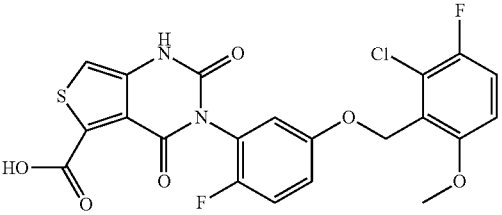 [SMILES: COc1ccc(F)c(Cl)c1COc1ccc(F)c(-n2c(=O)[nH]c3csc(C(=O)O)c3c2=O)c1] | (DMSO-d6) 3.84 (3H, s), 5.1 (2H, s), 7.13 (1H, dd, J = 9.2 Hz, 4.0 Hz), 7.15-7.3 (2H, m), 7.3-7.4 (2H, m), 7.45-7.55 (1H, m), 12.03 (1H, s) |
| 343 | 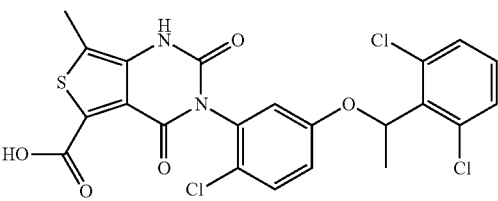 [SMILES: Cc1sc(C(=O)O)c2c(=O)n(-c3cc(OC(C)c4c(Cl)cccc4Cl)ccc3Cl)c(=O)[nH]c12] | (DMSO-d6) 1.73 (3H, d, J = 6.7 Hz), 2.5-2.55 (3H, m), 6.07 (1H, q, J = 6.7 Hz), 6.85-6.95 (1H, m), 7.15-7.2 (1H, m), 7.3-7.4 (1H, m), 7.45-7.55 (3H, m), 11.89 (1H, s), 14.37 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 344 | 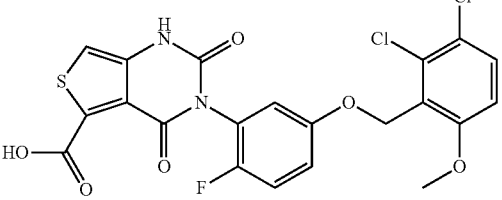 | (DMSO-d6) 3.86 (3H, s), 5.12 (2H, s), 7.1-7.3 (3H, m), 7.3-7.4 (2H, m), 7.69 (1H, d, J = 8.7 Hz), 12.03 (1H, s), 14.41 (1H, s) |
| 345 | 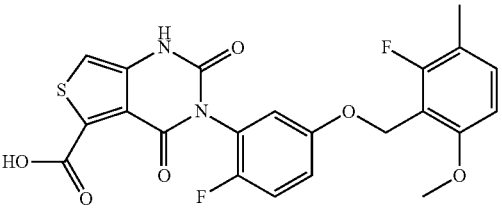 [SMILES: COc1ccc(C)c(F)c1COc1ccc(F)c(-n2c(=O)[nH]c3csc(C(=O)O)c3c2=O)c1] | (DMSO-d6) 2.15-2.2 (3H, m), 3.81 (3H, s), 5.0 (2H, s), 6.84 (1H, d, J = 8.5 Hz), 7.15-7.25 (2H, m), 7.25-7.4 (3H, m), 12.03 (1H, s), 14.42 (1H, s) |
| 346 | 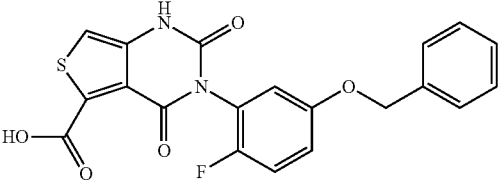 [SMILES: O=C(O)c1scc2[nH]c(=O)n(-c3cc(OCc4ccccc4)ccc3F)c(=O)c12] | (DMSO-d6) 5.08 (2H, s), 7.1-7.5 (9H, m), 12.01 (1H, s), 14.42 (1H, s) |
| 347 | 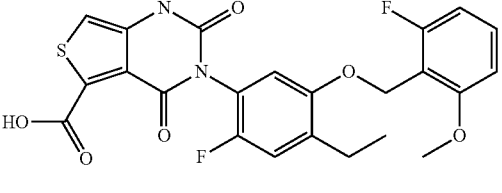 | (DMSO-d6) 1.1 (3H, t, J = 7.5 Hz), 2.45-2.55 (2H, m), 3.84 (3H, s), 4.97 (2H, s), 6.85-7.0 (2H, m), 7.22 (1H, d, J = 10.2 Hz), 7.33 (1H, d, J = 6.4 Hz), 7.35-7.5 (2H, m), 12.02 (1H, s), 14.47 (1H, brs) |
| 348 | 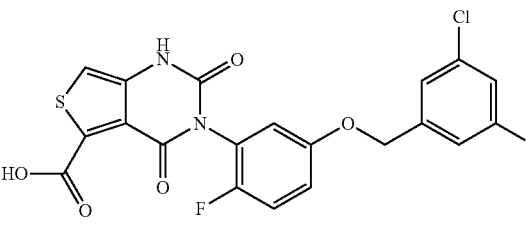 | (DMSO-d6) 5.11 (2H, s), 7.1-7.3 (2H, m), 7.3-7.45 (2H, m), 7.5-7.65 (3H, m), 12.0 (1H, brs), 14.41 (1H, brs) |
| 349 | 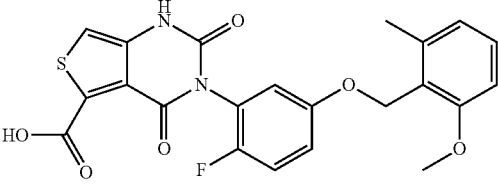 [SMILES: COc1cccc(C)c1COc1ccc(F)c(-n2c(=O)[nH]c3csc(C(=O)O)c3c2=O)c1] | (DMSO-d6) 2.33 (3H, s), 3.78 (3H, s), 5.04 (2H, s), 6.8-6.95 (2H, m), 7.1-7.3 (3H, m), 7.3-7.4 (2H, m), 12.01 (1H, s), 14.42 (1H, brs) |
| 350 | 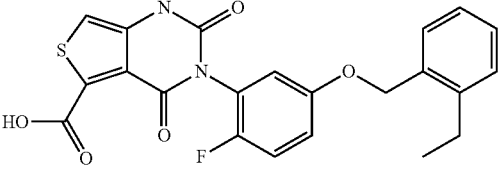 | (DMSO-d6) 1.19 (3H, t, J = 7.5 Hz), 2.68 (2H, q, J = 7.5 Hz), 5.07 (2H, s), 7.15-7.4 (7H, m), 7.4-7.5 (1H, m), 12.0 (1H, brs), 14.3-14.55 (1H, br) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 351 | | (DMSO-d6) 3.84 (3H, s), 5.09 (2H, s), 7.2-7.25 (1H, m), 7.25-7.35 (1H, m), 7.35-7.45 (2H, m), 7.58 (1H, d, J = 2.7 Hz), 7.68 (1H, d, J = 2.7 Hz), 12.01 (1H, brs), 14.41 (1H, brs) |
| 352 | | (DMSO-d6) 5.25 (2H, s), 7.2-7.35 (2H, m), 7.35-7.45 (2H, m), 7.95-8.05 (1H, m), 8.1- 8.2 (1H, m), 12.01 (1H, brs), 14.4 (1H, brs) |
| 353 | | (DMSO-d6) 1.19 (3H, t, J = 7.6 Hz), 2.62 (2H, q, J = 7.6 Hz), 5.05 (2H, s), 7.1-7.4 (8H, m), 12.01 (1H, brs), 14.43 (1H, brs) |
| 354 | | (DMSO-d6) 3.3 (3H, s), 4.53 (2H, s), 5.13 (2H, s), 7.1-7.3 (2H, m), 7.3-7.45 (5H, m), 7.45-7.55 (1H, m), 12.01 (1H, brs), 14.42 (1H, brs) |
| 355 | | (DMSO-d6) 3.29 (3H, s), 4.43 (2H, s), 5.09 (2H, s), 7.1-7.2 (1H, m), 7.2-7.45 (7H, m), 12.01 (1H, brs), 14.42 (1H, brs) |
| 356 | | (DMSO-d6) 5.19 (2H, s), 7.15-7.25 (1H, m), 7.25-7.3 (1H, m), 7.35-7.45 (2H, m), 7.92 (1H, t, J = 8.0 Hz), 8.21 (2H, d, J = 28.0 Hz), 12.01 (1H, s), 14.38 (1H, brs) |
| 357 | | (DMSO-d6) 2.25 (3H, s), 2.44 (3H, s), 3.7 (3H, s), 5.02 (2H, s), 7.1-7.25 (3H, m), 7.25-7.3 (1H, m), 7.3-7.4 (2H, m), 12.01 (1H, brs), 14.3-14.55 (1H, br) |

TABLE 1-continued
Exemplary Thieno[3,4d]pyrimidine GnRH Antagonists Useful for the Treatment of Adenomyosis and Rectovaginal Endometriosis
| No. | Compound | Reported $^1$H NMR spectral properties |
|---|---|---|
| 358 | 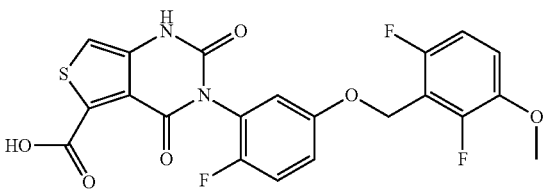 [SMILES: COc1ccc(F)c(COc2ccc(F)c(-n3c(=O)[nH]c4csc(C(=O)O)c4c3=O)c2)c1F] | (DMSO-d6) 3.85 (3H, s), 5.09 (2H, s), 7.05-7.35 (4H, m), 7.35-7.45 (2H, m), 12.02 (1H, brs), 14.39 (1H, brs) |
| 359 | 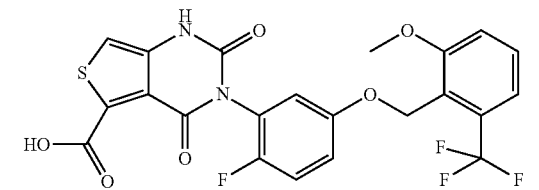 [SMILES: COc1cccc(C(F)(F)F)c1COc1ccc(F)c(-n2c(=O)[nH]c3csc(C(=O)O)c3c2=O)c1] | (DMSO-d6) 3.89 (3H, s), 5.07 (2H, s), 7.15-7.13 (2H, m), 7.3-7.5 (4H, m), 7.6-7.7 (1H, m), 12.01 (1H, s), 14.4 (1H, brs) |
| 360 | 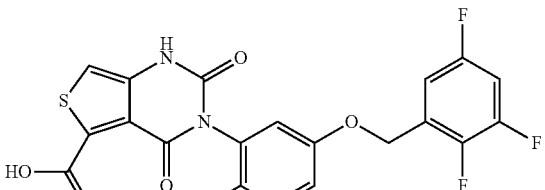 | (DMSO-d6) 5.18 (2H, s), 7.2-7.45 (5H, m), 7.5-7.65 (1H, m) 12.02 (1H, s), 14.4 (1H, brs) |
| 361 | 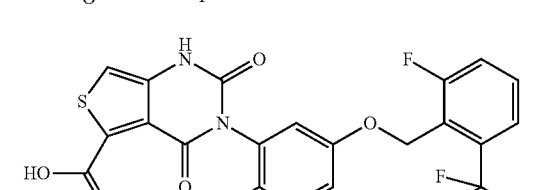 | (DMSO-d6) 5.14 (2H, s), 7.15-7.3 (2H, m), 7.3-7.45 (2H, m), 7.6-7.8 (3H, m), 12.02 (1H, s), 14.39 (1H, s) |
| 362 | 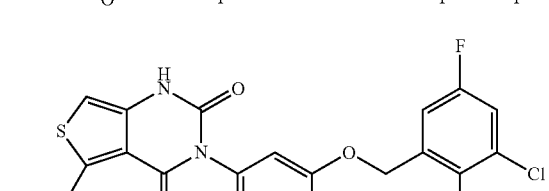 | (DMSO-d6) 3.82 (3H, s), 5.1 (2H, s), 7.15-7.45 (5H, m), 7.45-7.55 (1H, m), 12.01 (1H, s), 14.4 (1H, s) |
| 363 | 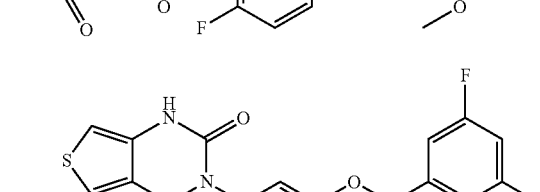 | (DMSO-d6) 2.27 (3H, s), 3.71 (3H, s), 5.05 (2H, s), 7.05-7.25 (3H, m), 7.25-7.3 (1H, m), 7.3-7.4 (2H, m), 12.02 (1H, s), 14.42 (1H, brs) |
| 364 | 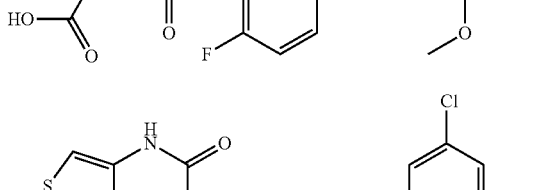 | (DMSO-d6) 3.76 (3H, s), 3.85 (3H, s), 5.03 (2H, s), 7.05-7.3 (4H, m), 7.3-7.4 (2H, m), 12.02 (1H, brs), 14.42 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 365 | 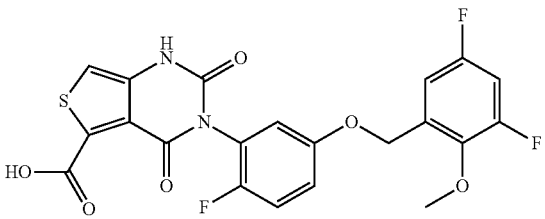 | (DMSO-d6) 3.8-3.9 (3H, m), 5.08 (2H, s), 7.15-7.25 (2H, m), 7.25-7.45 (4H, m), 12.02 (1H, brs), 14.41 (1H, brs) |
| 366 | 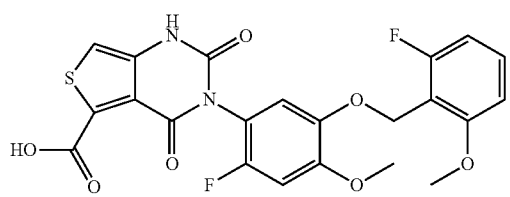 | (DMSO-d6) 3.79 (3H, s), 3.83 (3H, s), 4.92 (2H, s), 6.8-7.0 (2H, m), 7.11 (1H, d, J = 11.2 Hz), 7.27 (1H, d, J = 27.6 Hz), 7.38 (1H, s), 7.4-7.5 (1H, m), 11.99 (1H, brs), 14.55 (1H, brs) |
| 367 | 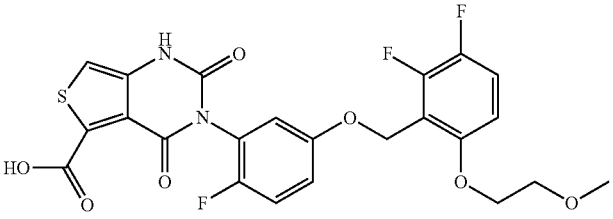 [SMILES: COCCOc1ccc(F)c(F)c1COc1ccc(F)c(-n2c(=O)[nH]c3csc(C(=O)O)c3c2=O)c1] | (DMSO-d6) 3.23 (3H, s), 3.55-3.65 (2H, m), 4.1-4.2 (2H, m), 5.09 (2H, s), 6.9-7.0 (1H, m), 7.15-7.3 (2H, m), 7.3-7.4 (2H, m), 7.4-7.5 (1H, m), 12.03 (1H, brs), 14.42 (1H, brs) |
| 368 | 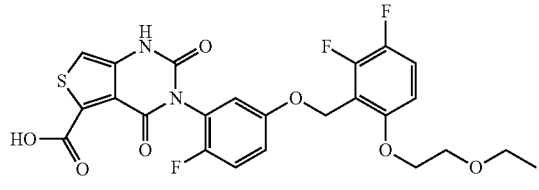 | (DMSO-d6) 1.02 (3H, t, J = 6.9 Hz), 3.43 (2H, q, J = 6.9 Hz), 3.6-3.7 (2H, m), 4.1-4.2 (2H, m), 5.08 (2H, s), 6.9-7.0 (1H, m), 7.15-7.25 (2H, m), 7.3-7.4 (2H, m), 7.4-7.5 (1H, m), 12.02 (1H, s), 14.42 (1H, brs) |
| 369 | 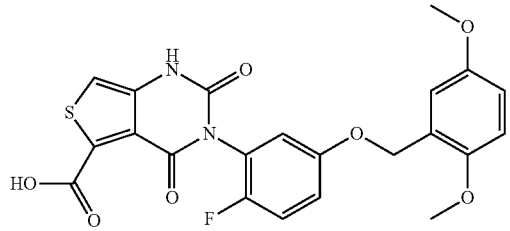 [SMILES: COc1ccc(OC)c(COc2ccc(F)c(-n3c(=O)[nH]c4csc(C(=O)O)c4c3=O)c2)c1] | (DMSO-d6) 3.71 (3H, s), 3.77 (3H, s), 4.99 (2H, s), 6.85-6.95 (1H, m), 6.95-7.05 (2H, m), 7.1-7.2 (1H, m), 7.2-7.3 (1H, m), 7.3-7.4 (2H, m), 12.01 (1H, s), 14.44 (1H, brs) |
| 370 | 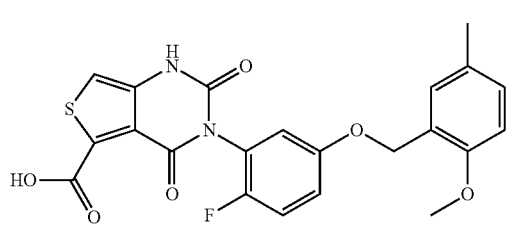 [SMILES: COc1ccc(C)cc1COc1ccc(F)c(-n2c(=O)[nH]c3csc(C(=O)O)c3c2=O)c1] | (DMSO-d6) 2.25 (3H, s), 3.78 (3H, s), 4.98 (2H, s), 6.94 (1H, d, J = 7.9 Hz), 7.1-7.2 (2H, m), 7.2-7.3 (2H, m), 7.3-7.4 (2H, m), 12.01 (1H, brs), 14.45 (1H, brs) |
| 371 | 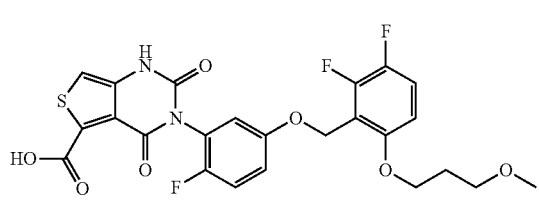 [SMILES: COCCCOc1ccc(F)c(F)c1COc1ccc(F)c(-n2c(=O)[nH]c3csc(C(=O)O)c3c2=O)c1] | (DMSO-d6) 1.85-1.95 (2H, m), 3.16 (3H, s), 3.39 (2H, t, J = 6.2 Hz), 4.08 (2H, t, J = 6.2 Hz), 5.06 (2H, s), 6.85-6.95 (1H, m), 7.15-7.3 (2H, m), 7.3-7.5 (3H, m), 12.03 (1H, s), 14.42 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 372 | 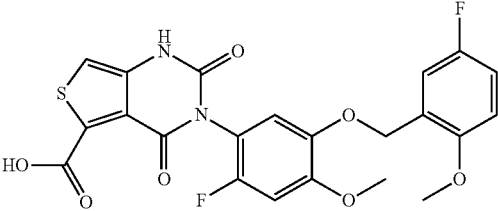 [SMILES: COc1ccc(F)cc1COc1cc(-n2c(=O)[nH]c3csc(C(=O)O)c3c2=O)c(F)cc1OC] | (DMSO-d6) 3.78 (3H, s), 3.85 (3H, s), 4.94 (2H, s), 7.0-7.1 (1H, m), 7.1-7.2 (2H, m), 7.2-7.35 (2H, m), 7.36 (1H, s), 11.96 (1H, brs), 14.56 (1H, brs) |
| 373 | 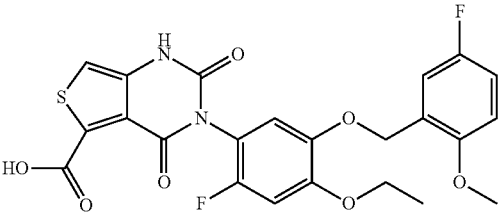 [SMILES: CCOc1cc(F)c(-n2c(=O)[nH]c3csc(C(=O)O)c3c2=O)cc1OCc1cc(F)ccc1OC] | (DMSO-d6) 1.36 (3H, t, J = 6.9 Hz), 3.78 (3H, s), 4.13 (2H, q, J = 6.9 Hz), 4.96 (2H, s), 7.0-7.1 (1H, m), 7.1-7.2 (2H, m), 7.2-7.35 (2H, m), 7.37 (1H, s), 11.97 (1H, brs), 14.56 (1H, brs) |
| 374 | 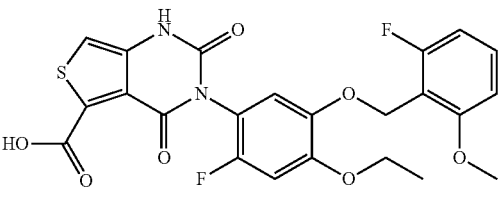 [SMILES: CCOc1cc(F)c(-n2c(=O)[nH]c3csc(C(=O)O)c3c2=O)cc1OCc1c(F)cccc1OC] | (DMSO-d6) 1.3 (3H, t, J = 7.0 Hz), 3.82 (3H, s), 4.08 (2H, q, J = 27.0 Hz), 4.94 (2H, s), 6.8-7.0 (2H, m), 7.1 (1H, d, J = 11.6 Hz), 7.26 (1H, d, J = 7.6 Hz), 7.35-7.5 (2H, m), 11.99 (1H, s), 14.55 (1H, brs) |
| 375 | 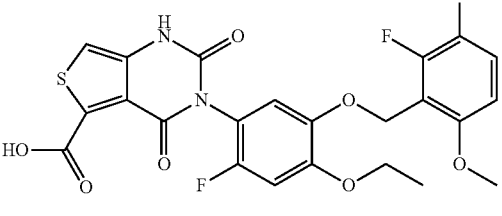 | (DMSO-d6) 1.31 (3H, t, J = 7.0 Hz), 3.79 (3H, s), 4.09 (2H, q, J = 7.0 Hz), 4.95-5.05 (2H, m), 6.85-6.95 (1H, m), 7.12 (1H, d, J = 11.7 Hz), 7.23 (1H, d, J = 7.3 Hz), 7.38 (1H, s), 7.4-7.5 (1H, m), 11.99 (1H, s), 14.54 (1H, brs) |
| 376 | 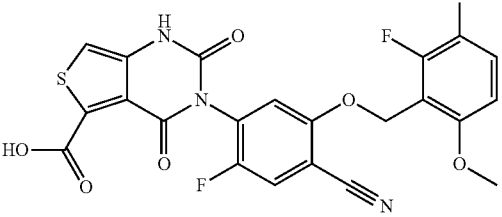 | (DMSO-d6) 3.83 (3H, s), 5.18 (2H, s), 6.9-7.0 (1H, m), 7.38 (1H, s), 7.45-7.6 (1H, m), 7.7-7.85 (1H, m), 8.0-8.1 (1H, m), 12.08 (1H, s), 14.16 (1H, brs) |
| 377 | 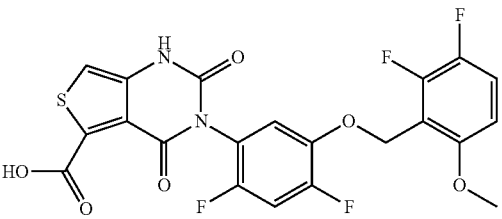 [SMILES: COc1ccc(F)c(F)c1COc1cc(-n2c(=O)[nH]c3csc(C(=O)O)c3c2=O)c(F)cc1F] | (DMSO-d6) 3.81 (3H, s), 5.07 (2H, s), 6.9-6.95 (1H, m), 7.39 (1H, s), 7.45-7.55 (1H, m), 7.55-7.65 (2H, m), 12.06 (1H, s), 14.37 (1H, brs) |

245 246

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 378 | 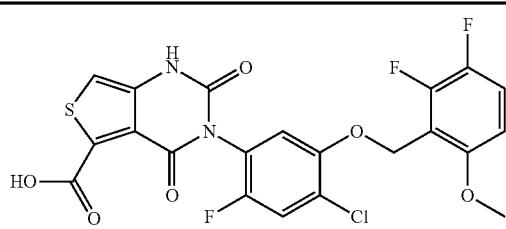 | (DMSO-d6) 3.82 (3H, s), 5.08 (2H, s), 6.9-7.0 (1H, m), 7.39 (1H, s), 7.45-7.6 (1H, m), 7.61 (1H, d, J = 6,7 Hz), 7.73 (1H, d J = 9.1 Hz), 12.07 (1H, s), 14.33 (1H, brs) |
| 379 | 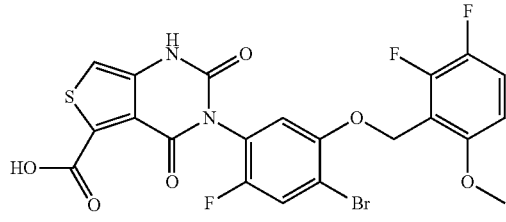 [SMILES: COc1ccc(F)c(F)c1COc1cc(-n2c(=O)[nH]c3csc(C(=O)O)c3c2=O)c(F)cc1Br] | (DMSO-d6) 3.82 (3H, s), 5.07 (2H, s), 6.9-7.0 (1H, m), 7.39 (1H, s), 7.45-7.55 (1H, m), 7.58 (1H, d, J = 6.5 Hz), 7.84 (1H, d, J = 8.8 Hz), 12.07 (1H, s), 14.33 (1H, s) |
| 380 | 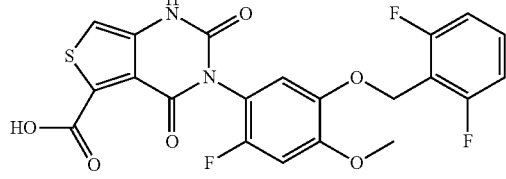 | (DMSO-d6) 3.81 (3H, s), 5.0 (2H, s), 7.1-7.25 (3H, m), 7.29 (1H, d, J = 7.4 Hz), 7.39 (1H, s), 7.45-7.6 (1H, m), 12.01 (1H, s), 14.54 (1H, s) |
| 381 | 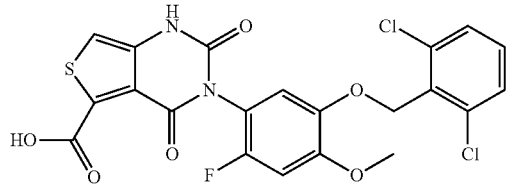 [SMILES: COc1cc(F)c(-n2c(=O)[nH]c3csc(C(=O)O)c3c2=O)cc1OCc1c(Cl)cccc1Cl] | (DMSO-d6) 3.82 (3H, s), 5.13 (2H, s), 7.15 (1H, d, J = 11.4 Hz), 7.33 (1H, d, J = 7.3 Hz), 7.39 (1H, s), 7.45-7.6 (3H, m), 12.01 (1H, s), 14.54 (1H, s) |
| 382 | 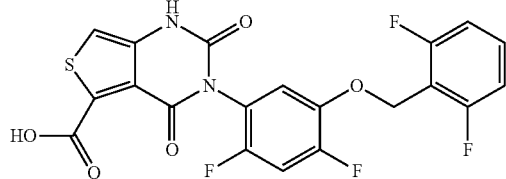 | (DMSO-d6) 5.12 (2H, s), 7.15-7.25 (2H, m), 7.39 (1H, s), 7.5-7.7 (3H, m), 12.06 (1H, s), 14.36 (1H, brs) |
| 383 | 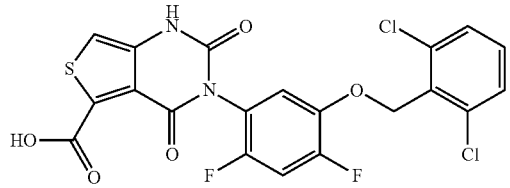 [SMILES: O=C(O)c1scc2[nH]c(=O)n(-c3cc(OCc4c(Cl)cccc4Cl)c(F)cc3F)c(=O)c12] | (DMSO-d6) 5.24 (2H, s), 7.39 (1H, s), 7.45-7.55 (1H, m), 7.55-7.75 (4H, m), 1206. (1H, s), 14.36 (1H, brs) |
| 384 | 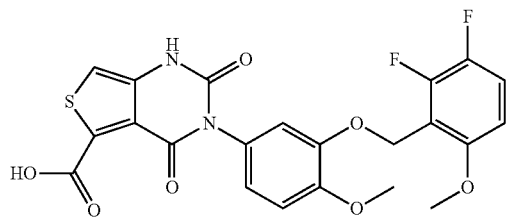 [SMILES: COc1ccc(-n2c(=O)[nH]c3csc(C(=O)O)c3c2=O)cc1OCc1c(OC)ccc(F)c1F] | (DMSO-d6) 3.78 (3H, s), 3.81 (3H, s), 4.96 (2H, s), 6.85-7.0 (2H, m), 7.07 (1H, d, J = 8.4 Hz), 7.18 (1H, d, J = 2.4 Hz), 7.37 (1H, s), 7.4-7.55 (1H, m), 11.87 (1H, s), 14.97 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 385 | | (DMSO-d6) 3.2 (3H, s), 3.5-3.6 (2H, m), 3.81 (3H, s), 4.05-4.15 (2H, m), 5.01 (2H, s); 6.85-6.95 (1H, m), 7.13 (1H, d, J = 11.2 Hz), 7.23 (1H, d, J = 7.0 Hz), 7.39 (1H, s), 7.4-7.5 (1H, m), 11.99 (1H, s), 14.52 (1H, s) |
| 386 | | (DMSO-d6) 1.0 (3H, t, J = 7.0 Hz), 3.4 (2H, q, J = 7.0 Hz), 3.55-3.65 (2H, m), 3.81 (3H, s), 4.05-4.15 (2H, m), 5.0 (2H, s), 6.85-6.95 (1H, m), 7.13 (1H, d, J = 11.4 Hz), 7.23 (1H, d, J = 7.7 Hz), 7.38 (1H, s), 7.4-7.5 (1H, m), 11.99 (1H, s), 14.53 (1H, brs) |
| 387 | | (DMSO-d6) 3.19 (3H, s), 3.5-3.65 (2H, m), 4.05-4.2 (2H, m), 5.13 (2H, s), 6.9-7.0 (1H, m), 7.38 (1H, s), 7.4-7.65 (3H, m), 12.03 (1H, s), 14.34 (1H, brs) |
| 388 | | (DMSO-d6) 0.99 (3H, t, J = 7.0 Hz), 3.4 (2H, q, J = 7.0 Hz), 3.55-3.7 (2H, m), 4.05-4.2 (2H, m), 5.11 (2H, s), 6.9-7.0 (1H, m), 7.38 (1H, s), 7.4-7.65 (3H, m), 12.03 (1H, s), 14.35 (1H, brs) |
| 389 | | (DMSO-d6) 1.75-1.9 (1H, m), 1.9-2.05 (1H, m), 2.5-2.7 (4H, m), 6.55-6.6 (1H, m), 6.9-6.95 (1H, m), 7.1-7.2 (1H, m), 7.25-7.45 (4H, m), 7.45-7.55 (2H, m), 11.96 (1H, s), 14.41 (1H, s) |
| 390 | | (DMSO-d6) 3.82 (3H, s), 5.08 (2H, s), 6.9-7.0 (1H, m), 7.0-7.1 (1H, m), 7.3-7.4 (2H, m), 7.4-7.55 (2H, m), 11.91 (1H, brs), 14.82 (1H, brs) |
| 391 | | (DMSO-d6) 1.8-1.95 (1H, m), 2.25-2.4 (1H, m), 2.6-2.8 (4H, m), 3.6 (3H, s), 6.65-6.75 (1H, m), 7.05-7.15 (1H, m), 7.25-7.35 (2H, m), 7.35-7.5 (1H, m), 11.7-12.2 (1H, br), 14.1-14.8 (1H, br) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 392 | 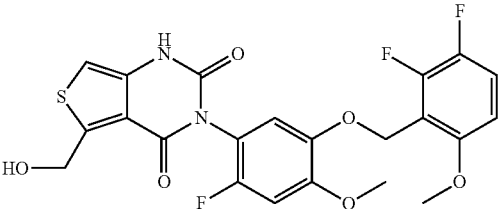 [SMILES: COc1cc(F)c(-n2c(=O)[nH]c3csc(CO)c3c2=O)cc1OCc1c(OC)ccc(F)c1F] | (DMSO-d6) 3.78 (3H, s), 3.81 (3H, s), 4.9-5.1 (4H, m), 5.95 (1H, t, J = 5.6 Hz), 6.71 (1H, s), 6.85-6.95 (1H, m), 7.05 (1H, d, J = 11.2 Hz), 7.17 (1H, d, J = 7.4 Hz), 7.4-7.55 (1H, m), 11.32 (1H, s) |
| 393 | 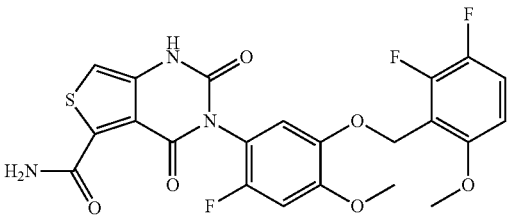 [SMILES: COc1cc(F)c(-n2c(=O)[nH]c3csc(C(N)=O)c3c2=O)cc1OCc1c(OC)ccc(F)c1F] | (DMSO-d6) 3.8 (3H, s), 3.81 (3H, s), 4.95 (2H, s), 6.85-6.95 (1H, m), 7.1 (1H, d, J = 11.5 Hz), 7.2-7.3 (2H, m), 7.4-7.55 (1H, m), 8.05-8.15 (1H, m), 9.65-9.75 (1H, m), 11.77 (1H, s) |
| 394 | 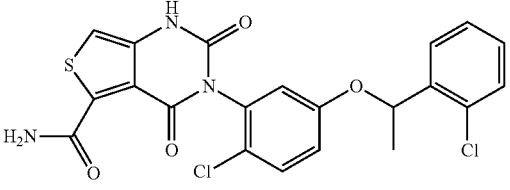 [SMILES: CC(Oc1ccc(Cl)c(-n2c(=O)[nH]c3csc(C(N)=O)c3c2=O)c1)c1ccccc1Cl] | (DMSO-d6) 1.58 (3H, d, J = 6.4 Hz), 5.65-5.75 (1H, m), 6.85-6.9 (1H, m), 7.2-7.25 (2H, m), 7.3-7.45 (2H, m), 7.45-7.55 (3H, m), 8.05-8.15 (1H, m), 9.6-9.7 (1H, m), 11.7-11.8 (1H, m) |
| 395 | 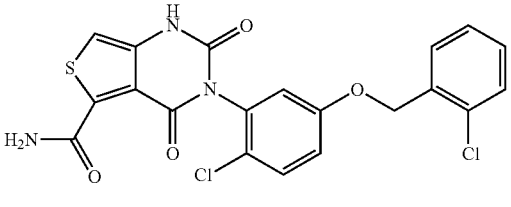 [SMILES: NC(=O)c1scc2[nH]c(=O)n(-c3cc(OCc4ccccc4Cl)ccc3Cl)c(=O)c12] | (DMSO-d6) 5.16 (2H, s), 7.19 (1H, dd, J = 8.9 Hz, 3.2 Hz), 7.24 (1H, s), 7.35-7.45 (3H, m), 7.5-7.7 (3H, m), 8.11 (1H, d, J = 2.1 Hz), 9.65-9.7 (1H, m), 11.8 (1H, s) |
| 396 | 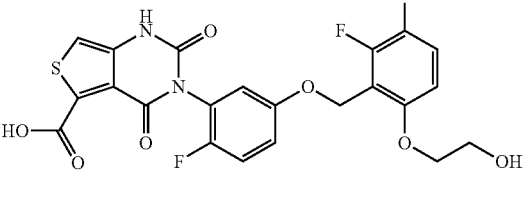 | (DMSO-d6) 3.6-3.75 (2H, m), 4.04 (2H, t, J = 4.9 Hz), 4.8-4.95 (1H, m), 5.13 (2H, s), 6.9-6.95 (1H, m), 7.15-7.3 (2H, m), 7.3-7.4 (2H, m), 7.4-7.5 (1H, m), 12.01 (1H, s), 14.4 (1H, brs) |
| 397 | 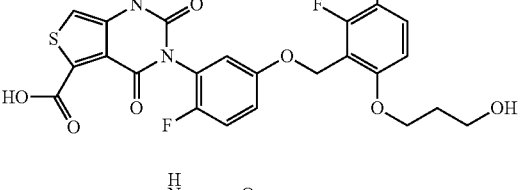 | (DMSO-d6) 1.75-1.9 (2H, m), 3.45-3.55 (2H, m), 4.1 (2H, t, J = 6.2 Hz), 4.9-5.0 (1H, m), 5.06 (2H, s), 6.85-6.95 (1H, m), 7.15-7.25 (2H, m), 7.3-7.4 (2H, m), 7.4-(1H, m), 12.02 (1H, s), 14.4 (1H, brs) |
| 398 | 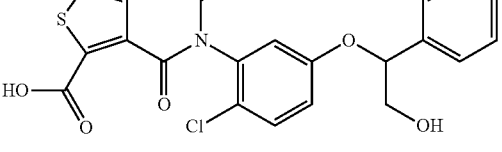 | (DMSO-d6) 3.55-3.65 (1H, m), 3.7-3.8 (1H, m), 5.15-5.25 (1H, m), 5.25-5.35 (1H, m), 7.0-7.05 (1H, m), 7.2-7.5 (8H, m), 11.95-12.05 (1H, m), 14.42 (1H, s) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 399 | | (DMSO-d6) 4.61 (2H, s), 5.16 (2H, s), 5.21 (1H, brs), 7.15-7.5 (7H, m), 7.57 (1H, d, J = 8.6 Hz), 12.0 (1H, s) |
| 400 | | (DMSO-d6) 4.51 (2H, d, J = 5.2 Hz), 5.1 (2H, s), 5.22 (1H t, J = 5.2 Hz), 7.15-7.2 (1H, m), 7.25-7.45 (6H, m), 7.57 (1H, d, J = 8.6 Hz), 12.03 (1H, s), 14.44 (1H, s) |
| 401 | | (DMSO-d6) 4.61 (2H, s), 5.15 (2H, s), 7.15-7.5 (6H, m), 7.57 (1H, d, J = 9.2 Hz), 7.95 (1H, s), 13.95 (1H, s) |
| 402 | | (DMSO-d6) 3.55-3.65 (1H, m), 3.7-3.8 (1H, m), 5.0-5.4 (2H, m), 7.0-7.1 (1H, m), 7.15-7.5 (7H, m), 7.95 (1H, d, J = 5.9 Hz), 12.98 (1H, brs), 13.95 (1H, s) |
| 403 | | (DMSO-d6) 1.55 (3H, d, J = 6.3 Hz), 3.6-3.8 (2H, m), 3.95-4.15 (2H, m), 4.85-4.95 (1H, m), 5.75-5.9 (1H, m), 6.9-7.05 (3H, m), 7.15-7.5 (5H, m), 11.95-12.05 (1H, m), 14.43 (1H, s) |
| 404 | | (DMSO-d6) 1.55 (3H, d, J = 6.3 Hz), 3.6-3.8 (2H, m), 3.95-4.15 (2H, m), 4.8-5.0 (1H, br), 5.75-5.85 (1H, m), 6.9-7.05 (3H, m), 7.15-7.35 (3H, m), 7.43 (1H, d, J = 8.9 Hz), 7.9-8.0 (1H, m), 12.8-13.2 (1H, br), 13.99 (1H, s) |
| 405 | | (DMSO-d6) 1.57 (3H, d, J = 6.2 Hz), 4.55-4.65 (1H, m), 4.65-4.75 (1H, m), 5.3-5.35 (1H, m), 5.7-5.8 (1H, m), 6.95-7.05 (1H, m), 7.2-7.5 (7H, m), 11.95-12.05 (1H, m), 1442 (1H, s) |
| 406 | | (DMSO-d6) 3.65-3.75 (2H, m), 4.0-4.1 (2H, m), 4.87 (1H, brs), 5.12 (2H, s), 6.95-7.0 (1H, m), 7.05 (1H, d, J = 8.1 Hz), 7.19 (1H, dd, J = 9.0 Hz, 3.0 Hz), 7.25-7.45 (4H, m), 7.56 (1H, d, J = 9.0 Hz), 12.04 (1H, s), 14.46 (1H, s) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 407 | 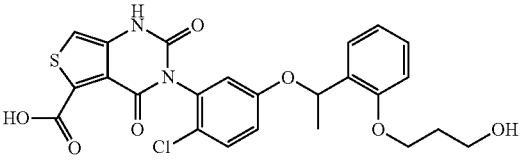 [SMILES: CC(Oc1ccc(Cl)c(-n2c(=O)[nH]c3csc(C(=O)O)c3c2=O)c1)c1ccccc1OCCCO] | (DMSO-d6) 1.54 (3H, d, J = 6.3 Hz), 1.85-1.95 (2H, m), 3.55-3.65 (2H, m), 4.05-4.2 (2H, m), 4.54 (1H, brs), 5.65-5.75 (1H, m), 6.85-7.0 (2H, m), 7.0-7.1 (1H, m), 7.15-7.2 (1H, m), 7.2-7.35 (2H, m), 7.4 (1H, d, J = 4.6 Hz), 7.47 (1H, d, J = 9.0 Hz), 11.95-12.05 (1H, m), 14.42 (1H, s) |
| 408 | 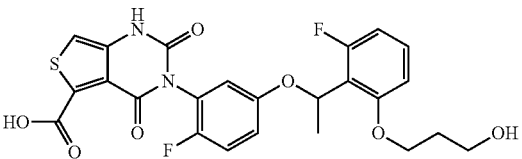 [SMILES: CC(Oc1ccc(F)c(-n2c(=O)[nH]c3csc(C(=O)O)c3c2=O)c1)c1c(F)cccc1OCCCO] | (DMSO-d6) 1.66 (3H, d, J = 6.4 Hz), 1.85-1.95 (2H, m), 3.5-3.6 (2H, m), 4.05-4.2 (2H, m), 5.75-5.85 (1H, m), 6.7-7.1 (4H, m), 7.2-7.4 (3H, 7), 11.95-12.05 (1H, m), 14.35-14.45 (1H, m) |
| 409 | 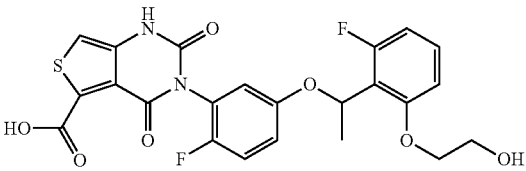 [SMILES: CC(Oc1ccc(F)c(-n2c(=O)[nH]c3csc(C(=O)O)c3c2=O)c1)c1c(F)cccc1OCCO] | (DMSO-d6) 1.66 (3H, d, J = 6.6 Hz), 3.55-3.8 (2H, m), 3.85-4.0 (1H, m), 4.05-4.2 (1H, m), 4.9-5.05 (1H, m), 5.9-6.0 (1H, m), 6.7-6.9 (2H, m), 7.0-7.4 (5H, m), 11.95-12.05 (1H, m), 14.44 (1H, s) |
| 410 | 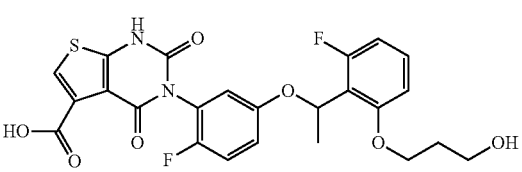 [SMILES: CC(Oc1ccc(F)c(-n2c(=O)[nH]c3scc(C(=O)O)c3c2=O)c1)c1c(F)cccc1OCCCO] | (DMSO-d6) 1.66 (3H, d, J = 6.4 Hz), 1.8-1.95 (2H, m), 3.5-3.6 (2H, m), 4.0-4.2 (2H, m), 5.8 (1H, q, J = 6.4 Hz), 6.7-6.8 (1H, m), 6.8-7.0 (2H, m), 7.0-7.05 (1H, m), 7.2-7.35 (2H, m), 7.9-7.95 (1H, m), 13.93 (1H, s) |
| 411 | 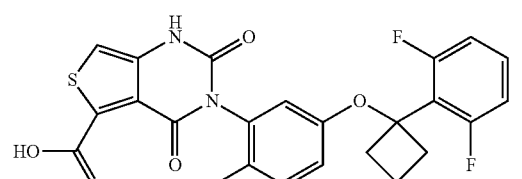 | (DMSO-d6) 1.85-2.0 (1H, m), 2.2-2.35 (1H, m), 2.65-2.85 (4H, m), 6.75-6.85 (1H, m), 7.0-7.1 (3H, m), 7.24 (1H, t, J = 9.3 Hz), 7.3-7.45 (2H, m), 11.97 (1H, brs), 13.5-15.0 (1H, br) |
| 412 | 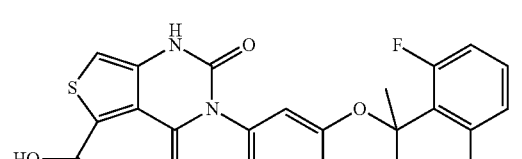 | (DMSO-d6) 1.820 (3H, s), 1.823 (3H, s), 6.75-6.8 (1H, m), 6.95-7.1 (3H, m), 7.15-7.25 (1H, m), 7.3-7.45 (2H, m), 11.96 (1H, brs), 14.43 (1H, brs) |
| 413 | 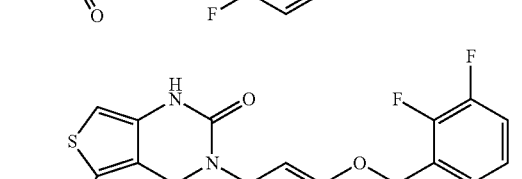 | (DMSO-d6) 3.79 (3H, s), 5.05-5.2 (2H, m), 6.8-6.9 (1H, m), 7.05-7.2 (1H, m), 7.37 (1H, s), 7.5-7.6 (1H, m), 7.65-7.75 (1H, m), 12.02 (1H, s), 14.35 (1H, s) |
| 414 | 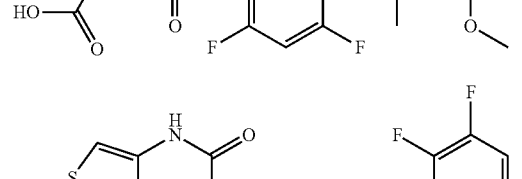 | (DMSO-d6) 3.79 (3H, s), 3.85 (3H, s), 5.0-5.1 (2H, m), 6.8-6.9 (1H, m), 7.05-7.2 (2H, m), 7.38 (1H, s), 7.51 (1H, d, J = 8.5 Hz), 11.98 (1H, s), 14.54 (1H, brs) |

TABLE 1-continued

Exemplary Thieno[3,4d]pyrimidine GnRH Antagonists Useful for the Treatment of Adenomyosis and Rectovaginal Endometriosis

| No. | Compound | Reported $^1$H NMR spectral properties |
|---|---|---|
| 415 | | (DMSO-d6) 3.27 (3H, s), 3.6-3.7 (2H, m), 4.1-4.2 (2H, m), 5.13 (2H, s), 6.85-6.95 (1H, m), 7.05-7.2 (1H, m), 7.39 (1H, s), 7.4-7.5 (1H, m), 7.6-7.7 (2H, m), 12.05 (1H, s), 14.42 (1H, s) |
| 416 | | (DMSO-d6) 1.05 (3H, t, J = 7.1 Hz), 3.46 (2H, q, J = 7.1 Hz), 3.65-3.75 (2H, m), 4.1-4.2 (2H, m), 5.14 (2H, s), 6.85-6.95 (1H, m), 7.05-7.2 (1H, m), 7.38 (1H, s), 7.4-7.5 (1H, m), 7.55-7.7 (2H, m), 12.05 (1H, s), 14.41 (1H, s) |
| 417 | | (DMSO-d6) 1.27 (3H, t, J = 7.1 Hz), 3.68 (2H, t, J = 4.8 Hz), 4.05 (2H, t, J = 4.8 Hz), 4.3 (2H, q, J = 7.1 Hz), 5.12 (2H, s), 6.85-6.95 (1H, m), 7.1-7.25 (3H, m), 7.25-7.35 (1H, m), 7.4-7.5 (1H, m), 11.63 (1H, s) |
| 418 | | (DMSO-d6) 1.13 (3H, t, J = 7.0 Hz), 1.27 (3H, t, J = 7.1 Hz), 4.03 (2H, q, J = 7.0 Hz), 4.25-4.35 (4H, m), 4.35-4.45 (2H, m), 5.07 (2H, s), 6.9-7.0 (1H, m), 7.1-7.2 (3H, m), 7.25-7.35 (1H, m), 7.4-7.55 (1H, m), 11.63 (1H, s) |
| 419 | | (DMSO-d6) 1.04 (9H, s), 1.27 (3H, t, J = 7.1 Hz), 4.2-4.35 (6H, m), 5.05 (2H, s), 6.9-7.05 (1H, m), 7.05-7.2 (3H, m), 7.25-7.35 (1H, m), 7.4-7.55 (1H, m), 11.63 (1H, s) |
| 420 | | (DMSO-d6) 2.7-2.75 (3H, m), 3.71 (3H, s), 4.1-4.25 (2H, m), 6.95-7.15 (4H, m), 7.38 (1H, s), 7.41 (1H, d, J = 8.6 Hz), 11.95 (1H, s), 14.57 (1H, brs) |
| 421 | | (DMSO-d6) 2.73 (3H, s), 3.74 (3H, s), 4.15-4.25 (2H, m), 7.08 (1H, d, J = 12.4 Hz), 7.15-7.2 (1H, m), 7.36 (1H, s), 7.4-7.45 (2H, m), 7.56 (1H, d, J = 8.7 Hz), 11.96 (1H, brs), 14.61 (1H, brs) |

TABLE 1-continued

Exemplary Thieno[3,4d]pyrimidine GnRH Antagonists Useful for the Treatment of
Adenomyosis and Rectovaginal Endometriosis

| No. | Compound | Reported $^1$H NMR spectral properties |
|---|---|---|
| 422 | 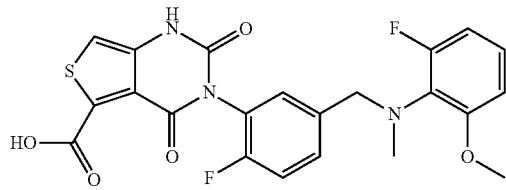 [SMILES: COc1cccc(F)c1N(C)Cc1ccc(F)c(-n2c(=O)[nH]c3csc(C(=O)O)c3c2=O)c1] | (DMSO-d6) 2.68 (3H, s), 3.81 (3H, s), 4.15 (2H, s), 6.7-6.85 (2H, m), 7.0-7.1 (1H, m), 7.3-7.4 (2H, m), 7.45-7.55 (2H, m), 11.98 (1H, s), 14.45 (1H, s) |
| 423 | 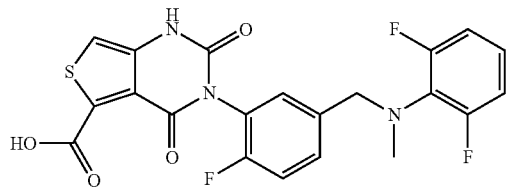 [SMILES: CN(Cc1ccc(F)c(-n2c(=O)[nH]c3csc(C(=O)O)c3c2=O)c1)c1c(F)cccc1F] | (DMSO-d6) 2.72 (3H, s), 4.3 (2H, s), 6.95-7.15 (3H, m), 7.35-7.45 (2H, m), 7.45-7.5 (2H, m), 12.02 (1H, s) |
| 424 | 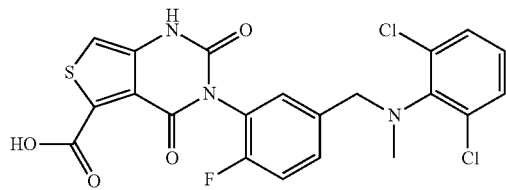 [SMILES: CN(Cc1ccc(F)c(-n2c(=O)[nH]c3csc(C(=O)O)c3c2=O)c1)c1c(Cl)cccc1Cl] | (DMSO-d6) 2.72 (3H, s), 4.3 (2H, s), 7.15-7.25 (1H, m), 7.35-7.5 (4H, m), 7.55-7.65 (2H, m), 12.03 (1H, s) |
| 425 | 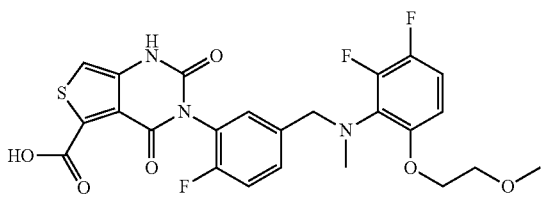 [SMILES: COCCOc1ccc(F)c(F)c1N(C)Cc1ccc(F)c(-n2c(=O)[nH]c3csc(C(=O)O)c3c2=O)c1] | (DMSO-d6) 2.7-2.75 (3H, m), 3.23 (3H, s), 3.6-3.7 (2H, m), 4.05-4.1 (2H, m), 4.22 (2H, s), 6.7-6.8 (1H, m), 7.0-7.1 (1H, m), 7.3-7.4 (2H, m), 7.45-7.55 (2H, m), 12.03 (1H, s), 14.46 (1H, brs) |
| 426 | 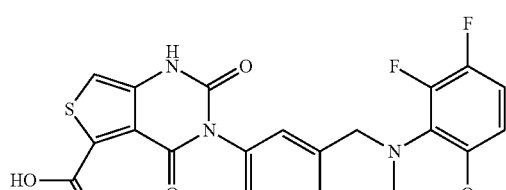 | (DMSO-d6) 2.7-2.75 (3H, m), 3.79 (3H, s), 4.2 (2H, s), 6.7-6.8 (1H, m), 7.0-7.15 (1H, m), 7.3-7.4 (2H, m), 7.45-7.55 (2H, m), 12.02 (1H, s), 14.47 (1H, brs) |
| 427 | 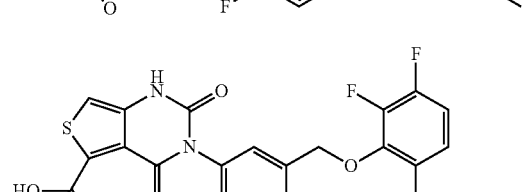 | (DMSO-d6) 3.7-3.8 (2H, m), 4.04 (2H, t, J = 4.6 Hz), 4.85-4.95 (1H, m), 5.17 (2H, s), 6.85-6.95 (1H, m), 7.05-7.15 (1H, m), 7.39 (1H, s), 7.4-7.5 (1H, m), 7.6-7.7 (2H, m), 12.05 (1H, s), 14.44 (1H, s) |
| 428 | 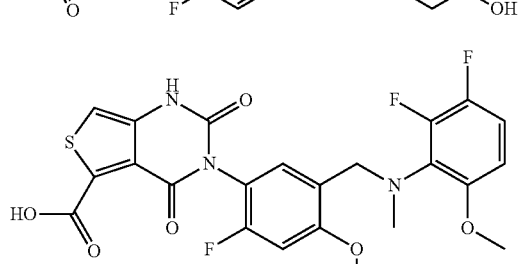 | (DMSO-d6) 2.7-2.75 (3H, m), 3.7- 3.8 (6H, m), 4.1-4.2 (2H, m), 6.7-6.75 (1H, m), 6.95-7.1 (2H, m), 7.37 (1H, s), 7.41 (1H, d, J = 8.8 Hz), 11.95 (1H, s), 14.57 (1H, s) |

For example, the GnRH antagonist may be 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid, or a pharmaceutically acceptable salt thereof. The salt may be, for instance, the choline salt thereof, represented by formula (VIa), below.

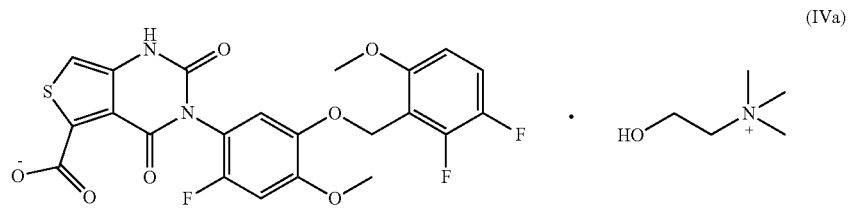
(IVa)

Compound (VI) and pharmaceutically acceptable salts thereof, such as the choline salt thereof (compound (VIa)), can be synthesized, for example, using the methodology described in WO 2014/042176, the disclosure of which is incorporated herein by reference in its entirety. An exemplary synthetic scheme that may be used for the preparation of compound (VI) and the choline salt thereof is shown in Scheme 1, below.

-continued

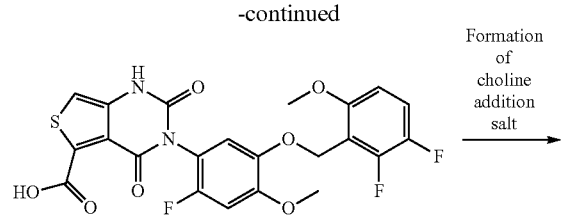
Formation of choline addition salt

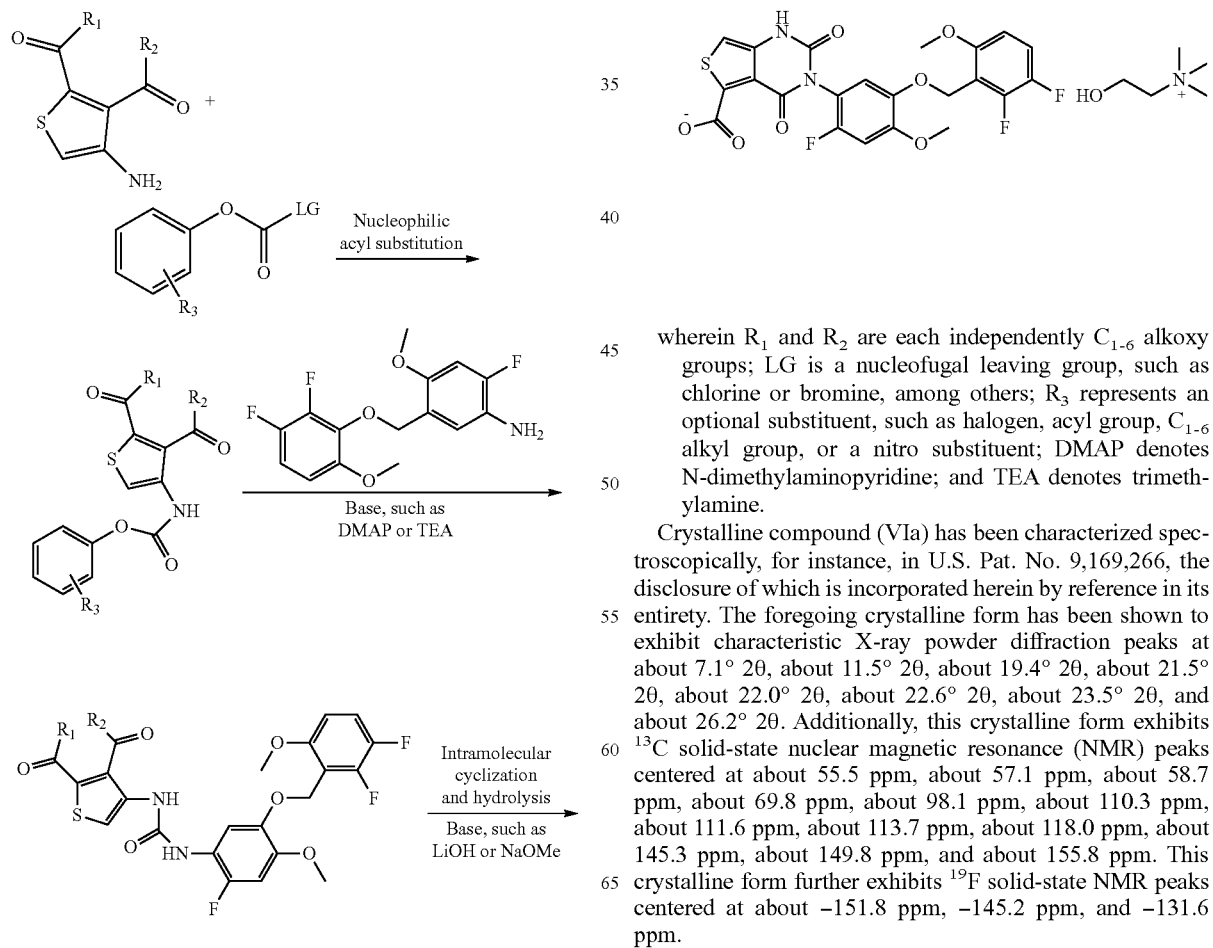

Scheme 1. Exemplary preparation of compound (VI) and the choline salt thereof wherein $R_1$ and $R_2$ are each independently $C_{1-6}$ alkoxy groups; LG is a nucleofugal leaving group, such as chlorine or bromine, among others; $R_3$ represents an optional substituent, such as halogen, acyl group, $C_{1-6}$ alkyl group, or a nitro substituent; DMAP denotes N-dimethylaminopyridine; and TEA denotes trimethylamine.

Crystalline compound (VIa) has been characterized spectroscopically, for instance, in U.S. Pat. No. 9,169,266, the disclosure of which is incorporated herein by reference in its entirety. The foregoing crystalline form has been shown to exhibit characteristic X-ray powder diffraction peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ. Additionally, this crystalline form exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm. This crystalline form further exhibits $^{19}F$ solid-state NMR peaks centered at about −151.8 ppm, −145.2 ppm, and −131.6 ppm.

Compound (VI), as well as pharmaceutically acceptable salts thereof, such as the choline salt thereof, exhibit a high affinity for human GnRH receptor (27.4 nM). Using the compositions and methods described herein, a patient that is presenting with or has been diagnosed as having, adenomyosis or rectovaginal endometriosis may be administered a compound of formula (VI), or a pharmaceutically acceptable salt thereof, such as the choline salt thereof, to treat the disease or ameliorate one or more symptoms of the disease. Exemplary doses of compound (VI) and pharmaceutically acceptable salts thereof, such as the choline salt thereof, include doses of from 25 mg to 500 mg daily, such as doses of 100 mg per day and 200 mg per day. Additional dosing information is provided below.

3-Aminoalkyl pyrimidine-2,4(1H,3H)-diones

Additional GnRH antagonists that may be used in conjunction with the compositions and methods described herein include optionally substituted 3-aminoalkyl pyrimidine-2,4(1H,3H)-dione derivatives, such as compounds represented by formula (VII)

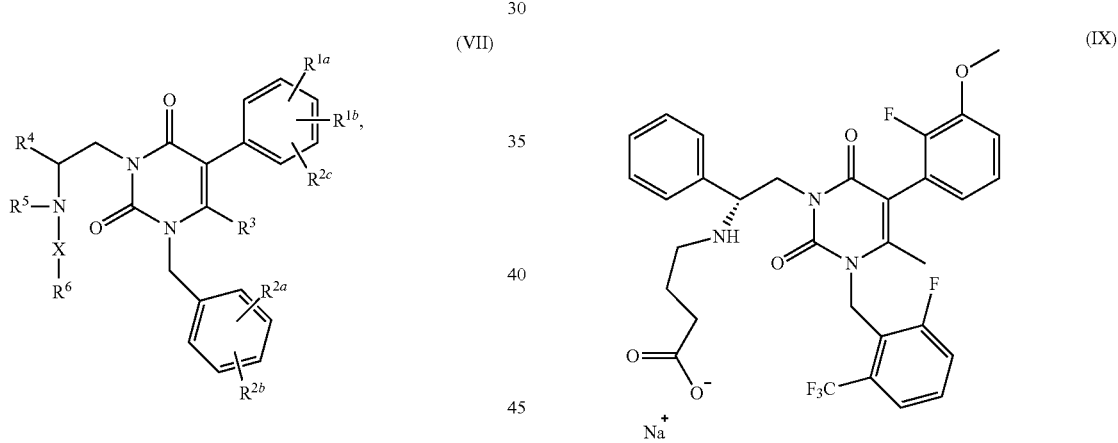

(VII)

wherein $R_{1a}$, $R_{1b}$ and $R_{1c}$ are the same or different and are each independently hydrogen, halogen, $C_{1-4}$alkyl, hydroxy or alkoxy, or $R_{1a}$ and $R_{1b}$ taken together form —OCH$_2$O— or —OCH$_2$CH$_2$—;

$R_{2a}$ and $R_{2b}$ are the same or different and are each independently hydrogen, halogen, trifluoromethyl, cyano or —SO$_2$CH$_3$;

$R_3$ is hydrogen or methyl;

$R_4$ is phenyl or $C_{3-7}$alkyl;

$R_5$ is hydrogen or $C_{1-6}$alkyl;

$R_5$ is —COOH or an acid isostere; and

X is $C_{1-6}$ alkanediyl optionally substituted with from 1 to 3 $C_{1-6}$alkyl groups;

or a pharmaceutically acceptable salt thereof.

For example, the GnRH antagonist may be the conjugate acid of elagolix, which is represented by formula (VIII),

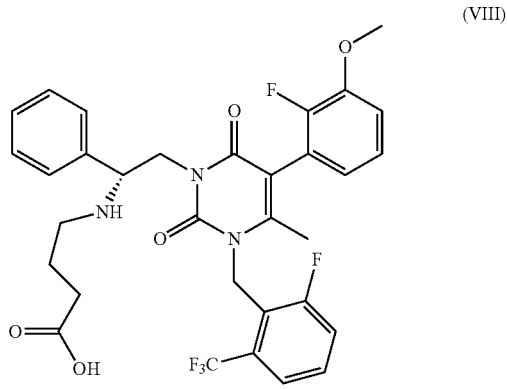 [SMILES: COc1cccc(-c2c(C)n(Cc3c(F)cccc3C(F)(F)F)c(=O)n(C[C@H](NCCCC(=O)O)c3ccccc3)c2=O)c1F]

or a pharmaceutically acceptable salt thereof. In some embodiments, the GnRH antagonist is the sodium salt of the compound represented by formula (VIII), which is represented by formula (IX), below.

(IX)

Compound (IX), also referred to as sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate, is known as elagolix. Other GnRH antagonists of this chemical class that may be used for the treatment of adenomyosis and/or rectovaginal endometriosis in accordance with the compositions and methods of the disclosure include compounds described in U.S. Pat. No. 7,056,927, the contents of which are incorporated herein by reference. Exemplary GnRH antagonists of this chemical class that may be used for the treatment of adenomyosis and/or rectovaginal endometriosis in accordance with the present disclosure include the compounds set forth in Table 2, below.

TABLE 2
Exemplary 3-Aminoalkyl pyrimidine-2,4(1H,3H)-dione GnRH Antagonists Useful for the Treatment of Adenomyosis and Rectovaginal Endometriosis
| No. | Compound | Reported spectral properties |
|---|---|---|
| 1 | 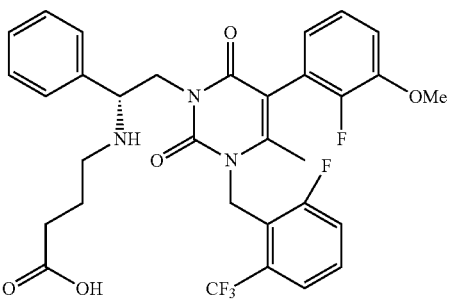 | HPLC-MS (Cl) m/z 632.2 (MH+), tR = 26.45 |
| 2 | 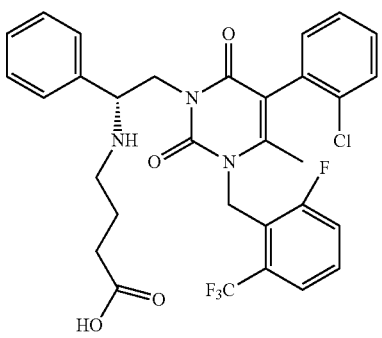 [SMILES: Cc1c(-c2ccccc2Cl)c(=O)n(C[C@H](NCCCC(=O)O)c2ccccc2)c(=O)n1Cc1c(F)cccc1C(F)(F)F] | MS (Cl) m/z 618.2 (MH+) tR = 1.005 |
| 3 | 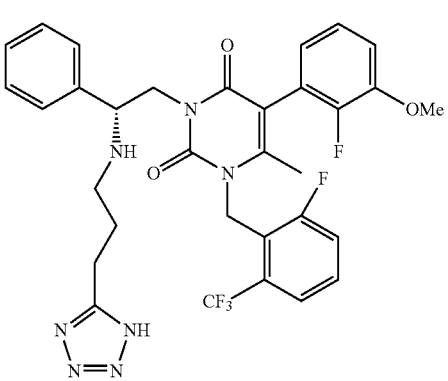 [SMILES: COc1cccc(-c2c(C)n(Cc3c(F)cccc3C(F)(F)F)c(=O)n(C[C@H](NCCCc3nnn[nH]3)c3ccccc3)c2=O)c1F] | HPLC-MS (Cl) m/z 656.2 (MH+), tR = 2.128 min |
| 4 | 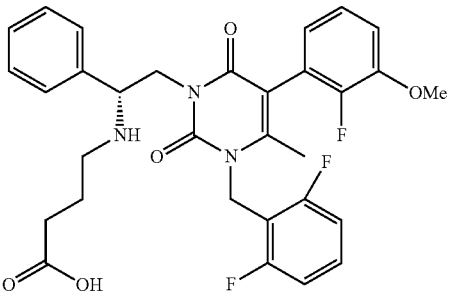 [SMILES: COc1cccc(-c2c(C)n(Cc3c(F)cccc3F)c(=O)n(C[C@H](NCCCC(=O)O)c3ccccc3)c2=O)c1F] | MS (Cl) m/z 588.3 (MH+) |

TABLE 2-continued
Exemplary 3-Aminoalkyl pyrimidine-2,4(1H,3H)-dione GnRH Antagonists Useful for the Treatment of Adenomyosis and Rectovaginal Endometriosis
| No. | Compound | Reported spectral properties |
|---|---|---|
| 5 | 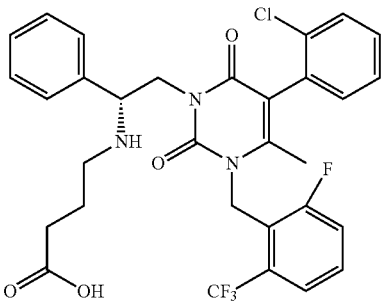 | HPLC-MS (Cl) m/z 604.1, 606.1 (MH+), tR = 2.511 |
| 6 | 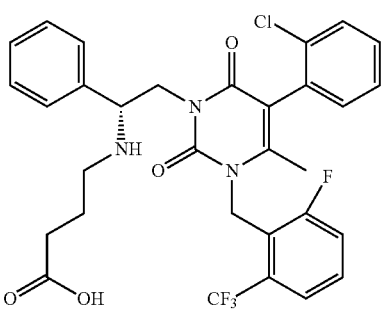 | HPLC-MS (Cl) m/z 604.1, 606.1 (MH+), tR = 26.98 |
| 7 | 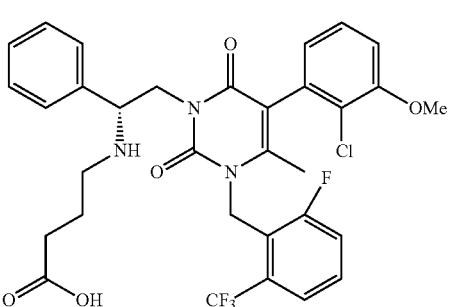 | HPLC-MS (Cl) m/z 634.2, 636.2 (MH+), tR-24.925 |
| 8 | 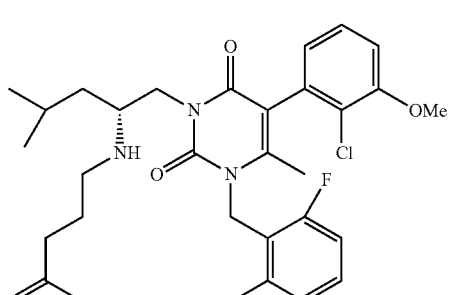 | MS (Cl) m/z 614.1, 616.1 (MH+), tR = 6.550 min |

TABLE 2-continued

Exemplary 3-Aminoalkyl pyrimidine-2,4(1H,3H)-dione GnRH Antagonists Useful for the Treatment of Adenomyosis and Rectovaginal Endometriosis

| No. | Compound | Reported spectral properties |
|---|---|---|
| 9 | | HPLC-MS (Cl) m/z 592.3 (MH+), tR = 2.150 |
| 10 | | HPLC-MS (Cl) m/z = 556.2 (M + H+), tR = 2.354 |
| 11 | | |

Thieno[2,3d]pyrimidines

Additional GnRH antagonists that may be used in conjunction with the compositions and methods described herein include optionally substituted thieno[2,3d]pyrimidine derivatives, such as compounds represented by formula (X)

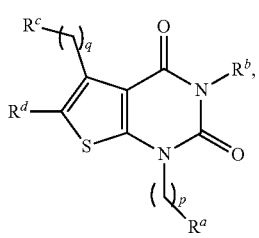

(X)

wherein $R^a$ is a hydrogen atom, an optionally substituted aryl group (such as an aryl group that may have 1 to 5 substituents selected from halogen, nitro, cyano, amino, a carboxyl group that may be esterified or amidated, an alkylenedioxy, alkyl, alkoxy, alkylthio, alkylsulfinyl, and alkylsulfonyl), an optionally substituted cycloalkyl group, or an optionally substituted heterocyclic group;

$R^b$ is an optionally substituted nitrogen-containing heterocyclic group;

$R^c$ is an optionally substituted amino group;

$R^d$ is an optionally substituted aryl group;

p is an integer from 0 to 3; and q is an integer from 0 to 3;

or a pharmaceutically acceptable salt thereof.

In some embodiments, the GnRH antagonist is a thieno[2,3d]pyrimidine compound represented by formula (XI)

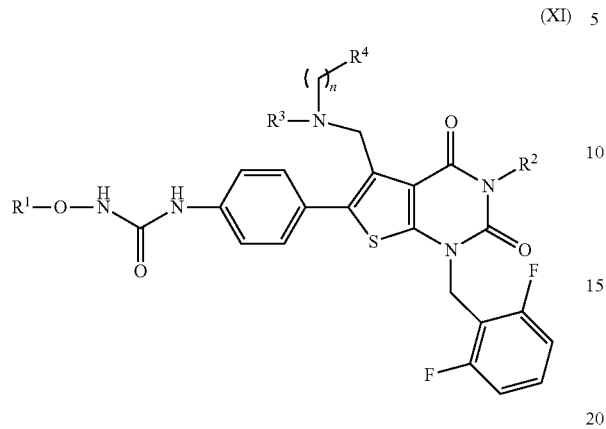

(XI)

wherein $R^1$ is $C_{1-4}$alkyl;
$R^2$ is (1) a $C_{1-6}$alkyl which may have a substituent selected from the group consisting of (1') a hydroxy group, (2') a $C_{1-4}$alkoxy, (3') a $C_{1-4}$alkoxy-carbonyl, (4') a di-$C_{1-4}$alkyl-carbamoyl, (5') a 5- to 7-membered nitrogen-containing heterocyclic group, (6') a $C_{1-4}$alkyl-carbonyl and (7') a halogen, (2) a $C_{3-8}$ cycloalkyl which may have (1') a hydroxy group or (2') a mono-$C_{1-4}$alkyl-carbonylamino, (3) a 5- to 7-membered nitrogen-containing heterocyclic group which may have a substituent selected from the group consisting of (1') a halogen, (2') a hydroxy group, (3') a $C_{1-4}$alkyl and (4') a $C_{1-4}$alkoxy, (4) a phenyl which may have a substituent selected from the group consisting of (1') a halogen, (2') a $C_{1-4}$alkoxy-$C_{1-4}$alkyl, (3') a mono-$C_{1-4}$alkyl-carbamoyl-$C_{1-4}$alkyl, (4') a $C_{1-4}$alkoxy and (5') a mono-$C_{1-4}$alkylcarbamoyl-$C_{1-4}$alkoxy, or (5) a $C_{1-4}$alkoxy;
$R^3$ is $C_{1-4}$alkyl;
$R^4$ is (1) hydrogen, (2) $C_{1-4}$alkoxy, (3) $C_{6-10}$aryl, (4) N—$C_{1-4}$alkyl-N—$C_{1-4}$alkylsulfonylamino, (5) hydroxyl, or (6) a 5- to 7-membered nitrogen-containing heterocyclic group which may have a substituent selected from the group consisting of (1') oxo, (2') a $C_{1-4}$alkyl, (3') a hydroxy-$C_{1-4}$alkyl, (4') a $C_{1-4}$alkoxy-carbonyl, (5') a mono-$C_{1-4}$alkyl-carbamoyl and (6') a $C_{1-4}$alkylsulfonyl; and
n is an integer from 1 to 4;
optionally provided that when $R^2$ is a phenyl which may have a substituent, $R^4$ is a 5- to 7-membered nitrogen-containing heterocyclic group which may have a substituent selected from the group consisting of (1) oxo, (2) hydroxy-$C_{1-4}$alkyl, (3) $C_{1-4}$alkoxy-carbonyl, (4) mono-$C_{1-4}$alkyl-carbamoyl and (5) $C_{1-4}$alkylsulfonyl;
or a pharmaceutically acceptable salt thereof. For example, the GnRH antagonist may be a compound represented by formula (XII), below.

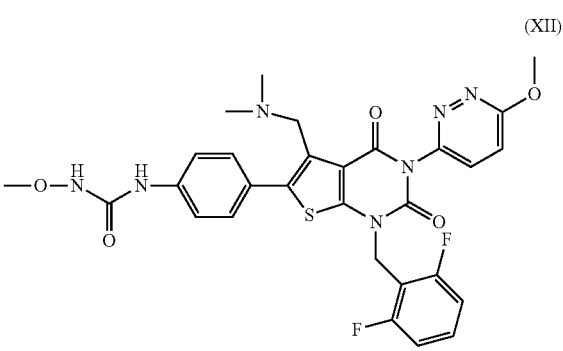

(XII)

Compound (XII), also referred to as N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, is known as relugolix. Other GnRH antagonists of this chemical class that may be used for the treatment of adenomyosis and/or rectovaginal endometriosis in accordance with the compositions and methods of the disclosure include compounds described in U.S. Pat. No. 7,300,935, the contents of which are incorporated herein by reference. Exemplary GnRH antagonists of this chemical class that may be used for the treatment of adenomyosis and/or rectovaginal endometriosis in accordance with the present disclosure include the compounds set forth in Table 3, below.

TABLE 3

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 1 | | $^1$H-NMR (CDCl$_3$) δ: 2.05 (3H, s), 3.56 (2H, s), 3.82 (3H, s), 3.89 (2H, s), 5.34 (2H, brs), 6.91 (2H, t, J = 8.0 Hz), 7.1-7.45 (9H, m), 756 (2H, d, J = 8.8 Hz), 7.65 (1H, s), 7.75 (2H, d, J = 8.8 Hz), 7.91 (1H, dt, J = 2.0, 7.7 Hz), 8.7-8.75 (1H, m). |

TABLE 3-continued
Exemplary Thieno[2,3d]pyrimidine GnRH Antagonists Useful for the Treatment of Adenomyosis and Rectovaginal Endometriosis
| No. | Compound | Reported spectral properties |
|---|---|---|
| 2 | 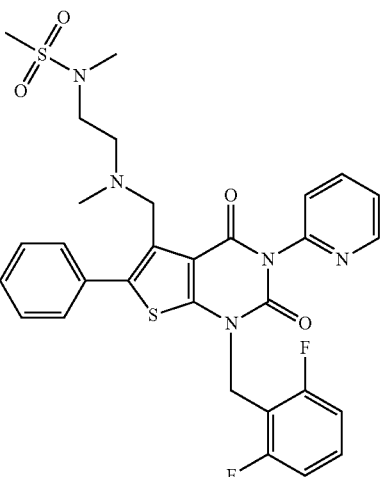 | $^1$H-NMR (CDCl$_3$) δ: 2.11 (3H, s), 2.45-2.6 (2H, m), 2.70 (3H, s), 2.75 (3H, s), 3.1-3.25 (2H, m), 3.80 (2H, s), 3.83 (3H, s), 5.36 (2H, brs), 6.93 (2H, t, J = 8.2 Hz), 7.14 (1H, s), 7.2-7.6 (7H, m), 765 (1H, s), 7.85-7.95 (1H, m), 8.65-8.75 (1H, m). |
| 3 | 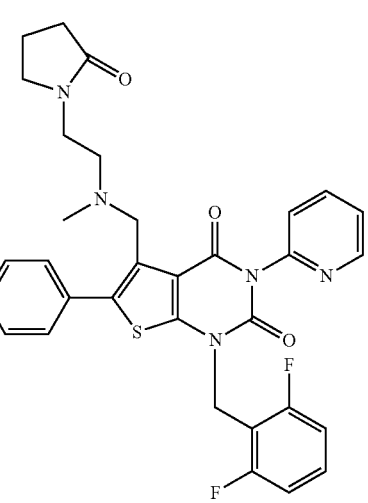 | $^1$H-NMR (CDCl$_3$) δ: 1.7-1.85 (2H, m), 2.17 (3H, s), 2.15-2.3 (2H, m), 2.5-2.6 (2H, m), 3.15 (2H, t, J = 7.0 Hz), 3.2-3.4 (2H, m), 3.76 (2H, s), 3.83 (3H, s), 5.36 (2H, brs), 6.93 (2H, t, J = 8.4 Hz), 7.16 (1H, s), 7.2-7.7 (8H, m), 7.85-7.95 (1H, m), 8.65-8.75 (1H, m). |
| 4 | 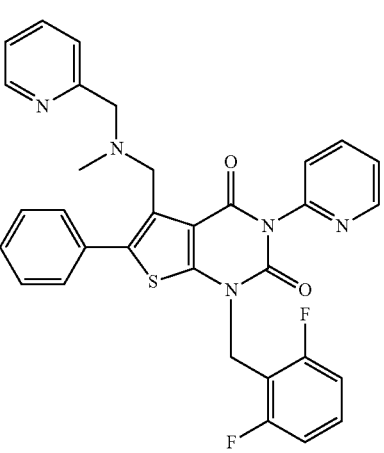 | $^1$H-NMR (CDCl$_3$) δ: 2.10 (3H, s), 3.70 (2H, s), 3.82 (3H, s), 3.96 (3H, s), 5.34 (2H, brs), 6.85-7.7 (14H, m), 7.85-7.95 (1H, m), 8.4-8.5 (1H, m), 8.65-8.75 (1H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 5 | 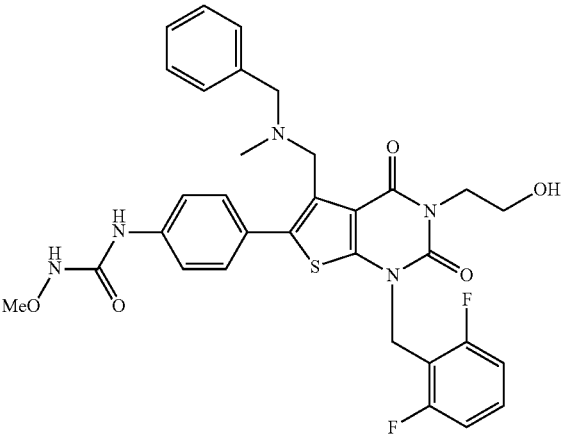 [SMILES: CONC(=O)Nc1ccc(-c2sc3c(c2CN(C)Cc2ccccc2)c(=O)n(CCO)c(=O)n3Cc2c(F)cccc2F)cc1] | $^1$H-NMR (CDCl$_3$) δ: 2.04 (3H, s), 2.5-2.65 (1H, m), 3.58 (2H, s), 3.83 (3H, s), 3.91 (2H, s), 3.9-4.0 (2H, m), 4.37 (2H, t, J = 5.0 Hz), 5.34 (2H, s), 6.92 (2H, t, J = 8.2 Hz), 7.1-7.4 (7H, m), 7.54 (2H, d, J = 8.6 Hz), 7.66 (2H, d, J = 8.6 Hz), 7.6-7.7(1H, m). |
| 6 | 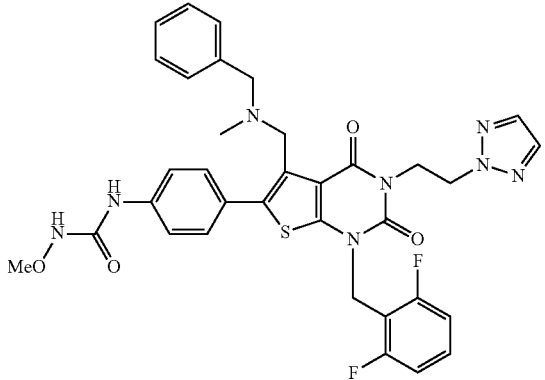 [SMILES: CONC(=O)Nc1ccc(-c2sc3c(c2CN(C)Cc2ccccc2)c(=O)n(CCn2ncnn2)c(=O)n3Cc2c(F)cccc2F)cc1] | $^1$H-NMR (CDCl$_3$) δ: 2.04 (3H, s), 3.51 (2H, s), 3.82 (3H, s), 3.86 (2H, s), 4.57 (2H, t, J = 6.2 Hz), 4.81 (2H, t, J = 6.2 Hz), 5.28 (2H, s), 6.91 (2H, t, J = 8.4 Hz), 7.15-7.35 (6H, m), 7.46 (2H, s), 7.53 (2H, d, J = 8.6 Hz), 762 (1H, s), 7.70 (2H, t, J = 8.6 Hz), 7.75 (1H, s). |
| 7 | 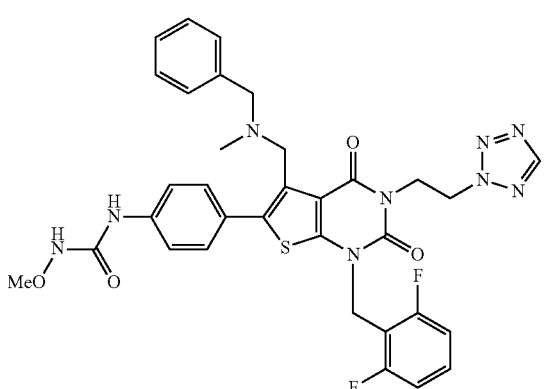 | 2-yl Form (1)<br>$^1$H-NMR (CDCl$_3$) δ: 2.02 (3H, s), 3.51 (2H, s), 3.83 (5H, s), 4.6-4.7 (2H, m), 5.0-5.1 (2H, m), 5.28 (2H, s), 6.92 (2H, t, J = 8.2 Hz), 7.12 (1H, s), 7.2-7.75 (11H, m), 8.38 (1H, s). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| | 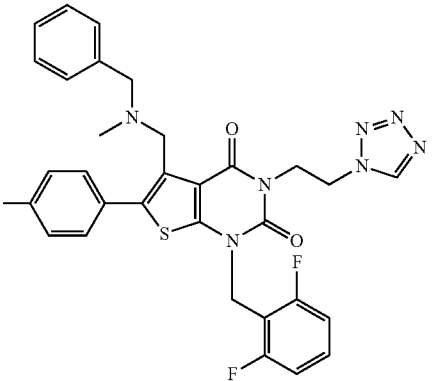 | 1-yl Form (2)<br>$^1$H-NMR (CDCl$_3$) δ: 2.01 (3H, s), 3.51 (2H, s), 3.83 (3H, s), 3.8-4.0 (2H, m), 4.6-4.7 (2H, m), 4.8-4.9 (2H, m), 5.30 (2H, s), 6.65-6.75 (1H, m), 6.85-7.0 (2H, m), 7.1-7.7 (11H, m), 8.68 (1H, s). |
| 8 | 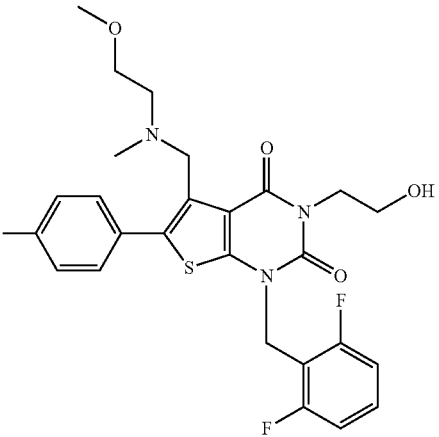 | $^1$H-NMR (CDCl$_3$) δ: 2.11 (3H, s), 2.65 (2H, t, J = 5.8 Hz), 3.30 (3H, s), 3.46 (2H, t, J = 5.8 Hz), 3.82 (5H, s), 3.9-4.0 (2H, m), 4.35 (2H, t, J = 5.2 Hz), 5.34 (2H, s), 6.92 (2H, t, J = 8.0 Hz), 7.14 (1H, s), 7.2-7.35 (1H, m), 7.5-7.65 (5H, m). |
| 9 | 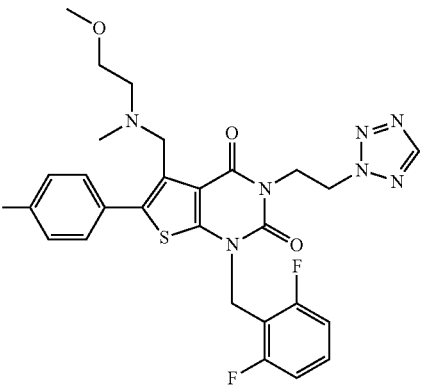 | 2-yl Form (1)<br>$^1$H-NMR (CDCl$_3$) δ: 2.10 (3H, brs), 2.55-2.65 (2H, m), 3.31 (3H, s), 3.4-3.5 (2H, m), 3.76 (2H, s), 3.82 (3H, s), 4.62 (2H, t, J = 5.8 Hz), 5.02 (2H, t, J = 5.8 Hz), 5.27 (2H, s), 6.92 (2H, t, J = 8.2 Hz), 7.13 (1H, s), 7.25-7.4 (1H, m), 7.5-7.65 (5H, m), 8.43 (1H, s). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
|  | 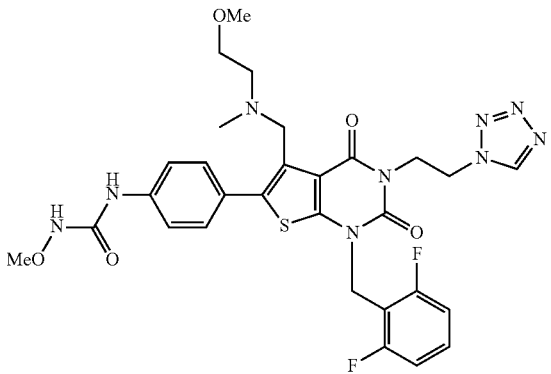 [SMILES: COCCN(C)Cc1c(-c2ccc(NC(=O)NOC)cc2)sc2c1c(=O)n(CCn1cnnn1)c(=O)n2Cc1c(F)cccc1F] | 1-yl Form (2)<br>$^1$H-NMR (CDCl$_3$) δ: 2.07 (3H, s), 2.55-2.65 (2H, m), 3.30 (3H, s), 3.4-3.5 (2H, m), 3.74 (2H, s), 3.82 (3H, s), 4.55-4.65 (2H, m), 4.8-4.9 (2H, m), 5.30 (2H, s), 6.93 (2H, t, J = 7.8 Hz), 7.5-7.65 (5H, m), 8.69 (1H, s). |
| 10 | 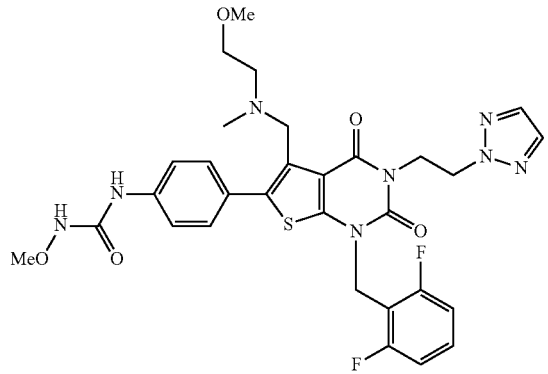 [SMILES: COCCN(C)Cc1c(-c2ccc(NC(=O)NOC)cc2)sc2c1c(=O)n(CCn1nccn1)c(=O)n2Cc1c(F)cccc1F] | $^1$H-NMR (CDCl$_3$) δ: 2.11 (3H, s), 2.62 (2H, t, J = 5.8 Hz), 3.31 (3H, s), 3.44 (2H, t, J = 5.8 Hz), 3.78 (2H, s), 3.82 (3H, s), 4.55 (2H, t, J = 5.6 Hz), 4.79 (2H, t, J = 5.6 Hz), 5.27 (2H, s), 6.91 (2H, t, J = 8.2 Hz), 7.10 (1H, s), 7.2-7.4 (2H, m), 7.51 (2H, s), 7.45-7.65 (4H, m). |
| 11 |  | 2-yl Form (1)<br>$^1$H-NMR (CDCl$_3$) δ: 2.23 (3H, s), 3.00 (2H, t, J = 6.3 Hz), 3.78 (2H, s), 3.82 (3H, s), 4.45 (2H, t, J = 6.3 Hz), 5.37 (2H, s), 6.92 (2H, t, J = 8.2 Hz), 6.85-6.95 (1H, m), 7.11 (1H, s), 7.2-7.6 (12H, m). |

TABLE 3-continued
Exemplary Thieno[2,3d]pyrimidine GnRH Antagonists Useful for the Treatment of Adenomyosis and Rectovaginal Endometriosis
| No. | Compound | Reported spectral properties |
|---|---|---|
|  | 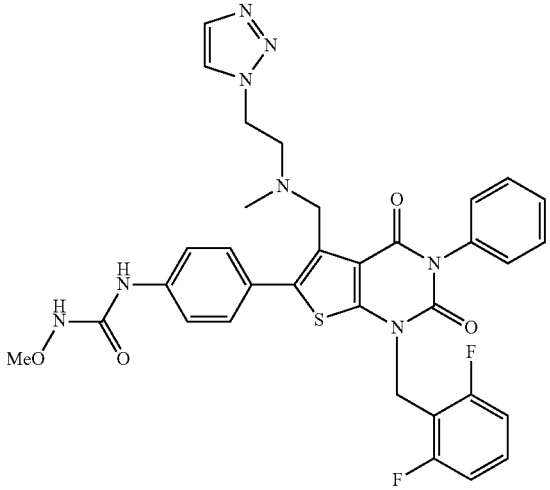 [SMILES: CONC(=O)Nc1ccc(-c2sc3c(c2CN(C)CCn2ccnn2)c(=O)n(-c2ccccc2)c(=O)n3Cc2c(F)cccc2F)cc1] | 1-yl Form (2)<br>$^1$H-NMR (CDCl$_3$) δ: 2.14 (3H, s), 2.82 (2H, t, J = 6.0 Hz), 3.80 (2H, s), 3.82 (3H, s), 4.39 (2H, t, J = 6.0 Hz), 5.37 (2H, s), 6.92 (2H, t, J = 8.2 Hz), 6.85-6.95 (1H, m), 7.14 (1H, s), 7.2-7.55 (11H, m), 7.63 (1H, s). |
| 12 | 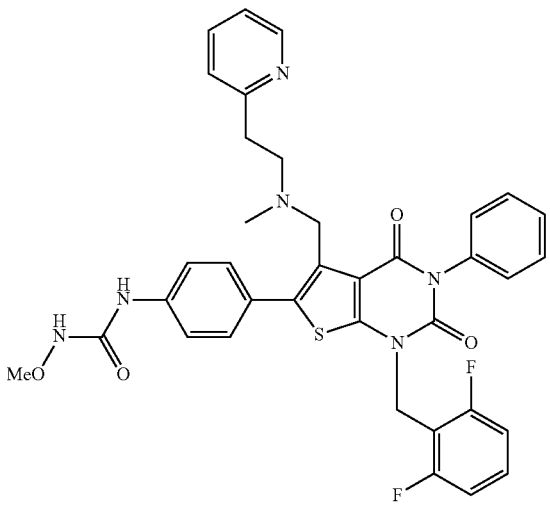 [SMILES: CONC(=O)Nc1ccc(-c2sc3c(c2CN(C)CCc2ccccn2)c(=O)n(-c2ccccc2)c(=O)n3Cc2c(F)cccc2F)cc1] | $^1$H-NMR (CDCl$_3$) δ: 2.20 (3H, s), 2.85 (4H, s), 3.82 (5H, s), 5.37 (2H, s), 6.93 (2H, t, J = 8.2 Hz), 6.95-7.1 (2H, m), 7.14 (1H, s), 7.2-7.55 (11H, m), 760 (1H, s), 8.43(1H d, J = 4.0 Hz). |
| 13 | 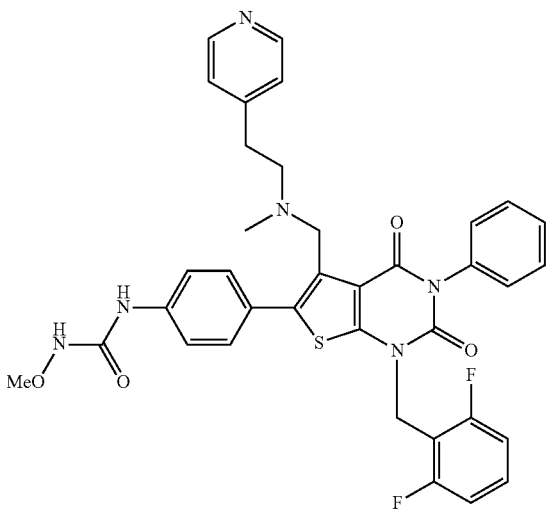 [SMILES: CONC(=O)Nc1ccc(-c2sc3c(c2CN(C)CCc2ccncc2)c(=O)n(-c2ccccc2)c(=O)n3Cc2c(F)cccc2F)cc1] | $^1$H-NMR (CDCl$_3$) δ: 2.18 (3H, s), 2.68 (4H, s), 3.83 (5H, s), 5.37 (2H, s), 6.85-7.0 (5H, m), 7.16 (1H, s), 7.2-7.65 (10H, m), 8.35-8.4 (2H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
| --- | --- | --- |
| 14 | | $^1$H-NMR (CDCl$_3$) δ: 2.10 (3H, s), 3.71 (2H, s), 3.83 (3H, s), 3.99 (2H, s), 5.36 (2H, s), 6.92 (2H, t, J = 8.2 Hz), 7.0-7.1 (1H, m), 7.15 (1H, s), 7.2-7.35 (4H, m), 7.4-7.65 (9H, m), 8.4-8.5 (1H, m). |
| 15 | | $^1$H-NMR (CDCl$_3$) δ: 2.10 (3H, s), 3.71 (2H, s), 3.83 (3H, s), 3.97 (2H, s), 5.35 (2H, s), 6.93 (2H, t, J = 8.2 Hz), 7.0-7.7 (14H, m), 8.4-8.5 (1H, m). |
| 16 | | $^1$H-NMR (CDCl$_3$) δ: 2.19 (3H, s), 2.85 (4H, s), 3.82 (5H, s), 5.36 (2H, s), 6.9-7.55 (13H, m), 7.60 (1H, s), 8.4-8.45 (1H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 17 | | $^1$H-NMR (CDCl$_3$) δ: 2.21 (3H, s), 2.8-2.9 (4H, m), 3.82 (5H, s), 5.34 (2H, brs), 6.85-7.75 (13H, m), 7.60 (1H, s), 7.85-7.95 (1H, m), 8.4-8.5 (1H, m), 8.65-8.75 (1H, m). |
| 18 | | $^1$H-NMR (CDCl$_3$) δ: 2.04 (3H, s), 3.58 (2H, s), 3.83 (3H, s), 3.92 (2H, s), 5.37 (2H, s), 6.92 (2H, t, J = 8.2 Hz), 7.05-7.7 (14H, m), 8.35-8.45 (2H, m). |
| 19 | | $^1$H-NMR (CDCl$_3$) δ: 2.13 (3H, s), 3.72 (2H, s), 3.83 (3H, s), 3.97 (2H, s), 4.05-4.1 (1H, m), 4.65-4.75 (2H, m), 5.37 (2H, s), 6.93 (2H, t, J = 8.2 Hz), 6.9-7.05 (1H, m), 7.1-7.2 (2H, m), 7.2-7.7 (12H, m). |

TABLE 3-continued
Exemplary Thieno[2,3d]pyrimidine GnRH Antagonists Useful for the Treatment of Adenomyosis and Rectovaginal Endometriosis
| No. | Compound | Reported spectral properties |
|---|---|---|
| 20 | 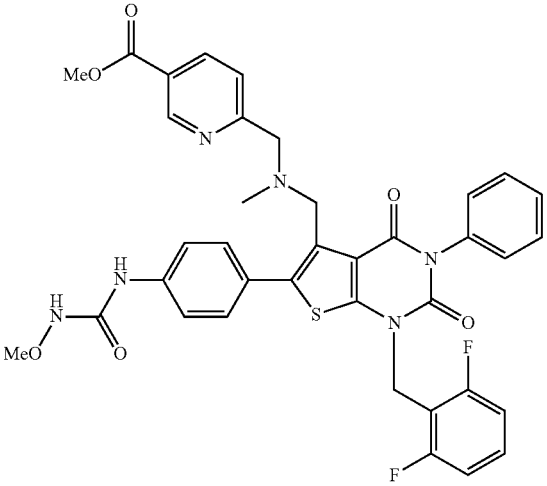 [SMILES: CONC(=O)Nc1ccc(-c2sc3c(c2CN(C)Cc2ccc(C(=O)OC)cn2)c(=O)n(-c2ccccc2)c(=O)n3Cc2c(F)cccc2F)cc1] | $^1$H-NMR (CDCl$_3$) δ: 2.09 (3H, s), 3.76 (2H, s), 3.83 (3H, s), 3.93 (3H, s), 3.99 (2H, s), 5.35 (2H, s), 6.92 (2H, t, J = 8.2 Hz), 7.26 (1H, s), 7.2-7.6 (11H, m), 7.64 (1H, s), 8.05-8.15 (1H, m), 9.0-9.05 (1H, s). |
| 21 | 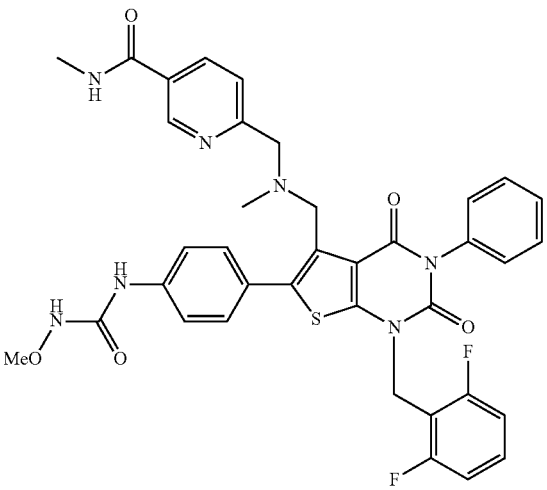 [SMILES: CNC(=O)c1ccc(CN(C)Cc2c(-c3ccc(NC(=O)NOC)cc3)sc3c2c(=O)n(-c2ccccc2)c(=O)n3Cc2c(F)cccc2F)nc1] | $^1$H-NMR (CDCl$_3$) δ: 2.21 (3H, s), 3.00 (3H, d, J = 4.6 Hz), 3.74 (2H, s), 3.84 (3H, s), 3.92 (2H, s), 5.36 (2H, s), 6.5-6.65 (1H, m), 6.92 (2H, t, J = 8.0 Hz), 7.15-7.6 (12H, m), 7.71 (1H, s), 7.9-8.0 (1H, m), 8.80-8.85 (1H, m). |
| 22 | 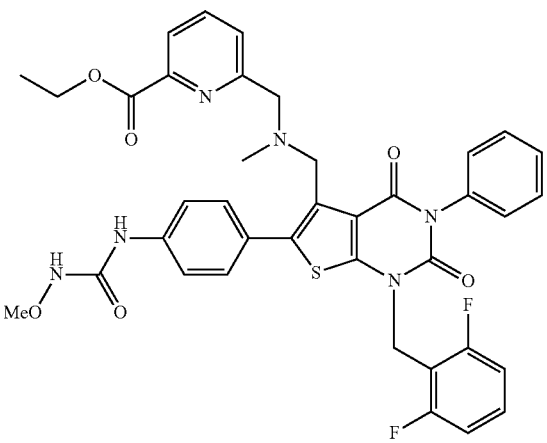 [SMILES: CCOC(=O)c1cccc(CN(C)Cc2c(-c3ccc(NC(=O)NOC)cc3)sc3c2c(=O)n(-c2ccccc2)c(=O)n3Cc2c(F)cccc2F)n1] | $^1$H-NMR (CDCl$_3$) δ: 1.40 (3H, t, J = 7.2 Hz), 2.10 (3H, s), 3.79 (2H, s), 3.83 (3H, s), 4.01 (2H, s), 4.43 (2H, q, J = 7.2 Hz), 5.35 (2H, s), 6.92 (2H, t, J = 8.2 Hz), 7.15 (1H, s), 7.2-7.7 (13H, m), 7.88 (1H, d, J = 7.4 Hz). |

TABLE 3-continued
Exemplary Thieno[2,3d]pyrimidine GnRH Antagonists Useful for the Treatment of Adenomyosis and Rectovaginal Endometriosis
| No. | Compound | Reported spectral properties |
|---|---|---|
| 23 | 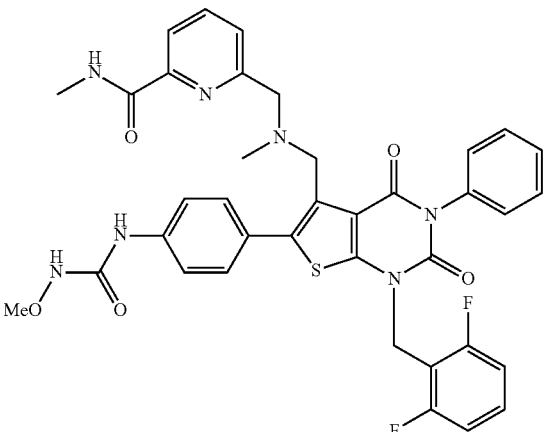 | $^1$H-NMR (CDCl$_3$) δ: 2.13 (3H, s), 2.95 (3H, d, J = 5.2 Hz), 3.74 (2H, s), 3.84 (3H, s), 3.99 (2H, J = 8.2 Hz), 7.15-7.7 (13H, m), 7.9-8.1 (3H, m). |
| 24 | 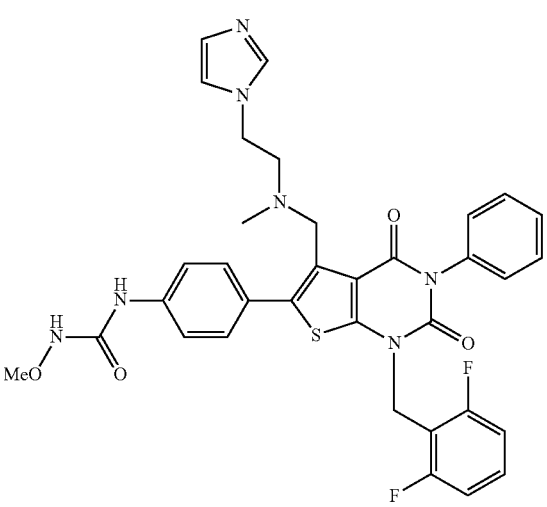 [SMILES: CONC(=O)Nc1ccc(-c2sc3c(c2CN(C)CCn2ccnc2)c(=O)n(-c2ccccc2)c(=O)n3Cc2c(F)cccc2F)cc1] | $^1$H-NMR (CDCl$_3$) δ: 2.17 (3H, s), 2.6-2.8 (2H, m), 3.80 (2H, s), 3.83 (3H, s), 3.9-4.0 (2H, m), 5.38 (2H, s), 6.78 (1H, s), 6.85-7.0 (3H m), 7.2-7.6 (12H m), 7.71 (1H, s). |
| 25 | 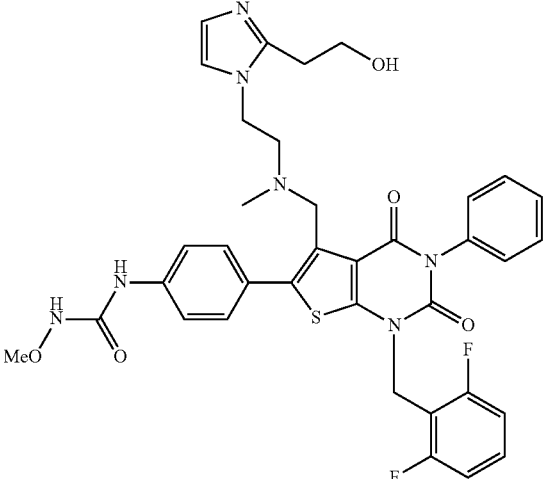 | $^1$H-NMR (CDCl$_3$) δ: 1.9-2.1 (2H, m), 2.16 (3H, s), 2.6-2.8 (4H, m), 3.78 (2H, s), 3.83 (2H, s), 3.9-4.0 (2H, m), 5.38 (2H, s), 6.70 (1H, s), 6.80 (1H, s), 6.94 (2H, t, J = 8.0 Hz), 7.2-7.6 (11H, m), 7.73 (1H, s). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| 26 | 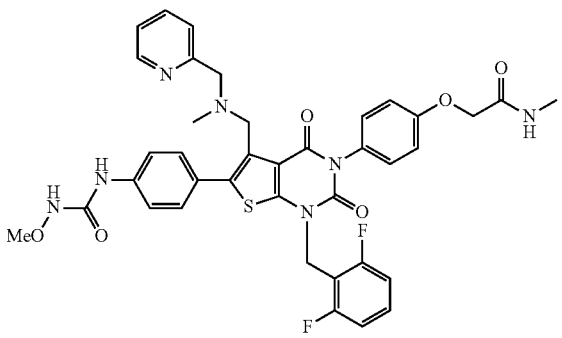 [SMILES: CNC(=O)COc1ccc(-n2c(=O)c3c(CN(C)Cc4ccccn4)c(-c4ccc(NC(=O)NOC)cc4)sc3n(Cc3c(F)cccc3F)c2=O)cc1] | $^1$H-NMR (CDCl$_3$) δ: 2.09 (3H, s), 2.93 (3H, d, J = 4.8 Hz), 3.72 (2H, s), 3.83 (3H, s), 3.97 (2H, s), 4.55 (2H, s), 5.35 (2H, s), 6.55-6.65 (1H, m), 6.92 (2H, t, J = 8.0 Hz), 7.0-7.65 (14H, m), 8.44 (1H, d, J = 6.0 Hz). |
| 27 | 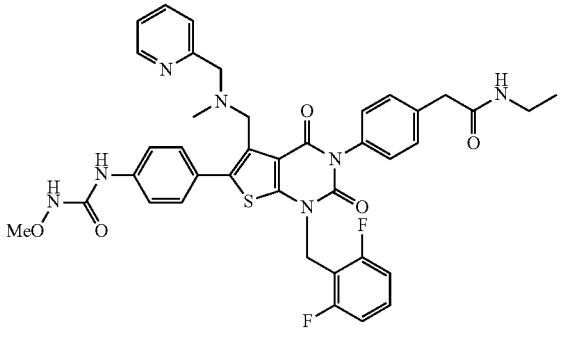 [SMILES: CCNC(=O)Cc1ccc(-n2c(=O)c3c(CN(C)Cc4ccccn4)c(-c4ccc(NC(=O)NOC)cc4)sc3n(Cc3c(F)cccc3F)c2=O)cc1] | $^1$H-NMR (CDCl$_3$) δ: 1.10 (3H, t, J = 7.2 Hz), 2.10 (3H, s), 3.2-3.4 (2H, m), 3.64 (2H, s), 3.72 (2H, s), 3.83 (3H, s), 3.98 (2H, s), 5.36 (2H, s), 5.45-5.55 (1H, m), 6.93 (2H, t, J = 8.0 Hz), 7.0-7.1 (1H, m), 7.16 (1H, s), 7.25-7.7 (12H, m), 8.44 (1H, d, J = 4.0 Hz). |
| 28 | 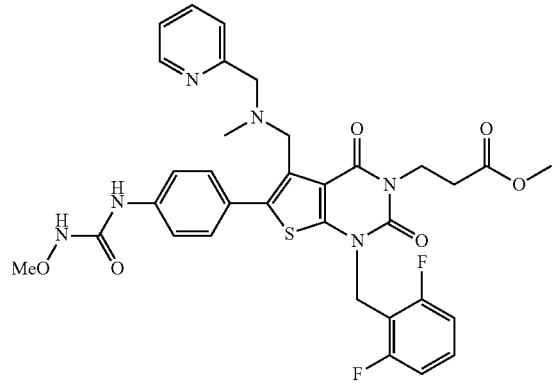 [SMILES: CONC(=O)Nc1ccc(-c2sc3c(c2CN(C)Cc2ccccn2)c(=O)n(CCC(=O)OC)c(=O)n3Cc2c(F)cccc2F)cc1] | $^1$H-NMR (CDCl$_3$) δ: 2.10 (3H, s), 2.65-2.8 (2H, m), 3.68 (3H, s), 3.72 (2H, s), 3.83 (3H, s), 3.98 (2H, s), 4.3-4.5 (2H, m), 5.31 (2H, s), 6.91 (2H, t, J = 7.6 Hz), 7.0-7.4 (5H, m), 7.45-7.65 (5H, m), 8.4-8.5 (1H, m). |
| 29 | 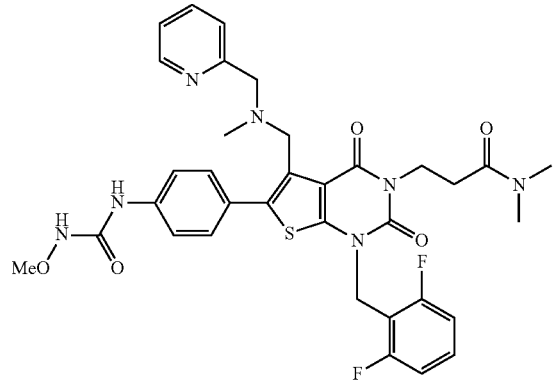 [SMILES: CONC(=O)Nc1ccc(-c2sc3c(c2CN(C)Cc2ccccn2)c(=O)n(CCC(=O)N(C)C)c(=O)n3Cc2c(F)cccc2F)cc1] | $^1$H-NMR (CDCl$_3$) δ: 2.09 (3H, s), 2.75 (3H, d, J = 7.8 Hz), 2.94 (3H, s), 3.02 (3H, s), 3.73 (2H, s), 3.83 (3H, s), 4.07 (2H, s), 4.40 (2H, t, J = 7.8 Hz), 5.33 (2H, s), 6.91 (2H, t, J = 8.2 Hz), 7.0-7.35 (5H m), 7.5-7.65 (5H, m), 8.45 (1H, d, J = 4.0 Hz). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| 30 | 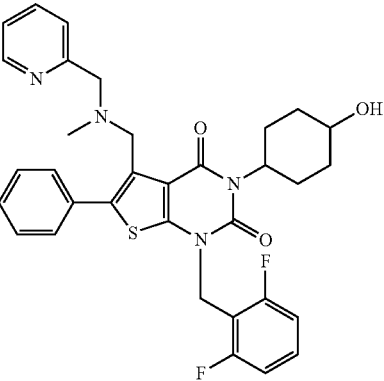 | $^{1}$H-NMR (CDCl$_{3}$) δ: 1.4-1.8 (4H, m), 2.0-2.1 (2H, m), 2.12 (3H, s), 2.55-2,75 (2H, m), 3.73 (2H, s), 3.7-3.8 (1H, m), 3.82 (3H, s), 3.98 (2H, s), 4.9-5.1 (1H, brm), 5.29 (2H, s), 6.91 (2H, t, J = 8.2 Hz), 7.0-7.4 (7H, m), 7.45-7.65 (5H, m), 8.45 (1H, d, J = 4.8 Hz). |
| 31 | 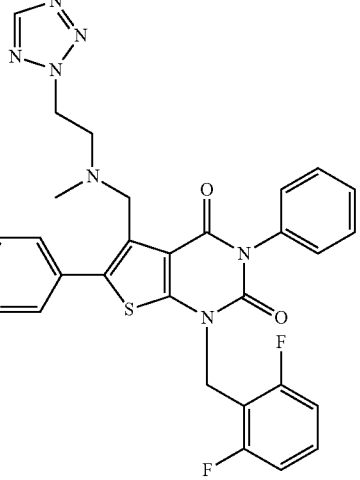 | 2-yl Form (1)<br>$^{1}$H-NMR (CDCl$_{3}$) δ: 2.25 (3H, s), 3.04 (2H, t, J = 6.2 Hz), 3.78 (2H, s), 3.83 (3H, s), 4.66 (2H, t, J = 6.2 Hz), 5.38 (2H, s), 6.94 (2H, t, J = 8.0 Hz), 7.16 (1H, s), 7.2-7.6 (10H, m), 7.64 (1H, s), 8.30 (1H, s). |
|  | 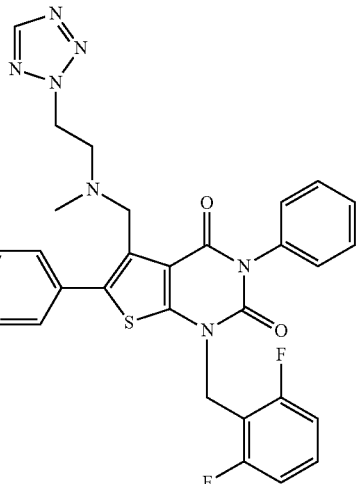 | 1-yl Form (2)<br>$^{1}$H-NMR (CDCl$_{3}$) δ: 2.02 (3H, s), 2.7-2.8 (2H, m), 3.78 (2H, s), 3.83 (3H, s), 4.4-4.5 (2H, m), 5.38 (2H, s), 6.92 (2H, t, J = 8.0 Hz), 7.17 (1H, s), 7.25-7.65 (10H, m), 7.66 (1H, s). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| 32 | 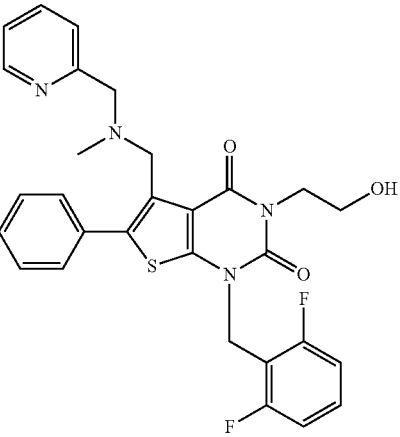 | $^1$H-NMR (CDCl$_3$) δ: 2.22 (3H, s), 3.3-3.5 (1H, br), 3.78 (2H, s), 3.83 (3H, s), 3.9-4.05 (2H, m), 3.99 (2H, s), 4.35-4.4 (2H, m), 5.27 (2H, s), 6.91 (2H, t, J = 8.0 Hz), 6.9-7.1 (1H, m), 7.15 (1H, s), 7.2-7.65 (8H, m), 8.35-8.4 (1H, m). |
| 33 | 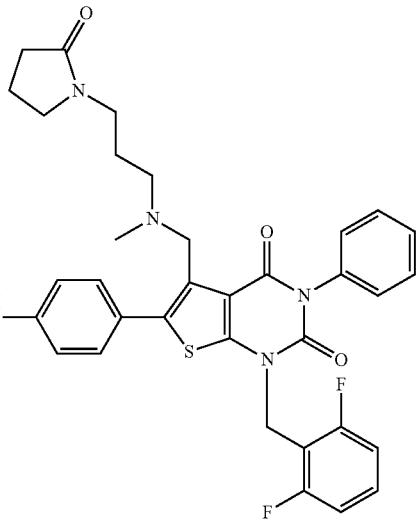 | $^1$H-NMR (CDCl$_3$) δ: 1.5-1.7 (2H, m), 1.8-2.0 (2H, m), 2.05 (3H, s), 2.25-2.45 (4H, m), 3.15 (2H, t, J = 7.8 Hz), 3.23 (2H, t, J = 7.2 Hz), 3.76 (2H, s), 3.83 (3H, s), 5.37 (2H, s), 6.93 (2H, t, J = 8.0 Hz), 7.15 (1H, s), 7.2-7.6 (10H, m), 7.67 (1H, s). |
| 34 | 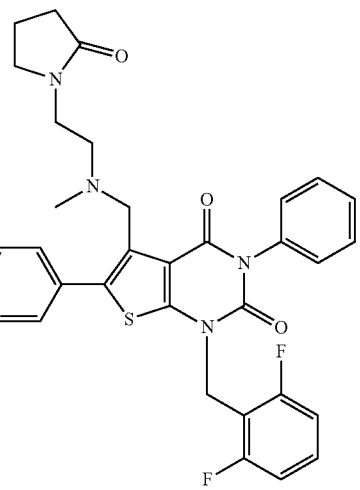 | $^1$H-NMR (CDCl$_3$) δ: 1.7-1.85 (2H, m), 2.14 (3H, s), 2.21 (2H, t, J = 8.1 Hz), 2.54 (2H, t, J = 6.2 Hz), 3.19 (2H, t, J = 7.0 Hz), 3.29 (2H, t, J = 6.2 Hz), 3.77 (2H, s), 3.83 (3H, s), 5.38 (2H, s), 6.93 (2H, t, J = 8.1 Hz), 7.18 (1H, s), 7.25-7.7 (11H, m). |

TABLE 3-continued
Exemplary Thieno[2,3d]pyrimidine GnRH Antagonists Useful for the Treatment of Adenomyosis and Rectovaginal Endometriosis
| No. | Compound | Reported spectral properties |
|---|---|---|
| 35 | 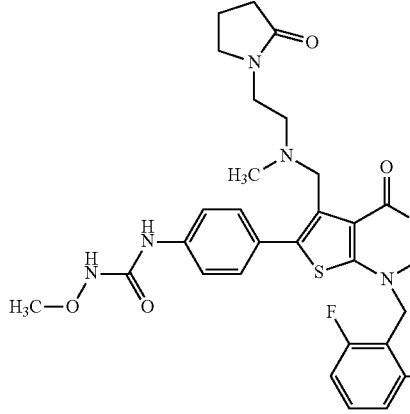 | $^1$H-NMR (CDCl$_3$) δ: 1.7-1.9 (2H, m), 2.15 (3H, s), 2.15-2.3 (2H, m), 2.52 (2H, t, J = 6.2 Hz), 3.20 (2H, t, J = 6.8 Hz), 3.29 (2H, t, J = 6.2 Hz), 3.77 (2H, s), 3.83 (3H, s), 5.37 (2H, s), 6.93 (2H, t, J = 8.2 Hz), 7.1-7.35 (6H, m), 7.5-7.65 (4H, m), 7.64 (1H, s). |
| 36 | 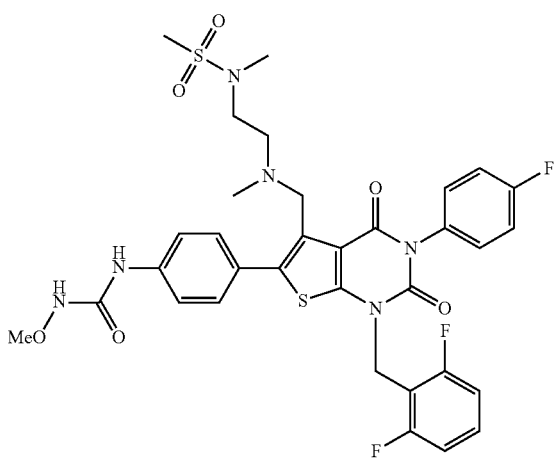 [SMILES: CONC(=O)Nc1ccc(-c2sc3c(c2CN(C)CCN(C)S(C)(=O)=O)c(=O)n(-c2ccc(F)cc2)c(=O)n3Cc2c(F)cccc2F)cc1] | $^1$H-NMR (CDCl$_3$) δ: 2.13 (3H, s), 2.55 (2H, t, J = 6.4 Hz), 2.70 (3H, s), 2.71 (3H, s), 3.15 (2H, t, J = 6.4 Hz), 3.81 (2H, s), 3.83 (3H, s), 5.37 (2H, s), 6.93 (2H, t, J = 8.2 Hz), 7.1-7.7 (11H, m). |
| 37 | 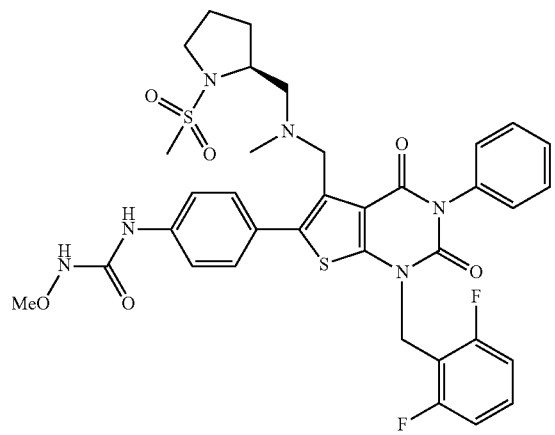 [SMILES: CONC(=O)Nc1ccc(-c2sc3c(c2CN(C)C[C@@H]2CCCN2S(C)(=O)=O)c(=O)n(-c2ccccc2)c(=O)n3Cc2c(F)cccc2F)cc1] | $^1$H-NMR (CDCl$_3$) δ: 1.7-1.85 (4H, m), 2.08 (3H, s), 2.2-2.4 (1H, m), 2.5-2.65 (1H, m), 2.72 (3H, s), 3.15-3.3 (2H, m), 3.7-3.9 (3H, m), 3.83 (3H, s), 5.37 (2H, s), 6.92 (2H, t, J = 8.2 Hz), 7.13 (1H, s), 7.2-7.7 (11H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 38 | 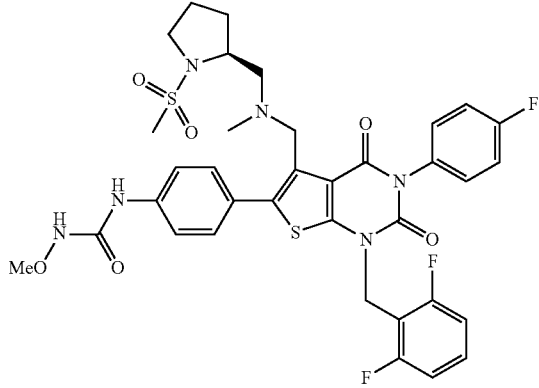 [SMILES: CONC(=O)Nc1ccc(-c2sc3c(c2CN(C)C[C@@H]2CCCN2S(C)(=O)=O)c(=O)n(-c2ccc(F)cc2)c(=O)n3Cc2c(F)cccc2F)cc1] | $^1$H-NMR (CDCl$_3$) δ: 1.7-1.85 (4H, m), 2.09 (3H, s), 2.25-2.35 (1H, m), 2.55-2.65 (1H, m), 2.71 (3H, s), 3.15-3.3 (2H, m), 3.65-3.7 (2H, m), 3.74 (1H, d, J = 12.0 Hz), 3.83 (3H, s), 3.87 (1H, d, J = 12.0 Hz), 5.36 (2H, s), 6.92 (2H, t, J = 8.2 Hz), 6.85-6.95 (1H, m), 7.1-7.35 (5H, m), 7.49 (2H, d, J = 8.4 Hz), 7.55 (2H, d, J = 8.4 Hz), 7.62 (1H, s). |
| 39 | 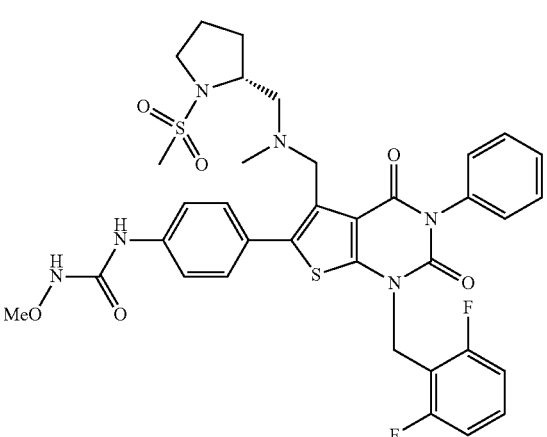 | $^1$H-NMR (CDCl$_3$) δ: 1.7-1.85 (4H, m), 2.08 (3H, s), 2.2-2.4 (1H, m), 2.5-2.65 (1H, m), 2.72 (3H, s), 3.15-3.3 (2H, m), 3.7-3.9 (3H, m), 3.83 (3H, s), 5.37 (2H, s), 6.92 (2H, t, J = 8.2 Hz), 7.13 (1H, s), 7.2-7.7 (11H, m). |
| 40 | 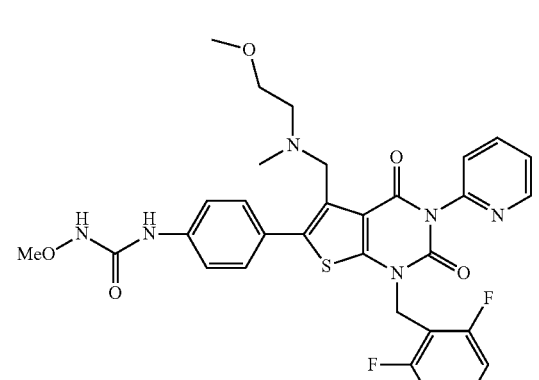 | $^1$H-NMR (CDCl$_3$) δ: 2.15 (3H, s), 2.62 (2H, t, J = 5.9 Hz), 3.26 (3H, s), 3.41 (2H, t, J = 5.9 Hz), 3.80 (3H, s), 3.81 (2H, brs), 5.34 (2H, brs), 6.91 (2H, t, J = 8.1 Hz), 7.24-7.40 (4H, m), 7.53 (2H, d, J = 8.4 Hz), 7.62 (2H, d, J = 8.4 Hz), 7.65 (1H, s), 7.88 (1H, dt, J = 1.5 Hz, 7.8 Hz), 8.67-8.69 (1H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 41 | *(structure)* | ¹H-NMR (CDCl₃) δ: 1.13(3H, t, J = 6.9 Hz), 2.15 (3H, s), 2.63 (2H, t, J = 6.2 Hz), 3.39 (2H, q, J = 6.9 Hz), 3.44 (2H, t, J = 6.2 Hz), 3.80 (2H, brs), 3.81 (3H, s), 5.34 (2H, brs), 6.91 (2H, t, J = 8.1 Hz), 7.19 (1H, s), 7.27-7.32 (1H, m), 7.35-7.41 (2H, m), 7.53 (2H, d, J = 8.4 Hz), 7.63 (1H, s), 7.64 (2H, d, J = 8.4 Hz), 7.88 (1H, dt, J = 1.2 Hz, 7.5 Hz), 8.68 (1H, dt, J = 0.9 Hz, 4.8 Hz). |
| 42 | *(structure)* | ¹H-NMR (CDCl₃) δ: 2.13 (3H, s), 2.62 (2H, t, J = 5.9 Hz), 3.26 (3H, s), 3.41 (2H, t, J = 5.9 Hz), 3.80 (2H, brs), 3.82 (3H, s), 5.33 (2H, brs), 6.92 (2H, t, J = 8.3 Hz), 7.19 (1H, s), 7.28-7.38 (2H, m), 7.52-7.63 (6H, m), 8.51 (1H, d, J = 3.0 Hz). |
| 43 | *(structure)* | ¹H-NMR (CDCl₃) δ: 2.13 (3H, s), 2.62 (2H, t, J = 5.9 Hz), 3.26 (3H, s), 3.41 (2H, t, J = 5.9 Hz), 3.78 (2H, brs), 3.80 (3H, s), 5.32 (2H, brs), 6.92 (2H, t, J = 8.1 Hz), 7.27 (1H, d, J = 8.4 Hz), 7.27-7.33 (1H, m), 7.37 (1H, s), 7.54 (2H, d, J = 9.0 Hz), 7.60 (2H, d, J = 9.0 Hz), 7.64 (1H, s), 7.98 (1H, dd, J = 2.7 Hz, 8.4 Hz), 8.72 (1H, d, J = 2.7 Hz). |
| 44 | *(structure)* | ¹H-NMR (CDCl₃) δ: 2.14 (3H, s), 2.39 (3H, s), 2.62 (2H, t, J = 5.7 Hz), 3.26 (3H, s), 3.41 (2H, t, J = 5.7 Hz), 3.77 (2H, brs), 3.80 (3H, s), 5.26 (1H, brs), 5.38 (1H, brs), 6.91 (2H, t, J = 8.3 Hz), 7.23-7.34 (2H, m), 7.42 (1H, s), 7.53 (2H, d, J = 8.7 Hz), 7.62 (2H, d, J = 8.7 Hz), 7.66 (1H, s), 7.66-7.69 (1H, m), 8.48 (1H, d, J = 2.4 Hz). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 45 | | $^1$H-NMR (CDCl$_3$) δ: 2.15 (3H, s), 2.60 (3H, s), 2.62 (2H, t, J = 5.8 Hz), 3.27 (3H, s), 3.41 (2H, t, J = 5.8 Hz), 3.66-3.94 (2H, m), 3.81 (3H, s), 5.15 (1H, d, J = 15.3 Hz), 5.48 (1H, d, J = 15.3 Hz), 6.91 (2H, t, J = 8.1 Hz), 716 (1H d, J = 7.8 Hz), 7.21 (1H, d, J = 7.8 Hz), 7.25 (1H, s), 7.26-7.35 (1H, m), 7.53 (2H, d, J = 8.7 Hz), 7.63 (1H, s), 7.53 (2H, d, J = 8.7 Hz), 7.64 (2H, d, J = 8.7 Hz), 7.76 (1H, t, J = 7.8 Hz). |
| 46 | | $^1$H-NMR (CDCl$_3$) δ: 2.13 (3H, s), 2.51 (3H, s), 2.62 (2H, t, J = 5.9 Hz), 3.26 (3H, s), 3.40 (2H, t, J = 5.9 Hz), 3.77 (1H, d, J = 12.3 Hz), 3.77 (3H, s), 3.79 (3H, s), 3.86 (1H, d, J = 12.3 Hz), 5.24 (1H, d, J = 15.6 Hz), 5.40 (1H, d, J = 15.6 Hz), 6.90 (2H, t, J = 8.1 Hz), 7.19 (1H, d, J = 8.4 Hz), 7.23-7.34 (1H, m), 7.27 (1H, d, J = 8.4 Hz), 7.51 (2H, d, J = 8.7 Hz), 7.58 (2H, d, J = 8.7 Hz), 7.65 (1H, s), 7.69 (1H, s). |
| 47 | | $^1$H-NMR (CDCl$_3$) δ: 2.11 (3H, s), 2.48 (3H, s), 2.51-2.59 (2H, m), 3.20 (3H, s), 3.30-3.46 (4H, m), 3.60 (1H, d, J = 12.3 Hz), 3.79 (3H, s), 4.05 (1H, d, J = 12.3 Hz), 5.21 (1H, d, J = 15.6 Hz), 5.31 (1H, d, J = 15.6 Hz), 6.88 (2H, t, J = 8.1 Hz), 7.07 (1H, d, J = 8.1 Hz), 7.21-7.31 (2H, m), 7.43-7.51 (4H, m), 7.69 (1H, s). |
| 48 | | $^1$H-NMR (CDCl$_3$) δ: 2.20 (3H, s), 2.63 (2H, t, J = 6.2 Hz), 3.28 (3H, s), 3.41 (2H, t, J = 6.2 Hz), 3.78 (1H, d, J = 12.3 Hz), 3.82 (3H, s), 3.84 (3H, s), 3.88 (1H, d, J = 12.3 Hz), 5.35 (2H, s), 6.92 (2H, t, J = 8.1 Hz), 7.17 (1H, s), 7.23-7.39 (3H, m), 7.54 (2H, d, J = 8.8 Hz), 7.57 (1H, s), 7.69 (2H, d, J = 8.8 Hz), 8.23-8.27 (1H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
| --- | --- | --- |
| 49 | | $^1$H-NMR (CDCl$_3$) δ: 1.60 (6H, s), 1.79 (1H, s), 2.14 (3H, s), 2.63 (2H, t, J = 5.9 Hz), 3.27 (3H, s), 3.41 (2H, t, J = 5.9 Hz), 3.81 (3H, s), 3.82 (2H, s), 5.36 (2H, s), 6.92 (2H, t, J = 8.3 Hz), 7.20-7.34 (4H, m), 7.53 (2H, d, J = 8.7 Hz), 7.60-7.63 (5H, m). |
| 50 | | $^1$H-NMR (CDCl$_3$) δ: 1.62 (6H, s), 1.77 (1H, s), 2.05 (3H, s), 3.56 (2H, s), 3.82 (3H, s), 3.90 (2H, s), 5.36 (2H, s), 6.91 (2H, t, J = 8.1 Hz), 7.14-7.38 (9H, m), 7.55 (2H, d, J = 9.0 Hz), 7.62 (1H, s), 7.64 (2H, d, J = 8.7 Hz), 7.72 (2H, d, J = 8.4 Hz). |
| 51 | | $^1$H-NMR (CDCl$_3$) δ: 1.55 (6H, s), 2.15 (3H, s), 2.64 (2H, t, J = 5.9 Hz), 3.11 (3H, s), 3.27 (3H, s), 3.41 (2H, t, J = 5.9 Hz), 3.82 (3H, s), 3.83 (2H, s), 5.36 (2H, s), 6.92 (2H, t, J = 8.3 Hz), 7.16 (1H, s), 7.24-7.36 (4H, m), 7.51-7.63 (6H, m). |
| 52 | | $^1$H-NMR (CDCl$_3$) δ: 2.15 (3H, s), 2.61 (2H, dt, J = 1.8 Hz, 6.90 Hz), 3.27 (3H, s), 3.40 (2H, dt, J = 1.8 Hz, 6.0 Hz), 3.53 (3H, s), 3.75 (1H, d, J = 12.3 Hz), 3.80 (3H, s), 3.81 (1H, d, J = 12.3 Hz), 5.12 (1H, d, J = 15.9 Hz), 5.57 (1H, d, J = 15.9 Hz), 6.91 (2H, t, J = 8.1 Hz), 6.99 (1H, d, J = 1.5 Hz), 7.14 (1H, d, J = 1.5 Hz), 7.28 (1H, s), 7.25-7.34 (1H, m), 7.53 (2H, d, J = 9.0 Hz), 7.60 (2H, d, J = 9.0 Hz), 7.70 (1H, s). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| 53 | | $^1$H-NMR (CDCl$_3$) δ: 0.98 (6H, d, J = 6.3 Hz), 1.52-1.58 (2H, m), 1.64-1.71 (1H, m), 2.14 (3H, s), 2.66 (2H, t, J = 5.9 Hz), 3.30 (3H, s), 3.45 (2H, t, J = 5.9 Hz), 3.81 (3H, s), 3.85 (2H, s), 4.04-4.09 (2H, m), 5.33 (2H, s), 6.90 (2H, t, J = 8.3 Hz), 7.17 (1H, s), 7.24-7.35 (1H, m), 7.51 (2H, d, J = 8.7 Hz), 7.57 (2H, d, J = 8.7 Hz), 7.60 (1H, s). |
| 54 | | $^1$H-NMR (CDCl$_3$) δ: 2.14 (3H, s), 2.65 (2H, t, J = 5.9 Hz), 3.30 (3H, s), 3.36 (3H, s), 3.45 (2H, t, J = 5.9 Hz), 3.66 (2H, t, J = 5.9 Hz), 3.81 (3H, s), 3.84 (2H, s), 4.30 (2H, t, J = 5.9 Hz), 5.33 (2H, s), 6.90 (2H, t, J = 8.3 Hz), 7.15 (1H, s), 7.24-7.34 (1H, m), 7.51 (2H, d, J = 9.0 Hz), 7.56 (2H, d, J = 9.0 Hz), 7.60 (1H, m). |
| 55 | | $^1$H-NMR (CDCl$_3$) δ: 1.15 (3H, t, J = 6.9 Hz), 2.14 (3H, s), 2.66 (2H, t, J = 6.0 Hz), 3.30 (3H, s), 3.45 (2H, t, J = 6.0 Hz), 3.54 (2H, q, J = 6.9 Hz), 3.69 (2H, t, J = 6.0 Hz), 3.81 (3H, s), 3.84 (2H, s), 4.29 (2H, t, J = 6.0 Hz), 5.32 (2H, s), 6.89 (2H, t, J = 8.1 Hz), 7.17 (1H, s), 7.23-7.34 (1H, m), 7.52 (2H, d, J = 8.7 Hz), 7.57 (2H, d, J = 8.7 Hz), 7.60 (1H, m). |
| 56 | | $^1$H-NMR (CDCl$_3$) δ: 1.52 (6H, d, J = 6.9 Hz), 2.13 (3H, s), 2.66 (2H, t, J = 5.9 Hz), 3.31 (3H, s), 3.46 (2H, t, J = 5.9 Hz), 3.82 (3H, s), 3.84 (2H, s), 5.31 (2H, s), 5.34 (1H, m), 6.90 (2H, t, J = 8.1 Hz), 7.16 (1H, s), 7.24-7.35 (1H, m), 7.52 (2H, d, J = 8.4 Hz), 7.55 (2H, d, J = 8.4 Hz), 7.60 (1H, m). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 57 | 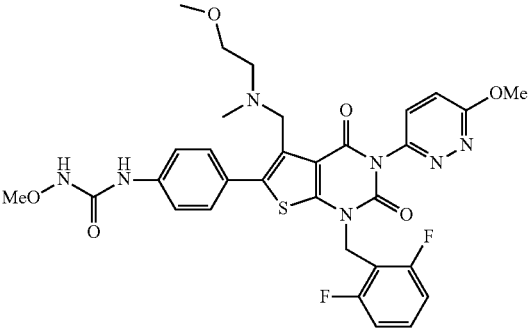 [SMILES: COCCN(C)Cc1c(-c2ccc(NC(=O)NOC)cc2)sc2c1c(=O)n(-c1ccc(OC)nn1)c(=O)n2Cc1c(F)cccc1F] | $^1$H-NMR (CDCl$_3$) δ: 2.13 (3H, s), 2.62 (2H, t, J = 5.7 Hz), 3.26 (3H, s), 3.41 (2H, t, J = 5.7 Hz), 3.74 (2H, brs), 3.82 (3H, s), 4.18 (3H, s), 5.32 (2H, brs), 6.92 (2H, t, J = 8.3 Hz), 7.12 (1H, d, J = 9.3 Hz), 7.24 (1H, s), 7.29-7.35 (1H, m), 7.41 (2H, d, J = 9.3 Hz), 7.54 (2H, d, J = 9.0 Hz), 7.59 (2H, d, J = 8.7 Hz), 7.66 (1H, s). |
| 58 | 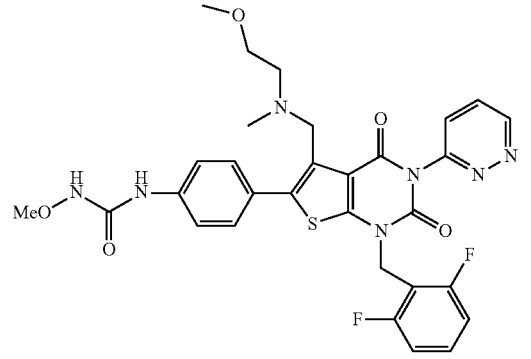 [SMILES: COCCN(C)Cc1c(-c2ccc(NC(=O)NOC)cc2)sc2c1c(=O)n(-c1cccnn1)c(=O)n2Cc1c(F)cccc1F] | $^1$H-NMR (CDCl$_3$) δ: 2.12 (3H, s), 2.61 (2H, t, J = 5.7 Hz), 3.26 (3H, s), 3.39 (2H, t, J = 5.7 Hz), 3.78 (2H, brs), 3.82 (3H, s), 5.34 (2H, brs), 6.93 (2H, t, J = 8.1 Hz), 7.26 (1H, s), 7.29-7.37 (1H, m), 7.53-7.61 (5H, m), 7.67 (1H, s), 7.69 (1H, dd, J = 4.8 Hz, 8.4 Hz), 9.28 (1H, dd, J = 1.8 Hz, 4.8 Hz). |
| 59 | 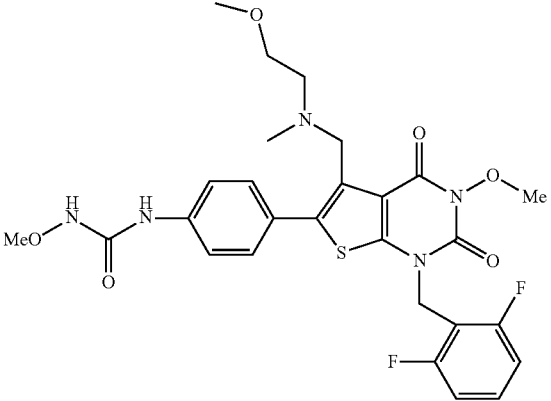 [SMILES: COCCN(C)Cc1c(-c2ccc(NC(=O)NOC)cc2)sc2c1c(=O)n(OC)c(=O)n2Cc1c(F)cccc1F] | $^1$H-NMR (CDCl$_3$) δ: 2.14 (3H, s), 2.68 (2H, t, J = 6.0 Hz), 3.31 (3H, s), 3.47 (2H, t, J = 6.0 Hz), 3.82 (3H, s), 3.83 (2H, s), 4.06 (3H, s), 5.35 (2H, s), 6.92 (2H, t, J = 8.3 Hz), 7.20 (1H, s), 7.29-7.35 (1H, m), 7.55 (4H, s), 7.63 (1H, s). |
| 60 | 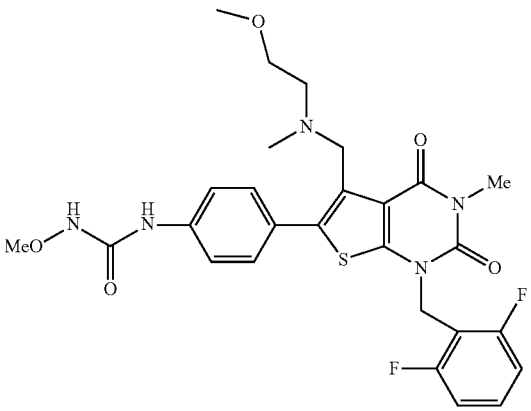 [SMILES: COCCN(C)Cc1c(-c2ccc(NC(=O)NOC)cc2)sc2c1c(=O)n(C)c(=O)n2Cc1c(F)cccc1F] | $^1$H-NMR (CDCl$_3$) δ: 2.13 (3H, s), 2.66 (2H, t, J = 5.9 Hz), 3.31 (3H, s), 3.45 (3H, s), 3.48 (2H, t, J = 5.9 Hz), 3.82 (3H, s), 3.84 (2H, s), 5.33 (2H, s), 6.91 (2H, t, J = 8.3 Hz), 7.17 (1H, s), 7.25-7.35 (1H, m), 7.55 (4H, s), 7.62 (1H, s). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 61 | 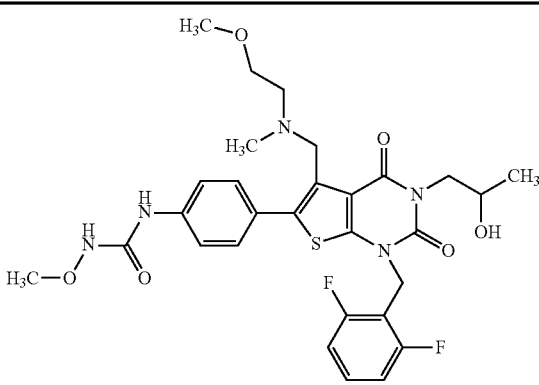 | $^1$H-NMR (CDCl$_3$) δ: 1.27 (3H, d, J = 5.6 Hz), 2.12 (3H, s), 2.64 (2H, t, J = 5.8 Hz), 2.9-3.05 (1H, m), 3.30 (3H, s), 3.45 (2H, d, J = 5.8 Hz), 3.82 (5H, s), 4.05-4.25 (1H, m), 4.18 (2H, s), 5.34 (2H, s), 6.91 (2H, t, J = 8.2 Hz), 7.2-7.4 (1H, m), 7.5-7.6 (3H, m), 7.63 (1H, s). |
| 62 | 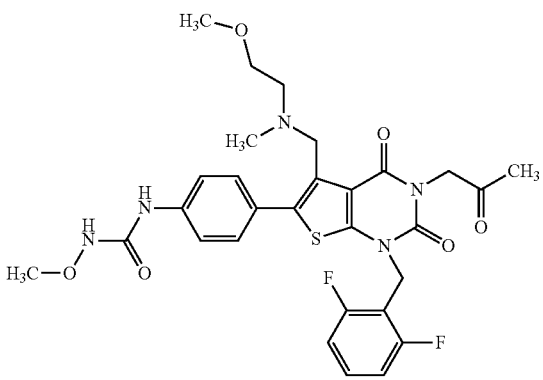 [SMILES: COCCN(C)Cc1c(-c2ccc(NC(=O)NOC)cc2)sc2c1c(=O)n(CC(C)=O)c(=O)n2Cc1c(F)cccc1F] | $^1$H-NMR (CDCl$_3$) δ: 2.13 (3H, s), 2.27 (3H, s), 2.55-2.65 (2H, m), 3.29 (3H, s), 3.4-3.5 (2H, m), 3.82 (5H, s), 4.88 (2H, s), 5.33 (2H, s), 6.91 (2H, t, J = 8.0 Hz), 7.2-7.35 (1H, m), 7.5-7.65 (4H, m). |
| 63 | 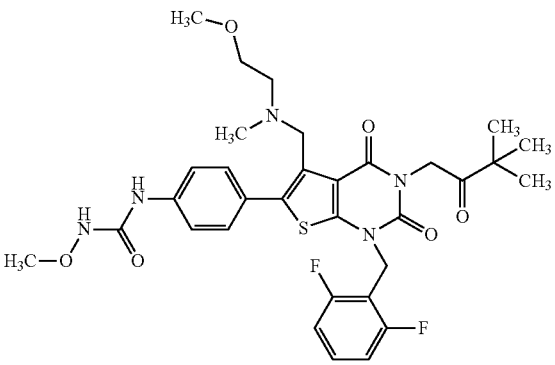 [SMILES: COCCN(C)Cc1c(-c2ccc(NC(=O)NOC)cc2)sc2c1c(=O)n(CC(=O)C(C)(C)C)c(=O)n2Cc1c(F)cccc1F] | $^1$H-NMR (CDCl$_3$) δ: 1.30 (9H, s) 2.12 (3H, s), 2.62 (2H, t, J = 5.8 Hz), 3.29 (3H, s), 3.44 (2H, d, J = 5.8 Hz), 3.80 (2H, s), 3.82 (3H, s), 5.04 (2H, s), 5.33 (2H, s), 6.91 (2H, t, J = 8.2 Hz), 7.14 (1H, s), 7.2-7.3 (1H, m), 7.5-7.6 (4H, m), 7.61 (1H, s). |
| 64 | 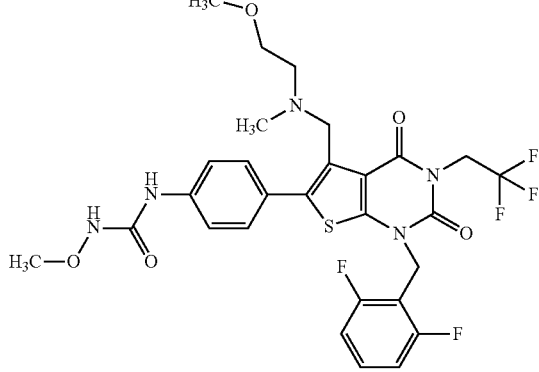 | $^1$H-NMR (CDCl$_3$) δ: 2.12 (3H, s), 2.65 (2H, t, J = 6.0 Hz), 3.31 (3H, s), 3.45 (2H, d, J = 6.0 Hz), 3.82 (5H, s), 4.75-4.85 (2H, m), 5.36 (2H, s), 6.92 (2H, t, J = 8.2 Hz), 7.13 (1H, s), 7.2-7.35 (1H, m), 7.55-7.6 (4H, m), 7.62 (1H, s). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 65 | | $^1$H-NMR (CDCl$_3$) δ: 1.04 (9H, s), 2.12 (3H, s), 2.64 (2H, t, J = 6.0 Hz), 2.96 (1H, d, J = 6.0 Hz), 3.31 (3H, s), 3.46 (2H, d, J = 6.0 Hz), 3.5-3.6 (1H, m), 3.82 (3H, s), 3.75-3.9 (2H, m), 4.05-4.2 (1H, m), 4.3-4.45 (1H, m), 5.25-5.45 (2H, m), 6.91 (2H, t, J = 8.2 Hz), 7.14 (1H, s), 7.2-7.35 (1H, m), 7.5-7.6 (4H, m), 7.61 (1H, s). |
| 66 | | $^1$H-NMR (CDCl$_3$) δ: 1.28 (6H, s), 2.3 (3H, s), 2.64 (2H, t, J = 5.8 Hz), 3.30 (3H, s), 3.45 (2H, t, J = 5.8 Hz), 3.82 (5H, s), 3.99 (1H, s), 4.25 (2H, s), 5.36 (2H, s), 6.91 (2H, t, J = 8.2 Hz), 7.12 (1H, s), 7.2-7.4 (1H, m), 7.5-7.6 (4H, m), 7.61 (1H, s). |
| 67 | | $^1$H-NMR (CDCl$_3$) δ: 0.96 (6H, s), 2.13 (3H, s), 2.64 (2H, t, J = 6.2 Hz), 3.13 (2H, s), 3.30 (3H, s), 3.45 (2H, t, J = 6.2 Hz), 3.82 (5H, s), 3.95-4.15 (2H, brm), 5.1-5.5 (2H, br), 6.91 (2H, t, J = 8.2 Hz), 7.14 (1H, s), 7.2-7.4 (1H, m), 7.5-7.6 (4H, m), 7.61 (1H, s). |
| 68 | | $^1$H-NMR (CDCl$_3$) δ: 0.46 (2H, t, J = 5.4 Hz), 0.85 (2H, t, J = 5.4 Hz), 2.11 (3H, s), 2.64 (2H, t, J = 6.0 Hz), 3.25 (2H, s), 3.31 (3H, s), 3.46 (2H, t, J = 6.0 Hz), 3.82 (5H, s), 3.95-4.15 (1H, br), 4.14 (2H, s), 5.37 (2H, s), 6.91 (2H, t, J = 8.0 Hz), 7.12 (1H, s), 7.2-7.4 (1H, m), 7.54 (4H, s), 7.61 (1H, s). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| 69 | | ¹H-NMR (CDCl₃) δ: 1.35-1.65 (3H, m), 1.65-1.8 (2H, m), 2.07 (3H, s), 2.5-2.8 (2H, m), 3.58 (2H, s), 3.7-3.9 (1H, m), 3.82 (3H, s), 3.91 (2H, s), 4.9-5.1 (1H, m), 5.29 (2H, s), 6.90 (2H, t, J = 7.8 Hz), 7.13 (1H, s), 7.15-7.35 (6H, m), 7.53 (2H, d, J = 8.6 Hz), 7.61 (1H, s), 7.66 (2H, d, J = 8.6 Hz). |
| 70 | | ¹H-NMR (CDCl₃) δ: 1.2-1.6 (3H, m), 1.6-1.8 (2H, m), 2.0-2.1 (2H, m), 2.14 (3H, s), 2.5-2.75 (4H, m), 3.31 (3H, s), 3.45 (2H, t, J = 5.8 Hz), 3.65-3.85 (3H, m), 3.82 (3H, s), 4.9-5.05 (1H, br), 5.30 (2H, s), 6.90 (2H, t, J = 8.0 Hz), 7.12 (1H, s), 7.25-7.4 (1H, m), 7.5-7.6 (4H, m), 7.60 (1H, s). |
| 71 | | ¹H-NMR (CDCl₃) δ: 2.13 (3H, s), 2.61 (2H, t, J = 5.8 Hz), 2.79 (3H, s), 3.26 (3H, s), 3.41 (2H, t, J = 5.8 Hz), 3.75-3.85 (2H, m), 3.82 (3H, s), 5.25-5.45 (2H, brm), 6.92 (2H, t, J = 8.2 Hz), 7.18 (1H, s), 7.2-7.7 (8H, m). |
| 72 | | ¹H-NMR (CDCl₃) δ: 1.30 (3H, d, J = 6.0 Hz), 2.06 (3H, s), 2.90 (1H, d, J = 5.2 Hz), 3.57 (2H, s), 3.82 (3H, s), 3.91 (2H, s), 4.1-4.25 (1H, m), 4.20 (2H, s), 5.34 (2H, s), 6.91 (2H, t, J = 8.0 Hz), 7.16 (1H, s), 7.2-7.4 (6H, m), 7.54 (2H, d, J = 8.8 Hz), 7.62 (1H, s), 7.67 (2H, d, J = 8.8 Hz). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 73 | 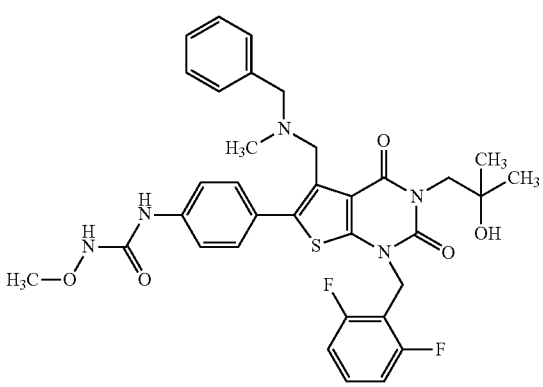 [SMILES: CONC(=O)Nc1ccc(-c2sc3c(c2CN(C)Cc2ccccc2)c(=O)n(CC(C)(C)O)c(=O)n3Cc2c(F)cccc2F)cc1] | $^1$H-NMR (CDCl$_3$) δ: 1.29 (6H, s), 2.06 (3H, s), 3.56 (2H, s), 3.83 (3H, s), 3.91 (2H, s), 3.96 (1H, s), 4.28 (2H, s), 5.36 (2H, s), 6.91 (2H, t, J = 8.2 Hz), 7.13 (1H, s), 7.2-7.35 (6H, m), 7.54 (2H, d, J = 8.8 Hz), 7.62 (1H, s), 7.67 (2H, d, J = 8.8 Hz). |
| 74 | 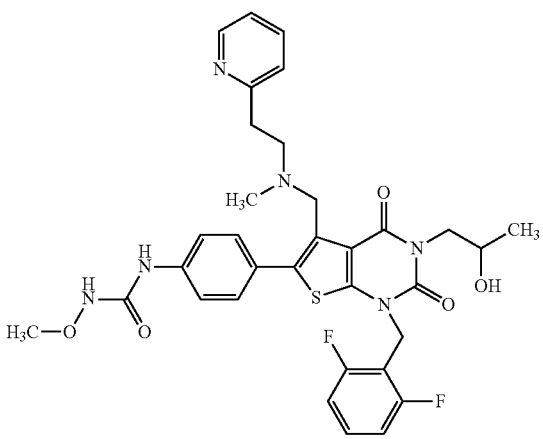 [SMILES: CONC(=O)Nc1ccc(-c2sc3c(c2CN(C)CCc2ccccn2)c(=O)n(CC(C)O)c(=O)n3Cc2c(F)cccc2F)cc1] | $^1$H-NMR (CDCl$_3$) δ: 1.28 (3H, d, J = 5.8 Hz), 2.21 (3H, s), 2.75-2.95 (4H, m), 3.0-3.1 (1H, m), 3.82 (5H, s), 4.1-4.2 (1H, m), 4.17 (2H, s), 5.34 (2H, s), 6.91 (2H, t, J = 8.2 Hz), 6.95-7.1 (2H, m), 7.14 (1H, s), 7.2-7.4 (1H, m), 7.4-7.55 (5H, m), 7.59 (1H, s), 8.43 (1H, d, J = 5.0 Hz). |
| 75 | 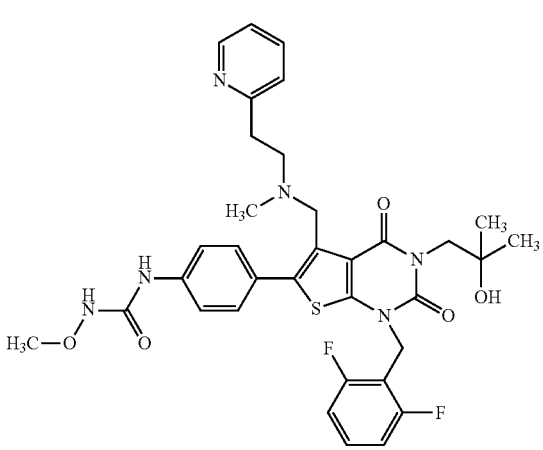 [SMILES: CONC(=O)Nc1ccc(-c2sc3c(c2CN(C)CCc2ccccn2)c(=O)n(CC(C)(C)O)c(=O)n3Cc2c(F)cccc2F)cc1] | $^1$H-NMR (CDCl$_3$) δ: 1.26 (6H, s), 2.21 (3H, s), 2.75-2.95 (4H, m), 3.82 (5H, s), 3.99 (1H, s), 4.24 (2H, s), 5.36 (2H, s), 6.91 (2H, t, J = 8.2 Hz), 7.0-7.1 (2H, m), 7.13 (1H, s), 7.2-7.35 (1H, m), 7.45-7.55 (5H, m), 7.59 (1H, s), 8.43 (1H, d, J = 4.0 Hz). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 76 | 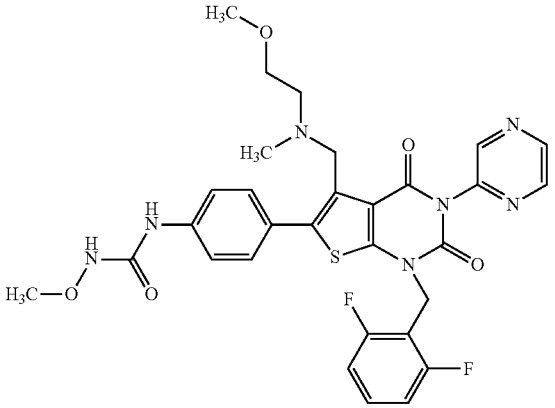 [SMILES: COCCN(C)Cc1c(-c2ccc(NC(=O)NOC)cc2)sc2c1c(=O)n(-c1cnccn1)c(=O)n2Cc1c(F)cccc1F] | ¹H-NMR (CDCl₃) δ: 2.13 (3H, s), 2.62 (2H, t, J = 6.0 Hz), 3.26 (3H, s), 3.41 (2H, t, J = 6.0 Hz), 3.79 (2H, s), 3.83 (1H, s), 5.36 (2H, s), 6.94 (2H, t, J = 8.0 Hz), 7.12 (1H, s), 7.2-7.4 (1H, m), 7.5-7.65 (5H, m), 8.65-8.7 (3H, m). |
| 77 | 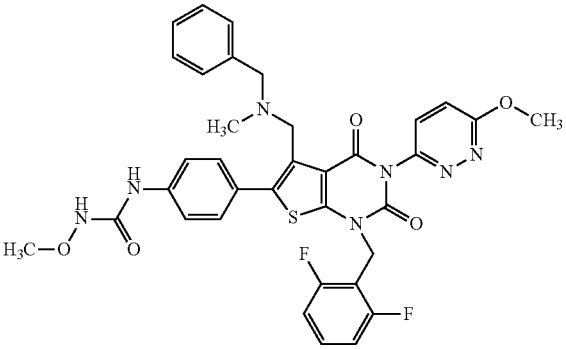 | ¹H-NMR (CDCl₃) δ: 2.06 (3H, s), 3.55 (2H, s), 3.83 (3H, s), 3.87 (2H, s), 4.19 (3H, s), 5.35 (2H, s), 6.92 (2H, t, J = 8.2 Hz), 7.1-7.45 (9H, m), 7.55 (2H, d, J = 8.4 Hz), 7.63 (1H, s), 7.72 (2H, d, J = 8.4 Hz). |
| 78 | 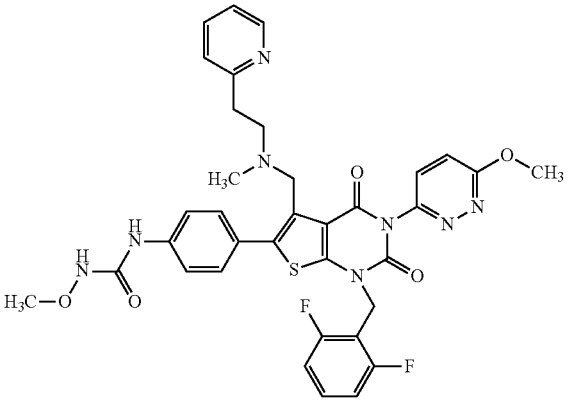 | ¹H-NMR (CDCl₃) δ: 2.20 (3H, s), 2.7-2.9 (4H, m), 3.78 (2H, s), 3.82 (3H, s), 4.19 (3H, s), 5.34 (2H, s), 6.85-7.2 (5H, m), 7.25-7.45 (2H, m), 7.45-7.7 (7H, m), 8.42 (1H, d, J = 4.0 Hz). |
| 79 | 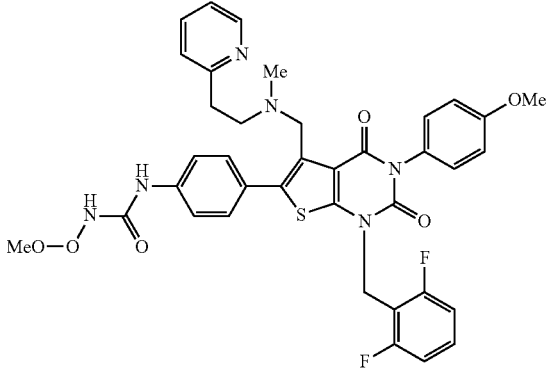 [SMILES: COONC(=O)Nc1ccc(-c2sc3c(c2CN(C)CCc2ccccn2)c(=O)n(-c2ccc(OC)cc2)c(=O)n3Cc2c(F)cccc2F)cc1] | ¹H NMR (CDCl₃) δ 2.20 (3H, s), 2.86 (4H, m), 3.82-3.84 (8H, m), 5.36 (2H, s), 6.92 (2H, d, J = 8.3 Hz), 7.00-7.06 (4H, m), 7.14-7.33 (4H, m), 7.46-7.51 (5H, m), 7.61 (1H, s), 8.42 (1H, d, J = 5.7 Hz). |

TABLE 3-continued

Exemplary Thieno[2,3d]pyrimidine GnRH Antagonists Useful for the Treatment of
Adenomyosis and Rectovaginal Endometriosis

| No. | Compound | Reported spectral properties |
|---|---|---|
| 80 | 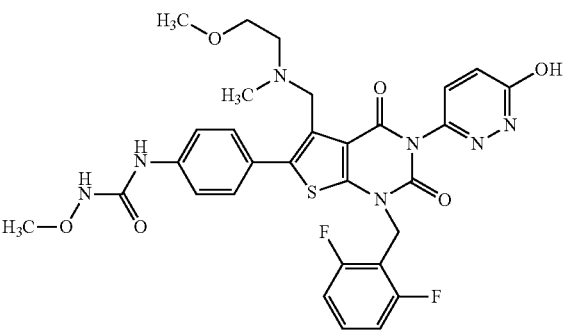 [SMILES: COCCN(C)Cc1c(-c2ccc(NC(=O)NOC)cc2)sc2c1c(=O)n(-c1ccc(O)nn1)c(=O)n2Cc1c(F)cccc1F] | $^1$H-NMR (CDCl$_3$) δ: 2.12 (3H, s), 2.63 (2H, t, J = 5.8 Hz), 3.28 (3H, s), 3.43 (2H, t, J = 5.8 Hz), 3.79 (2H, s), 3.83 (3H, s), 5.35 (2H, s), 6.94 (2H, t, J = 8.2 Hz), 7.0-7.1 (1H, m), 7.2-7.4 (3H, m), 7.5-7.65 (4H, m), 7.63 (1H, s), 10.5-10.6 (1H, brs). |
| 81 | 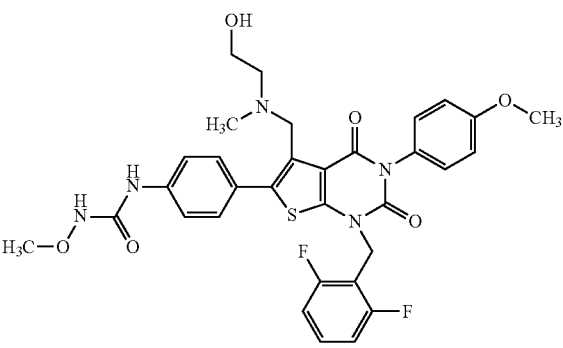 | $^1$H-NMR (CDCl$_3$) δ: 1.98 (3H, s), 2.45-2.5 (2H, m), 2.9-3.2 (1H, m), 3.5-3.55 (2H, m), 3.65-3.85 (2H, brm), 3.82 (3H, s), 4.18 (3H, s), 5.34 (2H, s), 6.93 (2H, t, J = 8.0 Hz), 7.11 (1H, d, J = 9.0 Hz), 7.18 (1H, s), 7.25-7.35 (1H, m), 7.35-7.45 (3H, m), 7.57 (2H, d, J = 8.7 Hz), 7.66 (1H, s). |
| 82 | 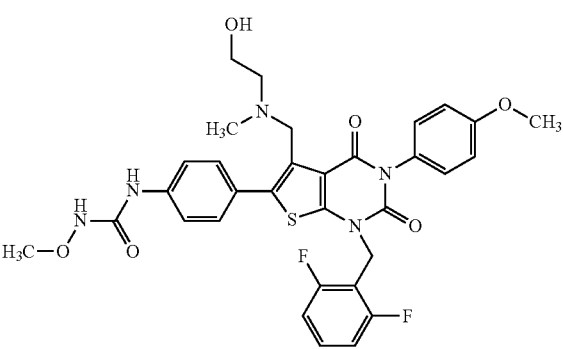 | $^1$H-NMR (CDCl$_3$) δ: 1.99 (3H, s), 2.45-2.55 (2H, m), 3.5-3.6 (2H, m), 3.79 (2H, s), 3.82 (3H, s), 3.83 (3H, s), 5.36 (2H, s), 6.92 (2H, t, J = 8.0 Hz), 6.99 (2H, d, J = 8.8 Hz), 7.1-7.3 (4H, m), 7.39 (2H, d, J = 8.8 Hz), 7.56 (2H, d, J = 8.8 Hz), 7.64 (1H, s). |
| 83 | 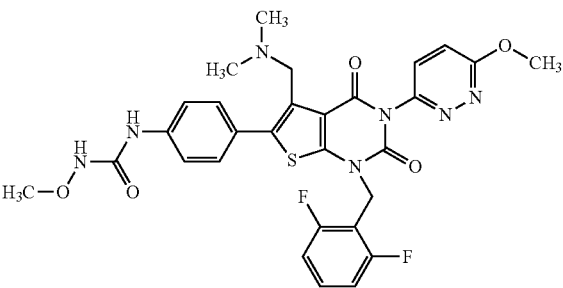 | $^1$H-NMR (CDCl$_3$) δ: 2.15 (6H, s), 3.6-3.8 (2H, m), 3.82 (3H, s), 4.18 (3H, s), 5.35 (2H), 6.92 (2H, t, J = 8.2 Hz), 7.12 (1H, d, J = 8.8 Hz), 7.2-7.65 (7H, m), 7.69 (1H, s). |

TABLE 3-continued

Exemplary Thieno[2,3d]pyrimidine GnRH Antagonists Useful for the Treatment of Adenomyosis and Rectovaginal Endometriosis

| No. | Compound | Reported spectral properties |
|---|---|---|
| 84 | (structure) | $^1$H-NMR (CDCl$_3$) δ: 2.13 (6H, s), 3.68 (2H, s), 3.83 (3H, s), 3.96 (3H, s), 5.36 (2H, s), 6.8-7.0 (3H, m), 7.13 (1H, s), 7.2-7.4 (1H, m), 7.45-7.65 (6H, m), 8.10 (1H, d, J = 2.6 Hz). |

Propane-1,3-diones

Additional GnRH antagonists that may be used in conjunction with the compositions and methods described herein include optionally substituted propane-1,3-dione derivatives, such as (2R)—N-{5-[3-(2,5-difluorophenyl)-2-(1,3-dihydro-2H-benzimidazol-2-ylidene)-3-oxopropanoyl]-2-fluorobenzene-1-sulfonyl}-2-hydroxypropanimidamide, also referred to as opigolix or ASP-1707. Other GnRH antagonists of this chemical class that may be used for the treatment of adenomyosis and/or rectovaginal endometriosis in accordance with the compositions and methods of the disclosure include compounds described in U.S. Pat. No. 6,960,591, the contents of which are incorporated herein by reference.

Add-Back Therapy

Among the potential side-effects of GnRH antagonist therapy is a reduction in bone mineral density due to excessive depletion of estrogen (Newhall-Perry et al., American Journal of Obstetrics and Gynecology 173:824-829 (1995)). To combat this potential side effect, a patient undergoing GnRH antagonist therapy using the compositions and methods described herein can be administered add-back therapy. Add-back therapy may contain an estrogen (such as @17-estradiol, ethinyl estradiol, or a conjugated estrogen, such as a conjugated equine estrogen) optionally in combination with a progestin (such as norethindrone or an ester thereof, e.g., norethindrone acetate, or another agent such as progesterone, norgestimate, medroxyprogesterone, or drospirenone).

Endogenous estrogens are largely responsible for the development and maintenance of the female reproductive system and secondary sexual characteristics. Although circulating estrogens exist in a dynamic equilibrium of metabolic interconversions, estradiol is the principal intracellular human estrogen and is substantially more potent than its metabolites, estrone and estriol, at the receptor level. The primary source of estrogen in normally cycling adult women is the ovarian follicle, which secretes 70 to 500 μg of estradiol daily, depending on the phase of the menstrual cycle. After menopause, most endogenous estrogen is produced by conversion of androstenedione, secreted by the adrenal cortex, to estrone by peripheral tissues. Thus, estrone and the sulfate conjugated form, estrone sulfate, are the most abundant circulating estrogens in postmenopausal women. Circulating estrogens modulate the pituitary secretion of the gonadotropins, LH and FSH, through a negative feedback mechanism. Estrogens act to reduce the elevated levels of these hormones seen in postmenopausal women.

Progestin compounds, such as norethindrone and esters thereof (e.g., norethindrone acetate), as well as progesterone, norgestimate, medroxyprogesterone, and drospirenone, enhance cellular differentiation and generally oppose the actions of estrogens by decreasing estrogen receptor levels, increasing local metabolism of estrogens to less active metabolites, or inducing gene products that blunt cellular responses to estrogen. Progestins exert their effects in target cells by binding to specific progesterone receptors that interact with progesterone response elements in target genes. Progesterone receptors have been identified in the female reproductive tract, breast, pituitary, hypothalamus, and central nervous system. Progestins produce similar endometrial changes to those of the naturally occurring hormone progesterone. Progestins may be included in combination with estrogen in add-back therapy. For instance, according to the methods described herein, one can administer estrogen (e.g., E2) in conjunction with a progestin (e.g., norethindrone or an ester thereof, such as norethindrone acetate) to a patient undergoing GnRH antagonist therapy as to counteract the hypoestrogenemia that may be induced by the antagonist. In this way, add-back therapy can be used to mitigate or prevent potentially deleterious side effects, such as a reduction in bone mineral density.

Add-back therapy may be formulated for oral administration. For instance, add-back therapy administered in conjunction with the compositions and methods described herein may be formulated as a tablet, capsule, gel cap, powder, liquid solution, or liquid suspension. In some embodiments, the add-back therapy includes both an estrogen, such as β17-estradiol, and a progestin, such as norethindrone or norethindrone acetate. The estrogen and progestin may be administered separately or admixed in a single composition, such as a single tablet, capsule, gel cap, powder, liquid solution, or liquid suspension. For example, add-back therapy may feature a co-formulation containing estrogen (e.g., in the form of E2) and an additional agent such as a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered to a patient in the form of a single tablet, capsule, gel cap, powder, liquid solution, or liquid suspension that contains both estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

Methods of Treating Adenomyosis and Rectovaginal Endometriosis

Adenomyosis and rectovaginal endometriosis are estrogen-dependent pathologies that are triggered when endogenous estrogen levels rise beyond a particular threshold level. Taking each condition in turn, the terms "adenomyosis" and "uterine adenomyosis" are used interchangeably to describes the presence of both endometrial glands and stroma deep within the myometrium. This condition is associated with hypertrophy and hyperplasia of the subjacent muscle cells, which may ultimately result in an altered size and globulous morphology of the uterus, although the clinical signs and symptoms are variable. One of the key symptoms of adenomyosis is strong menstrual and even non menstrual pelvic pain with abnormal uterine bleeding.

There is presently a lack of precise data regarding adenomyosis prevalence among general gynecologic patients. Women are more commonly diagnosed with adenomyosis during the later stages of reproductive age; however the majority of published reports describing adenomyosis prevalence rely on pathologic analysis of surgical specimens. With modern imaging methods like transvaginal ultrasound (TVUS) and magnetic resonance imaging (MRI) with T2-weighted images, more detailed evaluation of the changes in the smooth muscle cells is enabled.

Endometriosis is an estrogen-dependent gynecological condition, defined as the presence of endometrial-like tissue outside the uterus. It is one of the most common gynecological diseases. The condition is predominantly found in women in their reproductive years and disappears spontaneously after menopause. A chronic, inflammatory reaction, induced by the ectopic endometrial cells, results in a variety of pain symptoms including dysmenorrhea, dyspareunia, chronic pelvic pain, dysuria, and dyschezia. In particular, for deep rectovaginal endometriosis, dyschezia may appear due to rectal involvement, and dyspareunia may occur due to the presence of the endometrial lesion in the cul-de-sac and in the vagina. Localized tenderness along the uterosacral ligaments and cul-de-sac is often related to endometrial lesions in these sites.

The deep rectovaginal form of endometriosis originates most often from the posterior part of the cervix and may infiltrate the anterior wall of the rectum. Endometriosis can be classified based on, for example, MRI and the degree of involvement of the bowel. The pure rectovaginal node, without involvement of the rectum and cervix (type I) accounts for about 12% of cases. Type II rectovaginal endometriosis describes a rectovaginal endometriosis node which is attached to the cervix, and type III rectovaginal endometriosis describes a node which is infiltrating the wall of the rectum or sigmoid.

Using the compositions and methods described herein, a patient having adenomyosis and/or rectovaginal endometriosis may be administered a GnRH antagonist, such as a compound of formula (I), described above (e.g., 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid, or a pharmaceutically acceptable salt thereof, such as the choline salt thereof).

A variety of methods known in the art and described herein can be used to determine whether a patient is responding favorably to GnRH antagonist treatment. For instance, beneficial clinical results in response to GnRH antagonist therapy include, without limitation, alleviation of symptoms of the endometrial growth disorder. Exemplary indicia of successful treatment of an adenomyosis patient that is administered a gonadotropin-releasing hormone (GnRH) antagonist include, without limitation, (i) a reduction in serum concentration of FSH, LH, and/or E2 following administration of the GnRH antagonist to the patient, (ii) a reduction in uterine volume following administration of the GnRH antagonist to the patient, (iii) a reduction in the thickness of the anterior and/or posterior region of the uterine myometrium following administration of the GnRH antagonist to the patient, (iv) a reduction in pelvic pain following administration of the GnRH antagonist to the patient; (v) a reduction in dysmenorrhea following administration of the GnRH antagonist to the patient; (vi) a reduction in dyspareunia following administration of the GnRH antagonist to the patient; (vii) a reduction in dyschezia following administration of the GnRH antagonist to the patient; (viii) a reduction in uterine tenderness following administration of the GnRH antagonist to the patient; (ix) a reduction in uterine bleeding following administration of the GnRH antagonist to the patient; (x) achievement of amenorrhea following administration of the GnRH antagonist to the patient; (xi) a reduction in the diameter of a junctional zone of adenomyosis following administration of the GnRH antagonist to the patient; and (xii) an improvement in the patient's overall well-being as determined by an improvement in the patients Endometriosis Health Profile questionnaire (EHP-30) score following administration of the GnRH antagonist to the patient and/or by way of a positive Patient Global Impression of Change (PGIC) score following administration of the GnRH antagonist to the patient.

Similarly, exemplary indicia of successful treatment of a rectovaginal endometriosis patient that is administered a GnRH antagonist include, without limitation, (i) a reduction in serum concentration of FSH, LH, and/or E2 following administration of the GnRH antagonist to the patient, (ii) a reduction in the volume of one or more rectovaginal endometriosis nodes following administration of the GnRH antagonist to the patient, (iii) a reduction in bowel involvement of one or more type III endometriosis nodes following administration of the GnRH antagonist to the patient, (iv) a reduction in pelvic pain following administration of the GnRH antagonist to the patient; (v) a reduction in dysmenorrhea following administration of the GnRH antagonist to the patient; (vi) a reduction in dyspareunia following administration of the GnRH antagonist to the patient; (vii) a reduction in dyschezia following administration of the GnRH antagonist to the patient; (viii) a reduction in uterine bleeding following administration of the GnRH antagonist to the patient; (ix) achievement of amenorrhea following administration of the GnRH antagonist to the patient; and (x) an improvement in the patient's overall well-being as determined by an improvement in the patients EHP-30 score following administration of the GnRH antagonist to the patient and/or by way of a positive PGIC score following administration of the GnRH antagonist to the patient.

Modified Biberoglu and Behrman Symptom Severity Scale

Exemplary methods for assessing a patient's response to GnRH antagonist therapy for the treatment of adenomyosis and/or rectovaginal endometriosis include administration of a modified Biberoglu and Behrman questionnaire, as described herein. An exemplary mB&B questionnaire for use in conjunction with the compositions and methods described herein is shown in FIG. 1.

Endometriosis Health Profile Questionnaire

Additional methods for assessing patient respond to GnRH antagonist therapy for the treatment of adenomyosis and/or rectovaginal endometriosis include analyzing the patient's score on an Endometriosis Health Profile questionnaire. An exemplary Endometriosis Health Profile questionnaire for use in conjunction with the compositions and methods described herein is the EHP-30 questionnaire shown in FIGS. 2A-2D.

Patient Global Impression of Change Score

Additional methods for assessing patient response to GnRH antagonist therapy for the treatment of adenomyosis and/or rectovaginal endometriosis include analyzing the patient's score on a Patient Global Impression of Change (PGIC) scale. An exemplary PGIC questionnaire for use in conjunction with the compositions and methods described herein is shown in FIG. 3.

Quantitation of Uterine Blood Loss by the Alkaline Hematin Method

Techniques for quantifying uterine blood loss are known in the art and include, for instance, the alkaline hematin method, as described, for instance, in Hallberg et al., Scand. J. Clin. Lab. Invest. 16:244-248 (1964), the disclosure of which is incorporated herein by reference as it pertains to techniques for assessing the volume of blood lost by a patient. In the alkaline hematin approach, uterine blood soaked into, for example, a sanitary napkin, vaginal tampon, or cotton pad, is reconstituted in a basic aqueous solution, such as a solution of 5% (w/v) sodium hydroxide. This incubation enables (i) extraction of the iron-containing porphyrin of hemoglobin and (ii) oxidation of the ferrous ion to a hydroxy-coordinated ferric ion in each chelate, thus forming hematin. Hematin is a detectable chromophore, absorbing light at between 550 and 546 nm. By comparing the concentration of hematin obtained from incubation of a soaked menstrual blood sample with aqueous sodium hydroxide to the concentration of hematin obtained from incubation of a sample of venous blood with aqueous sodium hydroxide, one can stoichiometrically determine the volume of menstrual blood lost by a patient, such as a patient having adenomyosis and/or rectovaginal endometriosis. Improvements to the original alkaline hematin method are known in the art and are described, for example, in Newton et al., Contraception 16:269-282 (1977), and in van Eijkeren et al., Eur. J. Obstet. Gynecol. Reprod. Biol. 22:345-351 (1986), the disclosures of each of which are incorporated herein by reference as they pertain to methods of determining the volume of blood lost by a patient.

Routes of Administration and Dosing of GnRH Antagonists

The GnRH antagonists described herein may be administered to a patient in need thereof (e.g., a patient suffering from adenomyosis and/or rectovaginal endometriosis) by a variety of routes of administration. For instance, the GnRH antagonists described herein may be formulated for oral administration, among other routes. Exemplary non-oral routes of administration of the GnRH antagonists described herein include, without limitation, parenteral administration, subcutaneous administration, intramuscular administration, and intradermal administration, among others.

In some embodiments, the GnRH antagonist is a compound of any one of formulas (I)-(VIa), above, and is administered to the patient in an amount of from about 25 mg to about 500 mg per dose, and may be administered in one or more doses per day, for example, in accordance with a dosing schedule described above. For instance, the GnRH antagonist may a compound of any one of formulas (I)-(VIa), above, and may be administered to the patient in an amount of from 25 mg to 500 mg, 30 mg to 495 mg, 35 mg to 490 mg, 40 mg to 485 mg, 45 mg to 480 mg, 50 mg to 475 mg, 55 mg to 470 mg, 60 mg to 465 mg, 65 mg to 460 mg, 70 mg to 455 mg, 75 mg to 450 mg, 80 mg to 445 mg, 85 mg to 440 mg, 90 mg to 435 mg, 95 mg to 430 mg, 100 mg to 425 mg, 105 mg to 420 mg, 110 mg to 415 mg, 115 mg to 410 mg, 120 mg to 405 mg, 125 mg to 400 mg, 130 mg to 395 mg, 135 mg to 390 mg, 140 mg to 385 mg, 145 mg to 380 mg, or 150 mg to 375 mg, per dose, and may be administered in one or more doses per day (e.g., in a single daily dose). In some embodiments, the GnRH antagonist is a compound of any one of formulas (I)-(VIa), above, and is administered to the patient once daily in an amount of from 100 mg to 300 mg, per dose, such as from 105 mg to 295 mg, 110 mg to 290 mg, 115 mg to 285 mg, 120 mg to 280 mg, 125 mg to 275 mg, 130 mg to 270 mg, 135 mg to 265 mg, 140 mg to 260 mg, 145 mg to 255 mg, 150 mg to 250 mg, 155 mg to 245 mg, 160 mg to 240 mg, 165 mg to 235 mg, 170 mg to 230 mg, 175 mg to 225 mg, 180 mg to 220 mg, 185 mg to 215 mg, 190 mg to 210 mg, or 195 mg to 205 mg, per dose. In some embodiments, the GnRH antagonist is a compound of any one of formulas (I)-(VIa), above, and is administered to the patient once daily in an amount of about 100 mg per dose or 200 mg per dose.

The GnRH antagonists described herein may be administered to a patient a plurality of times over the course of a treatment period. For instance, the GnRH antagonists described herein may be administered to a patient periodically over a treatment period of at least two weeks (e.g., a treatment period of from about two weeks to about six months, about three weeks to about five months, about four weeks to about four months, or about one month to about three months). The GnRH antagonist may be administered to the patient, for example, over a treatment period of from about four weeks to about six months (e.g., from about 28 days to about 180 days, about 30 days to about 175 days, about 35 days to about 170 days, about 40 days to about 165 days, about 45 days to about 160 days, about 50 days to about 155 days, about 55 days to about 150 days, about 60 days to about 145 days, about 65 days to about 140 days, about 70 days to about 135 days, about 75 days, to about 130 days, about 80 days to about 125 days, about 85 days, to about 120 days, or about 90 days to about 115 days). In some embodiments, the GnRH antagonist is periodically administered to the patient over the course of from about eight weeks to about sixteen weeks (e.g., from about 60 days to about 110 days, about 65 days to about 105 days, about 70 days to about 100 days, about 75 days to about 95 days, or about 80 days, to about 90 days). In some embodiments, the GnRH antagonist is periodically administered to the patient over a treatment period of about 12 weeks. In some embodiments, the GnRH antagonist is periodically administered to the patient over a treatment period of about 24 weeks.

Additional dosing schedules for the treatment of adenomyosis and rectovaginal endometriosis using other GnRH antagonists disclosed herein are described in detail above.

Pharmaceutical Compositions

GnRH antagonists suitable for use with the compositions and methods described herein can be formulated into a pharmaceutical composition for administration to a patient, such as a female human patient, in a biologically compatible form suitable for administration in vivo. A pharmaceutical composition containing a GnRH antagonist, such as a compound described herein (e.g., 3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid or a pharmaceutically acceptable salt thereof, such as the choline salt thereof), may additionally contain a suitable diluent, carrier, or excipient. GnRH antagonists can be administered to a patient, for example, orally or by intravenous injection. Under ordinary conditions of storage and use, a pharmaceutical composition may contain a preservative, e.g., to prevent the growth of microorganisms. Conventional procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a patient in need of treatment.

A pharmaceutical composition may be administered to a patient, e.g., a human patient, alone or in combination with one or more pharmaceutically acceptable carriers, e.g., as described herein, the proportion of which may be determined by the solubility and/or chemical nature of the compound, chosen route of administration, and standard pharmaceutical practice.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example 1. Use of a GnRH Antagonist for the Treatment of a Patient Having Adenomyosis Using the compositions and methods described herein, a patient may be administered a GnRH antagonist so as to treat, and/or ameliorate the symptoms of, adenomyosis. The GnRH antagonist (e.g., a compound of formula (I), above, such as compound (VI) or the choline salt thereof) may be administered to the patient in an amount sufficient to reduce the serum concentration of luteinizing hormone (LH), follicle-stimulating hormone (FHS), and/or β17-estradiol (E2) in circulation. The GnRH antagonist may be administered, for example, in an amount of from about 25 mg to about 500 mg per dose. Exemplary doses of the GnRH antagonist include, without limitation, an amount of from 25 mg to 500 mg, 30 mg to 495 mg, 35 mg to 490 mg, 40 mg to 485 mg, 45 mg to 480 mg, 50 mg to 475 mg, 55 mg to 470 mg, 60 mg to 465 mg, 65 mg to 460 mg, 70 mg to 455 mg, 75 mg to 450 mg, 80 mg to 445 mg, 85 mg to 440 mg, 90 mg to 435 mg, 95 mg to 430 mg, 100 mg to 425 mg, 105 mg to 420 mg, 110 mg to 415 mg, 115 mg to 410 mg, 120 mg to 405 mg, 125 mg to 400 mg, 130 mg to 395 mg, 135 mg to 390 mg, 140 mg to 385 mg, 145 mg to 380 mg, or 150 mg to 375 mg, per dose. For example, when the GnRH antagonist is compound (VI) or the choline salt thereof, the compound may be administered at a dose of 200 mg.

The GnRH antagonist may be administered to the patient periodically, for instance, over a treatment period of at least two weeks. To determine the responsiveness of the patient to the GnRH antagonist, a physician may monitor the patient's uterine volume, as well as the level of pain experienced by the patient. For example, the physician may observe one or more of the following responses of the patient as an indicator of successful treatment: (i) a reduction in uterine volume following administration of the GnRH antagonist to the patient, (ii) a reduction in the thickness of the anterior and/or posterior region of the uterine myometrium following administration of the GnRH antagonist to the patient, (iii) a reduction in pelvic pain following administration of the GnRH antagonist to the patient; (iv) a reduction in dysmenorrhea following administration of the GnRH antagonist to the patient; (v) a reduction in dyspareunia following administration of the GnRH antagonist to the patient; (vi) a reduction in dyschezia following administration of the GnRH antagonist to the patient; (vii) a reduction in uterine tenderness following administration of the GnRH antagonist to the patient; (viii) a reduction in uterine bleeding following administration of the GnRH antagonist to the patient; (ix) achievement of amenorrhea following administration of the GnRH antagonist to the patient; (x) a reduction in the diameter of a junctional zone of adenomyosis following administration of the GnRH antagonist to the patient; and (xi) an improvement in the patient's overall well-being as determined by an improvement in the patients Endometriosis Health Profile questionnaire (EHP-30) score following administration of the GnRH antagonist to the patient and/or by way of a positive Patient Global Impression of Change (PGIC) score following administration of the GnRH antagonist to the patient.

Example 2. Use of Compound (VI) for the Treatment of a Patient Having Adenomyosis This example describes the results of an open-label, Phase II clinical trial examining the safety and efficacy of the GnRH antagonist, compound (VI) (3-[2-fluoro-5-(2,3-difluoro-6-methoxybenzyloxy)4-methoxyphenyl]-2,4-dioxo-1,2,3,4-tetrahydrothieno [3,4d]pyrimidine-5-carboxylic acid), for treating human female patients suffering from adenomyosis. The study began with a 4-week patient screening period, followed by two consecutive 12-week treatment periods. During the first 12-week treatment period, patients were administered compound (VI) in a single daily dose of 200 mg. During the second 12-week treatment period, patients were administered compound (VI) in a single daily dose of 100 mg. Patients then entered a post-treatment follow-up period during which the effects of compound (VI) were further assessed.

The sections that follow describe the experimental design of the clinical trial in further detail and provide results for a representative patient.

Study Design

The total duration of this study (from the screening visit to the end-of-study visit) was 40 weeks per subject. The study began with a 4-week screening period evaluating the symptoms of uterine adenomyosis and assessing the volume of each patient's adenomyosis-affected uterus by way of MRI. During this period, the patients received no study drug.

At the start of menstruation, the patients were administered 200 mg of compound (VI), once daily, in the form of the corresponding choline salt. The administration continued over the course of a 12-weel treatment period, referred to as the "initiation phase," so as to maximize the effect of the treatment. After the first 12-week treatment period, the therapeutic effect of the GnRH antagonist was maintained by administering 100 mg of compound (VI), once daily, over the course of a second 12-week treatment period. This second treatment period was referred to as the "maintenance phase."

At the end of the maintenance phase (at week 24), the patients entered a 12-week follow-up period without any active treatment.

Study Population

The target population for this study was composed of pre-menopausal women aged 18-48 years with symptomatic uterine adenomyosis and having specified pain symptoms as assessed on the modified Biberoglu & Behrman (mB&B) scale. Patients were subject to the following eligibility criteria:

Main Inclusion Criteria:

To be eligible for inclusion into this study, patients fulfilled the following inclusion criteria:

1. Patients provided written informed consent prior to initiation of any study related procedures.

2. Patients were pre-menopausal women, aged between 18 and 48 years inclusive at screening.

3. Patients had a history of regular menstrual cycles every 21-35 days and without intermenstrual bleeding heavier than spotting or staining.

4. Patients had Follicle-Stimulating Hormone (FSH) levels s 20 IU/L at screening.

5. Patients had uterine adenomyosis confirmed by MRI with:

Junctional-Zone width on T2 weighted images 12 mm, and

Moderate to severe pain according to the mB&B classification for two criteria out of deep dyspareunia, pelvic pain or dysmenorrhea, and Presence of abnormal uterine bleeding.

6. Patients had a Body Mass Index (BMI) ≥18 and ≤35 kg/m$^2$.

7. If of childbearing potential, patients agreed to use one of the following birth control methods during the entire length of the treatment period of the study:

Sexual abstinence from heterosexual intercourse if routinely and consistently practiced Partner with vasectomy performed at least 6 months prior to the screening visit and with confirmed azoospermia Double non-hormonal barrier contraception such as condom or diaphragm each combined with spermicide.

8. If of non-childbearing potential, patients had tubal ligation sterilization at least 2 months before the screening visit.

Efficacy Endpoints

The primary efficacy endpoint of this study was a change, from baseline to week 24, in volume of the adenomyosis-affected uterus, as measured by MRI. Secondary endpoints under investigation in this study were as follows:

Change from baseline to weeks 12 and 36 in volume of the uterus with adenomyosis measured by MRI Change from baseline to weeks 12, 24 and 36 in volume of the uterus with adenomyosis measured by TVUS Change from baseline to weeks 12, 24 and 36 in the largest thickness of the anterior and posterior part of the uterus myometrium (sagittal assessment)

Change from baseline to weeks 12, 24 and 36 in the largest diameter of the junctional zone of the uterine adenomyosis measured by MRI Presence of blood spots on the MRI images Change from baseline to weeks 12, 24 and 36 in uterus volume assessed at vaginal examination Change from baseline to weeks 12, 24 and 36 in uterine tenderness assessed at vaginal examination Change from baseline to weeks 12, 24 and 36 in dysmenorrhea, pelvic pain and dyspareunia according to the mB&B scale Change from baseline to weeks 4, 8, 12, 16, 20, 24 and 36 for global pelvic pain assessed over the preceding 4-week period using a Numerical Rating Scale (NRS) with a monthly recall Change from baseline to weeks 4, 8, 12, 16, 20, 24, 28, 32 and 36 in the mean monthly dyspareunia score defined as the mean of available daily dyspareunia scores over the preceding 4-week period assessed on the Verbal Rating Scale (VRS) dyspareunia scale and on a NRS Change from baseline to weeks 4, 8, 12, 16, 20 and 24 fin the mean monthly dyschezia score defined as the mean of weekly dyschezia scores over the preceding 4-week period using a NRS No uterine bleeding (or spotting only), during the 4-week period preceding weeks 4, 8, 12, 16, 20 and 24 using a simplified bleeding scale Time to amenorrhea Change from baseline to weeks 12, 24 and 36 in the Endometriosis Health Profile questionnaire (EHP-30)

Patient Global Impression of Change (PGIC) score at weeks 12, 24 and 36

Data Analysis and Statistics

Hypothesis testing was conducted based on change from baseline assessments, testing the null hypothesis of no change from baseline versus the alternative hypothesis of a change (increase/decrease from baseline). Two sided hypotheses tests were carried out, each at a nominal type I error rate (alpha) of 0.05. Calculated p-values were used primarily as a measure of evidence against the null hypothesis rather than just for a formal statement of statistical significance.

Descriptive statistics were produced for all measured as well as derived endpoints. For continuous data and for ordered categorical data, if appropriate, the number of non-missing observations, mean, standard deviation, median, minimum and maximum were calculated. For ordered categorical data and nominal data, absolute and relative frequencies (in %) were calculated.

Results

Table 4, below, provides primary and secondary endpoint results for a representative patient in this study. The patient had an age of 42 years, weight of 61.5 kg, and height of 1.74 m at screening. Table 4 shows the patient's reduction in uterine volume from just prior to initiation of 24 weeks of treatment with compound (VI) ("baseline") to the end of the initiation phase (week 12) and maintenance phase (week 24) of treatment. Table 4 also shows the patient's reduction in pain, as assessed by way of a mB&B score, numerical rating score, EHP-30 score, and PGIC score.

TABLE 4

Effects of GnRH Antagonist Treatment on Representative Patient Having Adenomyosis

| Patient Characteristic | Timepoint | | | Notes |
|---|---|---|---|---|
| | Baseline | Week 12 | Week 24 | |
| Uterus volume by MRI (cm$^3$) | 198 | 84 | 75 | Volume calculated by radiologist |

TABLE 4-continued

Effects of GnRH Antagonist Treatment on Representative Patient Having Adenomyosis

| Patient Characteristic | Baseline | Week 12 | Week 24 | Notes |
|---|---|---|---|---|
| Change from baseline in uterine volume by MRI (cm³) | — | −114 | −123 | |
| Uterus volume by transvaginal ultrasound (TVUS) (cm³) | 128 cm³ Length: 6.7 cm Height: 5.6 cm Depth: 6.5 cm | 48 cm³ Length: 4.5 cm Height: 4.1 cm Depth: 5.0 cm | 48 cm³ Length: 4.6 cm Height: 4.0 cm Depth: 5.0 cm | Volume = l × h × d × 0.523 (prolate ellipsoid volume) |
| Change from baseline in uterine volume by TVUS (cm³) | — | −79 | −79 | |
| mB&B score | 6.0 (Severe) | 2.0 (Mild) | 2.0 (Mild) | Composite Score (0-15) None (0) Mild (1-2) Moderate (3-5) Severe (6-10) Very severe (11-15) |
| Change from baseline in mB&B score | — | −4 | −4 | |
| Global pelvic pain by numerical rating scale (NRS) | 7 | 0 | 1 | Scale 0 to 10 0 (no pain) 10 (worst pain imaginable) |
| Change from baseline in global pelvic pain by NRS | — | −7 | −6 | |
| EHP-30 Score: Pain (Questions 1-11 of EHP-30) | 63.6 | 0.0 | 6.8 | Scale rated 0 to 100 Each domain rated independently 0 = (best possible health status as measured by the questionnaire 100 = (worst possible health status as measured by the questionnaire) |
| Change from baseline in EHP-30 score for pain | — | −63.6 | −56.8 | |
| EHP-30 Score: Control and Powerlessness (Questions 12-17 of EHP-30) | 70.8 | 0 | 0 | Scale rated 0 to 100 Each domain rated independently 0 = (best possible health status as measured by the questionnaire 100 = (worst possible health status as measured by the questionnaire) |
| Change from baseline in EHP-30 score for control and powerlessness | — | −70.8 | −70.8 | |
| EHP-30 Score: Emotional Well-being (Questions 18-23 of EHP-30) | 66.7 | 0 | 0 | Scale rated 0 to 100 Each domain rated independently 0 = (best possible health status as measured by the questionnaire 100 = (worst possible health status as measured by the questionnaire) |
| Change from baseline in EHP-30 score for emotional well-being | — | −66.7 | −66.7 | |
| EHP-30 Score: Social Support (Questions 24-27 of EHP-30) | 43.8 | 0 | 0 | Scale rated 0 to 100 Each domain rated independently 0 = (best possible health status as measured by the questionnaire 100 = (worst possible health status as measured by the questionnaire) |
| Change from baseline in EHP-30 score for social support | — | −43.8 | −43.8 | |
| EHP-30 Score: Self-Image (Questions 28-30 of EHP-30) | 50.0 | 0 | 0 | Scale rated 0 to 100 Each domain rated independently 0 = (best possible health status as measured by the questionnaire 100 = (worst possible health status as measured by the questionnaire) |
| Change from baseline in EHP-30 score for self-image | — | −50.0 | −50.0 | |
| Patient Global Impression of Change since Baseline (PGIC) | — | 1—Very much improved | 1—Very much improved | Scale rated 1 to 7 1 (Very much improved) 7 (very much worse) |

Conclusion

As shown in Table 4, the results of this study demonstrate that compound (VI) effectuates a sustained reduction in uterine volume, as well as substantial reduction in adenomyosis-associated pain, as assessed by way of various metrics.

Example 3. Use of a GnRH Antagonist for the Treatment of a Patient Having Rectovaginal Endometriosis Using the compositions and methods described herein, a patient may be administered a GnRH antagonist so as to treat, and/or ameliorate the symptoms of, rectovaginal endometriosis. The GnRH antagonist (e.g., a compound of formula (I), above, such as compound (VI) or the choline salt thereof) may be administered to the patient in an amount sufficient to reduce the serum concentration of LH, FHS, and/or E2 in circulation. The GnRH antagonist may be administered, for example, in an amount of from about 25 mg to about 500 mg per dose. Exemplary doses of the GnRH antagonist include, without limitation, an amount of from 25 mg to 500 mg, 30 mg to 495 mg, 35 mg to 490 mg, 40 mg to 485 mg, 45 mg to 480 mg, 50 mg to 475 mg, 55 mg to 470 mg, 60 mg to 465 mg, 65 mg to 460 mg, 70 mg to 455 mg, 75 mg to 450 mg, 80 mg to 445 mg, 85 mg to 440 mg, 90 mg to 435 mg, 95 mg to 430 mg, 100 mg to 425 mg, 105 mg to 420 mg, 110 mg to 415 mg, 115 mg to 410 mg, 120 mg to 405 mg, 125 mg to 400 mg, 130 mg to 395 mg, 135 mg to 390 mg, 140 mg to 385 mg, 145 mg to 380 mg, or 150 mg to 375 mg, per dose. For example, when the GnRH antagonist is compound (VI) or the choline salt thereof, the compound may be administered at a dose of 200 mg.

The GnRH antagonist may be administered to the patient periodically, for instance, over a treatment period of at least two weeks. To determine the responsiveness of the patient to the GnRH antagonist, a physician may monitor the length of one or more rectovaginal endometriosis lesions in the patient, for example, by way of magnetic resonance imaging (MRI) and/or transvaginal ultrasound (TVUS). For example, the physician may observe one or more of the following responses of the patient as an indicator of successful treatment: (i) a reduction in the volume of one or more rectovaginal endometriosis nodes following administration of the GnRH antagonist to the patient, (ii) a reduction in bowel involvement of one or more type III endometriosis nodes following administration of the GnRH antagonist to the patient, (iii) a reduction in pelvic pain following administration of the GnRH antagonist to the patient; (iv) a reduction in dysmenorrhea following administration of the GnRH antagonist to the patient; (v) a reduction in dyspareunia following administration of the GnRH antagonist to the patient; (vi) a reduction in dyschezia following administration of the GnRH antagonist to the patient; (vii) a reduction in uterine bleeding following administration of the GnRH antagonist to the patient; (viii) achievement of amenorrhea following administration of the GnRH antagonist to the patient; and (xi) an improvement in the patient's overall well-being as determined by an improvement in the patients EHP-30 score following administration of the GnRH antagonist to the patient and/or by way of a positive PGIC score following administration of the GnRH antagonist to the patient.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of treating adenomyosis in a human patient in need thereof, the method comprising administering to the patient a therapeutically effective amount of a compound, 3-[2-fluoro-5-(2,3-difluoro-6-methoxybenzyloxy)-4-methoxyphenyl]-2,4-dioxo-1,2,3,4-tetrahydrothieno [3,4d] pyrimidine-5-carboxylic acid, represented by formula (VI)

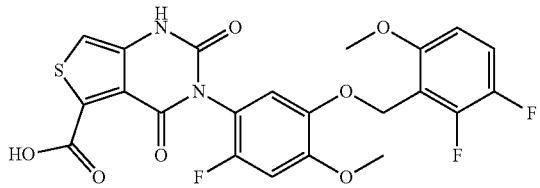

(VI)

or a pharmaceutically acceptable salt thereof.

2. The method of claim 1, wherein the compound is administered to the patient in the form of a pharmaceutically acceptable salt thereof.

3. The method of claim 2, wherein the pharmaceutically acceptable salt is a choline salt of (VI), choline 3-[2-fluoro-5-(2,3-difluoro-6-methoxybenzyloxy)4-methoxyphenyl]-2, 4-dioxo-1,2,3,4-tetrahydrothieno [3,4d]pyrimidine-5-carboxylate.

4. The method of claim 1, wherein the compound is administered to the patient orally.

5. The method of claim 1, wherein the compound is administered to the patient one or more times daily.

6. The method of claim 5, wherein the compound is administered to the patient once daily.

7. The method of claim 1, wherein the compound is administered to the patient in an amount of about 100 mg per day.

8. The method of claim 1, wherein the compound is administered to the patient in an amount of about 200 mg per day.

9. The method of claim 1, wherein the patient exhibits a reduction in uterine volume following administration of the compound to the patient.

10. The method of claim 9, wherein the reduction in uterine volume is assessed by way of MRI or transvaginal ultrasound (TVUS).

11. The method of claim 1, wherein the patient exhibits a reduction in pelvic pain, dysmenorrhea, dyspareunia, and/or dyschezia following administration of the compound to the patient.

* * * * *